(12) United States Patent
Shresta et al.

(10) Patent No.: US 10,308,689 B2
(45) Date of Patent: Jun. 4, 2019

(54) DENGUE VIRUS (DV) POLYPEPTIDE SEQUENCES, T CELL EPITOPES AND METHODS AND USES THEREOF

(71) Applicant: LA JOLLA INSTITUTE FOR ALLERGY AND IMMUNOLOGY, La Jolla, CA (US)

(72) Inventors: Sujan Shresta, San Diego, CA (US); Lauren Yauch, La Jolla, CA (US); Alessandro Sette, San Diego, CA (US); Daniela Weiskopf, San Diego, CA (US)

(73) Assignee: LA JOLLA INSTITUTE FOR ALLERGY AND IMMUNOLOGY, La Jolla, CA (US)

( * ) Notice: Subject to any disclaimer, the term of this patent is extended or adjusted under 35 U.S.C. 154(b) by 0 days.

(21) Appl. No.: 14/800,468

(22) Filed: Jul. 15, 2015

(65) Prior Publication Data
US 2016/0130305 A1 May 12, 2016

Related U.S. Application Data

(63) Continuation-in-part of application No. 13/719,227, filed on Dec. 18, 2012, now abandoned, which is a continuation-in-part of application No. PCT/US2011/041889, filed on Jun. 24, 2011.

(60) Provisional application No. 62/024,943, filed on Jul. 15, 2014, provisional application No. 61/391,882, filed on Oct. 11, 2010, provisional application No. 61/358,142, filed on Jun. 24, 2010.

(51) Int. Cl.
| | |
|---|---|
| *C07K 14/005* | (2006.01) |
| *A61K 39/12* | (2006.01) |
| *C12N 7/00* | (2006.01) |
| *G01N 33/569* | (2006.01) |
| *A61K 39/00* | (2006.01) |

(52) U.S. Cl.
CPC ............ *C07K 14/005* (2013.01); *A61K 39/12* (2013.01); *C12N 7/00* (2013.01); *G01N 33/56983* (2013.01); *A61K 2039/55566* (2013.01); *C07K 2319/00* (2013.01); *C07K 2319/21* (2013.01); *C12N 2770/24122* (2013.01); *C12N 2770/24134* (2013.01)

(58) Field of Classification Search
None
See application file for complete search history.

(56) References Cited

U.S. PATENT DOCUMENTS

| | | | | |
|---|---|---|---|---|
| 6,017,535 | A | * | 1/2000 | Fu ................. C07K 14/005 424/186.1 |
| 2003/0175304 | A1 | | 9/2003 | Peters et al. |
| 2004/0009469 | A1 | | 1/2004 | Apt et al. |
| 2005/0010043 | A1 | | 5/2005 | Whitehead et al. |
| 2006/0062803 | A1 | | 3/2006 | Kinney et al. |
| 2007/0092534 | A1 | | 4/2007 | Whitehead et al. |
| 2010/0035231 | A1 | | 2/2010 | Kumarsil et al. |
| 2010/0068147 | A1 | | 3/2010 | Hibberd et al. |
| 2011/0033449 | A1 | | 2/2011 | Glennie et al. |
| 2013/0064843 | A1 | | 3/2013 | Brusic et al. |

FOREIGN PATENT DOCUMENTS

| | | |
|---|---|---|
| EP | 1944038 | 7/2008 |
| WO | 2007/031034 | 3/2004 |
| WO | 2009/152147 | 12/2009 |
| WO | 2011/163628 | 12/2011 |

OTHER PUBLICATIONS

Gagnon, S.J., et al., Identification of Two Epitopes onthe Dengue 4 Virus Capsid Protein Recognized by a Serotype-Specific and a Panel of Serotype-Specific and Panel of Serotype-Cross-Reactive Human CD4+ Cytotoxic T Lymphocyte Clones, J. Virol., 1996, 70(01):141-147.

Halstead, S.B., Pathogenesis of Dengue: Challenges to Molecular Biology, 1988, Science, 239:476-481.

Mangada, M.M., et al., Altered Cytokine Responses of Dengle-Specific CD8+ T Cells to Heterologous Serotypes, J. Immunol., 2005, 175(4):2676-2683.

Medin, C.L., et al., Dengue Virus Nonstructural Protein NS5 Induces Interleukin 8 Transcription and Secretion, J. Virol., 2005, 79(17):11053-11061.

Simmons, C.P., et al., Early T Cell Responses to Dengue Virus Epitopes in Vietnamesse Adults with Secondary Dengue Virus Infections, J. Virol., 2005, 79(9):5665-5675.

Weiskopf, D., et al., Insights into HLA-Restricted T Cell Responses in a Novel Mouse Model of Dengue Virus Infection Point Toward New Implications for Vaccine Design, J. Immunol., 2011, 187(8):4268-4279.

Weiskopf, D., et al., T Cell Assay Information, Assay ID 1854385, Immune Epitope Database, Jan. 1, 2011, Retrieved from Internet: URL: http://www.immuneepitope.org/assayID/1854385.

(Continued)

*Primary Examiner* — Stacy B Chen
(74) *Attorney, Agent, or Firm* — Pillsbury Winthrop Shaw Pittman LLP

(57) ABSTRACT

Dengue virus (DV) peptides, including T cell epitopes, structural and non-structural (NS) polypeptide sequences, subsequences and modifications thereof, nucleotide sequences encoding such peptides, and compositions including such peptides and encoding nucleotide sequences, and cells expressing such peptides, are provided. Such DV peptides, nucleotide sequences and compositions, can be used to elicit, stimulate, induce, promote, increase, enhance or activate an anti-DV CD8+ T cell response or an anti-DV CD4+ T cell response. Such peptides, nucleotide sequences and compositions can also be used for and in methods of vaccination/immunization of a subject against Dengue virus (DV) (e.g., to provide protection against DV infection and/or pathology), and for treatment of a subject in need thereof, for example, treatment of the subject for a Dengue virus (DV) infection or pathology.

8 Claims, 46 Drawing Sheets

Specification includes a Sequence Listing.

(56) References Cited

OTHER PUBLICATIONS

Yauch, L.E., et al., A Protective Role for Dengue Virus-Specific CD8+ T Cells, J. Immunol., 2009, 189(8):4865-4873.
Zellweger, R.M., et al., Mouse Models to Study Dengue Virus Immunology and Pathogenesis, Frontiers in Immunology, 2014, 4(151):1-9.
Extended European Search Report, European Application No. 09763437 dated Oct. 25, 2011.
International Patent Application No. PCT/US2009/046740, International Search Report and Written Opinion dated Jan. 7, 2010.
International Patent Application No. PCT/US2009/046740, International Preliminary Report on Patentability dated Dec. 23, 2010.
International Patent Application No. PCT/US2011/041889, International Search Report and Written Opinion dated May 25, 2012.
International Patent Application No. PCT/US2011/041889, International Preliminary Report on Patentability dated Dec. 28, 2012.
International Patent Application No. PCT/US2012/k044071, International Search Report and Written Opinion dated Dec. 12, 2012.

* cited by examiner

Fig. 1A
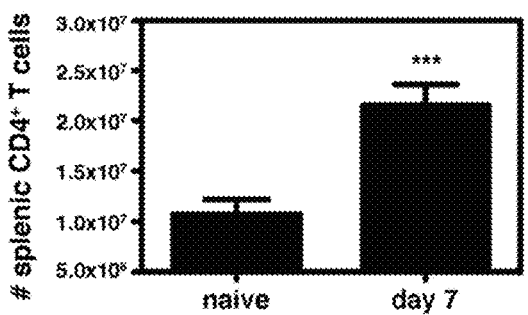
Fig. 1D
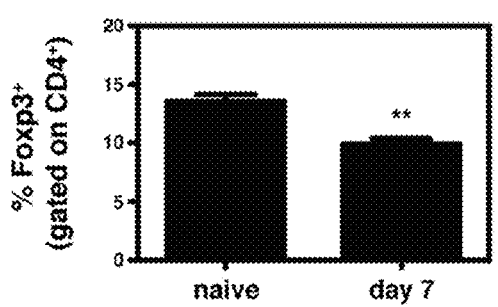
Fig. 1B
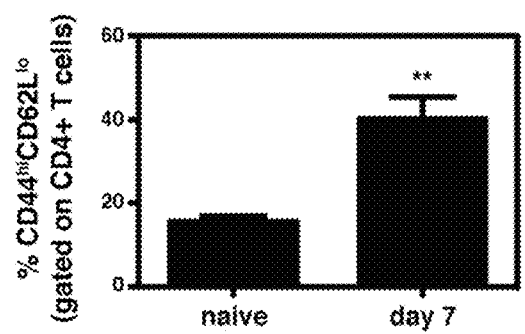
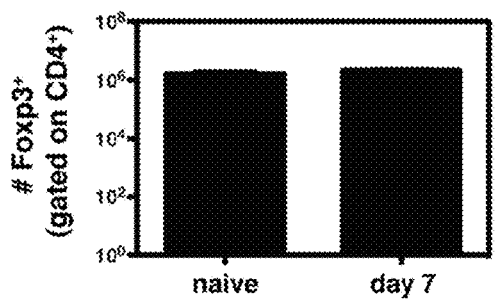
Fig. 1C
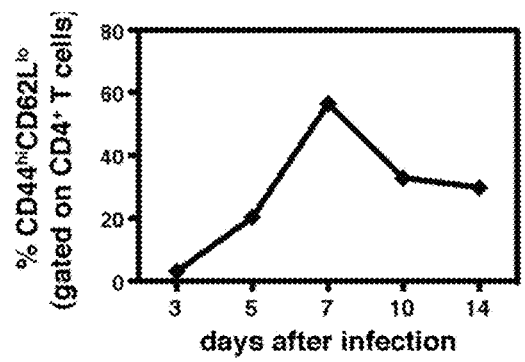

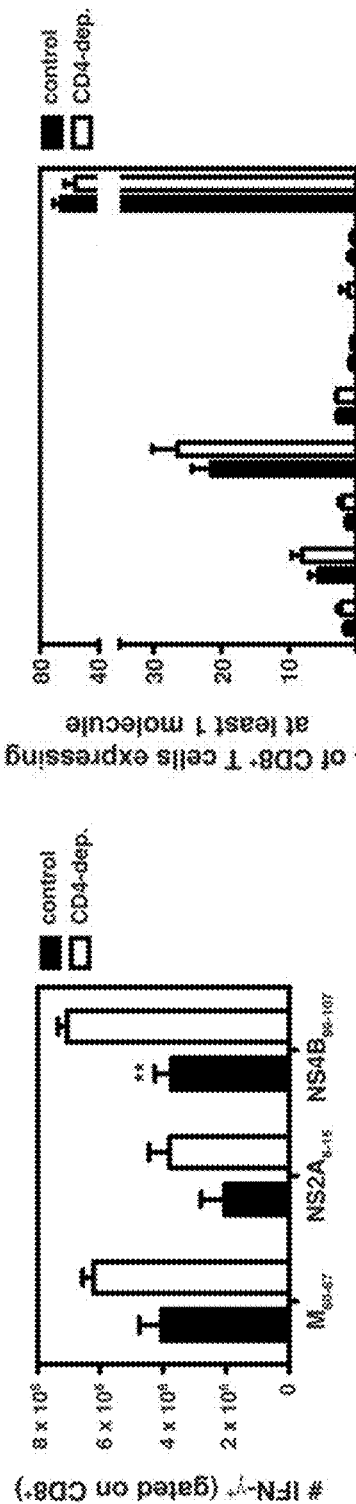
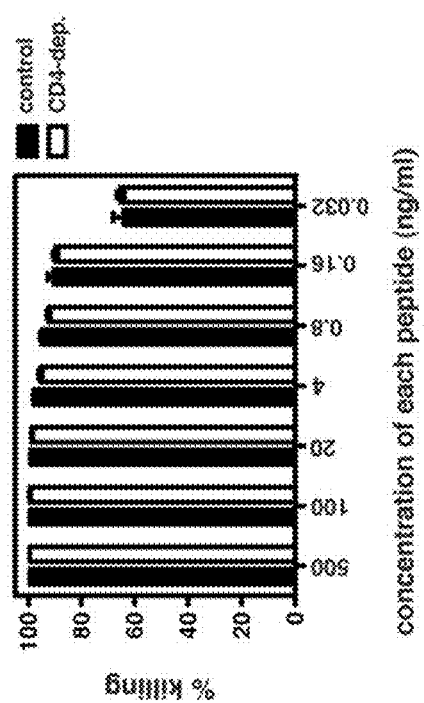
Fig. 6A
Fig. 6B
Fig. 6C

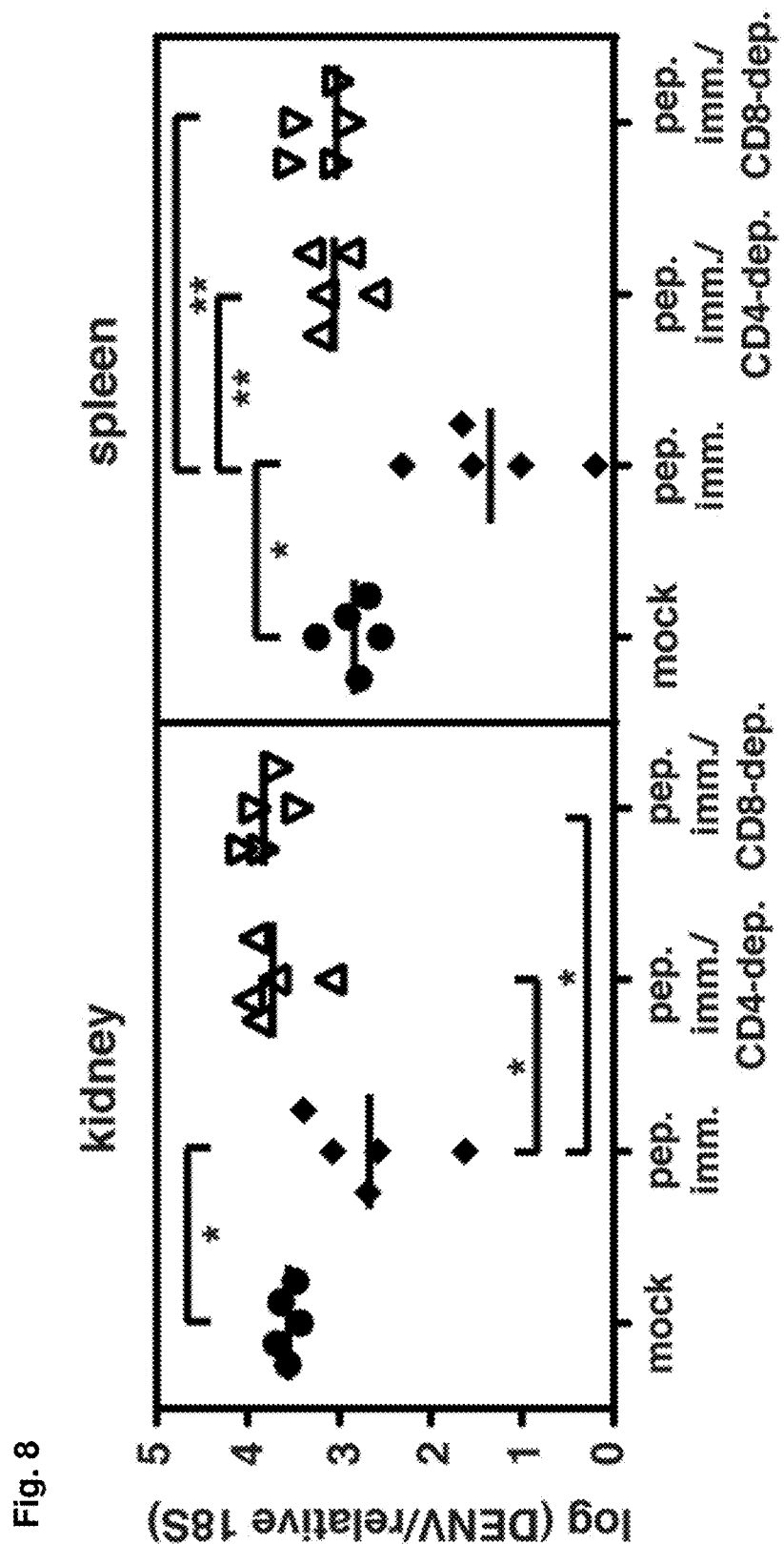

Fig. 10 conserved specific

DENGUE VIRUS (DV) POLYPEPTIDE SEQUENCES, T CELL EPITOPES AND METHODS AND USES THEREOF

RELATED APPLICATIONS

This application is a continuation in part of U.S. patent application Ser. No. 13/719,227 filed Dec. 18, 2012, which is a continuation in part of International Application No. PCT/US2011/041889, filed Jun. 24, 2011, which claims the benefit of priority to U.S. Provisional Application No. 61/391,882, filed Oct. 11, 2010, and U.S. Provisional-Application No. 61/358,142, filed Jun. 24, 2010, and this application claims the benefit of priority to U.S. Provisional Application No. 62/024,943 filed Jul. 15, 2014, all of which applications are expressly incorporated herein by reference in their entirety.

GOVERNMENT SUPPORT

This invention received government support under National Institutes of Health grants AI060989, AI077099, U54 AI057157 and National Institutes of Health contract HHSN272200900042C. The government has certain rights in the invention.

SEQUENCE LISTING

The instant application contains a Sequence Listing which has been submitted electronically in ASCII format and is hereby incorporated by reference in its entirety. Said ASCII copy, created on Sep. 29, 2015, is named LIAI0440555.txt and is 149,389 bytes in size.

INTRODUCTION

Dengue virus (DENV, DV) is a mosquito-borne RNA virus in the Flaviviridae family, which also includes West Nile Virus (WNV), Yellow Fever Virus (YFV), and Japanese Encephalitis Virus (JEV). The four serotypes of DENV (DENV1-4) share approximately 65-75% homology at the amino acid level (Fu, et al. *Virology* 188:953 (1992)). Infections with DENV can be asymptomatic, or cause disease ranging from dengue fever (DF) to dengue hemorrhagic fever (DHF) and dengue shock syndrome (DSS) (WHO, *Dengue: Guidelines for diagnosis, treatment, prevention and control* (2009)). DF is a self-limiting illness with symptoms that include fever, headache, myalgia, retro-orbital pain, nausea, and vomiting. DHF and DSS are characterized by increased vascular permeability, thrombocytopenia, hemorrhagic manifestations, and in the case of DSS, shock, which can be fatal. The incidence of DENV infections has increased 30-fold in the past 50 years (WHO, *Dengue: Guidelines for diagnosis, treatment, prevention and control* (2009)). DF and DHF/DSS are a significant cause of morbidity and mortality worldwide, and therefore a DENV vaccine is a global public health priority. However, vaccine development has been challenging, as a vaccine should protect against all four DENV serotypes (Whitehead, et al. *Nat Rev Microbiol* 5:518 (2007)).

Severe dengue disease (DHF/DSS) most often occurs in individuals experiencing a secondary infection with a heterologous DENV serotype, suggesting the immune response contributes to the pathogenesis (Sangkawibha, et al. *Am J Epidemiol* 120:653 (1984); Guzman, et al. *Am J Epidemiol* 152:793 (1997)). One hypothesis is that serotype cross-reactive antibodies enhance infection of FcγR+ cells during a secondary infection resulting in higher viral loads and more severe disease via a phenomenon known as antibody-dependent enhancement (ADE) (Morens, et al. *Clin Infect Dis* 19:500 (1994); Halstead, *Adv Virus Res* 60:421 (2003)). Recent studies have demonstrated DENV-specific antibody can enhance disease in mice (Zellweger, et al. *Cell Host Microbe* 7:128 (2010); Balsitis, et al. *PLoS Pathog* 6:e1000790 (2010)). It has also been proposed that serotype cross-reactive memory T cells may respond sub-optimally during secondary infection and contribute to the pathogenesis (Mathew, et al. *Immunol Rev* 225:300 (2008)). Accordingly, studies have shown serotype cross-reactive T cells can exhibit an altered phenotype in terms of cytokine production and degranulation (Mangada, et al. *J Immunol* 175:2676 (2005); Mongkolsapaya, et al. *Nat Med* 9:921 (2003); Mongkolsapaya, et al. *J Immunol* 176:3821 (2006)). However, another study found the breadth and magnitude of the T cell response during secondary DENV infection was not significantly associated with disease severity (Simmons, et al. *J Virol* 79:5665 (2005)). Although many studies have investigated the role of T cells in DENV pathogenesis, few studies have examined the contribution of T cells to protection against DENV. Consequently, the role of T cells in protection versus pathogenesis during DENV infections is presently unknown. This is primarily due to the lack of an adequate animal model, as mice are resistant to infection with this human pathogen (Yauch, et al. *Antiviral Res* 80:87 (2008)). A mouse-passaged DENV2 strain, S221, does not replicate to detectable levels in wild-type C57BL/6 mice, but does replicate in IFN-α/βR$^{-/-}$ mice (Yauch, et al. *J Immunol* 182:4865 (2009)). Using S221 and IFN-α/βR$^{-/-}$ mice, a protective role for CD8+ T cells in the response to primary DENV2 infection was reported (Yauch, et al. *J Immunol* 182:4865 (2009)).

CD4+ T cells can contribute to the host response to pathogens in a variety of ways. They produce cytokines and can mediate cytotoxicity. They also help B cell responses by inducing immunoglobulin class switch recombination (CSR), and help prime the CD8+ T cell response. CD4+ T cells can help the CD8+ T cell response indirectly by activating APCs, for example via CD40L/CD40 (Bevan, *Nat Rev Immunol* 4:595 (2004)). CD40L on CD4+ T cells is important in activating B cells as well (Elgueta, et al. *Immunol Rev* 229:152 (2009)). CD4+ T cells can also induce chemokine production that attracts CD8+ T cells to sites of infection (Nakanishi, et al. *Nature* 462:510 (2009)). However, the requirement for CD4+ T cell help for antibody and CD8+ T cell responses is not absolute, and may be specific to the pathogen and/or experimental system. For instance, it has been shown that CSR can occur in the absence of CD4+ T cells (Stavnezer, et al. *Annu Rev Immunol* 26:261 (2008)), and the primary CD8+ T cell response is CD4-independent under inflammatory conditions (Bevan, *Nat Rev Immunol* 4:595 (2004)).

Numerous studies have investigated the phenotype of DENV serotype cross-reactive T cells, which have been hypothesized to contribute to the pathogenesis of secondary heterologous infections, yet the actual contribution of T cells during DENV infection is unknown.

This suspected dual role of T cells in protection and pathogenesis is difficult to study in humans, since in most donor cohorts the time point and in case of secondary infections the sequence of infection is unknown, and does not allow direct correlations with T cell responses. A mouse model, which allows investigation of adaptive immune responses restricted by human histocompatibility complex (MHC) molecules to DENV infection, would shed light on the role of T cells in protection and/or pathogenesis. Mice transgenic for human leukocyte antigens (HLA) are widely used to study T cell responses restricted by human MHC molecules and studies in other viral systems have shown the valuable impact of HLA transgenic mice in epitope identification (Kotturi, et al. *Immunome Res* 6:4 (2010); Kotturi, et al. *Immunome Res* 5:3 (2009); Pasquetto, et al. *J Immunol* 175:5504 (2005)). It has been reported that mice lacking the IFNR-α/β support a productive DENV infection and allow the study of T cell responses after DENV infection (Yauch, et al. *J Immunol* 185:5405 (2010); Yauch, et al. *J Immunol* 182:4865 (2009); Shresta, et al. *J Virol* 78:2701 (2004)). To cover a wide range of HLA phenotypes, IFN-α/βR$^{-/-}$ mice were backcrossed with HLA, A*0201, A*0101, A*1101, B*0701 and DRB1*0101 transgenic mice and the T cell response against infection with DENV was determined.

SUMMARY

As disclosed herein, the contribution of CD4$^+$ T cells to the host response to primary DENV2 infection using IFN-α/βR$^{-/-}$ mice is defined. Infection with DENV2 resulted in CD4$^+$ T cell expansion and activation. The DENV-specific CD4$^+$ T cells expressed intracellular IFN-γ, TNF, IL-2, and CD40L, and could mediate in vivo cytotoxicity (e.g., kill peptide-pulsed target cells in vivo). Surprisingly, depletion of CD4$^+$ T cells before DENV infection had no effect on viral loads, and CD4$^+$ T cells were not required for the induction of the DENV2-specific antibody or CD8$^+$ T cell responses. Candidate MHC class II (I-A$^b$)-binding peptides from the entire proteome of DENV2, which is approximately 3390 amino acids and encodes three structural (core (C), envelope (E), and membrane (M)), and seven non-structural (NS) (NS1, NS2A, NS2B, NS3, NS4A, NS4B, NS5) proteins, were identified. Numerous additional CD4$^+$ T cell and CD8$^+$ T cell epitopes from the structural and non-structural (NS) proteins are also disclosed herein (e.g., Tables 1-4, 8, 10, 11 14 &15). Immunization with T cell epitopes, such as CD8$^+$ or CD4$^+$ T cell epitopes, before DENV infection resulted in significantly lower viral loads. While CD4$^+$ T cells do not appear to be required for controlling primary DENV infection, immunization contributes to viral clearance.

By way of example, 42 epitopes derived from 9 of the 10 DENV proteins were identified. 80% of the epitopes identified were able to elicit a T cell response in human donors, previously exposed to DENV. The mouse model described herein also reflected response patterns observed in humans. These findings indicate that inducing anti-DENV CD4$^+$ T and/or CD8+ T cell responses by immunization/vaccination will be an effective prophylactic or therapeutic treatment for DENV infection and/or pathology.

By way of a further example, HLA class I binding predicted epitopes for 16 HLA A and 11 HLA B alleles for all four DENV serotypes were tested in ex vivo IFNγ ELISPOT assays in HLA-matched PBMC of 250 blood donors from Sri Lanka where DENV is hyper-epidemic. This proteome-wide screen h identified a total of 408 epitopes across all 10 DENV proteins. Clustering epitopes that share more than 80% sequence homology resulted in the definition of 267 antigenic regions, with the 25 most immunodominant regions accounting for 50% of the total response observed.

In accordance with the invention, there are provided peptides, methods and uses, in which the peptides include or consist of a subsequence, portion, or an amino acid modification of Dengue virus (DV) structural or non-structural (NS) polypeptide sequence, and the peptide elicits, stimulates, induces, promotes, increases, or enhances an anti-DV CD8$^+$ T cell response or an anti-DV CD4$^+$ T cell response. In one embodiment, a peptide includes or consists of a subsequence, portion, or an amino acid modification of Dengue virus (DV) structural core (C), membrane (M) or envelope (E) polypeptide sequence, for example, based upon or derived from a DENV1, DENV2, DENV3 or DENV4 serotype. In another embodiment, a peptide includes or consists of a subsequence, portion, or an amino acid modification of Dengue virus (DV) NS1, NS2A, NS2B, NS3, NS4A, NS4B or NS5 polypeptide sequence, for example, based upon or derived from a DENV1, DENV2, DENV3 or DENV4 serotype.

In particular aspects, a peptide includes or consists of a sequence set forth in Tables 1-4, 8, 10, 11, 14 or 15, or a subsequence thereof or a modification thereof. Exemplary modifications include 1, 2, 3, 4, 5 or 6, 7, 8, 9, 10 or more conservative, non-conservative, or conservative and non-conservative amino acid substitutions.

In certain embodiments, a peptide elicits an anti-DV response. In particular aspects, an anti-DV response includes a CD8$^+$ T cell response and/or a CD4$^+$ T cell response. Such responses can be ascertained, for example, by increased IFN-gamma, TNF-alpha, IL-1alpha, IL-6 or IL-8 production by CD8$^+$ T cells in the presence of the peptide; and/or increased CD4$^+$ T cell production of IFN-gamma, TNF, IL-2, or CD40L in the presence of the peptide, or killing of peptide-pulsed target cells.

The invention also provides compositions including the peptides (e.g., T cell epitopes), such as pharmaceutical compositions. Compostions can include one or more peptides selected from Tables 1-4, 8, 10, 11, 14 &15, or a subsequence thereof or a modification thereof, as well as optionally adjuvants.

Peptides, and subsequences, portions, and modifications thereof (e.g., T cell epitopes) can be used for stimulating, inducing, promoting, increasing, or enhancing an immune response against Dengue virus (DV) in a subject. In one embodiment, a method includes administering to a subject an amount of a peptide sufficient to stimulate, induce, promote, increase, or enhance an immune response against Dengue virus (DV) in the subject, and/or provide the subject with protection against a Dengue virus (DV) infection or pathology, or one or more physiological conditions, disorders, illness, diseases or symptoms caused by or associated with DV infection or pathology.

Peptides, and subsequences, portions, and modifications thereof (e.g., T cell epitopes) can also be used for treating a subject for a Dengue virus (DV) infection. In one embodiment, a method includes administering to a subject an amount of a peptide sufficient to treat the subject for the Dengue virus (DV) infection.

Exemplary responses, in vitro, ex vivo or in vivo, elicited by T cell epitopes include, stimulating, inducing, promoting, increasing, or enhancing an anti-DV CD8$^+$ T cell response or an anti-DV CD4$^+$ T cell response. In particular aspects, CD8$^+$ T cells produce IFN-gamma, TNF-alpha, IL-1alpha, IL-6 or IL-8 in response to T cell epitope, and/or CD4$^+$ T cells produce IFN-gamma, TNF, IL-2 or CD40L, or kill peptide-pulsed target cells in response to a T cell epitope. Accordingly, peptides, and subsequences, portions, and modifications thereof (e.g., T cell epitopes) can also be used for inducing, increasing, promoting or stimulating anti-Dengue virus (DV) activity of CD8$^+$ T cells or CD4+ T cells in a subject.

In various embodiments, multiple peptides, for example, multiple Dengue virus (DV) T cell epitopes are employed in the methods and uses of the invention. In particular aspects, the Dengue virus (DV) T cell epitope includes or consists of one or more sequences set forth in Tables 1-4, 8, 10, 11, 14 &15, or a subsequence thereof or a modification thereof.

In some embodiments, provided herein is a peptide comprising or consisting of a subsequence, portion, or an amino acid modification of Dengue virus (DV) structural or non-structural (NS) polypeptide sequence comprising or consisting of a sequence set forth in Tables 11, 14 & 15, or a subsequence thereof or a modification thereof, where the peptide elicits, stimulates, induces, promotes, increases, or enhances an anti-DV CD8+ T cell response or an anti-DV CD4+ T cell response. In certain embodiments a composition or pharmaceutical composition comprises the peptide. In certain embodiments the peptide comprises or consists of a subsequence, portion, or an amino acid modification of Dengue virus (DV) structural core (C), membrane (M) or envelope (E) polypeptide sequence. In certain embodiments the structural core (C), membrane (M) or envelope (E) polypeptide sequence is identical to or derived from a DENV1, DENV2, DENV3 or DENV4 serotype. In certain aspects the peptide comprises or consists of a subsequence, portion, or an amino acid modification of Dengue virus (DV) NS1, NS2A, NS2B, NS3, NS4A, NS4B or NS5 polypeptide sequence. In some aspects the peptide comprises or consists of a subsequence, portion, or an amino acid modification of Dengue virus (DV) NS1, NS2A, NS2B, NS3, NS4A, NS4B or NS5 polypeptide sequence. In some embodiments the NS1, NS2A, NS2B, NS3, NS4A, NS4B or NS5 polypeptide sequence is identical to or derived from a DENV1, DENV2, DENV3 or DENV4 serotype. In some embodiments said amino acid modification is 1, 2, 3, 4, 5 or 6 conservative, non-conservative, or conservative and non-conservative amino acid substitutions. In certain embodiments the peptide is isolated or purified. In certain aspects the anti-DV CD8+ T cell response comprises increased IFN-gamma, TNF-alpha, IL-1alpha, IL-6 or IL-8 production by CD8+ T cells in the presence of the peptide. In certain aspects the CD4+ T cells produce IFN-gamma, TNF, IL-2, or CD40L in the presence of the peptide, or kill peptide-pulsed target cells.

In some embodiment, a composition comprises 2, 3, 4, 5, 6, 7, 8, 9, 10, 11, 12, 13, 14, 15, 16, 17, 18, 19, 20, 21, 22, 23, 24, 25, or more peptides selected from Tables 11, 14 & 15 or a subsequence thereof or a modification thereof. In certain aspects the composition comprises a pharmaceutical composition and/or a pharmaceutically acceptable carrier, excipient and/or adjuvant, optionally sterile. In some embodiments, the composition is formulated as a vaccine, that is optionally sterile. The composition can be a powder, for example in freeze-dried form, optionally sterile. In certain embodiments the composition is adapted to be re-dissolved before use, for example in an aqueous optionally sterile solution, for example a solution having a pH in the range of 4 to 8 or a pH of 6 to 8. In some embodiments the composition comprises saline, optionally sterile, and optionally further comprising a pH controlling or buffering agent, a wetting agent, a dispersant, a thickener or a preservative or anti-microbial agent.

In some embodiments presented herein is a kit comprising a compartment and instructions, where the compartment comprises one or more of the compositions described herein and where the instructions are for use in eliciting, stimulating, inducing, promoting, increasing or enhancing an anti-DV CD8+ T cell response or an anti-DV CD4+ T cell response.

In some embodiments presented herein is a method of stimulating, inducing, promoting, increasing, or enhancing an immune response against Dengue virus (DV) in a subject, comprising administering to a subject an amount of a peptide or composition described herein that is sufficient to stimulate, induce, promote, increase, or enhance an immune response against Dengue virus (DV) in the subject. In certain aspects the immune response provides the subject with protection against a Dengue virus (DV) infection or pathology, or one or more physiological conditions, disorders, illness, diseases or symptoms caused by or associated with DV infection or pathology.

In some embodiments presented herein is a method of a method of treating a subject for a Dengue virus (DV) infection, comprising administering to a subject a peptide or composition described herein in an amount sufficient to treat the subject for a Dengue virus (DV) infection. In certain embodiments, the Dengue virus comprises a DENV1, DENV2, DENV3 or DENV4 serotype. In some aspects a peptide comprises or consists of a Dengue virus (DV) T cell epitope. In some aspects a T cell epitope described herein elicits, stimulates, induces, promotes, increases, or enhances an anti-DV CD8+ T cell response or an anti-DV CD4+ T cell response. In some embodiments a Dengue virus (DV) T cell epitope is a structural or non-structural (NS) T cell epitope. In some embodiments a Dengue virus T cell epitope comprises or consists of a subsequence or portion of Dengue virus C, M or E protein. In certain embodiments a Dengue virus T cell epitope comprises or consists of a subsequence or portion of NS1, NS2A, NS2B, NS3, NS4A, NS4B or NS5 protein. In some embodiments a Dengue virus (DV) infection is acute. In certain embodiments a subject is a mammal. In certain embodiments a subject is a human. In certain aspects a method described herein reduces one or more adverse physiological conditions, disorders, illness, diseases, symptoms or complications caused by or associated with Dengue virus (DV) infection or pathology. In certain aspects a method described herein improves one or more adverse physiological conditions, disorders, illness, diseases, symptoms or complications caused by or associated with Dengue virus (DV) infection or pathology. In certain aspects a method described herein reduces or inhibits susceptibility to Dengue virus (DV) infection or pathology. In some embodiments of a method described herein the Dengue virus (DV) T cell epitope is administered prior to, substantially contemporaneously with or following exposure to or infection of the subject with Dengue virus (DV). In certain aspects of the method, a plurality of Dengue virus (DV) T cell epitopes are administered prior to, substantially contemporaneously with or following exposure to or infection of the subject with Dengue virus (DV). A Dengue virus can comprise a DENV1, DENV2, DENV3 or DENV4 serotype. In some embodiments the method reduces one or more adverse physiological conditions, disorders, illness, diseases, symptoms or complications caused by or associated with Dengue virus (DV) infection or pathology. In some embodiments the method improves one or more adverse physiological conditions, disorders, illness, diseases, symptoms or complications caused by or associated with Dengue virus (DV) infection or pathology. In some embodiments the method reduces or inhibits susceptibility to Dengue virus (DV) infection or pathology. In some embodiments the Dengue virus (DV) T cell epitope is administered prior to, substantially contemporaneously with or following exposure to or infection of the subject with Dengue virus (DV). In certain embodiments a plurality of Dengue virus (DV) T cell epitopes are administered prior to, substantially contemporaneously with or following exposure to or infection of the subject with Dengue virus (DV).

DESCRIPTION OF DRAWINGS

FIGS. 1A-1D show that DENV2 infection results in CD4+ T cell activation and expansion in IFN-α/βR−/− mice. FIG. 1A) The numbers of splenic CD4+ T cells in naïve IFN-α/βR−/− mice (n=6) and IFN-α/βR−/− mice infected with $10^{10}$ genomic equivalents (GE) of DENV2 (n=11) are shown. * p<0.001 for naïve versus infected mice. FIG. 1B) The percentage of CD62L$^{lo}$CD44$^{hi}$ cells (gated on CD4+ cells) is shown for naïve (n=4) and IFN-α/βR−/− mice infected with $10^{10}$ GE of DENV2 (n=8).  p<0.01 for naïve versus infected mice. FIG. 1C) Blood lymphocytes were obtained from IFN-α/βR−/− mice on days 3, 5, 7, 10, and 14 after infection with $10^{10}$ GE of DENV2. The percentage of CD44$^{hi}$CD62L$^{lo}$ cells (gated on CD4+ T cells)±SEM (n=6) is shown. FIG. 1D) The percentage and number of splenic Foxp3+ cells (gated on CD4+ cells) are shown for naïve (n=4) and infected IFN-α/βR−/− mice (n=4).

FIG. 2A) Splenocytes were obtained from IFN-α/βR−/− mice 7 days after infection with $10^{10}$ GE of DENV2 and re-stimulated in vitro with DENV2-derived 15-mer peptides predicted to bind I-A$^b$. Cells were then stained for surface CD4 and intracellular IFN-γ and analyzed by flow cytometry. The 4 positive peptides identified are shown. In the dot plots, the percentage of CD4+ T cells producing IFN-γ is indicated. The responses of individual mice as well as the mean and SEM are also shown (n=7-11). The response of unstimulated cells was subtracted from the response to each DENV2 peptide, and the net percentage and number of splenic CD4+ T cells producing IFN-γ are indicated. FIG. 2B, Splenocytes were obtained from wild-type C57BL/6 mice 7 days after infection with $10^{10}$ GE of DENV2 and stimulated and stained as in A (n=6).

FIGS. 6A-6C show that CD4+ T cells are not required for the primary DENV2-specific CD8+ T cell response. Fig. A) Splenocytes were obtained from IFN-α/βR−/− mice (control or CD4-depleted) 7 days after infection with $10^{10}$ GE of DENV2, and stimulated in vitro with immunodominant DENV2-derived H-2$^b$-restricted CD8+ T cell epitopes. Cells were then stained for CD8 and IFN-γ and analyzed by flow cytometry, and the number of CD8+ T cells producing IFN-γ is shown. Results are expressed as the mean±SEM of 4 mice per group. ** p<0.01. Fig. B) Splenocytes were obtained as in A and stimulated with NS4B$_{99-107}$ in the presence of an anti-CD107 Ab, and then stained for CD8, IFN-γ, TNF, and IL-2. The response of unstimulated cells was subtracted from the response to each DENV2 peptide, and the net percentages of the CD8+ T cells that are expressing at least one molecule are indicated. The mean and SEM of 3 mice is shown. Fig. C) CD8+ T cell-mediated killing. IFN-α/βR−/− mice (control or CD4-depleted) infected 7 days previously with $10^{10}$ GE of DENV2 were injected i.v. with CFSE-labeled target cells pulsed with a pool of DENV2-derived immunodominant H-2$^b$-restricted peptides (C$_{51-59}$, NS2A$_{8-15}$, NS4B$_{99-107}$, and NS5$_{237-245}$) at the indicated concentrations (n=3-6 mice per group). After 4 h, splenocytes were harvested, analyzed by flow cytometry, and the percentage killing was calculated.

FIG. 8 shows that peptide immunization with CD4+ T cell epitopes results in enhanced DENV2 clearance. IFN-α/βR−/− mice were immunized s.c. with 50 μg each of the three DENV peptides that contain only CD4+ T cell epitopes (NS2B$_{108-122}$, NS3$_{198-212}$, NS3$_{237-51}$) in CFA, or mock-immunized with DMSO in CFA. Mice were boosted 11 days later with peptide in IFA, then challenged with $10^{11}$ GE of DENV2 13 days later, and sacrificed 4 days after infection. Separate groups of peptide-immunized mice were depleted of CD4+ or CD8+ T cells prior to infection. DENV2 RNA levels in the tissues were quantified by real-time RT-PCR and are expressed as DENV2 units normalized to 18S rRNA. Each symbol represents one mouse and the bar represents the geometric mean. * p<0.05, ** p<0.01.

(FIG. 9B) A*1101; (FIG. 9C) A*0101; (FIG. 9D) B*0702. For all strains tested, IFNγ ELISPOT was performed using splenic T cells isolated from HLA transgenic IFN-α/βR−/− mice (black bars) and HLA transgenic IFN-α/βR$^{+/+}$ mice (white bars). Mice were infected i.v. retro-orbitally with 1×10$^{10}$ GE of DENV2 (S221) in 100 µl PBS. Seven days post-infection, CD8$^+$ T cells were purified and tested against a panel of S221 predicted peptides. The data are expressed as mean number of SFC/10$^6$ CD8$^+$ T cells of two independent experiments. Error bars represent SEM. Responses against peptides were considered positive if the stimulation index (SI) exceeded double the mean negative control wells (effector cells plus APCs without peptide) and net spots were above the threshold of 20 SFCs/10$^6$ CD8$^+$ T cells in two independent experiments. Asterisks indicate peptides, which were able to elicit a significant IFNγ response in each individual experiment, according to the criteria described above.

FIG. 10 shows identification of DENV-derived epitopes recognized by CD4$^+$ T cells. IFNγ ELISPOT was performed using CD4$^+$ T cells isolated from DRB1*0101 transgenic IFN-α/βR$^{-/-}$ (black bars) and IFN-α/βR$^{+/+}$ (white bars) mice. Mice were infected i.v. retro-orbitally with 1×10$^{10}$ GE of DENV2 (S221) in 100 µl PBS. Seven days postinfection, CD4$^+$ T cells were purified and tested against a panel of S221 predicted peptides. The data are expressed as mean number of SFC/10$^6$ CD4$^+$ T cells of two independent experiments. Error bars represent SEM. Responses against peptides were considered positive if the stimulation index (SI) exceeded double the mean negative control wells (effector cells plus APCs without peptide) and net spots were above the threshold of 20 SFCs/10$^6$ CD4$^+$ T cells in two individual experiments. Asterisks indicate peptides, which were able to elicit a significant IFNγ response, according to the criteria described above.

FIG. 11A) shows pairs of peptides where the 9-mer and the 10mer were able to elicit a significant T cell response; FIG. 11B) shows the 3 B*0702 restricted peptides which did show an IC$_{50}$>1000 nM in the respective binding assay. Peptides were retested in parallel with their corresponding 8-, 10- and 11-mers. The peptides, which were able to elicit stronger IFNγ responses at various concentrations, were then considered the dominant epitope.

FIGS. 13A-E) show IFNγ responses/10$^6$ PBMC after stimulation with A*0101, A*0201, A*1101, B*0702 and DRB1*0101 restricted peptides, respectively. Donors, seropositive for DENV, were grouped in HLA matched and non-HLA matched cohorts, as shown in panels 1 and 2 of each figure. All epitopes identified were further tested in DENV seronegative individuals. The average IFNγ responses elicited by PBMC from DENV seropositive non-HLA matched and DENV seronegative donors plus 3 times the standard deviation (SD) was set as a threshold for positivity, as indicated by the dashed line. FIG. 13F) shows the mean IFNγ response/10$^6$ T cells from HLA transgenic mice (black bars) and HLA matched donors (white bars) grouped by HLA restriction of the epitopes tested.

(FIG. 15A) HLA allele coverage in the Sri Lankan cohort is shown. Bars represent the relative number of donors where the donor specific HLA alleles have been exactly matched (black bars) or matched within the same supertype (white bars) with one of the 27 alleles selected for our study. The black line represents the cumulative number of donors where at least 1 allele has been matched exactly. (FIG. 15B) The relative number of donors with neutralizing antibodies against one, two, three or all four serotypes is shown. Donors have experienced either primary (white bars) or secondary infection (black bars). (FIG. 15C) Summary of all donors experiencing primary infection (n=55). Neutralization titers against donors infected with DENV1 (n=14), DENV2 (n=18), DENV3 (n=20) or DENV4 (n=3) are shown.

(FIG. 16A) The genomic position of DENV encoded proteins ((capsid (C), pre-membrane (prM/M), envelope (E), NS1, NS2A, NS2B, NS3, NS4A, NS4B, NS5) and the total observed response magnitude for every amino acid along the proteome is shown (black bars). The data are expressed as total number of IFNγ SFC/10$^6$ PBMC. The heat map indicates the number of donors that showed a positive cytokine response to peptides within these regions. (FIG. 16B) Identified antigenic regions were plotted as a function of the percentage of the total response. Lines indicate the number of regions needed to account for 25, 75 and 90% of the total response, respectively.

(FIG. 17A) Magnitude of serotype specific and conserved T cell responses. Total of responses observed against serotype specific regions (black bars) or regions being conserved/homologous (white bars) are shown. Conserved regions are defined as sequences found in two or more serotypes, also allowing one residue substitutions to account for potential cross-reactivity of highly homologous sequences. The data are expressed as total number of IFNγ SFC/10$^6$ PBMC. Responses magnitudes (as SFC/10$^6$ PBMC values) directed against conserved regions (FIG. 17B), specific for DENV2 (FIG. 17C) or DENV3 (FIG. 17D) were plotted as a function of the genomic position in the DENV polyprotein.

(FIG. 19A) Differential frequency and magnitude of HLA restricted responses. Frequency (black bars) and the magnitude (white bars) of T cell responses (as total SFC/$10^6$ PBMC values) sorted according to their restriction element is shown. (FIG. 19B) Association of HLA restricted T cell responses with disease susceptibility. A meta-analysis of all data associating HLA allele with disease susceptibility available in the literature was performed. For each of the studies, all investigated alleles were ranked according to their association with disease (dengue fever [DF], dengue hemorrhagic fever [DHF] and dengue shock syndrome [DSS]). A calculated percentile ranking across all studies for the 18 alleles detected in significant frequencies in our own cohort was performed and correlated the rankings with T cell responses. Disease susceptibility was correlated with the average magnitudes of HLA restricted responses (left panel), with the frequency and the magnitude of T cell responses per donor (middle panel) and with the magnitude per epitope as well as breath of (right panel) One-tailed Spearman test was then used to calculate correlations using Prism Graph Pad Software, Inc (La Jolla, Calif.). (FIG. 19C) Multi-functionality of HLA restricted responses. Representative donors were stimulated with HLA restricted donor-specific peptide pools. [1 µg/ml] for 6 hours in the presence of BFA. Cells were then stained with mAB against surface markers CD3, CD8 and mAB against intracellular IFNγ, TNFα and IL2. Pie charts represent cytokine profiles of individual donors. The relative number of cells producing one (dark grey areas), two (light grey areas) or three (white areas) of the measured cytokines are shown. Percentages in the pie charts represent the number of cells, which produce 2 or more cytokines. Numbers under the pie charts represent the T cell responses (as IFNγ SFC/106 PBMC) of this specific donor/allele combination in the ELISPOT assay. Responses hierarchy was IFNγ>TNFα>IL2 in all experiments (n=4).

(FIG. 20A) DENV specific IgG titers of all donors investigated in this study are shown. Results are grouped according to the immune status of the donor (dengue negative, primary or secondary infection). Donors with history of dengue infection have additionally been grouped into responding donors (R) with non-responding donors (NR) referring to a detectable T cell response in the IFNγ ELISPOT assay. Serum sample from 80 donors were investigated and total dengue specific IgG titers (FIG. 20B), enhancement titers (FIG. 20C) and neutralization titers (FIG. 20D) were measured. These parameters were then compared to T cell responses observed in these specific donors. Data were analyzed using Prism Graph Pad Software, Inc (La Jolla, Calif.).

(FIG. 22A) To determine the optimal epitope CD8+ T cells were purified 7 days post infection and incubated for 24 hours with ascending concentrations of nested peptides. The peptides, which were able to elicit stronger IFNγ responses at various concentrations, were then considered the optimal epitope. Cell lines expressing either the A*0201 (FIG. 22B) or the B*4001 (FIG. 22C) but no murine MHC molecule were used as APCs to establish HLA restriction as described in Materials and Methods. Purified CD8+ T cells from DENV3 infected mice were incubated with ascending concentrations of peptides and tested for IFNγ production in an ELISPOT assay. Representative graphs of CD8+ T cell responses, when incubated with HLA expressing cell lines (FIG. 22B and FIG. 22C; black lines) and control cell lines (FIG. 22B and FIG. 22C, grey lines) are shown.

FIGS. 25A-25C show an effect of Heterologous infection on the T cell repertoire. Groups of B*0702 transgenic IFN-α/βR-/- mice were infected with DENV3 as described in Materials and Methods. For primary infection experiments the mice were sacrificed 7 days post infection and splenic CD8+ were tested against a panel of previous identified epitopes in IFNγ ELISPOT assays (FIG. 25A, white bars). For secondary infection experiments mice were infected with DENV2 28 days after primary DENV3 infection. 7 days post secondary infection mice were sacrificed and splenic CD8+ T cells were used in mouse IFNγ ELISPOT assays (FIG. 25A, black bars). The data are expressed as mean number of SFC/10⁶ CD8+ T cells of two independent experiments. (FIG. 25B) Groups of B*0702 transgenic IFN-α/βR-/- mice were infected with DENV2 as described in Materials and Methods. 28 days after primary DENV2 infection mice were either infected with DENV2 (FIG. 25B, white bars) or DENV3 (FIG. 25B, black bars). 7 days post secondary infection mice were sacrificed and splenic CD8+ T cells were used in mouse IFNγ ELISPOT assays. The data are expressed as mean number of SFC/10⁶ CD8+ T cells of two independent experiments. (FIG. 25C) All responses measured after primary or secondary infection (average SFC/10⁶ CD8+ T cells in two independent experiments) were added up and the relative responses against DENV3 specific (dark grey pie), DENV2 specific (light grey pie) or conserved epitopes (black pie) after primary (left chart) or secondary (right charts) infection are shown.

(FIG. 27A) Shown are responses detected in study participants vaccinated with tetravalent attenuated dengue vaccine (TV003). Responses are expressed as the number of IFNγ secreting cells per 10⁶ PBMC. (FIG. 27B) Analysis of conservancy of epitopes identified. Relative responses have been analyzed as function of the serotype (DENV1 white, DENV2 light grey, DENV3 grey and DENV4 dark grey) they are derived. The relative response by epitopes derived from regions conserved between serotype is shown in black. (FIGS. 27C-D) Phenotype and cytokine profile of responding cells. PBMC from tetravalent vaccinees (n=4) have been incubated with HLA matched epitope pools and assayed for the production of IFNγ and TNFα as described in Materials and Methods. Each sample has been stained additionally with antibodies against CD45RA and CCR7 to determine the proportion of cells in the following subsets: CCR7−CD45RA− (TEM; effector memory T cells), CCR7+CD45RA− (TCM; central memory T cells), CCR7+CD45RA+ (TN; naïve T cells), and CCR7−CD45RA+ (TEMRA; effector memory T cells re-expressing CD45RA). Shown is the relative distribution of T cell subsets within the IFNγ positive cells (FIG. 27C) and the relative distribution of cells positive for one of the cytokines (FIG. 27D, IFNγ black circles; TNFα black triangles) or double positive for both cytokines (FIG. 27D, black triangles). (FIG. 27E) Representative example of co-expression of IFNγ and the marker for cytotoxicity CD107a after stimulation with HLA-matched epitope pools.

(FIG. 28A) Conservancy of epitopes identified within field isolates of DENV. 162 DENV1, 171 DENV2, 169 DENV3 and 53 DENV4 sequences were retrieved from the NCBI Protein database. The relative conservancy within the sequences of the respective serotypes for all epitopes identified after monovalent (left panel) or tetravalent vaccination (middle panel) is shown. The right panel shows all epitope reactivity to either the monovalent or tetravalent vaccination. (FIG. 28B) Phenotype and (FIG. 28C) cytokine profile of T cell responses in donors exposed to natural secondary infection with DENV epitopes. PBMC samples (n=4) have been incubated with HLA matched vaccine-specific epitope pools and assayed for the production of IFNγ and TNFα as described in Materials and Methods. Each sample has been stained additionally with antibodies against CD45RA and CCR7 to determine the proportion of cells in the following subsets: CCR7−CD45RA− (TEM; effector memory T cells), CCR7+CD45RA− (TCM; central memory T cells), CCR7+CD45RA+ (TN; naïve T cells), and CCR7−CD45RA+ (TEMRA; effector memory T cells re-expressing CD45RA). Responses have been detected in 3 out of 4 donors tested. Shown is the relative distribution of T cell subsets within the IFNγ positive cells (FIG. 28B) and the relative distribution of cells positive for one of the cytokines (FIG. 28C, IFNγ black circles; TNFα black triangles) or double positive for both cytokines (FIG. 28C, black triangles).

DETAILED DESCRIPTION

Figure 2A:
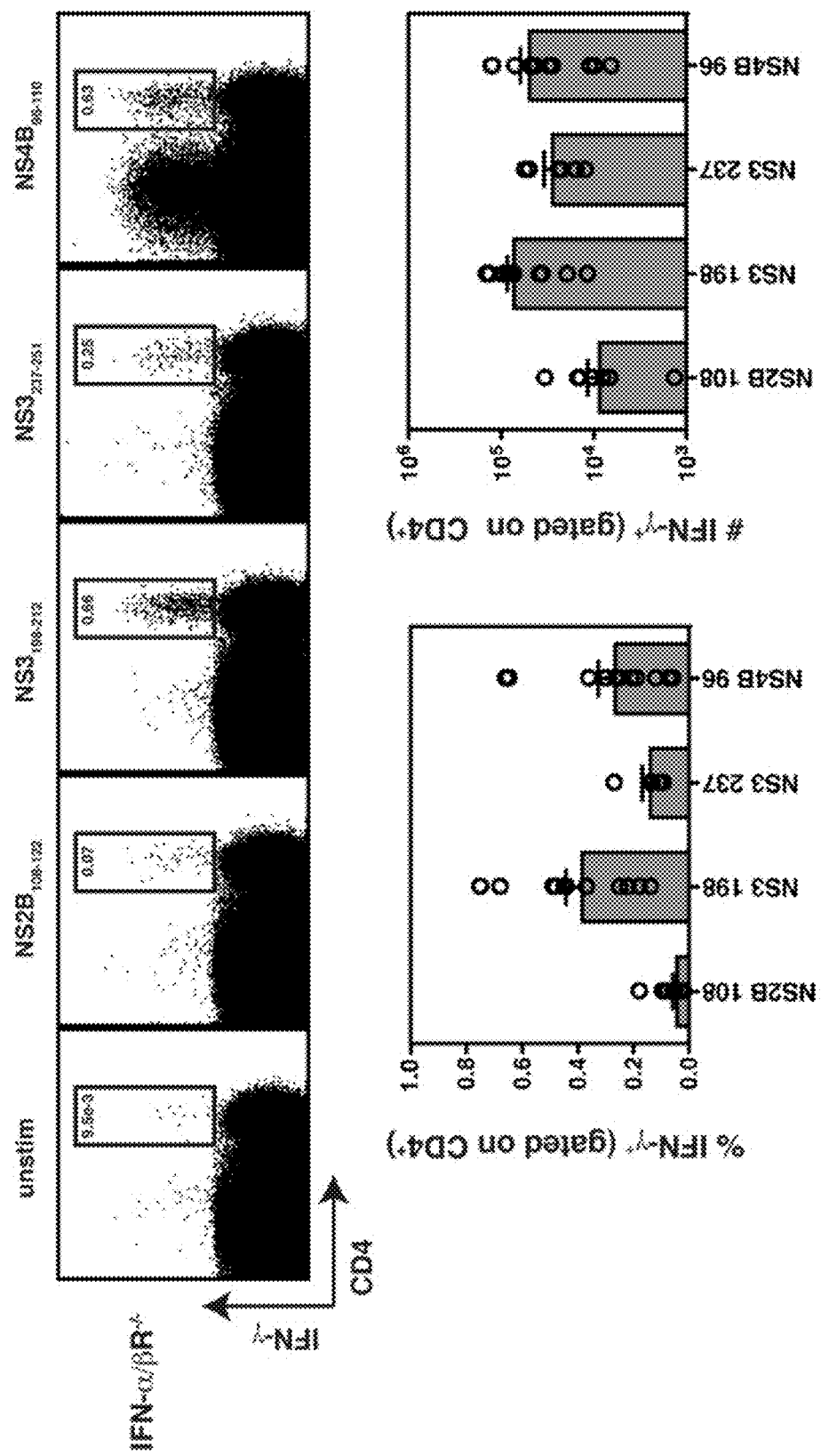
FIGS. 2A-2B show the identification of DENV2-derived epitopes recognized by CD4+ T cells.

The invention is based at least in part on Dengue virus (DV) peptides, subsequences and portions, and amino acid modifications of DV peptides, subsequences and portions. Invention Dengue virus (DV) peptides, subsequences, portions and modifications thereof, including T cell epitopes that elicit, stimulate, induce, promote, increase, enhance, or activate an anti-DV CD4⁺ T cell and/or an anti-DV CD8⁺ T cell response in vitro or in vivo, are useful in vaccination and immunization (e.g., prophylactic), as well as treatment uses and methods. For example, an invention Dengue virus (DV) peptide, subsequence, portion or modification thereof, can be used to immunize or vaccinate a subject, or to treat a subject having or at risk of having Dengue virus (DV) infection or pathology.

Dengue virus (DV) peptide, subsequences, portions and modifications thereof include T cell epitopes. A T cell epitope can elicit, stimulate, induce, promote, increase, enhance, or activate an anti-DV CD4⁺ T cell and/or an anti-DV CD8⁺ T cell response in vitro (e.g., in solution, in solid phase, in tissue culture) or in vivo. Such anti-DV CD4⁺ T cell and/or an anti-DV CD8⁺ T cell responses can be detected using various assays disclosed herein or known to the skilled artisan. For example, an anti-DV CD8⁺ T cell response can include one or more of increased IFN-gamma, TNF-alpha, IL-1alpha, IL-6 or IL-8 production by CD8⁺ T cells in the presence of the peptide; and an anti-DV CD4+ T cell response can include one or more of increased IFN-gamma, TNF, IL-2, or CD40L production by CD4+ T cells in the presence of the peptide, or CD4+ T cell killing of peptide-pulsed target cells.

Exemplary T cell epitopes can include or consist of a subsequence, a portion or modification of Dengue virus (DV) structural Core, Membrane or Envelope polypeptide sequence, or a subsequence or portion of a Dengue virus (DV) non-structural (NS) NS1, NS2A, NS2B, NS3, NS4A, NS4B or NS5 polypeptide sequence. Specific non-limiting examples of Dengue virus (DV) structural protein and non-structural (NS) protein subsequences, portions and modifications include or consist of a sequence set forth in Tables 1-4, 8, 10, 11, 14 &15 (SEQ ID NOs: 11-1163), as well as subsequences and portions, and amino acid modifications of sequences set forth in Tables 1-4, 8, 10, 11, 14 &15 (SEQ ID NOs: 11-1163).

Additional Dengue virus (DV) peptide, subsequences and portions thereof can be based upon or derived from DENV serotypes, such as DENV1, DENV2, DENV3 or DENV4 serotypes. For example, a subsequence or portion of a Dengue virus (DV) structural polypeptide such as a core (C), membrane (M) or envelope (E) polypeptide, or a non-structural (NS) NS1, NS2A, NS2B, NS3, NS4A, NS4B or NS5 polypeptide, can be a sequence having 75% or more (e.g., 80%, 85%, 90%, 95%, 96%, 97%, 98%, 99%, 100%) sequence identity to all or a region of a structural or non-structural (NS) Dengue virus (DV) serotype, such as a DENV1, DENV2, DENV3 or DENV4 serotype (e.g., a peptide listed in any of Tables 1-4, 8, 10, 11, 14 &15 SEQ ID NOs: 11-1163)).

Thus, in accordance with the invention, there are also provided Dengue virus (DV) peptides, subsequences, portions and modifications thereof that exhibit sequence identity to a reference Dengue virus (DV) peptide, subsequence or portion, or modification thereof (e.g., as set forth in Tables 1-4, 8, 10, 11, 14 &15 (SEQ ID NOs: 11-1163)). In one embodiment, an Dengue virus (DV) peptide, subsequence, portion or modification thereof includes or consists of a sequence at least 60% or more (e.g., 65%, 70%, 75%, 80%, 85%, 90%, 95%, etc.) identical to a reference Dengue virus (DV) peptide, subsequence, portion or modification thereof (e.g., a subsequence, portion or modification of any peptide listed in Tables 1-4, 8, 10, 11, 14 &15 (SEQ ID NOs: 11-1163)).

In another embodiment, Dengue virus (DV) peptides, subsequences and portions thereof include or consist of a Dengue virus (DV) peptide, subsequence or portion thereof set forth as any peptide listed in Tables 1-4, 8, 10, 11, 14 &15 (SEQ ID NOs: 11-1163), wherein the Dengue virus (DV) peptide, subsequence or portion thereof has one or more modifications, such as an amino acid addition to, deletion of, or substitution of any amino acid residue in any peptide listed in Tables 1-4, 8, 10, 11, 14 &15 (SEQ ID Nos: 11-1163). In particular aspects, a modified sequence is at least 80% or more, e.g., 80-85%, 85-90%, 90-95%, 95-100% identical, to Dengue virus (DV) peptide, subsequence or portion thereof set forth any peptide listed in Tables 1-4, 8, 10, 11, 14 &15 (SEQ ID NOs: 11-1163), or has 1, 2, 3, 4, 5, 6, 7, 8, 9, 10, 1, 12, 13, 14, 15, 16, 17, 18, 19, 20, 20-25, 25-30, 30-50, 50-100, or more, additions to, deletions of, or substitutions.

T cell epitopes typically are short amino acid sequences, e.g. about five to 15 amino acids in length (or 5-10 amino acids in length). Linear or contiguous T cell epitopes include a continuous amino acid sequence, such as a 5 to 15 amino acid sequence, which can elicit an anti-DV CD4+ T cell or anti-DV CD8+ T cell response in vitro or in vivo.

A non-limiting example of a subsequence or portion of a Dengue virus (DV) polypeptide sequence includes or consists of a subsequence or portion of Dengue virus (DV) structural Core, Membrane or Envelope polypeptide sequence. A non-limiting example of a subsequence or portion of a Dengue virus (DV) polypeptide sequence includes or consists of a subsequence or portion of Dengue virus (DV) non-structural (NS) NS1, NS2A, NS2B, NS3, NS4A, NS4B or NS5 polypeptide sequence.

A non-limiting Core sequence from which a subsequence, portion or modification can be based upon is a sequence set forth as:

```
                                        (SEQ ID NO: 210)
MNNQRKKARNTPFNMLKRERNRVSTVQQLTKRFSLGMLQGRGPLKLFMA

LVAFLRFLTIPPTAGILKRWGTIKKSKAINVLRGFRKEIGRMLNILNRR

RRTAGMIIMLIPTVMA.
```

A non-limiting Membrane sequence from which a subsequence, portion or modification can be based upon is a sequence set forth as:

```
                                        (SEQ ID NO: 211)
FHLTTRNGEPHMIVSRQEKGKSLLFKTGDGVNMCTLMAMDLGELCEDTI

TYKCPLLRQNEPEDIDCWCNSTSTWVTYGTCTTTGEHRREKRSVALVPH

VGMGLETRTETWMSSEGAWKHAQRIETWILRHPGFTIMAAILAYTIGTT

HFQRALIFILLTAVAPSMT.
```

A non-limiting Envelope sequence from which a subsequence, portion or modification can be based upon is a sequence set forth as:

```
                                        (SEQ ID NO: 212)
MRCIGISNRDFVEGVSGGSWVDIVLEHGSCVTTMAKNKPTLDFELIKTE

AKQSATLRKYCIEAKLTNTTTESRCPTQGEPSLNEEQDKRFVCKHSMVD

RGWGNGCGLFGKGGIVTCAMFTCKKNMKGKVVQPENLEYTIVITPHSGE

EHAVGNDTGKHGKEIKITPQSSITEAELTGYGTVTMECSPRTGLDFNEM

VLLQMENKAWLVHRQWFLDLPLPWLPGADTQGSNWIQKETLVTFKNPHA

KKQDVVVLGSQEGAMHTALTGATEIQMSSGNLLFTGHLKCRLRMDKLQL

KGMSYSMCTGKFKVVKEIAETQHGTIVIRVQYEGDGSPCKIPFEIMDLE

KRHVLGRLITVNPIVTEKDSPVNIEAEPPFGDSYIIIGVEPGQLKLNWF

KKGSSIGQMLETTMRGAKRMAILGDTAWDFGSLGGVFTSIGKALHQVFG

AIYGAAFSGVSWTMKILIGVIITWIGMNSRSTSLSVSLVLVGVVTLYLG

VMVQA.
```

A non-limiting non-structural NS1 sequence from which a subsequence, portion or modification can be based upon is a sequence set forth as:

```
                                        (SEQ ID NO: 213)
ADSGCVVSWKNKELKCGSGIFITDNVHTWTEQYKFQPESPSKLASAIQK

AHEEGICGIRSVTRLENLMWKQITPELNHILSENEVKLTIMTGDIKGIM
```

QAGKRSLRPQPTELKYSWKTWGKAKMLSTESHNQTFLIDGPETAECPNT

NRAWNSLEVEDYGFGVFTTNIWLKLREKQDVFCDSKLMSAAIKDNRAVH

ADMGYWIESALNDTWKIEKASFIEVKSCHWPKSHTLWSNEVLESEMIIP

KNFAGPVSQHNYRPGYHTQTAGPWHLGKLEMDFDFCEGTTVVVTEDCGN

RGPSLRTTTASGKLITEWCCRSCTLPPLRYRGEDGCWYGMEIRPLKEKE

ENLVNSLVTA.

A non-limiting non-structural NS2A sequence from which a subsequence, portion or modification can be based upon is a sequence set forth as:

(SEQ ID NO: 214)
GHGQIDNFSLGVLGMALFLEEMLRTRVGTKHAILLVAVSFVTLITGNMS

FRDLGRVMVMVGATMTDDIGMGVTYLALLAAFKVRPTFAAGLLLRKLTS

KELMMTTIGIVLLSQSTIPETILELTDALALGMMVLKMVRKMEKYQLAV

TIMAILCVPNAVILQNAWKVSCTILAVVSVSPLFLTSSQQKADWIPLAL

TIKGLNPTAIFLTTLSRTNKKR.

A non-limiting non-structural NS2B sequence from which a subsequence, portion or modification can be based upon is a sequence set forth as:

(SEQ ID NO: 215)
SWPLNEAIMAVGMVSILASSLLKNDIPMTGPLVAGGLLTVCYVLTGRSA

DLELERAADVKWEDQAEISGSSPILSITISEDGSMSIKNEEEEQTLTIL

IRTGLLVISGLFPVSLPITAAAWYLWEVKKQR.

A non-limiting non-structural NS3 sequence from which a subsequence, portion or modification can be based upon is a sequence set forth as:

(SEQ ID NO: 216)
AGVLWDVPSPPPVGKAELEDGAYRIKQKGILGYSQIGAGVYKEGTFHTM

WHVTRGAVLMHKGKRIEPSWADVKKDLISYGGGWKLEGEWKEGEEVQVL

ALEPGKNPRAVQTKPGLFKTNAGTIGAVSLDFSPGTSGSPIIDKKGKVV

GLYGNGVVTRSGAYVSAIAQTEKSIEDNPEIEDDIFRKRKLTIMDLHPG

AGKTKRYLPAIVREAIKRGLRTLILAPTRVVAAEMEEALRGLPIRYQTP

AIRAEHTGREIVDLMCHATFTMRLLSPVRVPNYNLIIMDEAHFTDPASI

AARGYISTRVEMGEAAGIFMTATPPGSRDPFPQSNAPIMDEEREIPERS

WSSGHEWVTDFKGKTVWFVPSIKAGNDIAACLRKNGKKVIQLSRKTFDS

EYVKTRTNDWDFVVTTDISEMGANFKAERVIDPRRCMKPVILTDGEERV

ILAGPMPVTHSSAAQRRGRIGRNPKNENDQYIYMGEPLENDEDCAHWKE

AKMLLDNINTPEGIIPSMFEPEREKVDAIDGEYRLRGEARKTFVDLMRR

GDLPVWLAYRVAAEGINYADRRWCFDGIKNNQILEENVEVEIWTKEGER

KKLKPRWLDARIYSDPLALKEFKEFAAGRK.

A non-limiting non-structural NS4A sequence from which a subsequence, portion or modification can be based upon is a sequence set forth as:

(SEQ ID NO: 217)
SLTLSLITEMGRLPTFMTQKARDALDNLAVLHTAEAGGRAYNHALSELP

ETLETLLLLTLLATVTGGIFLFLMSGRGIGKMTLGMCCIITASILLWYA

QIQPHWIAASIILEFFLIVLLIPEPEKQRTPQDNQLTYVVIAILTVVAA

TMA.

A non-limiting non-structural NS4B sequence from which a subsequence, portion or modification can be based upon is a sequence set forth as:

(SEQ ID NO: 218)
NEMGFLEKTKKDLGLGSITTQQPESNILDIDLRPASAWTLYAVATTFVT

PMLRHSIENSSVNVSLTAIANQATVLMGLGKGWPLSKMDIGVPLLAIGC

YSQVNPITLTAALFLLVAHYAIIGPGLQAKATREAQKRAAAGIMKNPTV

DGITVIDLDPIPYDPKFEKQLGQVMLLVLCVTQVLMMRTTWALCEALTL

ATGPISTLWEGNPGRFWNTTIAVSMANIFRGSYLAGAGLLFSIMKNTTN

TRR.

A non-limiting non-structural NS5 sequence from which a subsequence, portion or modification can be based upon is a sequence set forth as:

(SEQ ID NO: 219)
GTGNIGETLGEKWKSRLNALGKSEFQIYKKSGIQEVDRTLAKEGIKRGE

TDHHAVSRGSAKLRWFVERNMVTPEGKVVDLGCGRGGWSYYCGGLKNVR

EVKGLTKGGPGHEEPIPMSTYGWNLVRLQSGVDVFFTPPEKCDTLLCDI

GESSSPNPTVEAGRTLRVLNLVENWLNNNTQFCIKVLNPYMPSVIEKMEA

LQRKYGGALVRNPLSRNSTHEMYVVVSNASGNIVSSVNMISRMLINRFT

MRHKKATYEPDVDLGSGTRNIGIESEIPNLDIIGKRIEKIKQEHETSWH

YDQDHPYKTWAYHGSYETKQTGSASSMVNGVVRLLTKPWDVVPMVTQMA

MTDTTPFGQQRVFKEKVDTRTQEPKEGTKKLMKITAEWLWKELGKKKTP

RMCTREEFTRKVRSNAALGAIFTDENKWKSAREAVEDSRFWELVDKERN

LHLEGKCETCVYNMMGKREKKLGEFGKAKGSRAIWYMWLGARFLEFEAL

GFLNEDHWFSRENSLSGVEGEGLHKLGYILRDVSKKEGGAMYADDTAGW

DTRITLEDLKNEEMVTNHMEGEHKKLAEAIFKLTYQNKVVRVQRPTPRG

TVMDIISRRDQRGSGQVGTYGLNTFTNMEAQLIRQMEGEGVFKSIQHLT

VTEEIAVQNWLARVGRERLSRMAISGDDCVVKPLDDRFASALTALNDMG

KVRKDIQQWEPSRGWNDWTQVPFCSHHFHELIMKDGRVLVVPCRNQDEL

IGRARISQGAGWSLRETACLGKSYAQMWSLMYFHRRDLRLAANAICSAV

PSHWVPTSRTTWSIHAKHEWMTAEDMLTVWNRVWIQENPWMEDKTPVES

WEEIPYLGKREDQWCGSLIGLTSRATWAKNIQTAINQVRSLIGNEEYTD

YMPSMKRFRREEEEAGVLW.

As disclosed herein, Dengue virus (DV) peptides, subsequences, portions and modifications thereof of the invention include those having at least partial sequence identity to one or more exemplary Dengue virus (DV) peptides, subsequences, portions or modifications thereof (e.g., sequences set forth in Tables 1-4, 8, 10, 11, 14 &15 (SEQ ID NOs: 11-1163)). The percent identity of such sequences can be as little as 60%, or can be greater (e.g., 65%, 70%, 75%, 80%, 85%, 90%, 95%, 96%, 97%, 98%, 99%, etc.). The percent identity can extend over the entire sequence length or a portion of the sequence. In particular aspects, the length of the sequence sharing the percent identity is 2, 3, 4, 5 or more contiguous amino acids, e.g., 6, 7, 8, 9, 10, 11, 12, 13, 14, 15, 16, 17, 18, 19, 20, etc. contiguous amino acids. In additional particular aspects, the length of the sequence sharing the percent identity is 20 or more contiguous amino acids, e.g., 20, 21, 22, 23, 24, 25, 26, 27, 28, 29, 30, 31, 32, 33, 34, 35, etc. contiguous amino acids. In further particular aspects, the length of the sequence sharing the percent identity is 35 or more contiguous amino acids, e.g., 35, 36, 37, 38, 39, 40, 41, 42, 43, 44, 45, 45, 47, 48, 49, 50, etc., contiguous amino acids. In yet further particular aspects, the length of the sequence sharing the percent identity is 50 or more contiguous amino acids, e.g., 50-55, 55-60, 60-65, 65-70, 70-75, 75-80, 80-85, 85-90, 90-95, 95-100, 100-110, etc. contiguous amino acids.

The term "identity" and grammatical variations thereof, mean that two or more referenced entities are the same. Thus, where two Dengue virus (DV) peptides, subsequences, portions and modifications thereof are identical, they have the same amino acid sequence. The identity can be over a defined area (region or domain) of the sequence. "Areas, regions or domains" of homology or identity mean that a portion of two or more referenced entities share homology or are the same.

The extent of identity between two sequences can be ascertained using a computer program and mathematical algorithm known in the art. Such algorithms that calculate percent sequence identity (homology) generally account for sequence gaps and mismatches over the comparison region or area. For example, a BLAST (e.g., BLAST 2.0) search algorithm (see, e.g., Altschul et al., *J. Mol. Biol.* 215:403 (1990), publicly available through NCBI) has exemplary search parameters as follows: Mismatch −2; gap open 5; gap extension 2. For polypeptide sequence comparisons, a BLASTP algorithm is typically used in combination with a scoring matrix, such as PAM100, PAM 250, BLOSUM 62 or BLOSUM 50. FASTA (e.g., FASTA2 and FASTA3) and SSEARCH sequence comparison programs are also used to quantitate the extent of identity (Pearson et al., *Proc. Natl. Acad. Sci. USA* 85:2444 (1988); Pearson, *Methods Mol Biol.* 132:185 (2000); and Smith et al., *J. Mol. Biol.* 147:195 (1981)). Programs for quantitating protein structural similarity using Delaunay-based topological mapping have also been developed (Bostick et al., *Biochem Biophys Res Commun.* 304:320 (2003)).

In accordance with the invention, modified and variant forms of Dengue virus (DV) peptides, subsequences and portions there are provided. Such forms, referred to as "modifications" or "variants" and grammatical variations thereof, mean a Dengue virus (DV) peptide, subsequence or portion thereof that deviates from a reference sequence. For example, certain sequences set forth in Tables 1-4, 8, 10, 11, 14 &15 (SEQ ID NOs: 11-1163) are considered a modification or variant of Dengue virus (DV) peptide, subsequence or portion thereof. Such modifications may have greater or less activity or function than a reference Dengue virus (DV) peptide, subsequence or portion thereof, such as ability to elicit, stimulate, induce, promote, increase, enhance or activate a CD4+ or a CD8+ T cell response. Thus, Dengue virus (DV) peptides, subsequences and portions thereof include sequences having substantially the same, greater or less relative activity or function as a T cell epitope than a reference T cell epitope (e.g., any of the sequences in Tables 1-4, 8, 10, 11, 14 &15), for example, an ability to elicit, stimulate, induce, promote, increase, enhance or activate an anti-DV CD4+ T cell or anti-DV CD8+ T cell response in vitro or in vivo.

Non-limiting examples of modifications include one or more amino acid substitutions (e.g., 1, 2, 3, 4, 5, 6, 7, 8, 9, 10, 1, 12, 13, 14, 15, 16, 17, 18, 19, 20, 20-25, 25-30, 30-50, 50-100, or more residues), additions and insertions (e.g., 1, 2, 3, 4, 5, 6, 7, 8, 9, 10, 1, 12, 13, 14, 15, 16, 17, 18, 19, 20, 20-25, 25-30, 30-50, 50-100, or more residues) and deletions (e.g., 1, 2, 3, 4, 5, 6, 7, 8, 9, 10, 1, 12, 13, 14, 15, 16, 17, 18, 19, 20, 20-25, 25-30, 30-50, 50-100) of a reference Dengue virus (DV) peptide, subsequence or portion thereof. In particular embodiments, a modified or variant sequence retains at least part of a function or an activity of unmodified sequence, which can have less than, approximately the same, or greater, but at least a part of, a function or activity of a reference sequence, for example, the ability to elicit, stimulate, induce, promote, increase, enhance or activate an anti-DV CD4+ T cell or anti-DV CD8+ T cell response in vitro or in vivo. Such CD4+ T cell and CD8+ T cell responses elicited include, for example, among others, induced, increased, enhanced, stimulate or activate expression or production of a cytokine (e.g., IFN-gamma, TNF, IL-2 or CD40L), release of a cytotoxin (perforin or granulysin), or apoptosis of a target (e.g., DV infected) cell.

Specific non-limiting examples of substitutions include conservative and non-conservative amino acid substitutions. A "conservative substitution" is the replacement of one amino acid by a biologically, chemically or structurally similar residue. Biologically similar means that the substitution does not destroy a biological activity. Structurally similar means that the amino acids have side chains with similar length, such as alanine, glycine and serine, or a similar size. Chemical similarity means that the residues have the same charge or are both hydrophilic or hydrophobic. Particular examples include the substitution of one hydrophobic residue, such as isoleucine, valine, leucine or methionine for another, or the substitution of one polar residue for another, such as the substitution of arginine for lysine, glutamic for aspartic acids, or glutamine for asparagine, serine for threonine, and the like.

An addition can be the covalent or non-covalent attachment of any type of molecule to the sequence. Specific examples of additions include glycosylation, acetylation, phosphorylation, amidation, formylation, ubiquitination, and derivatization by protecting/blocking groups and any of numerous chemical modifications. Additional specific non-limiting examples of an addition is one or more additional amino acid residues. Accordingly, DV sequences including T cell epitopes, subsequences, portions, and modifications thereof can be a part of or contained within a larger molecule, such as another peptide sequence, such as a fusion or chimera with a different DV sequence, or a non-DV peptide sequence. In particular embodiments, an addition is a fusion (chimeric) sequence, an amino acid sequence having one or more molecules not normally present in a reference native (wild type) sequence covalently attached to the sequence.

The term "chimeric" and grammatical variations thereof, when used in reference to a sequence, means that the sequence contains one or more portions that are derived from, obtained or isolated from, or based upon other physical or chemical entities. For example, a chimera of two or more different proteins may have one part a Dengue virus (DV) peptide, subsequence, portion or modification, and a second part of the chimera may be from a different Dengue virus (DV) peptide sequence, or a non-Dengue virus (DV) sequence.

Another particular example of a modified sequence having an amino acid addition is one in which a second heterologous sequence, i.e., heterologous functional domain is attached (covalent or non-covalent binding) that confers a distinct or complementary function. Heterologous functional domains are not restricted to amino acid residues. Thus, a heterologous functional domain can consist of any of a variety of different types of small or large functional moieties. Such moieties include nucleic acid, peptide, carbohydrate, lipid or small organic compounds, such as a drug (e.g., an antiviral), a metal (gold, silver), and radioisotope. For example, a tag such as T7 or polyhistidine can be attached in order to facilitate purification or detection of a T cell epitope. Thus, in other embodiments the invention provides Dengue virus (DV) peptides, subsequences, portions and modifications thereof and a heterologous domain, wherein the heterologous functional domain confers a distinct function, on the Dengue virus (DV) peptides, subsequences, portions and modifications thereof. Such constructs containing Dengue virus (DV) peptides, subsequences, portions and modifications thereof and a heterologous domain are also referred to as chimeras.

Linkers, such as amino acid or peptidomimetic sequences may be inserted between the sequence and the addition (e.g., heterologous functional domain) so that the two entities maintain, at least in part, a distinct function or activity. Linkers may have one or more properties that include a flexible conformation, an inability to form an ordered secondary structure or a hydrophobic or charged character which could promote or interact with either domain. Amino acids typically found in flexible protein regions include Gly, Asn and Ser. Other near neutral amino acids, such as Thr and Ala, may also be used in the linker sequence. The length of the linker sequence may vary without significantly affecting a function or activity of the fusion protein (see, e.g., U.S. Pat. No. 6,087,329). Linkers further include chemical moieties and conjugating agents, such as sulfo-succinimidyl derivatives (sulfo-SMCC, sulfo-SMPB), disuccinimidyl suberate (DSS), disuccinimidyl glutarate (DSG) and disuccinimidyl tartrate (DST).

Further non-limiting examples of additions are detectable labels. Thus, in another embodiment, the invention provides Dengue virus (DV) peptides, subsequences and portions thereof that are detectably labeled. Specific examples of detectable labels include fluorophores, chromophores, radioactive isotopes (e.g., $S^{35}$, $P^{32}$, $I^{125}$), electron-dense reagents, enzymes, ligands and receptors. Enzymes are typically detected by their activity. For example, horseradish peroxidase is usually detected by its ability to convert a substrate such as 3,3-',5,5-'-tetramethylbenzidine (TMB) to a blue pigment, which can be quantified.

Another non-limiting example of an addition is an insertion of an amino acid within any Dengue virus (DV) sequence, subsequence, portions or modification thereof (e.g., any sequence set forth in Tables 1-4, 8, 10, 11, 14 &15 (SEQ ID NOs: 11-1163)). In particular embodiments, an insertion is of one or more amino acid residues inserted into a Dengue virus (DV) peptide, subsequence portion or modification thereof, such as any sequence set forth in Tables 1-4, 8, 10, 11, 14 &15.

Modified and variant Dengue virus (DV) peptides, subsequences and portions thereof also include one or more D-amino acids substituted for L-amino acids (and mixtures thereof), structural and functional analogues, for example, peptidomimetics having synthetic or non-natural amino acids or amino acid analogues and derivatized forms. Modifications include cyclic structures such as an end-to-end amide bond between the amino and carboxy-terminus of the molecule or intra- or inter-molecular disulfide bond. Dengue virus (DV) peptides, subsequences and portions thereof may be modified in vitro or in vivo, e.g., post-translationally modified to include, for example, sugar residues, phosphate groups, ubiquitin, fatty acids, lipids, etc.

Specific non-limiting examples of substitutions include at least one amino acid deletion from full length Dengue virus (DV) peptide sequence. In particular embodiments, a peptide subsequence or portion is from about 5 to 300 amino acids in length, provided that said subsequence or portion is at least one amino acid less in length than the full-length Dengue virus (DV) structural sequence or the non-structural (NS) sequence. In additional particular embodiments, a peptide subsequence or portion is from about 2 to 5, 5 to 10, 10 to 15, 15 to 20, 20 to 25, 25 to 50, 50 to 100, 100 to 150, 150 to 200, or 200 to 300 amino acids in length, provided that said subsequence or portion is at least one amino acid less in length than the full-length Dengue virus (DV) structural sequence or non-structural (NS) sequence.

Dengue virus (DV) peptides, subsequences and portions thereof including modified forms can be produced by any of a variety of standard protein purification or recombinant expression techniques. For example, a Dengue virus (DV) peptide, subsequence, portion or modification thereof can be produced by standard peptide synthesis techniques, such as solid-phase synthesis. A portion of the protein may contain an amino acid sequence such as a T7 tag or polyhistidine sequence to facilitate purification of expressed or synthesized protein. The protein may be expressed in a cell and purified. The protein may be expressed as a part of a larger protein (e.g., a fusion or chimera) by recombinant methods.

Dengue virus (DV) peptides, subsequences and portions thereof including modified forms can be made using recombinant DNA technology via cell expression or in vitro translation. Polypeptide sequences including modified forms can also be produced by chemical synthesis using methods known in the art, for example, an automated peptide synthesis apparatus (see, e.g., Applied Biosystems, Foster City, Calif.).

The invention provides isolated and/or purified Dengue virus (DV) peptides, including or consisting of a subsequence, portion or modification of a structural core (C), membrane (M) or envelope (E) polypeptide sequence, or a non-structural (NS) NS1, NS2A, NS2B, NS3, NS4A, NS4B or NS5 polypeptide sequence. In particular embodiments, an isolated and/or purified subsequence, portion or modification of the Dengue virus (DV) polypeptide sequence includes a T cell epitope, e.g., as set forth in Tables 1-4, 8, 10, 11, 14 &15 (SEQ ID NOs: 11-1163).

The term "isolated," when used as a modifier of a composition (e.g., Dengue virus (DV) peptides, subsequences, portions and modifications thereof, nucleic acids encoding same, etc.), means that the compositions are made by the hand of man or are separated, completely or at least in part, from their naturally occurring in vivo environment. Generally, isolated compositions are substantially free of one or more materials with which they normally associate with in nature, for example, one or more protein, nucleic acid, lipid, carbohydrate, cell membrane. The term "isolated" does not exclude alternative physical forms of the composition, such as fusions/chimeras, multimers/oligomers, modifications (e.g., phosphorylation, glycosylation, lipidation) or derivatized forms, or forms expressed in host cells produced by the hand of man.

An "isolated" composition (e.g., Dengue virus (DV) peptide, subsequence, portion or modification thereof) can also be "substantially pure" or "purified" when free of most or all of the materials with which it typically associates within in nature. Thus, an isolated Dengue virus (DV) peptide, subsequence, portion or modification thereof, that also is substantially pure or purified does not include polypeptides or polynucleotides present among millions of other sequences, such as peptides of an peptide library or nucleic acids in a genomic or cDNA library, for example.

A "substantially pure" or "purified" composition can be combined with one or more other molecules. Thus, "substantially pure" or "purified" does not exclude combinations of compositions, such as combinations of Dengue virus (DV) peptides, subsequences, portions and modifications thereof (e.g., multiple, T cell epitopes), and other antigens, agents, drugs or therapies.

The invention also provides nucleic acids encoding Dengue virus (DV) peptides, subsequences, portions and modifications thereof. Such nucleic acid sequences encode a sequence at least 60% or more (e.g., 65%, 70%, 75%, 80%, 85%, 90%, 95%, etc.) identical to a Dengue virus (DV) peptide, subsequence or portion thereof. In an additional embodiment, a nucleic acid encodes a sequence having a modification, such as one or more amino acid additions (insertions), deletions or substitutions of a Dengue virus (DV) peptide, subsequences or portion thereof, such as any sequence set forth in Tables 1-4, 8, 10, 11, 14 &15 (SEQ ID NOs: 11-1163).

The terms "nucleic acid" and "polynucleotide" and the like refer to at least two or more ribo- or deoxy-ribonucleic acid base pairs (nucleotides) that are linked through a phosphoester bond or equivalent. Nucleic acids include polynucleotides and polynucleotides. Nucleic acids include single, double or triplex, circular or linear, molecules. Exemplary nucleic acids include but are not limited to: RNA, DNA, cDNA, genomic nucleic acid, naturally occurring and non naturally occurring nucleic acid, e.g., synthetic nucleic acid.

Nucleic acids can be of various lengths. Nucleic acid lengths typically range from about 20 nucleotides to 20 Kb, or any numerical value or range within or encompassing such lengths, 10 nucleotides to 10 Kb, 1 to 5 Kb or less, 1000 to about 500 nucleotides or less in length. Nucleic acids can also be shorter, for example, 100 to about 500 nucleotides, or from about 12 to 25, 25 to 50, 50 to 100, 100 to 250, or about 250 to 500 nucleotides in length, or any numerical value or range or value within or encompassing such lengths. In particular aspects, a nucleic acid sequence has a length from about 10-20, 20-30, 30-50, 50-100, 100-150, 150-200, 200-250, 250-300, 300-400, 400-500, 500-1000, 1000-2000, nucleotides, or any numerical value or range within or encompassing such lengths. Shorter polynucleotides are commonly referred to as "oligonucleotides" or "probes" of single- or double-stranded DNA. However, there is no upper limit to the length of such oligonucleotides.

Nucleic acid sequences further include nucleotide and nucleoside substitutions, additions and deletions, as well as derivatized forms and fusion/chimeric sequences (e.g., encoding recombinant polypeptide). For example, due to the degeneracy of the genetic code, nucleic acids include sequences and subsequences degenerate with respect to nucleic acids that encode Dengue virus (DV) peptides, subsequences and portions thereof, as well as variants and modifications thereof (e.g., substitutions, additions, insertions and deletions).

Nucleic acids can be produced using various standard cloning and chemical synthesis techniques. Techniques include, but are not limited to nucleic acid amplification, e.g., polymerase chain reaction (PCR), with genomic DNA or cDNA targets using primers (e.g., a degenerate primer mixture) capable of annealing to the encoding sequence. Nucleic acids can also be produced by chemical synthesis (e.g., solid phase phosphoramidite synthesis) or transcription from a gene. The sequences produced can then be translated in vitro, or cloned into a plasmid and propagated and then expressed in a cell (e.g., a host cell such as eukaryote or mammalian cell, yeast or bacteria, in an animal or in a plant).

Nucleic acid may be inserted into a nucleic acid construct in which expression of the nucleic acid is influenced or regulated by an "expression control element." An "expression control element" refers to a nucleic acid sequence element that regulates or influences expression of a nucleic acid sequence to which it is operatively linked. Expression control elements include, as appropriate, promoters, enhancers, transcription terminators, gene silencers, a start codon (e.g., ATG) in front of a protein-encoding gene, etc.

An expression control element operatively linked to a nucleic acid sequence controls transcription and, as appropriate, translation of the nucleic acid sequence. Expression control elements include elements that activate transcription constitutively, that are inducible (i.e., require an external signal for activation), or derepressible (i.e., require a signal to turn transcription off; when the signal is no longer present, transcription is activated or "derepressed"), or specific for cell-types or tissues (i.e., tissue-specific control elements).

Nucleic acid may be inserted into a plasmid for propagation into a host cell and for subsequent genetic manipulation. A plasmid is a nucleic acid that can be propagated in a host cell, plasmids may optionally contain expression control elements in order to drive expression of the nucleic acid encoding Dengue virus (DV) peptides, subsequences, portions and modifications thereof in the host cell. A vector is used herein synonymously with a plasmid and may also include an expression control element for expression in a host cell (e.g., expression vector). Plasmids and vectors generally contain at least an origin of replication for propagation in a cell and a promoter. Plasmids and vectors are therefore useful for genetic manipulation and expression of Dengue virus (DV) peptides, subsequences and portions thereof. Accordingly, vectors that include nucleic acids encoding or complementary to Dengue virus (DV) peptides, subsequences, portions and modifications thereof, are provided.

In accordance with the invention, there are provided transformed and host cells that are transformed with a nucleic acid that encodes and/or express Dengue virus (DV) peptides, subsequences, portions and modifications thereof. Transformed and host cells include but are not limited to prokaryotic and eukaryotic cells such as bacteria, fungi (yeast), plant, insect, and animal (e.g., mammalian, including primate and human, CHO cells and hybridomas) cells. For example, bacteria transformed with recombinant bacteriophage nucleic acid, plasmid nucleic acid or cosmid nucleic acid expression vectors; yeast transformed with recombinant yeast expression vectors; plant cell systems infected with recombinant virus expression vectors (e.g., cauliflower mosaic virus, CaMV; tobacco mosaic virus, TMV) or transformed with recombinant plasmid expression vectors (e.g., Ti plasmid); insect cell systems infected with recombinant virus expression vectors (e.g., baculovirus); and animal cell systems infected with recombinant virus expression vectors (e.g., retroviruses, adenovirus, vaccinia virus), or transformed animal cell systems engineered for stable expression. The cells may be a primary cell isolate, cell culture (e.g., passaged, established or immortalized cell line), or part of a plurality of cells, or a tissue or organ ex vivo or in a subject (in vivo).

The term "transformed" or "transfected" when used in reference to a cell (e.g., a host cell) or organism, means a genetic change in a cell following incorporation of an exogenous molecule, for example, a protein or nucleic acid (e.g., a transgene) into the cell. Thus, a "transfected" or "transformed" cell is a cell into which, or a progeny thereof in which an exogenous molecule has been introduced by the hand of man, for example, by recombinant DNA techniques.

The nucleic acid or protein can be stably or transiently transfected or transformed (expressed) in the host cell and progeny thereof. The cell(s) can be propagated and the introduced protein expressed, or nucleic acid transcribed. A progeny of a transfected or transformed cell may not be identical to the parent cell, since there may be mutations that occur during replication.

Introduction of Dengue virus (DV) peptides, subsequences, portions and modifications thereof, and nucleic acid into target cells (e.g., host cells) can also be carried out by methods known in the art such as osmotic shock (e.g., calcium phosphate), electroporation, microinjection, cell fusion, etc. Introduction of nucleic acid and polypeptide in vitro, ex vivo and in vivo can also be accomplished using other techniques. For example, a polymeric substance, such as polyesters, polyamine acids, hydrogel, polyvinyl pyrrolidone, ethylene-vinylacetate, methylcellulose, carboxymethylcellulose, protamine sulfate, or lactide/glycolide copolymers, polylactide/glycolide copolymers, or ethylenevinylacetate copolymers. A nucleic acid can be entrapped in microcapsules prepared by coacervation techniques or by interfacial polymerization, for example, by the use of hydroxymethylcellulose or gelatin-microcapsules, or poly (methylmethacrolate) microcapsules, respectively, or in a colloid system. Colloidal dispersion systems include macromolecule complexes, nano-capsules, microspheres, beads, and lipid-based systems, including oil-in-water emulsions, micelles, mixed micelles, and liposomes.

Liposomes for introducing various compositions into cells are known in the art and include, for example, phosphatidylcholine, phosphatidylserine, lipofectin and DOTAP (e.g., U.S. Pat. Nos. 4,844,904, 5,000,959, 4,863,740, and 4,975,282; and GIBCO-BRL, Gaithersburg, Md.). Piperazine based amphilic cationic lipids useful for gene therapy also are known (see, e.g., U.S. Pat. No. 5,861,397). Cationic lipid systems also are known (see, e.g., U.S. Pat. No. 5,459,127). Polymeric substances, microcapsules and colloidal dispersion systems such as liposomes are collectively referred to herein as "vesicles." Accordingly, viral and non-viral vector means delivery into cells are included.

Dengue virus (DV) peptides, subsequences, portions and modifications thereof can be employed in various methods and uses. Such methods and uses include contact or administration of one or more peptides set forth in Tables 1-4, 8, 10, 11, 14 &15 (SEQ ID NOs: 11-1163), or contact or administration of a subsequence, portion or a modification of one or more peptides set forth in Tables 1-4, 8, 10, 11, 14 &15 (SEQ ID NOs: 11-1163), in vitro and in vivo.

In accordance with the invention, methods of stimulating, inducing, promoting, increasing, or enhancing an immune response against Dengue virus (DV) in a subject are provided. In one embodiment, a method includes administering to a subject an amount of a Dengue virus (DV) T cell epitope sufficient to stimulate, induce, promote, increase, or enhance an immune response against Dengue virus (DV) in the subject. Such immune response methods can in turn be used to provide a subject with protection against a Dengue virus (DV) infection or pathology, or one or more physiological conditions, disorders, illness, diseases or symptoms caused by or associated with DV infection or pathology.

In accordance with the invention, treatment methods are provided that include therapeutic (following Dengue virus (DV) infection) and prophylactic (prior to Dengue virus (DV) exposure, infection or pathology) methods. For example, therapeutic and prophylactic methods of treating a subject for a Dengue virus (DV) infection include treatment of a subject having or at risk of having a Dengue virus (DV) infection or pathology, treating a subject with a Dengue virus (DV) infection, and methods of protecting a subject from a Dengue virus (DV) infection (e.g., provide the subject with protection against Dengue virus (DV) infection), to decrease or reduce the probability of a Dengue virus (DV) infection in a subject, to decrease or reduce susceptibility of a subject to a Dengue virus (DV) infection, or to inhibit or prevent a Dengue virus (DV) infection in a subject, and to decrease, reduce, inhibit or suppress transmission of the Dengue virus (DV) from a host (e.g., a mosquito) to a subject.

Such methods include administering Dengue virus (DV) peptide, subsequence, portion or modification thereof to therapeutically or prophylactically treat (vaccinate or immunize) a subject having or at risk of having a Dengue virus (DV) infection or pathology. Accordingly, methods can treat the Dengue virus (DV) infection or pathology, or provide the subject with protection from infection (e.g., prophylactic protection).

In one embodiment, a method includes administering to a subject an amount of Dengue virus (DV) peptide, subsequence, portion or modification thereof sufficient to treat the subject for the Dengue virus (DV) infection or pathology. In another embodiment, a method includes administering to a subject an amount of a Dengue virus (DV) T cell epitope sufficient to provide the subject with protection against the Dengue virus (DV) infection or pathology, or one or more physiological conditions, disorders, illness, diseases or symptoms caused by or associated with the virus infection or pathology. In a further embodiment, a method includes administering a subject an amount of a Dengue virus (DV) T cell epitope sufficient to treat the subject for the Dengue virus (DV) infection.

Dengue virus (DV) peptides, subsequences, portions and modifications thereof include T cell epitopes. In one embodiment, a method includes administering an amount of Dengue virus (DV) peptide, subsequence, portion or modification thereof (e.g., a T cell epitope) to a subject in need thereof, sufficient to provide the subject with protection against Dengue virus (DV) infection or pathology. In another embodiment, a method includes administering an amount of a Dengue virus (DV) peptide, subsequence, portion or modification thereof (e.g., a T cell epitope) to a subject in need thereof sufficient to treat, vaccinate or immunize the subject against the Dengue virus (DV) infection or pathology.

In accordance with the invention, methods of inducing, increasing, promoting or stimulating anti-Dengue virus (DV) activity of $CD8^+$ T cells or $CD4^+$ T cells in a subject are provided. In one embodiment, a method includes administering to a subject an amount of a Dengue virus (DV) T cell epitope sufficient to induce, increase, promote or stimulate anti-Dengue virus (DV) activity of CD8$^+$ T cells or CD4$^+$ T cells in the subject.

In methods of the invention, any appropriate Dengue virus (DV) peptide, subsequence, portion or modification thereof can be administered. Non-limiting examples include Dengue virus (DV) peptide, subsequence, portion or modification thereof of a DENV1, DENV2, DENV3 or DENV4 serotype. Additional non-limiting examples include a Dengue virus structural protein (e.g., C, M or E) or non-structural (NS) protein (e.g., NS1, NS2A, NS2B, NS3, NS4A, NS4B or NS5) T cell epitope, such as a subsequence, portion or modification of a sequence in such structural and non-structural (NS) proteins. Particular non-limiting examples include a peptide sequence set forth in Tables 1-4, 8, 10, 11, 14 &15 (SEQ ID NOs: 11-1163), a subsequence thereof or a modification thereof.

In particular methods embodiments, one or more disorders, diseases, physiological conditions, pathologies and symptoms associated with or caused by a Dengue virus (DV) infection or pathology will respond to treatment. In particular methods embodiments, treatment methods reduce, decrease, suppress, limit, control or inhibit Dengue virus (DV) numbers or titer; reduce, decrease, suppress, limit, control or inhibit pathogen proliferation or replication; reduce, decrease, suppress, limit, control or inhibit the amount of a pathogen protein; or reduce, decrease, suppress, limit, control or inhibit the amount of a Dengue virus (DV) nucleic acid. In additional particular methods embodiments, treatment methods include an amount of a Dengue virus (DV) peptide, subsequence or portion thereof sufficient to increase, induce, enhance, augment, promote or stimulate an immune response against a Dengue virus (DV); increase, induce, enhance, augment, promote or stimulate Dengue virus (DV) clearance or removal; or decrease, reduce, inhibit, suppress, prevent, control, or limit transmission of Dengue virus (DV) to a subject (e.g., transmission from a host, such as a mosquito, to a subject). In further particular methods embodiments, treatment methods include an amount of Dengue virus (DV) peptide, subsequence or portion thereof sufficient to protect a subject from a Dengue virus (DV) infection or pathology, or reduce, decrease, limit, control or inhibit susceptibility to Dengue virus (DV) infection or pathology.

Methods of the invention include treatment methods, which result in any therapeutic or beneficial effect. In various methods embodiments, Dengue virus (DV) infection, proliferation or pathogenesis is reduced, decreased, inhibited, limited, delayed or prevented, or a method decreases, reduces, inhibits, suppresses, prevents, controls or limits one or more adverse (e.g., physical) symptoms, disorders, illnesses, diseases or complications caused by or associated with Dengue virus (DV) infection, proliferation or replication, or pathology (e.g., fever, rash, headache, pain behind the eyes, muscle or joint pain, nausea, vomiting, loss of appetite). In additional various particular embodiments, treatment methods include reducing, decreasing, inhibiting, delaying or preventing onset, progression, frequency, duration, severity, probability or susceptibility of one or more adverse symptoms, disorders, illnesses, diseases or complications caused by or associated with Dengue virus (DV) infection, proliferation or replication, or pathology (e.g., fever, rash, headache, pain behind the eyes, muscle or joint pain, nausea, vomiting, loss of appetite). In further various particular embodiments, treatment methods include improving, accelerating, facilitating, enhancing, augmenting, or hastening recovery of a subject from a Dengue virus (DV) infection or pathogenesis, or one or more adverse symptoms, disorders, illnesses, diseases or complications caused by or associated with Dengue virus (DV) infection, proliferation or replication, or pathology (e.g., fever, rash, headache, pain behind the eyes, muscle or joint pain, nausea, vomiting, loss of appetite). In yet additional various embodiments, treatment methods include stabilizing infection, proliferation, replication, pathogenesis, or an adverse symptom, disorder, illness, disease or complication caused by or associated with Dengue virus (DV) infection, proliferation or replication, or pathology, or decreasing, reducing, inhibiting, suppressing, limiting or controlling transmission of Dengue virus (DV) from a host (e.g., mosquito) to an uninfected subject.

A therapeutic or beneficial effect of treatment is therefore any objective or subjective measurable or detectable improvement or benefit provided to a particular subject. A therapeutic or beneficial effect can but need not be complete ablation of all or any particular adverse symptom, disorder, illness, disease or complication caused by or associated with Dengue virus (DV) infection, proliferation or replication, or pathology (e.g., fever, rash, headache, pain behind the eyes, muscle or joint pain, nausea, vomiting, loss of appetite). Thus, a satisfactory clinical endpoint is achieved when there is an incremental improvement or a partial reduction in an adverse symptom, disorder, illness, disease or complication caused by or associated with Dengue virus (DV) infection, proliferation or replication, or pathology, or an inhibition, decrease, reduction, suppression, prevention, limit or control of worsening or progression of one or more adverse symptoms, disorders, illnesses, diseases or complications caused by or associated with Dengue virus (DV) infection, Dengue virus (DV) numbers, titers, proliferation or replication, Dengue virus (DV) protein or nucleic acid, or Dengue virus (DV) pathology, over a short or long duration (hours, days, weeks, months, etc.).

A therapeutic or beneficial effect also includes reducing or eliminating the need, dosage frequency or amount of a second active such as another drug or other agent (e.g., anti-viral) used for treating a subject having or at risk of having a Dengue virus (DV) infection or pathology. For example, reducing an amount of an adjunct therapy, for example, a reduction or decrease of a treatment for a Dengue virus (DV) infection or pathology, or a vaccination or immunization protocol is considered a beneficial effect. In addition, reducing or decreasing an amount of a Dengue virus (DV) antigen used for vaccination or immunization of a subject to provide protection to the subject is considered a beneficial effect.

Adverse symptoms and complications associated with Dengue virus (DV) infection and pathology include, for example, e.g., fever, rash, headache, pain behind the eyes, muscle or joint pain, nausea, vomiting, loss of appetite, etc. Other symptoms of Dengue virus (DV) infection or pathogenesis are known to one of skill in the art and treatment thereof in accordance with the invention is provided. Thus, the aforementioned symptoms and complications are treatable in accordance with the invention.

Methods and compositions of the invention also include increasing, stimulating, promoting, enhancing, inducing or augmenting an anti-DENV CD4$^+$ and/or CD8$^+$ T cell responses in a subject, such as a subject with or at risk of a Dengue virus infection or pathology. In one embodiment, a method includes administering to a subject an amount of Dengue virus (DV) peptide, subsequence, portion or modification thereof sufficient to increase, stimulate, promote, enhance, augment or induce anti-DENV CD4$^+$ or CD8$^+$ T cell response in the subject. In another embodiment, a method includes administering to a subject an amount of Dengue virus (DV) peptide, subsequence, portion or modification thereof and administering a Dengue virus (DV) antigen, live or attenuated Dengue virus (DV), or a nucleic acid encoding all or a portion (e.g., a T cell epitope) of any protein or proteinaceous Dengue virus (DV) antigen sufficient to increase, stimulate, promote, enhance, augment or induce anti-Dengue virus (DV) $CD4^+$ T cell or $CD8^+$ T cell response in the subject.

Methods of the invention additionally include, among other things, increasing production of a Th1 cytokine (e.g., IFN-gamma, TNF-alpha, IL-1alpha, IL-2, IL-6, IL-8, etc.) or other signaling molecule (e.g., CD40L) in vitro or in vivo. In one embodiment, a method includes administering to a subject in need thereof an amount of Dengue virus (DV) peptide, subsequence or portion thereof sufficient to increase production of a Th1 cytokine in the subject (e.g., IFN-gamma, TNF-alpha, IL-1alpha, IL-2, IL-6, IL-8, etc.) or other signaling molecule (e.g., CD40L).

Methods and compositions of the invention include administration of Dengue virus (DV) peptide, subsequence, portion or modification thereof to a subject prior to contact, exposure or infection by a Dengue virus, administration prior to, substantially contemporaneously with or after a subject has been contacted by, exposed to or infected with a Dengue virus (DV), and administration prior to, substantially contemporaneously with or after Dengue virus (DV) pathology or development of one or more adverse symptoms. Methods, compositions and uses of the invention also include administration of Dengue virus (DV) peptide, subsequence, portion or modification thereof to a subject prior to, substantially contemporaneously with or following a Dengue virus (DV) peptide, subsequence or portion thereof or adverse symptom, disorder, illness or disease caused by or associated with a Dengue virus (DV) infection, or pathology. A subject infected with a Dengue virus (DV) may have an infection over a period of 1-5, 5-10, 10-20, 20-30, 30-50, 50-100 hours, days, months, or years.

Invention compositions (e.g., Dengue virus (DV) peptide, subsequence or portion thereof, including T cell epitopes) and uses and methods can be combined with any compound, agent, drug, treatment or other therapeutic regimen or protocol having a desired therapeutic, beneficial, additive, synergistic or complementary activity or effect. Exemplary combination compositions and treatments include multiple T cell epitopes as set for the herein, second actives, such as anti-Dengue virus (DV) compounds, agents and drugs, as well as agents that assist, promote, stimulate or enhance efficacy. Such anti-Dengue virus (DV) drugs, agents, treatments and therapies can be administered or performed prior to, substantially contemporaneously with or following any other method of the invention, for example, a therapeutic method of treating a subject for a Dengue virus (DV) infection or pathology, or a method of prophylactic treatment of a subject for a Dengue virus (DV) infection.

Dengue virus (DV) peptides, subsequences, portions and modifications thereof can be administered as a combination composition, or administered separately, such as concurrently or in series or sequentially (prior to or following) administering a second active, to a subject. The invention therefore provides combinations in which a method or use of the invention is used in a combination with any compound, agent, drug, therapeutic regimen, treatment protocol, process, remedy or composition, such as an anti-viral (e.g., Dengue virus (DV)) or immune stimulating, enhancing or augmenting protocol, or pathogen vaccination or immunization (e.g., prophylaxis) set forth herein or known in the art. The compound, agent, drug, therapeutic regimen, treatment protocol, process, remedy or composition can be administered or performed prior to, substantially contemporaneously with or following administration of one or more Dengue virus (DV) peptides, subsequences, portions or modifications thereof, or a nucleic acid encoding all or a portion (e.g., a T cell epitope) of a Dengue virus (DV) peptide, subsequence, portion or modification thereof, to a subject. Specific non-limiting examples of combination embodiments therefore include the foregoing or other compound, agent, drug, therapeutic regimen, treatment protocol, process, remedy or composition.

An exemplary combination is a Dengue virus (DV) peptide, subsequence, portion or modification thereof (e.g., a $CD4^+$ or $CD8^+$ T cell epitope) and a different Dengue virus (DV) peptide, subsequence, portion or modification thereof (e.g., a different T cell epitope) such as a T cell epitope, antigen (e.g., Dengue virus (DV) extract), or live or attenuated Dengue virus (DV) (e.g., inactivated Dengue virus (DV)). Such Dengue virus (DV) antigens and T cell epitopes set forth herein or known to one skilled in the art include a Dengue virus (DV) antigen that increases, stimulates, enhances, promotes, augments or induces a proinflammatory or adaptive immune response, numbers or activation of an immune cell (e.g., T cell, natural killer T (NKT) cell, dendritic cell (DC), B cell, macrophage, neutrophil, eosinophil, mast cell, $CD4^+$ or a $CD8^+$ cell, $B220^+$ cell, $CD14^+$, $CD11b^+$ or $CD11c^+$ cells), an anti-Dengue virus (DV) $CD4^+$ or $CD8^+$ T cell response, production of a Th1 cytokine, a T cell mediated immune response, etc.

Combination methods and use embodiments include, for example, second actives such as anti-pathogen drugs, such as protease inhibitors, reverse transcriptase inhibitors, virus fusion inhibitors and virus entry inhibitors, antibodies to pathogen proteins, live or attenuated pathogen, or a nucleic acid encoding all or a portion (e.g., an epitope) of any protein or proteinaceous pathogen antigen, immune stimulating agents, etc., and include contact with, administration in vitro or in vivo, with another compound, agent, treatment or therapeutic regimen appropriate for pathogen infection, vaccination or immunization Methods of the invention also include, among other things, methods that result in a reduced need or use of another compound, agent, drug, therapeutic regimen, treatment protocol, process, or remedy. For example, for a Dengue virus (DV) infection or pathology, vaccination or immunization, a method of the invention has a therapeutic benefit if in a given subject a less frequent or reduced dose or elimination of an anti-Dengue virus (DV) treatment results. Thus, in accordance with the invention, methods of reducing need or use of a treatment or therapy for a Dengue virus (DV) infection or pathology, or vaccination or immunization, are provided.

In invention methods in which there is a desired outcome, such as a therapeutic or prophylactic method that provides a benefit from treatment, vaccination or immunization Dengue virus (DV) peptide, subsequence, portion or modification thereof can be administered in a sufficient or effective amount. As used herein, a "sufficient amount" or "effective amount" or an "amount sufficient" or an "amount effective" refers to an amount that provides, in single (e.g., primary) or multiple (e.g., booster) doses, alone or in combination with one or more other compounds, treatments, therapeutic regimens or agents (e.g., a drug), a long term or a short term detectable or measurable improvement in a given subject or any objective or subjective benefit to a given subject of any degree or for any time period or duration (e.g., for minutes, hours, days, months, years, or cured).

An amount sufficient or an amount effective can but need not be provided in a single administration and can but need not be achieved by Dengue virus (DV) peptide, subsequence, portion or modification thereof alone, in a combination composition or method that includes a second active. In addition, an amount sufficient or an amount effective need not be sufficient or effective if given in single or multiple doses without a second or additional administration or dosage, since additional doses, amounts or duration above and beyond such doses, or additional antigens, compounds, drugs, agents, treatment or therapeutic regimens may be included in order to provide a given subject with a detectable or measurable improvement or benefit to the subject. For example, to increase, enhance, improve or optimize immunization and/or vaccination, after an initial or primary administration of one or more Dengue virus (DV) peptides, subsequences, portions or modifications thereof to a subject, the subject can be administered one or more additional "boosters" of one or more Dengue virus (DV) peptides, subsequences, portions or modifications thereof. Such subsequent "booster" administrations can be of the same or a different formulation, dose or concentration, route, etc.

An amount sufficient or an amount effective need not be therapeutically or prophylactically effective in each and every subject treated, nor a majority of subjects treated in a given group or population. An amount sufficient or an amount effective means sufficiency or effectiveness in a particular subject, not a group of subjects or the general population. As is typical for such methods, different subjects will exhibit varied responses to treatment.

The term "subject" refers to an animal, typically a mammalian animal (mammal), such as a non human primate (apes, gibbons, gorillas, chimpanzees, orangutans, macaques), a domestic animal (dogs and cats), a farm animal (poultry such as chickens and ducks, horses, cows, goats, sheep, pigs), experimental animal (mouse, rat, rabbit, guinea pig) and humans. Subjects include animal disease models, for example, mouse and other animal models of pathogen (e.g., DV) infection known in the art.

Subjects appropriate for treatment include those having or at risk of having Dengue virus infection or pathology. Target subjects therefore include subjects that have been exposed to or contacted with Dengue virus (DV), or that have an ongoing infection or have developed one or more adverse symptoms caused by or associated with Dengue virus (DV) infection or pathology, regardless of the type, timing or degree of onset, progression, severity, frequency, duration of the symptoms.

Target subjects also include those at risk of Dengue virus (DV) exposure, contact, infection or pathology or at risk of having or developing a Dengue virus (DV) infection or pathology. The invention methods are therefore applicable to treating a subject who is at risk of Dengue virus (DV) exposure, contact, infection or pathology, but has not yet been exposed to or contacted with Dengue virus (DV). Prophylactic methods are therefore included. Target subjects for prophylaxis can be at increased risk (probability or susceptibility) of exposure, contact, infection or pathology, as set forth herein. Such subjects are considered in need of treatment due to being at risk.

Target subjects for prophylaxis need not be at increased risk but may be from the general population in which it is desired to vaccinate or immunize a subject against a Dengue virus (DV) infection, for example. Such a subject that is desired to be vaccinated or immunized against a Dengue virus (DV) can be administered Dengue virus (DV) peptide, subsequence, portion or modification thereof. In another non-limiting example, a subject that is not specifically at risk of exposure to or contact with a Dengue virus (DV), but nevertheless desires protect against infection or pathology, can be administered a Dengue virus (DV) peptide, subsequence, portion or modification thereof. Such subjects are also considered in need of treatment.

At risk subjects appropriate for treatment also include subjects exposed to environments in which subjects are at risk of a Dengue virus (DV) infection due to mosquitos. Subjects appropriate for treatment therefore include human subjects exposed to mosquitos, or travelling to geographical regions or countries in which Dengue virus (DV) is know to infect subjects due, for example, an individual who risks exposure due to the presence of DENV in a particular geographical region or country or population, or transmission from mosquitos present in the region or country. At risk subjects appropriate for treatment also include subjects where the risk of Dengue virus (DV) infection or pathology is increased due to changes in infectivity or the type of region of Dengue virus (DV) carrying mosquitos. Such subjects are also considered in need of treatment due to such a risk.

"Prophylaxis" and grammatical variations thereof mean a method in which contact, administration or in vivo delivery to a subject is prior to contact with or exposure to or infection. In certain situations it may not be known that a subject has been contacted with or exposed to Dengue virus (DV), but administration or in vivo delivery to a subject can be performed prior to infection or manifestation of pathology (or an associated adverse symptom, condition, complication, etc. caused by or associated with a Dengue virus (DV)). For example, a subject can be immunized or vaccinated with a Dengue virus (DV) peptide, subsequence, portion or modification thereof. In such case, a method can eliminate, prevent, inhibit, suppress, limit, decrease or reduce the probability of or susceptibility towards a Dengue virus (DV) infection or pathology, or an adverse symptom, condition or complication associated with or caused by or associated with a Dengue virus (DV) infection or pathology.

Treatment of an infection can be at any time during the infection. Dengue virus (DV) peptide, subsequence or portion thereof can be administered as a combination (e.g., with a second active), or separately concurrently or in sequence (sequentially) in accordance with the methods as a single or multiple dose e.g., one or more times hourly, daily, weekly, monthly or annually or between about 1 to 10 weeks, or for as long as appropriate, for example, to achieve a reduction in the onset, progression, severity, frequency, duration of one or more symptoms or complications associated with or caused by Dengue virus (DV) infection, pathology, or an adverse symptom, condition or complication associated with or caused by a Dengue virus (DV). Thus, a method can be practiced one or more times (e.g., 1-10, 1-5 or 1-3 times) an hour, day, week, month, or year. The skilled artisan will know when it is appropriate to delay or discontinue administration. A non-limiting dosage schedule is 1-7 times per week, for 1, 2, 3, 4, 5, 6, 7, 8, 9, 10, 15, 20 or more weeks, and any numerical value or range or value within such ranges.

Methods of the invention may be practiced by any mode of administration or delivery, or by any route, systemic, regional and local administration or delivery. Exemplary administration and delivery routes include intravenous (i.v.), intraperitoneal (i.p.), intrarterial, intramuscular, parenteral, subcutaneous, intra-pleural, topical, dermal, intradermal, transdermal, transmucosal, intra-cranial, intra-spinal, rectal, oral (alimentary), mucosal, inhalation, respiration, intranasal, intubation, intrapulmonary, intrapulmonary instillation, buccal, sublingual, intravascular, intrathecal, intracavity, iontophoretic, intraocular, ophthalmic, optical, intraglandular, intraorgan, or intralymphatic.

Doses can be based upon current existing protocols, empirically determined, using animal disease models or optionally in human clinical trials. Initial study doses can be based upon animal studies set forth herein, for a mouse, which weighs about 30 grams, and the amount of Dengue virus (DV) peptide, subsequence, portion or modification thereof administered that is determined to be effective. Exemplary non-limiting amounts (doses) are in a range of about 0.1 mg/kg to about 100 mg/kg, and any numerical value or range or value within such ranges. Greater or lesser amounts (doses) can be administered, for example, 0.01-500 mg/kg, and any numerical value or range or value within such ranges. The dose can be adjusted according to the mass of a subject, and will generally be in a range from about 1-10 ug/kg, 10-25 ug/kg, 25-50 ug/kg, 50-100 ug/kg, 100-500 ug/kg, 500-1,000 ug/kg, 1-5 mg/kg, 5-10 mg/kg, 10-20 mg/kg, 20-50 mg/kg, 50-100 mg/kg, 100-250 mg/kg, 250-500 mg/kg, or more, two, three, four, or more times per hour, day, week, month or annually. A typical range will be from about 0.3 mg/kg to about 50 mg/kg, 0-25 mg/kg, or 1.0-10 mg/kg, or any numerical value or range or value within such ranges.

Doses can vary and depend upon whether the treatment is prophylactic or therapeutic, whether a subject has been previously exposed to, infected with our suffered from Dengue virus (DV), the onset, progression, severity, frequency, duration probability of or susceptibility of the symptom, condition, pathology or complication, or vaccination or immunization to which treatment is directed, the clinical endpoint desired, previous or simultaneous treatments, the general health, age, gender, race or immunological competency of the subject and other factors that will be appreciated by the skilled artisan. The skilled artisan will appreciate the factors that may influence the dosage and timing required to provide an amount sufficient for providing a therapeutic or prophylactic benefit.

Typically, for therapeutic treatment, Dengue virus (DV) peptide, subsequence, portion or modification thereof will be administered as soon as practical, typically within 1-2, 2-4, 4-12, 12-24 or 24-72 hours after a subject is exposed to or contacted with a Dengue virus (DV), or within 1-2, 2-4, 4-12, 12-24 or 24-48 hours after onset or development of one or more adverse symptoms, conditions, pathologies, complications, etc., associated with or caused by a Dengue virus (DV) infection or pathology. For prophylactic treatment in connection with vaccination or immunization, Dengue virus (DV) peptide, subsequence, portion or modification thereof can be administered for a duration of 0-4 weeks, e.g., 2-3 weeks, prior to exposure to, contact or infection with Dengue virus (DV), or at least within 1-2, 2-4, 4-12, 12-24, 24-48 or 48-72 hours prior to exposure to, contact or infection with Dengue virus (DV). For an acute infection, Dengue virus (DV) peptide, subsequence, portion or modification thereof is administered at any appropriate time.

The dose amount, number, frequency or duration may be proportionally increased or reduced, as indicated by the status of the subject. For example, whether the subject has a pathogen infection, whether the subject has been exposed to, contacted or infected with pathogen or is merely at risk of pathogen contact, exposure or infection, whether the subject is a candidate for or will be vaccinated or immunized. The dose amount, number, frequency or duration may be proportionally increased or reduced, as indicated by any adverse side effects, complications or other risk factors of the treatment or therapy.

Dengue virus (DV) peptides, subsequences, portions and modifications thereof can be incorporated into compositions, including pharmaceutical compositions, e.g., a pharmaceutically acceptable carrier or excipient. Such pharmaceutical compositions are useful for, among other things, administration to a subject in vivo or ex vivo.

As used herein the term “pharmaceutically acceptable” and “physiologically acceptable” mean a biologically acceptable formulation, gaseous, liquid or solid, or mixture thereof, which is suitable for one or more routes of administration, in vivo delivery or contact. Such formulations include solvents (aqueous or non-aqueous), solutions (aqueous or non-aqueous), emulsions (e.g., oil-in-water or water-in-oil), suspensions, syrups, elixirs, dispersion and suspension media, coatings, isotonic and absorption promoting or delaying agents, compatible with pharmaceutical administration or in vivo contact or delivery. Aqueous and non-aqueous solvents, solutions and suspensions may include suspending agents and thickening agents. Such pharmaceutically acceptable carriers include tablets (coated or uncoated), capsules (hard or soft), microbeads, powder, granules and crystals. Supplementary active compounds (e.g., preservatives, antibacterial, antiviral and antifungal agents) can also be incorporated into the compositions.

Pharmaceutical compositions can be formulated to be compatible with a particular route of administration. Thus, pharmaceutical compositions include carriers, diluents, or excipients suitable for administration by various routes. Exemplary routes of administration for contact or in vivo delivery which a composition can optionally be formulated include inhalation, respiration, intranasal, intubation, intrapulmonary instillation, oral, buccal, intrapulmonary, intradermal, topical, dermal, parenteral, sublingual, subcutaneous, intravascular, intrathecal, intraarticular, intracavity, transdermal, iontophoretic, intraocular, opthalmic, optical, intravenous (i.v.), intramuscular, intraglandular, intraorgan, or intralymphatic.

Formulations suitable for parenteral administration comprise aqueous and non-aqueous solutions, suspensions or emulsions of the active compound, which preparations are typically sterile and can be isotonic with the blood of the intended recipient. Non-limiting illustrative examples include water, saline, dextrose, fructose, ethanol, animal, vegetable or synthetic oils.

To increase an immune response, immunization or vaccination, Dengue virus (DV) peptides, subsequences, portions and modifications thereof can be coupled to another protein such as ovalbumin or keyhole limpet hemocyanin (KLH), thyroglobulin or a toxin such as tetanus or cholera toxin. Dengue virus (DV) peptides, subsequences, portions and modifications thereof can also be mixed with adjuvants.

Adjuvants include, for example: Oil (mineral or organic) emulsion adjuvants such as Freund’s complete (CFA) and incomplete adjuvant (IFA) (WO 95/17210; WO 98/56414; WO 99/12565; WO 99/11241; and U.S. Pat. No. 5,422,109); metal and metallic salts, such as aluminum and aluminum salts, such as aluminum phosphate or aluminum hydroxide, alum (hydrated potassium aluminum sulfate); bacterially derived compounds, such as Monophosphoryl lipid A and derivatives thereof (e.g., 3 De-O-acylated monophosphoryl lipid A, aka 3D-MPL or d3-MPL, to indicate that position 3 of the reducing end glucosamine is de-O-acylated, 3D-MPL consisting of the tri and tetra acyl congeners), and enterobacterial lipopolysaccharides (LPS); plant derived saponins and derivatives thereof, for example Quil A (isolated from the Quilaja Saponaria Molina tree, see, e.g., "Saponin adjuvants", Archiv. fur die gesamte Virusforschung, Vol. 44, Springer Verlag, Berlin, p 243-254; U.S. Pat. No. 5,057,540), and fragments of Quil A which retain adjuvant activity without associated toxicity, for example QS7 and QS21 (also known as QA7 and QA21), as described in WO96/33739, for example; surfactants such as, soya lecithin and oleic acid; sorbitan esters such as sorbitan trioleate; and polyvinylpyrrolidone; oligonucleotides such as CpG (WO 96/02555, and WO 98/16247), polyriboA and polyriboU; block copolymers; and immunostimulatory cytokines such as GM-CSF and IL-1, and Muramyl tripeptide (MTP). Additional examples of adjuvants are described, for example, in "Vaccine Design—the subunit and adjuvant approach" (Edited by Powell, M. F. and Newman, M. J.; 1995, *Pharmaceutical Biotechnology* (Plenum Press, New York and London, ISBN 0-306-44867-X) entitled "Compendium of vaccine adjuvants and excipients" by Powell, M. F. and Newman M.

Cosolvents may be added to a Dengue virus (DV) peptide, subsequence, portion or modification composition or formulation. Non-limiting examples of cosolvents contain hydroxyl groups or other polar groups, for example, alcohols, such as isopropyl alcohol; glycols, such as propylene glycol, polyethyleneglycol, polypropylene glycol, glycol ether; glycerol; polyoxyethylene alcohols and polyoxyethylene fatty acid esters. Non-limiting examples of cosolvents contain hydroxyl groups or other polar groups, for example, alcohols, such as isopropyl alcohol; glycols, such as propylene glycol, polyethyleneglycol, polypropylene glycol, glycol ether; glycerol; polyoxyethylene alcohols and polyoxyethylene fatty acid esters.

Supplementary compounds (e.g., preservatives, antioxidants, antimicrobial agents including biocides and biostats such as antibacterial, antiviral and antifungal agents) can also be incorporated into the compositions. Pharmaceutical compositions may therefore include preservatives, anti-oxidants and antimicrobial agents.

Preservatives can be used to inhibit microbial growth or increase stability of ingredients thereby prolonging the shelf life of the pharmaceutical formulation. Suitable preservatives are known in the art and include, for example, EDTA, EGTA, benzalkonium chloride or benzoic acid or benzoates, such as sodium benzoate. Antioxidants include, for example, ascorbic acid, vitamin A, vitamin E, tocopherols, and similar vitamins or provitamins.

An antimicrobial agent or compound directly or indirectly inhibits, reduces, delays, halts, eliminates, arrests, suppresses or prevents contamination by or growth, infectivity, replication, proliferation, reproduction, of a pathogenic or non-pathogenic microbial organism. Classes of antimicrobials include antibacterial, antiviral, antifungal and antiparasitics. Antimicrobials include agents and compounds that kill or destroy (-cidal) or inhibit (-static) contamination by or growth, infectivity, replication, proliferation, reproduction of the microbial organism.

Exemplary antibacterials (antibiotics) include penicillins (e.g., penicillin G, ampicillin, methicillin, oxacillin, and amoxicillin), cephalosporins (e.g., cefadroxil, ceforanid, cefotaxime, and ceftriaxone), tetracyclines (e.g., doxycycline, chlortetracycline, minocycline, and tetracycline), aminoglycosides (e g, amikacin, gentamycin, kanamycin, neomycin, streptomycin, netilmicin, paromomycin and tobramycin), macrolides (e.g., azithromycin, clarithromycin, and erythromycin), fluoroquinolones (e.g., ciprofloxacin, lomefloxacin, and norfloxacin), and other antibiotics including chloramphenicol, clindamycin, cycloserine, isoniazid, rifampin, vancomycin, aztreonam, clavulanic acid, imipenem, polymyxin, bacitracin, amphotericin and nystatin.

Particular non-limiting classes of anti-virals include reverse transcriptase inhibitors; protease inhibitors; thymidine kinase inhibitors; sugar or glycoprotein synthesis inhibitors; structural protein synthesis inhibitors; nucleoside analogues; and viral maturation inhibitors. Specific non-limiting examples of anti-virals include nevirapine, delavirdine, efavirenz, saquinavir, ritonavir, indinavir, nelfinavir, amprenavir, zidovudine (AZT), stavudine (d4T), larnivudine (3TC), didanosine (DDI), zalcitabine (ddC), abacavir, acyclovir, penciclovir, ribavirin, valacyclovir, ganciclovir, 1,-D-ribofuranosyl-1,2,4-triazole-3 carboxamide, 9->2-hydroxyethoxy methylguanine, adamantanamine, 5-iodo-2'-deoxyuridine, trifluorothymidine, interferon and adenine arabinoside.

Pharmaceutical formulations and delivery systems appropriate for the compositions and methods of the invention are known in the art (see, e.g., *Remington: The Science and Practice of Pharmacy* (2003) $20^{th}$ ed., Mack Publishing Co., Easton, Pa.; *Remington's Pharmaceutical Sciences* (1990) $18^{th}$ ed., Mack Publishing Co., Easton, Pa.; *The Merck Index* (1996) $12^{th}$ ed., Merck Publishing Group, Whitehouse, N.J.; *Pharmaceutical Principles of Solid Dosage Forms* (1993), Technonic Publishing Co., Inc., Lancaster, Pa.; Ansel ad Soklosa, *Pharmaceutical Calculations* (2001) $11^{th}$ ed., Lippincott Williams & Wilkins, Baltimore, Md.; and Poznansky et al., *Drug Delivery Systems* (1980), R. L. Juliano, ed., Oxford, N.Y., pp. 253-315).

Dengue virus (DV) peptides, subsequences, portions, and modifications thereof, along with any adjunct agent, compound drug, composition, whether active or inactive, etc., can be packaged in unit dosage form (capsules, tablets, troches, cachets, lozenges) for ease of administration and uniformity of dosage. A "unit dosage form" as used herein refers to physically discrete units suited as unitary dosages for the subject to be treated; each unit containing a predetermined quantity of active ingredient optionally in association with a pharmaceutical carrier (excipient, diluent, vehicle or filling agent) which, when administered in one or more doses, is calculated to produce a desired effect (e.g., prophylactic or therapeutic effect). Unit dosage forms also include, for example, ampules and vials, which may include a composition in a freeze-dried or lyophilized state; a sterile liquid carrier, for example, can be added prior to administration or delivery in vivo. Unit dosage forms additionally include, for example, ampules and vials with liquid compositions disposed therein. Individual unit dosage forms can be included in multi-dose kits or containers. Pharmaceutical formulations can be packaged in single or multiple unit dosage form for ease of administration and uniformity of dosage.

The invention provides kits that include Dengue virus (DV) peptide, subsequences, portions, and modifications thereof, optionally with a second active, and pharmaceutical formulations thereof, packaged into suitable packaging material. A kit typically includes a label or packaging insert including a description of the components or instructions for use in vitro, in vivo, or ex vivo, of the components therein. A kit can contain a collection of such components, e.g., Dengue virus (DV) peptide, subsequence, portion, or modification thereof, and optionally a second active, such as another compound, agent, drug or composition.

The term "packaging material" refers to a physical structure housing the components of the kit. The packaging material can maintain the components sterilely, and can be made of material commonly used for such purposes (e.g., paper, corrugated fiber, glass, plastic, foil, ampules, vials, tubes, etc.).

Kits of the invention can include labels or inserts. Labels or inserts include "printed matter," e.g., paper or cardboard, or separate or affixed to a component, a kit or packing material (e.g., a box), or attached to an ampule, tube or vial containing a kit component. Labels or inserts can additionally include a computer readable medium, such as a disk (e.g., hard disk, flash memory), optical disk such as CD- or DVD-ROM/RAM, DVD, MP3, magnetic tape, or an electrical storage media such as RAM and ROM or hybrids of these such as magnetic/optical storage media, FLASH media or memory type cards.

Labels or inserts can include identifying information of one or more components therein, dose amounts, does frequency or timing, clinical pharmacology of the active ingredient(s) including mechanism of action, pharmacokinetics and pharmacodynamics. Labels or inserts can include information identifying manufacturer information, lot numbers, manufacturer location and date.

Labels or inserts can include information on a condition, disorder or disease (e.g., viral infection, vaccination or immunization) for which a kit component may be used. Labels or inserts can include instructions for the clinician or subject for using one or more of the kit components in a method, or treatment protocol or therapeutic regimen. Instructions can include dosage amounts, frequency or duration, and instructions for practicing any of the methods, treatment protocols or prophylactic or therapeutic regimes described herein. Exemplary instructions include, instructions for treating a Dengue virus (DV) infection or pathology, and instructions for providing a subject with protection against Dengue virus (DV) infection or pathology, e.g., immune response stimulating, vaccination or immunization.

Labels or inserts can include information on any benefit that a component may provide, such as a prophylactic or therapeutic benefit. Labels or inserts can include information on potential adverse side effects, complications or reactions, such as warnings to the subject or clinician regarding situations where it would not be appropriate to use a particular composition. Adverse side effects or complications could also occur when the subject has, will be or is currently taking one or more other medications that may be incompatible with the composition, or the subject has, will be or is currently undergoing another treatment protocol or therapeutic regimen which would be incompatible with the composition and, therefore, instructions could include information regarding such incompatibilities.

Methods of the invention also include, among other things, methods of diagnosing DV infection in a subject, and DV exposure of a subject. In open embodiment, a method includes contacting cells from a subject to one or more DV T cell epitopes; and determining if the T cell epitope elicits a response (e.g., anti-DV response) from the contacted cells. A response identifies the cells as having been exposed to the T cell epitope, thereby diagnosing the subject from which the cells were obtained as having a DV infection or as having been exposed to DV. Exemplary cells include $CD8^+$ T cells and/or CD4+ T cells. Exemplary responses include inducing, increasing, promoting or stimulating an anti-Dengue virus (DV) activity of $CD8^+$ T cells or CD4+ T cells; and/or increased or stimulated IFN-gamma, TNF-alpha, IL-1alpha, IL-6 or IL-8 production by $CD8^+$ T cells in the presence of the T cell epitope; and/or increased or stimulated IFN-gamma, TNF, IL-2, or CD40L in the presence of the T cell epitope, or killing T cell epitope-pulsed target cells.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described herein.

All applications, publications, patents and other references, GenBank citations and ATCC citations cited herein are incorporated by reference in their entirety. In case of conflict, the specification, including definitions, will control.

As used herein, the singular forms "a," "and," and "the" include plural referents unless the context clearly indicates otherwise. Thus, for example, reference to a "Dengue virus (DV) peptide, subsequence, portion, or modification thereof," or a "Dengue virus (DV)" includes a plurality of Dengue virus (DV) peptides, subsequences, portions, and modifications thereof, such as $CD4^+$ and/or $CD8^+$ T cell epitopes, or serotypes of Dengue virus (DV), and reference to an "activity or function" can include reference to one or more activities or functions of a Dengue virus (DV) peptide, subsequence, portion, or modification thereof, including function as a T cell epitopes, an ability to elicit, stimulate, induce, promote, increase, enhance or activate a measurable or detectable anti-DV CD4+ T cell response or anti-DV CD8+ T cell response, and so forth.

As used herein, numerical values are often presented in a range format throughout this document. The use of a range format is merely for convenience and brevity and should not be construed as an inflexible limitation on the scope of the invention. Accordingly, the use of a range expressly includes all possible subranges, all individual numerical values within that range, and all numerical values or numerical ranges include integers within such ranges and fractions of the values or the integers within ranges unless the context clearly indicates otherwise. This construction applies regardless of the breadth of the range and in all contexts throughout this patent document. Thus, to illustrate, reference to a range of 90-100% includes 91-99%, 92-98%, 93-95%, 91-98%, 91-97%, 91-96%, 91-95%, 91-94%, 91-93%, and so forth. Reference to a range of 90-100%, includes 91%, 92%, 93%, 94%, 95%, 95%, 97%, etc., as well as 91.1%, 91.2%, 91.3%, 91.4%, 91.5%, etc., 92.1%, 92.2%, 92.3%, 92.4%, 92.5%, etc., and so forth. Reference to a range of 1-5 fold therefore includes 1, 2, 3, 4, 5, 6, 7, 8, 9, 10, 11, 12, 13, 14, 15, 16, 17, 18, 19, 20, fold, etc., as well as 1.1, 1.2, 1.3, 1.4, 1.5, fold, etc., 2.1, 2.2, 2.3, 2.4, 2.5, fold, etc., and so forth. Further, for example, reference to a series of ranges of 2-72 hours, 2-48 hours, 4-24 hours, 4-18 hours and 6-12 hours, includes ranges of 2-6 hours, 2, 12 hours, 2-18 hours, 2-24 hours, etc., and 4-27 hours, 4-48 hours, 4-6 hours, etc.

As also used herein a series of range formats are used throughout this document. The use of a series of ranges includes combinations of the upper and lower ranges to provide a range. Accordingly, a series of ranges include ranges which combine the values of the boundaries of different ranges within the series. This construction applies regardless of the breadth of the range and in all contexts throughout this patent document. Thus, for example, reference to a series of ranges such as 5-10, 10-20, 20-30, 30-40, 40-50, 50-75, 75-100, 100-150, and 150-171, includes ranges such as 5-20, 5-30, 5-40, 5-50, 5-75, 5-100, 5-150, 5-171, and 10-30, 10-40, 10-50, 10-75, 10-100, 10-150, 10-171, and 20-40, 20-50, 20-75, 20-100, 20-150, 20-171, and so forth.

The invention is generally disclosed herein using affirmative language to describe the numerous embodiments and aspects. The invention also specifically includes embodiments in which particular subject matter is excluded, in full or in part, such as substances or materials, method steps and conditions, protocols, procedures, assays or analysis. For example, in certain embodiments or aspects of the invention, antibodies or other materials and method steps are excluded. In certain embodiments and aspects of the invention, for example, a Dengue virus (DV) peptide, subsequence, portion, or modification thereof, is excluded. Thus, even though the invention is generally not expressed herein in terms of what is not included, embodiments and aspects that expressly exclude compositions (e.g., antibodies or pathogen antigens) or method steps are nevertheless disclosed and included in the invention.

A number of embodiments of the invention have been described. Nevertheless, it will be understood that various modifications may be made without departing from the spirit and scope of the invention. Accordingly, the following examples are intended to illustrate but not limit the scope of invention described in the claims.

EXAMPLES

Example 1

This example includes a description of various materials and methods.

Mice and Infections

C57BL/6 (H-$2^b$) mice were obtained from The Jackson Laboratory and subsequently bred. IFN-α/βR$^{-/-}$ mice on the C57BL/6 background were obtained from Dr. Wayne Yokoyama (Washington University, St. Louis, Mo.) via Dr. Carl Ware. HLA-A*0201/Kb, A*1101/Kb, A*0101, B*0702 and DRB1*0101 transgenic mice were bred at LIAI as previously described (Kotturi et al., *Immunome Res* 6:4 (2010); Pasquetto et al., *J Immunol* 175:5504 (2005); Alexander et al., *J Immunol* 159:4753 (1997); Alexander et al., *Hum Immunol* 64:211 (2003)). All transgenic mouse strains were subsequently backcrossed with the IFN-α/βR$^{-/-}$ mice at the animal facility at LIAI.B6.SJL mice were purchased from Taconic. Mice were used between 5 and 10 weeks of age.

Mice were infected intravenously (i.v.) in the lateral tail vein or retro-orbitally (r.o.) with 200 μl of the DENV2 strain, S221, in 5% FBS/PBS. Blood was obtained from anesthetized mice by r.o. puncture. For experiments with transgenic mice, mice were infected i.v.r.o. with $10^{10}$ genomic equivalents (GE) of S221 in 100 uL PBS. On day 7 post-infection, mice were sacrificed and splenic CD8+ or CD4+ T cells, respectively, were used in mouse IFNγ ELISPOT assays. All mouse experiments were approved by the Animal Care Committee.

Cell Culture and Viral Stocks

The hybridoma clones SFR3, GK1.5, and 2.43, which produce rat anti-human HLA-DR5, anti-mouse CD4, and anti-mouse CD8 IgG2b Ab, respectively, were from the American Type Culture Collection, and were grown in Protein-Free Hybridoma Medium supplemented with penicillin, streptomycin, HEPES, GlutaMAX, and 2-ME (all from Invitrogen) at 37° C., 5% $CO_2$. C6/36, an *A. albopictus* mosquito cell line, was cultured in Leibovitz's L-15 Medium (Invitrogen) supplemented with 10% FBS (Gemini Bio-Products), penicillin, streptomycin, and HEPES at 28° C. in the absence of $CO_2$. 5221, a plaque-purified DENV2 strain, was derived from the clinical isolate, PL046 (Lin et al., *J Virol* 72:9729 (1998)), as described previously (Yauch et al., *J Immunol* 182:4865 (2009)). Viral stocks were amplified in C6/36 cells and purified over a sucrose gradient as previously described (Prestwood et al., *J Virol* 82:8411 (2008)). Infectious doses were determined based on GE, which were quantified by real-time RT-PCR. There are approximately $5\times10^4$ GE/PFU for S221, based on plaque assay on baby hamster kidney cells.

Bioinfonnatic Analyses

Candidate epitopes were identified using a consensus approach (Wang et al., *PLoS Comput Biol* 4:e1000048 (2008)). Briefly, all 15-mer peptides that are encoded in the DENV2 PL046 polyprotein were predicted for binding to H-2 I-A". Two independent algorithms (Zhang et al., *Nucleic Acids Res* 36:W513 (2008)) were used to rank the peptides by predicted binding affinity. The median of the two ranks was used to select the top 73 out of 3383 peptides, corresponding to the top 2% of all peptides.

For human MHC class I binding predictions all 9 and 10mer peptides were predicted for their binding affinity to their respective alleles. Binding predictions were performed using the command-line version of the consensus prediction tool available on the IEDB web site (Zhang et al., *Nucleic Acids Res* 36:W513 (2008)). Peptides were selected if they are in the top 1% of binders in a given strain. For human MHC class II binding predictions all 15mer peptides were predicted for their binding affinity to the DRB1*0101 allele. As with class I, binding predictions were performed using the command-line version of the consensus prediction tool available on the IEDB web site. The top 2% of predicted binders were then selected for synthesis. All peptides evaluated in this study were derived from the DENV2 virus strain S221, which was also used as infectious agent in this study, as described above. For the conservancy analysis, full-length DENV polyprotein sequences were retrieved for each serotype from the NCBI Protein database using the following query: txid11053 AND polyprotein AND 3000:5000[slen]. The number of isolates from any one country was limited to 10 to eliminate geographical bias. Sequences were considered "unique" if they varied by at least 1 amino acid from all other sequences. In summary, 171 DENV2, 162 DENV1, 169 DENV3 and 53 DENV4 sequences from the NCBI protein database were investigated for conservancy of the identified epitopes within the respective serotypes.

Selection of DENV Sequences for Human HLAs

Full-length DENV polyprotein sequences were retrieved for each serotype from the NCBI Protein database using the following query: txid11053 AND polyprotein AND 3000:5000 (44). Table 7 shows the DENV sequences that were retrieved for DENV3 as an example. In summary 162 DENV1, 171 DENV2, 169 DENV3 and 53 DENV4 sequences have been retrieved. Sequences were considered "unique" if they varied by at least 1 amino acid from all other sequences. The number of isolates from any one country was limited to 10 to avoid geographical bias. Polyproteins were broken down into all possible 9, 10mer sequences for binding predictions as described below.

MHC Class I Binding Predictions and Peptide Selection

All 9 and 10mer peptides were predicted for their binding affinity to 27 MHC class I alleles (Table 8). Binding predictions were performed using the command-line version of the consensus prediction tool available on the Immune Epitope Data Base (IEDB), web site (www.iedb.org, (45)). For each allele and length combination, peptides from each included polyprotein were selected if they are in the top 1% of binders in a given strain and they exist in at least 30% of the isolates for that serotype. If the same peptide is selected from two or more serotypes, then it was placed in the "conserved" group. If two or more peptides at the same position in the alignment (i.e. completely overlapping) are selected from one serotype, the peptide that is more common is designated the representative and the less-common peptides were placed in the "variant" group. This resulted in a set of 8,088 peptides to be synthesized. Table 8 summarizes the peptide groups resulting from this selection.

Peptide Synthesis

Peptides utilized in initial screening studies were synthesized as crude material by A and A Labs. A total of 73 15-mer peptides were ordered and synthesized twice in different (alphabetical vs. predicted $IC_{50}$) order. Positive peptides were re-synthesized by A and A Labs and purified to >90% homogeneity by reverse-phase HPLC. Purity of these peptides was determined using mass spectrometry. The HPLC-purified peptides were used for all subsequent experiments.

All peptides using human MHC class I or II sequences were synthesized by Mimotopes (Victoria, Australia). A total of 8088 9-mer and 10-mer peptides were identified by MHC class I predictions and synthesized as crude material. Peptides were combined into pools of 10 individual peptides, according to their predicted HLA restriction.

Flow Cytometric Analyses

For surface staining of germinal center B cells, splenocytes were stained with anti-B220-Alexa Fluor 647 (Biolegend), anti-CD4-PerCP (BD Biosciences), GL7-FITC (BD Biosciences), anti-IgD-eFluor 450 (eBioscience), and anti-Fas-PE (BD Biosciences). For intracellular cytokine staining (ICS) of $CD4^+$ T cells, $2\times10^6$ splenocytes were plated in 96-well U-bottom plates and stimulated with individual DENV2 peptides (3 μg/ml) for 2 h (hours). Brefeldin A (GolgiPlug, BD Biosciences) was then added and cells were incubated for another 5 h (hours). Cells were washed, incubated with supernatant from 2.4G2-producing hybridoma cells, and labeled with anti-CD4-eFluor 450 (eBioscience) and anti-CD8α-PerCP-eFluor 710 (eBioscience) or PE-Cy7 (BD Biosciences). The cells were then fixed and permeabilized using the BD Cytofix/Cytoperm Kit, and stained with various combinations of anti-IFN-γ-APC (eBioscience), anti-TNF-PE-Cy7 (BD Biosciences), anti-IL-2-Alexa Fluor 488 (BD Biosciences) or -PE (Biolegend), and anti-CD40L-PE (eBioscience). Foxp3 staining was done using the mouse regulatory T cell staining kit from eBioscience. The criteria for positivity in $CD4^+$ T cell epitope identification were: 2× the percentage of IFN-γ produced by stimulated cells compared with unstimulated cells, positive in two independent crude peptide orders, and positive when ordered as HPLC-purified (>90% pure). For $CD8^+$ T cell ICS, splenocytes ($2\times10^6$) were stimulated in 96-well U-bottom plates for 5 h (hours) in the presence of 1 μg/ml $H-2^b$-restricted epitopes identified previously: $M_{60-67}$, $NS2A_{8-15}$, and $NS4B_{99-107}$ (Yauch et al., J Immunol 182: 4865 (2009)). Anti-CD107a-FITC (BD Biosciences) was added to the wells during the stimulation. Cells were then stained as described for $CD4^+$ T cell ICS. Samples were read on an LSR II (BD Biosciences) and analyzed using FloJo software (Tree Star).

Immunohistochemistry

Tissues were embedded in O.C.T. compound (Sakura). Sections (6 μm) were cut and stored at −80° C. Frozen sections were thawed and fixed for 10 minutes in acetone at 25° C., followed by 8 minutes in 1% paraformaldehyde (EMS) in 100 mM dibasic sodium phosphate containing 60 mM lysine and 7 mM sodium periodate pH 7.4 at 4° C. Sections were blocked first using the Avidin/Biotin Blocking Kit (Vector Labs) followed by 5% normal goat serum (Invitrogen) and 1% BSA (Sigma) in PBS. Sections were stained overnight with anti-F4/80-biotin (clone BM8, Biolegend), anti-CD4-PE (clone RM4-5, eBioscience), anti-CD8β-Alexa Fluor 647 (clone YTS156.7.7, Biolegend), and anti-B220-FITC (clone RA3-6B2, BD Pharmingen). Sections were then washed and stained with streptavidin-Alexa Fluor 750 and rabbit anti-FITC-Alexa Fluor 488 (Invitrogen). Images were recorded using a Leica TCS SP5 confocal microscope, processed using Leica Microsystems software, stitched together using Adobe Illustrator, and adjusted using ImageJ.

T Cell Depletions

Figure 4:
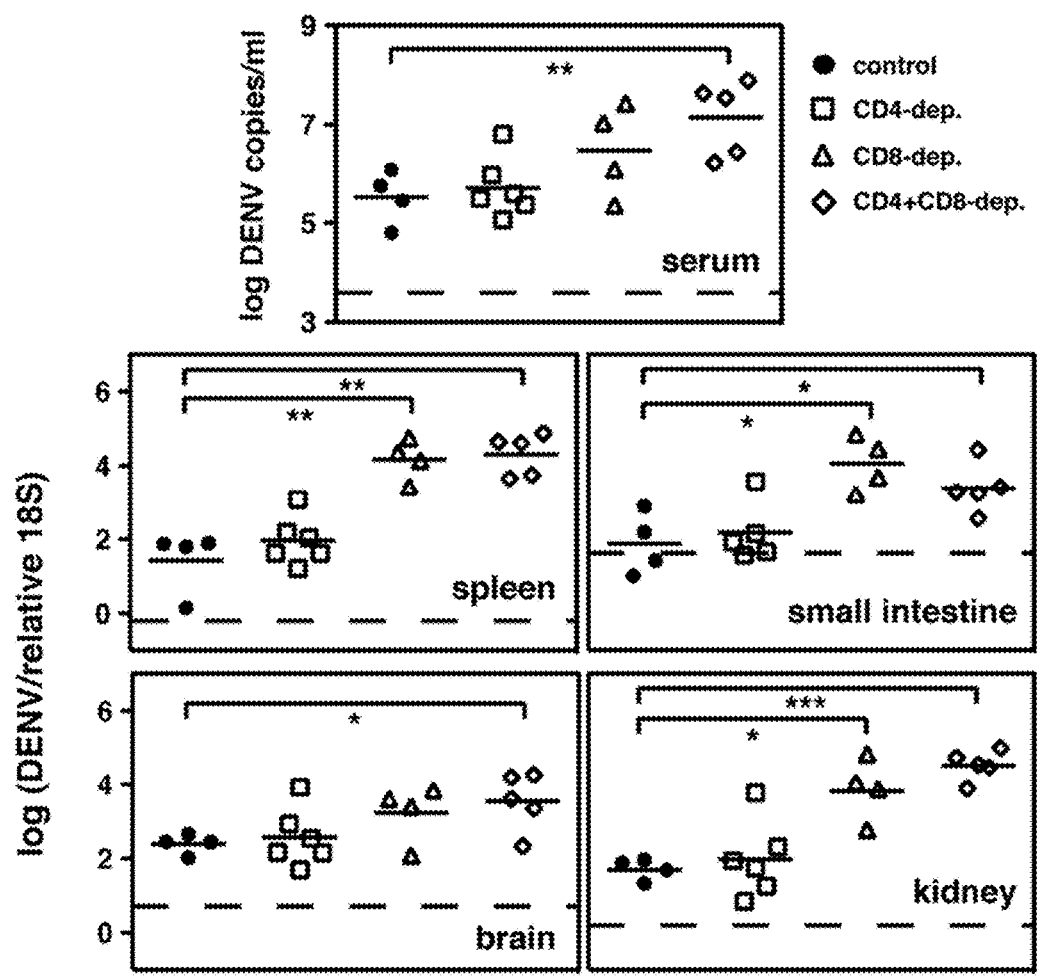
FIG. 4 shows that depletion of CD4+ T cells prior to DENV2 infection does not affect viral RNA levels. IFN-α/βR−/− mice were depleted of CD4+ or CD8+ cells, or both, by administration of GK1.5 or 2.43 Ab, respectively, (or given an isotype control Ab) 2 days before and 1 day after infection with $10^{10}$ GE of DENV2. Mice were sacrificed 5 days later, and DENV2 RNA levels in the serum, spleen, small intestine, brain, and kidney were quantified by real-time RT-PCR. Data are expressed as DENV2 copies per ml of sera, or DENV2 units normalized to 18S rRNA levels for the organs. Each symbol represents one mouse, the bar represents the geometric mean, and the dashed line is the limit of detection. * p<0.05,  p<0.01, and * p<0.001 for viral RNA levels comparing T cell-depleted mice with control mice.

Hybridoma supernatants were clarified by centrifugation, dialyzed against PBS, sterile-filtered, and quantified by BCA Protein Assay Reagent (Thermo Scientific). IFN-α/βR$^{-/-}$ mice were injected i.p. with 250 μg of SFR3, or GK1.5, or 2.43 in PBS (250 μl total volume) 3 days and 1 day before or 1 day before and 1 day after infection, which resulted in depletion of 90% of $CD8^+$ cells and ≥97% of $CD4^+$ cells. In FIG. 4, one CD4-depleted mouse received GK1.5 only on day 1, which still resulted in ≥97% depletion.

DENV2-Specific Antibody ELISA

Serum was harvested from control and CD4-depleted IFN-α/βR$^{-/-}$ mice 7 days after infection with $10^{10}$ GE of DENV2, or naïve mice. EIA/RIA 96-well plates (Costar) were coated with DENV2 ($10^9$ GE per well) in 50 μl 0.1M $NaHCO_3$. The virus was UV-inactivated and plates left overnight at 4° C. The plates were then washed to remove unbound virus using 0.05% (v/v) Tween 20 (Sigma) in PBS. After blocking with Blocker Casein Blocking Buffer (Thermo Scientific) for 1 h at room temperature, 1:3 serial dilutions of serum in a total volume of 100 μl were added to the wells. After 1.5 h, wells were washed and bound antibody was detected using HRP-conjugated goat anti-mouse IgG Fc portion or HRP-conjugated donkey anti-mouse IgMμ chain (Jackson Immunoresearch) and TMB (eBioscience).

Antibody-Virus Neutralization Assay

Serum was heat-inactivated at 56° C. for 30 min. Three-fold serial dilutions of serum were then incubated with $5\times10^8$ GE of DENV2 for 1 h at room temperature in a total volume of 100 μl PBS. Next, approximately $6\times10^5$ C6/36 cells per well of a 24-well plate were infected with 100 μl of the virus-antibody mix for one hour at 28° C. Cells were washed twice with 500 μl of PBS, and then incubated at 28° C. in 500 μl L-15 Medium containing 5% FBS, penicillin, and streptomycin for 24 h. For each antibody dilution, the percentage of infected cells was determined by flow cytometry as previously described (Lambeth et al., J Clin Microbiol 43:3267 (2005)) using 2H2-biotin (IgG2a anti-prM/M, DENV1-4 reactive) and streptavidin-APC (Biolegend). The percentage of infected cells was normalized to 100% (infection without serum).

CD8 In Vivo Cytotoxicity Assay

IFN-α/βR$^{-/-}$ mice (recipients) were infected with $10^{10}$ GE of DENV2. Some mice were depleted of $CD4^+$ T cells before infection. Splenocytes (targets) were harvested from donor B6.SJL congenic mice (CD45.1) 7 days later. RBC were lysed, and the target cells were pulsed with varying concentrations of a pool of 4 $H-2^b$-restricted DENV2 peptides ($M_{60-67}$, $NS2A_{8-15}$, $NS4B_{99-107}$, $NS5_{237}$-245) or DMSO for 1 h at 37° C. The cells were then washed and labeled with CFSE (Invitrogen) in PBS/0.1% BSA for 10 min at 37° C. Cells were labeled with 1 μM CFSE (CFSE$^{high}$) or 100 nM CFSE (CFSE$^{low}$) or left unlabeled. After washing, the cell populations were mixed and 5×10$^6$ cells from each population were injected i.v. into naïve or infected recipient mice. After 4 h, the mice were sacrificed and splenocytes stained with anti-CD45.1-APC (eBioscience) and analyzed by flow cytometry, gating on CD45.1$^+$ cells. The percentage killing was calculated as follows: 100−((percentage DENV peptide-pulsed in infected mice/percentage DMSO-pulsed in infected mice)/(percentage DENV peptide-pulsed in naïve mice/percentage DMSO-pulsed in naïve mice)×100).

CD4 In Vivo Cytotoxicity Assay

IFN-α/βR$^{-/-}$ mice (recipients) were infected with 10$^{10}$ GE of DENV2. Some mice were depleted of CD4$^+$ or CD8$^+$ cells before infection. Splenocytes (targets) were harvested from donor B6.SJL congenic mice (CD45.1) 7 days later. RBC were lysed and the target cells were pulsed with 1.7 μg (approximately 1 μM) each of NS2B$_{108-122}$, NS3$_{198-212}$, and NS3$_{237-251}$ (or DMSO) for 1 h at 37° C. The cells were then washed and labeled with CFSE in PBS/0.1% BSA for 10 min at 37° C. DENV2 peptide-pulsed cells were labeled with 1 μM CFSE (CFSE$^{high}$) and DMSO-pulsed cells with 100 nM CFSE (CFSE$^{low}$). After washing, the two cell populations were mixed and 5×10$^6$ cells from each population were injected i.v. into naïve or infected recipient mice. After 16 h, the mice were sacrificed and splenocytes stained and the percentage killing calculated as described for the CD8 in vivo cytotoxicity assay.

Quantitation of DENV Burden in Mice

Mice were euthanized by isoflurane inhalation and blood was collected via cardiac puncture. Serum was separated from whole blood by centrifugation in serum separator tubes (Starsted) Small intestines were put into PBS, flushed, filleted, chopped into small pieces, and put into RNAlater (Qiagen). Other organs were immediately placed into RNAlater and all organs were subsequently homogenized for 3 min in 1 ml tissue lysis buffer (Qiagen Buffer RLT) using a Mini-Beadbeater-8 (BioSpec Products) or QiagenTissueLyser Immediately after homogenization, all tissues were centrifuged (5 min, 4° C., 16,000×g) to pellet debris, and RNA was isolated using the RNeasy Mini Kit (Qiagen). Serum RNA was isolated using the QIAamp Viral RNA Mini Kit (Qiagen). After elution, viral RNA was stored at −80° C. Quantitative RT-PCR was performed according to a published protocol (Houng et al., *J Virol Methods* 86:1-11 (2000)), except a MyiQ Single-Color Real-Time PCR Detection System (Bio-Rad) with One-Step qRT-PCR Kit (Quanta BioSciences) were used. The DENV2 standard curve was generated with serial dilutions of a known concentration of DENV2 genomic RNA which was in vitro transcribed (MAXlscriptKit, Ambion) from a plasmid containing the cDNA template of S221 3'UTR. After transcription, DNA was digested with DNase I, and RNA was purified using the RNeasy Mini Kit and quantified by spectrophotometry. To control for RNA quality and quantity when measuring DENV in tissues, the level of 18S rRNA was measured using 18S primers described previously (Lacher, et al., *Cancer Res* 66:1648 (2006)) in parallel real-time RT-PCR reactions. A relative 18S standard curve was made from total splenic RNA.

Peptide Immunizations

IFN-α/βR$^{-/-}$ mice were immunized s.c. with 50 μg each of NS2B$_{108-122}$, NS3$_{198-212}$, and NS3$_{237-251}$ emulsified in CFA (Difco). After 11 days, mice were boosted with 50 μg peptide emulsified in IFA (Difco). Mock-immunized mice received PBS/DMSO emulsified in CFA or IFA. Mice were infected 13 days after the boost with 10$^{11}$ GE of DENV2 (some mice were depleted of CD4$^+$ or CD8$^+$ T cells 3 days and 1 day before infection). Four days later, the mice were sacrificed and tissues harvested, RNA isolated, and DENV2 RNA levels measured as described above. For Example 7, mice were immunized instead with 50 μg each of C$_{51-59}$, NS2A$_{8-15}$, NS4B$_{99-107}$, and NS5$_{237-245}$ as described in Yauch et al., *J Immunol* 182:4865 (2009).

MHC Peptide-Binding and Restriction Assays

MHC purification and quantitative assays to measure the binding affinity of peptides to purified A*0201, A*0101, A*1101, B*0702 and DRB1*0101 molecules were performed as described elsewhere (Sidney et al., *Immunome Res* 4:2 (2008); Sidney et al., *Curr Protoc Immunol Chapter* 18:Unit 18 13 (2001)). Briefly, after a 2-day incubation, binding of the radiolabeled peptide to the corresponding MHC molecule was determined by capturing MHC/peptide complexes on Greiner Lumitrac 600 microplates (Greiner Bio-One, Monroe, N.C.) coated with either the W6/32 (HLA class I specific) or L243 (HLA DR specific) monoclonal antibodies. Bound cpm were then measured using the Topcountmicroscintillation counter (Packard Instrument, Meriden, Conn.). The concentration of peptide yielding 50% inhibition of the binding of the radiolabeled probe peptide (IC$_{50}$) was then calculated.

The tumor cell line 721.221 (Shimizu et al., *J Immunol* 142:3320 (1989), which lacks expression of HLA-A, -B and C class I genes, was transfected with the HLA-A*0201/Kb or HLA*1101 chimeric genes, and was used as APC in the restriction assays. The non-transfected cell line was used as a negative control.

Human Blood Samples 250 peripheral blood samples were obtained from healthy adult blood donors from the National Blood Center, Ministry of Health, Colombo, Sri Lanka in an anonymous fashion. The institutional review boards of both the La Jolla Institute for and Genetech approved all protocols described in this study and donors gave written informed consent. Donors were of both sexes and between 18 and 60 years of age. Samples have been collected over a time course of 19 month between February 2010 and August 2011. PBMC were purified by density gradient centrifugation (Ficoll-Paque Premium, GE Healthcare Biosciences, Kowloon, Hong Kong) re-suspended in fetal bovine serum (Gemini Bio-products, Sacramento, Calif.) containing 10% dimethyl sulfoxide, and cryo-preserved in liquid nitrogen. 23 of the 250 blood samples obtained from the National Blood Center had to be excluded from the study due to poor viability of cells after shipment to LIAI as determined by trypan blue exclusion. For the remaining 227 samples DENV seropositivity was determined by dengue IgG ELISA as previously described (26). Flow cytometry-based neutralization assays were performed for further characterization of seropositve donors, as previously described (46).

Genomic DNA isolated from PBMC of the study subjects by standard techniques (QIAmp Qiagen, Valencia, Calif.) was used for HLA typing. High resolution Luminex-based typing for HLA Class I was utilized according to the manufacturer's protocol (Sequence-Specific Oligonucleotides (SSO) typing; One Lambda, Canoga Park, Calif.). Where needed, PCR based methods were used to provide high resolution sub-typing. (Sequence-Specific Primer (SSP) typing; One Lambda, Canoga Park, Calif.).

IFNγ ELISPOT Assay

For all murine studies, splenic CD4$^+$ or CD8$^+$ T cells were isolated by magnetic bead positive selection (MiltenyiBiotec, BergischGladbach, Germany) 7 days after infection. 2×10$^5$ T cells were stimulated with 1×10$^5$ uninfected splenocytes as APCs and 10 µg/ml of individual DENV peptides in 96-well flat-bottom plates (Immobilon-P; Millipore, Bedford, Mass.) coated with anti-IFNγ mAb (clone AN18; Mabtech, Stockholm, Sweden). Each peptide was evaluated in triplicate. Following a 20-h incubation at 37° C., the wells were washed with PBS/0.05% Tween 20 and then incubated with biotinylated IFNγ mAb (clone R4-6A2; Mabtech) for 2 h. The spots were developed using Vectastain ABC peroxidase (Vector Laboratories, Burlingame, Calif.) and 3-amino-9-ethylcarbazole (Sigma-Aldrich, St. Louis, Mo.) and counted by computer-assisted image analysis (KS-ELISPOT reader, Zeiss, Munich, Germany). Responses against peptides were considered positive if the net spot-forming cells (SFC) per $10^6$ were ≥20, a stimulation index of ≥2, and p<0.05 in a t test comparing replicates with those from the negative control.

To evaluate the antigenicity of the epitopes in humans, $2 \times 10^6$ PBMC/ml were stimulated in the presence of 1 µg/ml individual peptide for 7 days. Cells were cultured at 37° C., 5% $CO_2$, and recombinant IL2 (10 U/mL, eBiosciences, San Diego, Calif.) was added 3 days after antigenic stimulation. After one week, PBMC were harvested and tested at a concentration of $1 \times 10^5$/well in an IFNγ ELISPOT assay, as described above. The mAb 1-D1K and mAb 7-B6-1 (Mabtech) were used as coating and biotinylated secondary Ab, respectively. To be considered positive, IFNγ responses needed to exceed the threshold set as the mean responses of HLA non-matched and DENV seronegative donors plus 3 times the standard deviation.

Ex Vivo IFNγ ELISPOT Assay 96-well multiScreen plates (Immobilon-P; Millipore, Bedford, Mass.) were coated with anti-IFNγ mab (clone 1-DIK; [5 µg/ml]: Mabtech, Stockholm, Sweden) at 4° C. overnight. $2 \times 10^5$ PBMC were then incubated in triplicates with 0.1 ml complete RPMI 1640 in the presence of HLA-matched peptide pools [2 µg/ml]. Following a 20 h incubation at 37° C., the cells were washed with PBS/0.05% Tween 20 and then incubated with biotinylated IFNγ mAb (mAb 7-B6-1 Mabtech, Stockholm, Sweden) for 2 h. The spots were developed using Vectastain ABC peroxidase (Vector Laboratories, Burlingame, Calif.) and 3-amino-9-ethylcarbazole (Sigma-Aldrich, St. Louis, Mo.) and counted by computer-assisted image analysis (KS-ELISPOT reader, Zeiss, Munich, Germany). Responses were expressed as the number of IFNγ secreting cells per $10^6$ PBMC and were considered positive if the net spot-forming cells (SFC) per $10^6$ were ≥20, had a stimulation index of ≥2, and a p<0.05 in a t test comparing replicates with those from the negative control. Positive pools were subsequently deconvoluted and a peptide was considered positive according to the criteria described above.

Flow Cytometry and Intracellular Cytokine Staining (ICS)

The following monoclonal antibodies from eBioscience (eBioscience, San Diego, Calif.) were used in this study: anti-CD8a PerCP-Cy5.5 (clone RPA-T8), anti-CD3 efluor 450 (clone UCHT1), anti-CD107a FITC (clone ebioH4A3), anti-CD45RA PE-CY7 (clone H100), anti-CD27 PE (clone 0323), anti-CD197 (CCR7) APC efluor 780 (clone 3D12), anti-IFNγ APC (clone 4SB3), anti-IL 2 PE (clone MQ1-17H12), anti-TNFα (clone MAD 110).

PBMC were cultured in the presence of peptide pools [10 µg/ml] and GolgiPlug containing brefeldin A [1 µg/ml] (BD Biosciences, San Diego, Calif.) in 0.2 ml complete RPMI medium for 6 h. To determine the avidity of DENV specific T cells, PBMC were incubated with descending concentrations of peptide pools (10, 1, 0.1, 0.01, 0.001, and 0.0001 µg/ml] and the half maximal effective concentration ($EC_{50}$) was calculated. Cells stimulated with PMA/Ionomycin (Sigma Aldrich, St. Louis, Mo.) or media alone were used as positive and negative control respectively. After incubation, cells were washed and stained with directly conjugated anti-CD3 mAb, anti-CD8 mAb, anti-CD27 mAb, anti-CD45RA mAb and anti-CCR7 mAb for 30 minutes on ice, fixed with 1% of paraformaldehyde (Sigma-Aldrich, St. Louis, Mo.) and were kept at 4° C. over night. Cells were washed, incubated in Cytofix/cytoperm solution (BD Biosciences) for 20 minutes on ice, washed with Perm/Wash (BD Biosciences) and then stained for IL 2, IFNγ, TNFα and CD107a with directly conjugated Abs for 30 minutes on ice. Samples were acquired on a LSR II flow cytometer (BD Immunocytometry Systems), and analyzed with FlowJo software (Tree Star, San Carlos, Calif.).

Statistical Analyses

Data were analyzed with Prism software version 5.0 (GraphPad Software, Inc.). Statistical significance was determined using the unpaired t-test with Welch's correction.

Example 2

This example includes data demonstrating $CD4^+$ T cell activation and expansion following DENV2 infection.

DENV2 ($10^{10}$ GE of S221) infection of IFN-α/βR$^{-/-}$ mice results in an acute infection, with viral replication peaking between 2 and 4 days after infection (Yauch, et al. *J Immunol* 182:4865 (2009)). At this time the mice show signs of disease including hunched posture and ruffled fur, and the virus is subsequently cleared from the serum by day 6. To determine the role of $CD4^+$ T cells during the course of this primary DENV2 infection, the expansion of $CD4^+$ T cells in the spleens of IFN-α/βR$^{-/-}$ mice 7 days after infection with DENV2 was examined, and a 2-fold increase in $CD4^+$ T cell numbers was observed (FIG. 1A). The cells were activated, as measured by CD44 upregulation and CD62L downregulation on splenic $CD4^+$ T cells (FIG. 1B) and on circulating blood $CD4^+$ T cells, with the peak on day 7 after infection (FIG. 1C). To study the $CD4^+$ T cell response in the spleen in more detail, immunohistochemistry on spleen sections obtained from naïve mice and mice 3, 5, and 7 days after DENV2 infection was performed. Sections were stained for CD4, CD8, B220 to highlight B cell follicles, and F4/80 to show red pulp macrophages. As expected, in naïve mice, $CD4^+$ and $CD8^+$ T cells were dispersed throughout the spleen, but preferentially in T cell areas, also known as the periarteriolar lymphoid sheath (PALS). By day 3 after DENV2 infection, most of the $CD4^+$ and $CD8^+$ T cells had migrated to the PALS, with very few T cells observed in the red pulp. At day 5, the $CD4^+$ cells were still concentrated in the PALS, at the border between the T cell area and B cell follicles, and also in the B cell follicles. At day 7 after infection, the spleen had increased in size dramatically, and $CD4^+$ T cells were found primarily in the PALS and B cell follicles. The localization of $CD8^+$ T cells differed from the $CD4^+$ T cells mainly in that at day 5 after infection, many of the $CD8^+$ T cells had left the T cell area and were found distributed throughout the red pulp and marginal zone (MZ). By day 7, the $CD8^+$ T cells were observed in the PALS, MZ, and also the red pulp. These images illustrate the kinetics of the adaptive immune response to DENV2 in the spleen, and show $CD4^+$ T cells in close proximity to both $CD8^+$ T cells and B cells after DENV2 infection.

Regulatory T cells (Tregs) are a subset of $CD4^+$ T cells that are characterized by the expression of the transcription factor, Foxp3 (Josefowicz, et al. *Immunity* 30:616 (2009)), and have been found to facilitate the early host response to HSV-2 (Lund, et al. *Science* 320:1220 (2008)) and help control WNV infection (Lanteri, et al. *J Clin Invest* 119:3266 (2009)). To determine if DENV2 infection resulted in an expansion of Tregs, the number of CD4⁺Foxp3⁺ cells in the spleen 7 days after infection was determined. There was a decrease in the percentage of Tregs among total CD4⁺ cells, and no change in the number of Tregs, demonstrating that DENV2 infection does not lead to an expansion of Tregs in the spleen (FIG. 1D).

Example 3

This example includes data for the identification of DENV2 CD4⁺ T cell epitopes and phenotype of DENV2-specific CD4⁺ T cells.

Figure 2B:
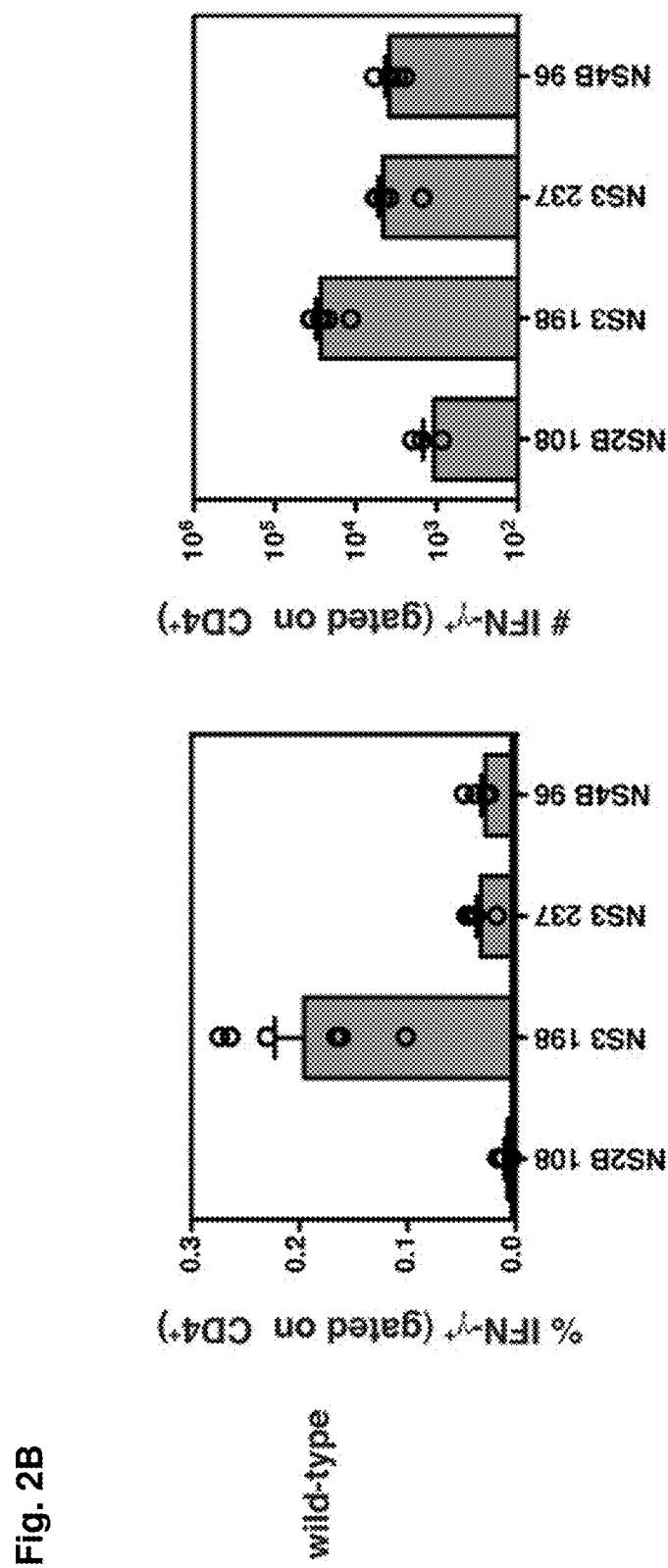

In order to study the DENV2-specific CD4⁺ T cell response, the identity of MHC class II (I-A$^b$)-restricted CD4⁺ T cell epitopes using a bioinformatics prediction method previously reported to map the CD4⁺ T cell response to mouse cytomegalovirus (Arens, et al. *J Immunol* 180: 6472 (2008)) was employed. Briefly, the proteome of DENV2 was screened and 73 15-mer peptides predicted to bind I-A$^b$ were identified. The peptides were tested by IFN-γ ICS using splenocytes from DENV2-infected IFN-α/βR$^{-/-}$ mice. Positive peptides (2× background) were then re-ordered as HPLC-purified (>90%) and re-tested. Four positive peptides were identified: $NS2B_{108-122}$, $NS3_{198-212}$, $NS3_{237-251}$, and $NS4B_{96-110}$ (FIG. 2A and Table 1). Similar to the DENV2-specific CD8⁺ T cell response (Yauch, et al. *J Immunol* 182:4865 (2009)), the epitopes identified in IFN-α/βR$^{-/-}$ mice were also recognized by CD4⁺ T cells from DENV2-infected wild-type mice (FIG. 2B), and the magnitude of the CD4⁺ T cell response was higher in IFN-α/βR$^{-/-}$ mice compared with wild-type mice, likely due to increased viral replication. Notably, $NS3_{200-214}$ has been identified as a human HLA-DR15-restricted CD4⁺ T cell epitope (Simmons, et al. *J Virol* 79:5665 (2005); Zeng, et al. *J Virol* 70:3108 (1996)). It was also of interest that $NS4B_{96-110}$ contains a CD8⁺ T cell epitope ($NS4B_{99-107}$) that was identified as the immunodominant epitope in both wild-type and IFN-α/βR$^{-/-}$ C57BL/6 mice infected with DENV2 (Yauch, et al. *J Immunol* 182:4865 (2009)).

Figure 3:
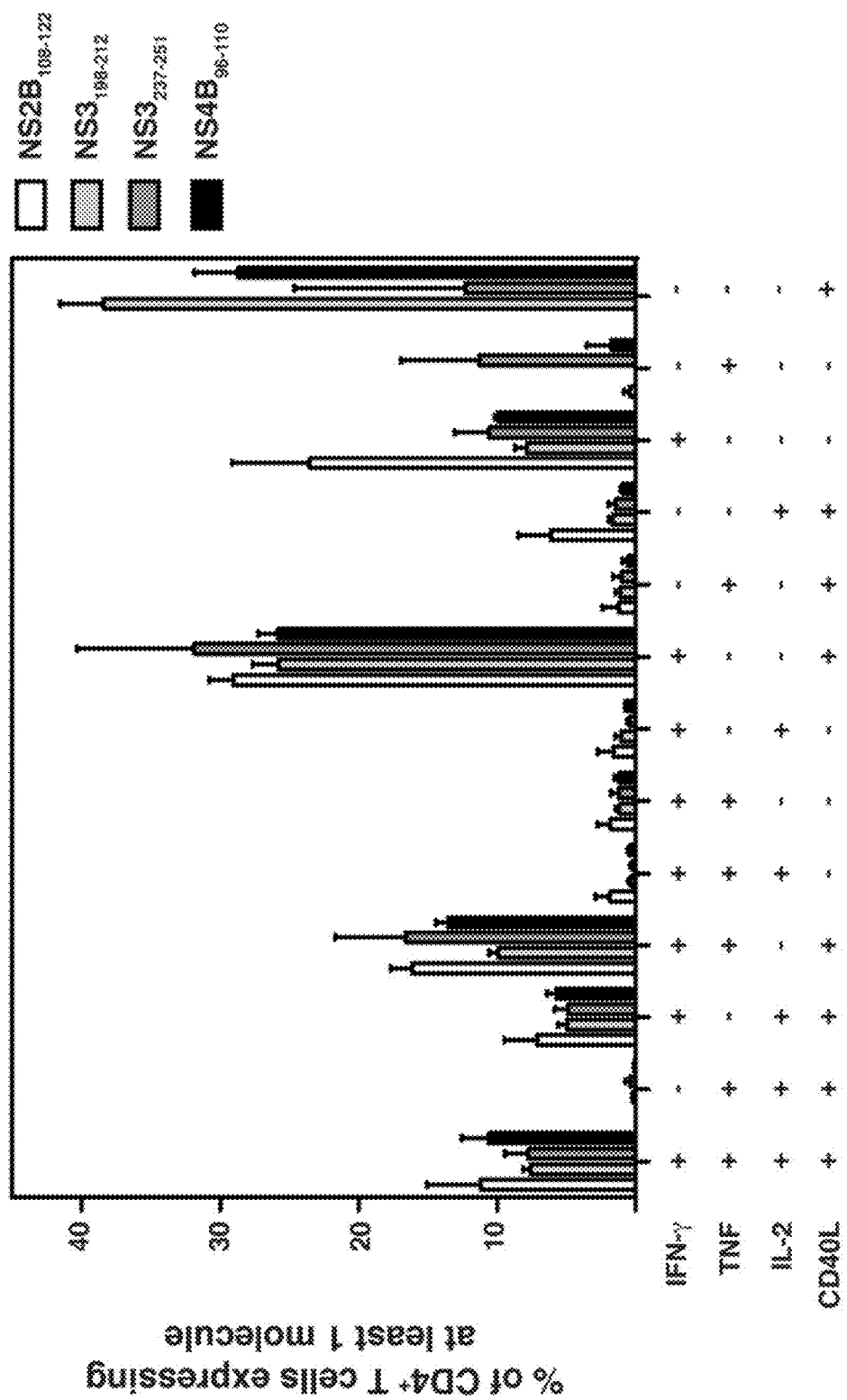
FIG. 3 shows that DENV2-specific CD4+ T cells are polyfunctional. Splenocytes were obtained from IFN-α/βR−/− mice 7 days after infection with $10^{10}$ GE of DENV2 and stimulated in vitro with individual peptides. Cells were then stained for surface CD4, and intracellular IFN-γ, TNF, IL-2, and CD40L, and analyzed by flow cytometry. The response of unstimulated cells was subtracted from the response to each DENV2 peptide, and the net percentages of the CD4+ T cells that are expressing at least one molecule are indicated. The mean and SEM of 3 mice is shown.

Multicolor flow cytometry was performed to study the phenotype of DENV2-specific CD4⁺ T cells. These cells produced IFN-γ, TNF, and IL-2 (FIG. 3). No intracellular IL-4, IL-5, IL-17, or IL-10 were detected. The DENV2-specific CD4⁺ T cells also expressed CD40L, suggesting they are capable of activating CD40-expressing cells, which include DCs and B cells. The four DENV2-derived CD4⁺ T cell epitopes induced responses that differed in magnitude, but were similar in terms of phenotype. The most polyfunctional cells (those expressing IFN-γ, TNF, IL-2, and CD40L) also expressed the highest levels of the cytokines and CD40L. These results demonstrate that DENV2 infection elicits a virus-specific Th1 CD4⁺ T cell response in IFN-α/βR$^{-/-}$ mice.

TABLE 1

DENV2-derived CD4⁺ T cell epitopes

| Epitope | Sequence |
|---|---|
| $NS2B_{108-122}$ | GLFPVSLPITAAAWY (SEQ ID NO: 220) |
| $NS3_{198-212}$ | GKTKRYLPAIVREAI (SEQ ID NO: 221) |
| $NS3_{237-251}$ | GLPIRYQTPAIRAEH (SEQ ID NO: 222) |
| $NS4B_{96-110}$ | IGCYSQVNPITLTAA (SEQ ID NO: 223) |

Example 4

This example includes a description of studies of the effects of CD4⁺ and/or CD8⁺ T cell depletions on DENV2 viral RNA levels, and data showing that CD4⁺ T cells are not required for the anti-DENV2 antibody response, and are also not necessary for the primary DENV2-specific CD8⁺ T cell response.

To determine how CD4⁺ T cells contribute to controlling DENV2 infection, CD4⁺ T cells, CD8⁺ T cells, or both were depleted from IFN-α/βR$^{-/-}$ mice and DENV2 RNA levels 5 days after infection with 10¹⁰ GE of DENV2 was measured. No difference in viral RNA levels between control undepleted mice and CD4-depleted mice in the serum, kidney, small intestine, spleen, or brain was observed (FIG. 4). CD8-depleted mice had significantly higher viral loads than control mice. Depletion of both CD4⁺ and CD8⁺ T cells resulted in viral RNA levels that were significantly higher than those in control mice in all tissues examined, and equivalent to the viral RNA levels in CD8-depleted mice. These data show that CD4⁺ T cells are not required to control primary DENV2 infection in IFN-α/βR$^{-/-}$ mice, and confirm an important role for CD8⁺ T cells in viral clearance.

Figure 5A:
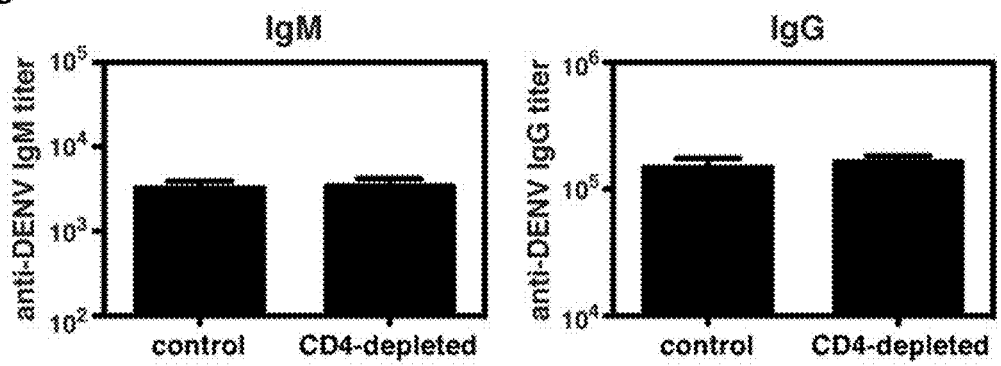
FIGS. 5A-5C show that CD4+ T cells are not required for the anti-DENV2 antibody response. IFN-α/βR−/− mice (control or CD4-depleted) were infected with $10^{10}$ GE of DENV2. Fig. A) IgM and IgG titers in the sera at day 7 were measured by ELISA (n=5 control and 6 CD4-depleted mice). Data are combined from two independent experiments. Fig. B) Neutralizing activity of sera from naïve (n=4) and control (n=6) or CD4-depleted mice (n=6) obtained 7 days after infection was determined by measuring the ability of the sera to reduce DENV2 infection of C6/36 cells. Fig. C) The percentage of germinal center B cells (GL7+Fas+, gated on B220+ cells) in the spleen 7 days after infection is shown. The plots are representative of 5 control and 5 CD4-depleted mice.
Figure 5B:
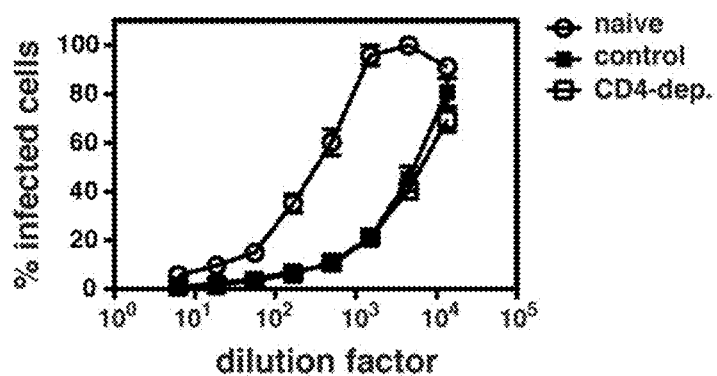
Figure 5C:
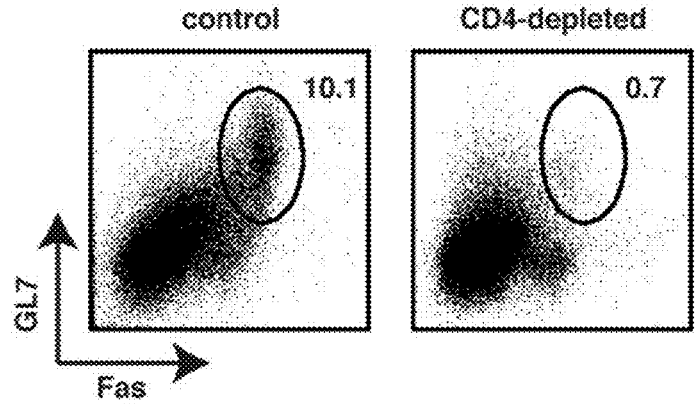

Although CD4⁺ T cells were not required for controlling DENV2 infection, the contribution to the anti-DENV immune response, for example by helping the B cell and/or CD8⁺ T cell responses, was investigated. CSR, the process by which the immunoglobulin heavy chain constant region is switched so the B cell expresses a new isotype of Ab, can be induced when CD40L-expressing CD4⁺ T cells engage CD40 on B cells (Stavnezer, et al. *Annu Rev Immunol* 26:261 (2008)). However, CSR can also occur in the absence of CD4⁺ T cell help. To determine whether the anti-DENV2 antibody response depends on CD4⁺ T cells, DENV2-specific IgM and IgG titers in the sera of control and CD4-depleted mice was measured 7 days after infection with 10¹⁰ GE of DENV2. As expected, there was no difference in IgM titers at day 7 between control and CD4-depleted mice (FIG. 5A). There was also no difference in IgG titers between control and CD4-depleted mice. To measure the functionality of these DENV2-specific antibody, a flow cytometry-based neutralization assay was performed, in which C6/36 mosquito cells were infected with DENV2 in the presence of heat-inactivated sera obtained from control and CD4-depleted mice 7 days after infection. The sera from control and CD4-depleted mice could neutralize DENV2 equally well (FIG. 5B). As reported previously (Zellweger, et al. *Cell Host Microbe* 7:128 (2010)), naïve serum was able to prevent DENV infection of C6/36 cells, although not as efficiently as DENV-immune serum. The presence of germinal center (GC) B cells, as the GC reaction is generally thought to be CD4⁺ T cell-dependent (Allen, et al. *Immunity* 27:190 (2007)), was also evaluated. As expected, GC B cells were absent in the CD4-depleted mice (FIG. 5C). Based on the lack of GC B cells in the DENV2-infected CD4-depleted mice, the early anti-DENV2 antibody response is CD4- and GC-independent.

Next, the role of CD4+ T cells in helping the CD8+ T cell response was assessed by examining the DENV2-specific CD8+ T cell response in control and CD4-depleted DENV2-infected mice. The numbers of splenic CD8+ T cells were equivalent in control and CD4-depleted mice. IFN-γ ICS was performed using DENV2-derived H-2$^b$-restricted immunodominant peptides identified ($M_{60-67}$, $NS2A_{8-15}$, and $NS4B_{99-107}$) (Yauch, et al. *J Immunol* 182:4865 (2009)). Somewhat surprisingly, there was an increase in the number of DENV2-specific IFN-γ+CD8+ T cells in CD4-depleted mice compared with control mice (FIG. 6A). To further characterize the phenotype of the CD8+ T cells generated in the absence of CD4+ T cells, expression of TNF, IL-2, and CD107a (a marker for degranulation) in cells stimulated with $NS4B_{99-107}$ was examined (FIG. 6B). As also shown in FIG. 6A, the magnitude of the CD8+ T cell response was larger in the CD4-depleted mice, but the cytokine and CD107a expression profiles were comparable. Similar results were observed when cells were stimulated with $M_{60-67}$ or $NS2A_{8-15}$. Next, the functionality of the DENV2-specific CD8+ T cells using an in vivo cytotoxicity assay, in which splenocytes were pulsed with a pool of 4 H-2$^b$-restricted immunodominant peptides and CFSE-labeled before injection into control or CD4-depleted DENV2-infected mice, was examined. CD8+ T cell-mediated-cytotoxicity was very efficient; almost 100% killing was observed at peptide concentrations of 500 ng/ml (FIG. 6C). Therefore, the peptide concentrations were titrated down, and no difference in killing was observed between control and CD4-depleted mice at any concentration tested. These data reveal that the primary anti-DENV2 CD8+ T cell response, in terms of expansion, cytokine production, degranulation, and cytotoxicity, does not depend on CD4+ T cell help.

Example 5

This example is a description of studies of in vivo killing of I-A$^b$-restricted peptide-pulsed target cells in DENV2-infected mice, and data showing that vaccination with DENV2 CD4+ T cell epitopes controls viral load.

Figure 7:
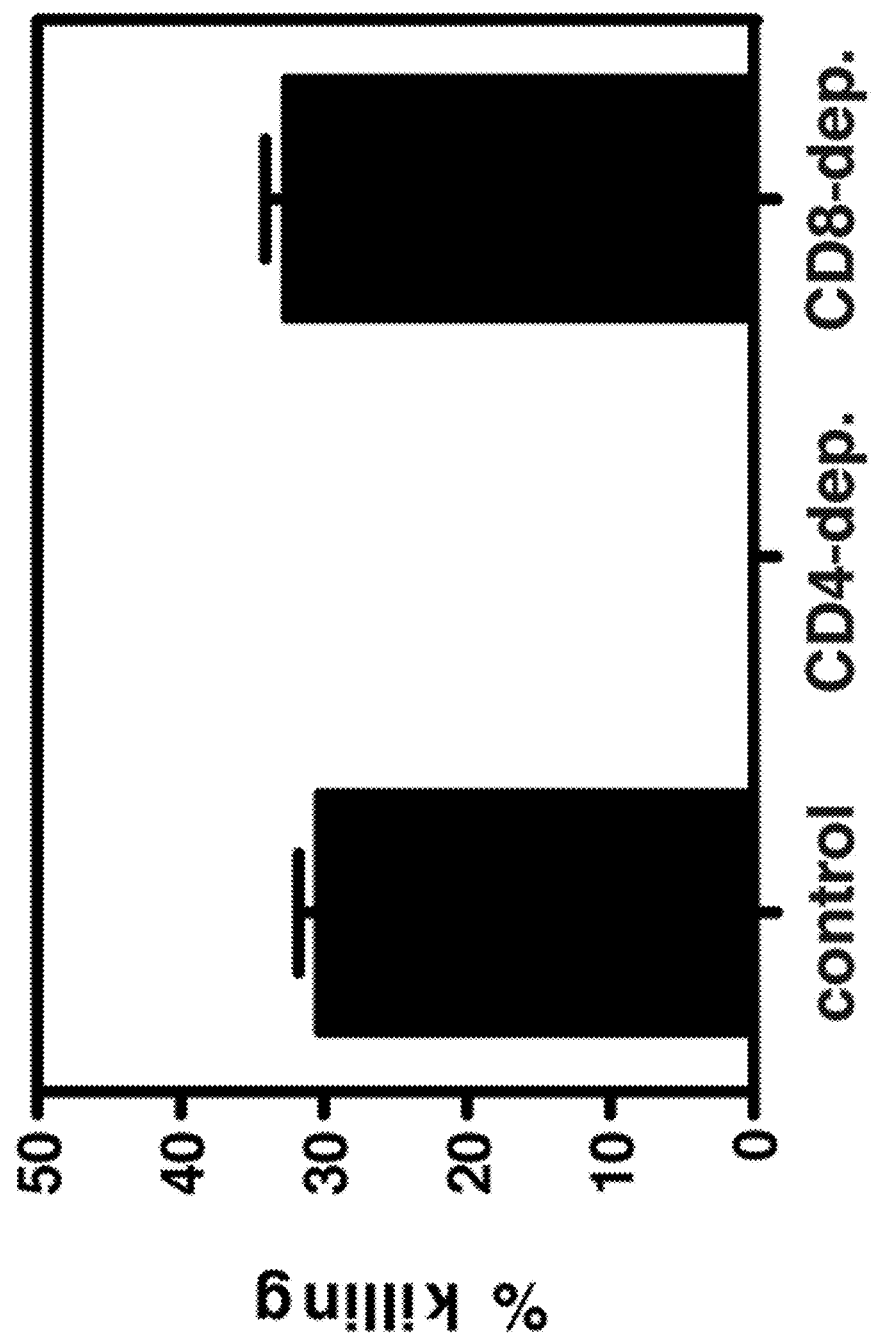
FIG. 7 shows cytotoxicity mediated by DENV2-specific CD4+ T cells. In vivo killing of DENV2-derived I-A$^b$-restricted peptide-pulsed cells. IFN-α/βR−/− mice (control, CD4-depleted, or CD8-depleted) infected 7 days previously with $10^{10}$ GE of DENV2 were injected i.v. with CFSE-labeled target cells pulsed with the three epitopes that contain only CD4+ T cell epitopes (NS2B$_{108-122}$, NS3$_{198-212}$, and NS3$_{237-51}$) (n=6 control, 3 CD4-depleted, and 3 CD8-depleted mice). After 16 h, splenocytes were harvested, analyzed by flow cytometry, and the percentage killing was calculated.

Although the absence of CD4+ T cells had no effect on viral RNA levels on day 5 after infection, it was possible that CD4+ T cells could still be contributing to the anti-DENV2 host response by killing infected cells. In vivo cytotoxicity assay was performed using splenocytes pulsed with the three peptides that contain only CD4+ T cell epitopes ($NS2B_{108-122}$, $NS3_{198-212}$, and $NS3_{237-251}$) and not $NS4B_{96-110}$ to measure only CD4+, not CD8+ T cell-mediated killing. Approximately 30% killing of target cells was observed (FIG. 7). No cytolytic activity was observed when CD4+ T cells were depleted, whereas depletion of CD8+ T cells had no effect on killing, demonstrating that the cytotoxicity was CD4+ T cell-mediated. Thus, DENV2-specific CD4+ T cells exhibit in vivo cytolytic activity, although this effector function does not appear to significantly contribute to controlling primary DENV2 infection.

Having found that DENV2-specific CD4+ T cells can kill target cells, immunization with CD4+ T cell epitopes was assessed for control of DENV2 infection. Mice were immunized with $NS2B_{108-122}$, $NS3_{198-212}$, and $NS3_{237-251}$ before DENV2 infection, and CD4+ T cell responses by ICS and viral RNA levels 4 days after infection measured. Peptide immunization resulted in enhanced CD4+ T cell cytokine responses, and significantly lower viral loads in the kidney and spleen (FIG. 8). The protective effect was mediated by CD4+ T cells, as CD4-depletion before infection abrogated the protective effect. Similarly, CD8-depletion resulted in no protection, demonstrating that protection after CD4+ T cell peptide immunization requires both CD4+ and CD8+ T cells. These data suggest that CD4+ T cells elicited by immunization protect by helping the CD8+ T cell response. Thus, although CD4+ T cells are not required for the primary CD8+ T cell or antibody response, and the absence of CD4+ T cells had no effect on viral RNA levels, vaccination with CD4+ T cell epitopes can reduce viral loads.

Example 6

This example includes a discussion of the data and a summary of the implications.

The data reveal that CD8+ T cells play an important protective role in the response to primary DENV2 infection, whereas CD4+ T cells do not. CD4+ T cells expanded, were activated, and were located near CD8+ T cells and B cells in the spleen after DENV2 infection, yet they did not seem to affect the induction of the DENV2-specific CD8+ T cell or antibody responses. In fact, CD4+ T cell depletion had no effect on viral clearance. However, the data demonstrate that vaccination with CD4+ T cell epitopes prior to DENV infection can provide significant protection, demonstrating that T cell peptide vaccination is a strategy for DENV immunization without the risk of ADE.

The DENV2-specific CD4+ T cells recognized epitopes from the NS2B, NS3, and NS4B proteins, and displayed a Th1 phenotype. CD4+ T cell epitopes have been identified in mice infected with other flaviviruses, including YFV, for which an I-A$^b$-restricted peptide from the E protein was identified (van der Most, et al. *Virology* 296:117 (2002)), and WNV, for which six epitopes from the E and NS3 proteins were identified (Brien, et al. *J Immunol* 181:8568 (2008)). DENV-derived epitopes recognized by human CD4+ T cells have been identified, primarily from NS proteins, including the highly conserved NS3 (Mathew, et al. *Immunol Rev* 225:300 (2008)). One study identified numerous epitopes from the $NS3_{200-324}$ region, and alignment of consensus sequences for DENV1-4 revealed that this region is more conserved (78%) than NS3 as a whole (68%) (Simmons, et al. *J Virol* 79:5665 (2005)), suggesting that the region contains good candidates for a DENV T cell epitope-based vaccine. Interestingly, one of the NS3-derived epitopes identified herein is also a human CD4+ T cell epitope, which may bind human HLAs promiscuously, making it a good vaccine candidate. Another finding was that one of the CD4+ T cell epitopes identified in this study contained the most immunodominant of the CD8+ T cell epitopes identified previously. Overlapping epitopes have also been found in LCMV (Homann, et al. *Virology* 363:113 (2007); Mothe, et al. *J Immunol* 179:1058-1067 (2007); Dow, et al. *J Virol* 82:11734 (2008)). The significance of overlapping epitopes is unknown, but is likely related to homology between MHC class I and MHC class II, and may be associated with proteasomal processing. Overlapping epitopes may turn out to be common once the complete CD4+ and CD8+ T cell responses to other pathogens are mapped.

CD4+ T cells are classically defined as helper cells, as they help B cell and CD8+ T cell responses. However, inflammatory stimuli can override the need for CD4+ T cell help, and therefore, the responses to many acute infections are CD4-independent (Bevan, *Nat Rev Immunol* 4:595 (2004)). DENV2 replicates to high levels in IFN-α/βR$^{-/-}$ mice, the mice appear hunched and ruffled at the time of peak viremia, and they have intestinal inflammation, suggesting that there is a significant inflammatory response to DENV2. Accordingly, CD4+ T cells did not play a critical role in the immune response to primary DENV2 infection. The contribution of CD4+ T cells has been examined during infections with other flaviviruses. The reports suggest that the contribution of CD4+ T cells to protection against flavivirus infection varies depending on the virus and experimental system (Brien, et al. *J Immunol* 181:8568 (2008); Murali-Krishna, et al. *J Gen Virol* 77 (Pt 4):705 (1996); Sitati, et al. *J Virol.* 80:12060 (2006)).

Antibody responses can be T cell-dependent or T cell-independent. In particular, the formation of GCs is thought to be CD4+ T cell-dependent, and is where high-affinity plasma cells and memory B cells are generated and where CSR can occur (Stavnezer, et al. *Annu Rev Immunol* 26:261 (2008); Allen, et al. *Immunity* 27:190 (2007); Fagarasan et al. *Science* 290:89 (2000)). T-independent antibody responses to viruses have been demonstrated for vesicular stomatitis virus (Freer, et al. *J Virol* 68:3650 (1994)), rotavirus (Franco, et al. *Virology* 238:169 (1997)), and polyomavirus (Szomolanyi-Tsuda, et al. *Virology* 280:160 (2001)). In addition, EBV (via LMP1) can induce CD40-independent CSR (He, et al. *J Immunol* 171:5215 (2003)), and mice deficient for CD40 or CD4+ T cells are able to mount an influenza-specific IgG response that is protective (Lee, et al. *J Immunol* 175:5827 (2005)).

The data herein demonstrate that the DENV2-specific IgG response at day 7 is CD4-independent. The lack of GC B cells in CD4-depleted mice shows that CD4-depletions have a functional effect, and indicate anti-DENV IgG is being produced by extrafollicular B cells. It is possible that the absence of CD4+ T cells would have an effect on DENV2-specific antibody titers and/or neutralizing activity at later time points, however, the goal of this study was to determine how CD4+ T cells contribute to clearance of primary DENV2 infection, and the early anti-DENV2 antibody response is CD4-independent.

Like pathogen-specific antibody responses, primary CD8+ T cell responses to many acute infections are also CD4-independent. CD4-independent CD8+ T cell responses have been demonstrated for *Listeria monocytogenes* (Sun, et al. *Science* 300:339 (2003); Shedlock, et al. *J Immunol* 170: 2053 (2003)), LCMV (Ahmed, et al. *J Virol* 62:2102 (1988)), and influenza (Belz, et al. *J Virol* 76:12388 (2002)). Recently a mechanism for how DCs can activate CD8+ T cells in the absence of CD4+ T cell help has been described (Johnson, et al. *Immunity* 30:218 (2009)). In accordance with the studies herein, the primary CD8+ T cell response to DENV2 did not depend on CD4+ T cells. In fact, an enhanced DENV2-specific CD8+ T cell response in CD4-deficient mice compared with control mice at day 7 was observed, which has also been reported for influenza-(Belz, et al. *J Virol* 76:12388 (2002)) and WNV— (Sitati, et al. *J Virol.* 80:12060 (2006)) specific CD8+ T cell responses. This could be due to the depletion of Tregs, or an increased availability of cytokines (e.g. IL-2) in mice lacking CD4+ T cells. This enhanced CD8+ T cell response may explain why CD4-depleted mice have no differences in viral titers despite the fact that DENV2-specific CD4+ T cells demonstrate in vivo cytotoxicity.

Although CD4+ T cells did not play an important role in helping antibody or CD8+ T cell responses, DENV2-specific CD4+ T cells could kill peptide-pulsed target cells in vivo. CD4+ T cells specific for other pathogens, including HIV (Norris, et al. *J Virol* 78:8844 (2004)) and influenza (Taylor, et al. *Immunol Lett* 46:67 (1995)) demonstrate in vitro cytotoxicity. In vivo cytotoxicity assays have been used to show CD4+ T cell-mediated killing following infection with LCMV (Jellison, et al. *J Immunol* 174:614 (2005)) and WNV (Brien, et al. *J Immunol* 181:8568 (2008)). DENV-specific cytolytic human CD4+ T cell clones (Gagnon, et al. *J Virol* 70:141 (1996); Kurane, et al. *J Exp Med* 170:763 (1989)) and a mouse (H-2$^d$) CD4+ T cell clone (Rothman, et al. *J Virol* 70:6540 (1996)) have been reported. Whether CD4+ T cells actually kill infected cells during DENV infection remains to be determined, but is possible, as MHC class II-expressing macrophages are targets of DENV infection (Zellweger, et al. *Cell Host Microbe* 7:128 (2010)). Based on the fact that CD4-depletion did not have a significant effect on viral clearance, it is unlikely that CD4+ T cell-mediated killing plays a major role in the anti-DENV2 response in this model.

A caveat to using the IFN-α/βR$^{-/-}$ mice is that type I IFNs are known to help T cell and B cell responses through their actions on DCs, and can act directly on T cells (Iwasaki, et al. *Nat Immunol* 5:987 (2004)). Type I IFNs were found to contribute to the expansion of CD4+ T cells following infection with LCMV, but not *Listeria monocytogenes* (Havenar-Daughton, et al. *J Immunol* 176:3315 (2006)). Type I IFNs can induce the development of Th1 IFN-γ responses in human CD4+ T cells, but cannot substitute for IL-12 in promoting Th1 responses in mouse CD4+ T cells (Rogge, et al. *J Immunol* 161:6567 (1998)). Following *Listeria* infection, IL-12 synergized with type I IFN to induce IFN-γ production by CD4+ T cells (Way, et al. *J Immunol* 178:4498 (2007)). Although DENV does not replicate to detectable levels in wild-type mice, examining the CD4+ T cell response in these mice revealed that the same epitopes were recognized as in the IFN-α/βR$^{-/-}$ mice, but the magnitude of the epitope-specific response was greater in the IFN-α/βR$^{-/-}$ mice. This suggests that the high levels of viral replication in the IFN-α/βR$^{-/-}$ mice are sufficient to drive a DENV2-specific CD4+ IFN-γ response. The results demonstrate a DENV2-specific CD4+ T cell response, including Th1-type cytokine production and cytotoxicity, in the absence of IFN-α/PR signaling; however, this response is not required for clearance of infection. It is possible that CD4+ T cells contribute to protection during DENV infection of hosts with intact IFN responses.

The results herein demonstrate that immunization with CD4+ T epitopes is also protective. These results have significant implications for DENV vaccine development, since designing a vaccine is challenging, as, ideally, a vaccine needs to protect against all four serotypes. DENV vaccine candidates in development, some of which are in phase II trials, focus on eliciting an antibody response. The challenge is to induce and maintain a robust neutralizing antibody response against all four serotypes, as it is becoming increasingly clear that non-neutralizing antibodies (or sub-neutralizing quantities of antibodies) can actually worsen dengue disease (Zellweger, et al. *Cell Host Microbe* 7:128 (2010); Balsitis, et al. *PLoS Pathog* 6:e1000790 (2010)). An alternative approach would be a peptide vaccine that induces cell-mediated immunity, including both CD4+ and CD8+ T cell responses, which, although not able to prevent infection, would reduce viral loads and disease severity, and would eliminate the risk of ADE. Such a vaccine should target highly conserved regions of the proteome, for example NS3, NS4B, and/or NS5, and ideally include epitopes conserved across all four serotypes. A vaccine containing only peptides from these particular NS proteins would also preclude the induction of any antibody against epitopes on the virion, which could enhance infection, or antibody against NS1, which could potentially contribute to pathogenesis (Lin, et al. *Viral Immunol* 19:127 (2006)). Peptide vaccination was given along with CFA, which is commonly used in mice to induce Th1 responses (Billiau, et al. *J Leukoc Biol* 70:849 (2001)), which was the type of response observed after natural DENV infection. CFA is not a vaccine adjuvant approved for human use, and thus, any peptide vaccine developed against DENV will be formulated with an adjuvant that is approved for human use.

Although the results herein indicate that CD4+ T cells do not make a significant contribution to controlling primary DENV2 infection, the characterization of the primary CD4+ T cell response and epitope identification allows the determination of the role of CD4+ T cells during secondary homologous and heterologous infections. CD4+ T cells are often dispensable for the primary CD8+ T cell response to infection, but have been shown to be required for the maintenance of memory CD8+ T cell responses after acute infection (Sun, et al. *Nat Immunol* 5:927 (2004)). Finally, the data herein support a DENV vaccine strategy that induces CD4+ T cell, in addition to CD8+ T cell, responses.

Example 7

This example includes a description of additional studies showing that vaccination with DENV CD8+ T cell epitopes controls viral load.

Since depleting CD8+ T cells resulted in increased viral loads and DENV-specific CD8+ T cells demonstrated in vivo cytotoxic activity, studies were performed to determine whether enhancing the anti-DENV CD8+ T cell response through peptide immunization would contribute to protection against a subsequent DENV challenge. Specifically, the effect of peptide vaccination on viremia was determined by immunizing IFN-α/βR$^{-/-}$ mice with DENV-2 derived H-2$^b$ peptides prior to infection with S221. Mice were immunized with four dominant DENV epitopes ($C_{51-59}$, $NS2A_{8-15}$, $NS4B_{99-107}$, and $NS5_{237-245}$) (Yauch et al., *J Immunol* 182:4865 (2009)) in an attempt to induce a multispecific T cell response, which is desirable to prevent possible viral escape through mutation (Welsh et al., *Nat Rev Microbiol* 5:555 (2007)). At day 4 after infection, viremia in the serum was measured by real-time RT-PCR, as described above. The peptide-immunization resulted in enhanced control of DENV infection, with 350-fold lower serum DENV RNA levels in peptide-immunized mice than mock-immunized mice (Yauch et al., *J Immunol* 182:4865 (2009)). To confirm that the protection was mediated by CD8+ T cells, CD8+ T cells were depleted from a group of peptide-immunized mice prior to infection, and it was found that this abrogated the protective effect (Yauch et al., *J Immunol* 182:4865 (2009)). Thus, the data demonstrate that a preexisting DENV-specific CD8+ T cell response induced by peptide vaccination enhances viral clearance.

Most dengue infections are asymptomatic or classified as DF, whereas DHF/DSS accounts for a small percentage of dengue cases, indicating that in most infections the host immune response is protective. These data indicate that CD8+ T cells contribute to protection during primary infection by reducing viral load and that CD8+ T cells are an important component to a protective immune response.

This study shows that immunization with four dominant epitopes prior to infection resulted in enhanced DENV clearance, and this protection was mediated by CD8+ T cells. These results indicate that vaccination with T cell epitopes can reduce viremia.

Results from the Examples described herein reveal a critical role for CD8+ T cells in the immune response to an important human pathogen, and provide a rationale for the inclusion of CD8+ T cell epitopes in DENV vaccines. Furthermore, identification of the CD8+ T cell epitopes recognized during DENV infection in combination with the disclosed mouse model can provide the foundation for elucidating the protective versus pathogenic role of CD8+ T cells during secondary infections.

Example 8

This example is a description of a novel system to identify DENV specific HLA*0201 epitopes.

Mouse-passaged DENV is able to replicate to significant levels in IFN-α/βR$^{-/-}$ mice. HLA*0201 transgenic and IFN-α/βR$^{-/-}$ mice strains were backcrossed to study DENV-specific HLA restricted T cell responses. These mice were then infected with mouse adapted DENV2 strain S221, and purified splenic T cells were used to study the anti-DENV CD8+ T cell responses.

Figure 9A:
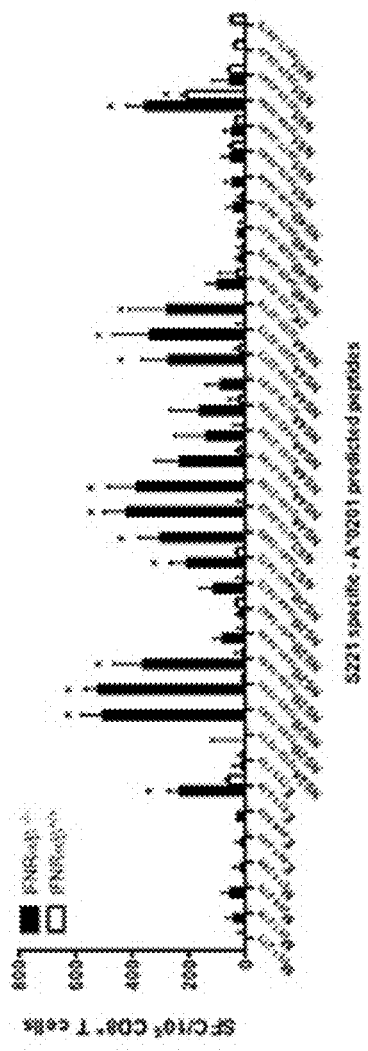
FIG. 9A-9D show identification of DENV-derived epitopes recognized by CD8+ T cells. DENV specific epitope identification was performed in four different HLA transgenic mouse strains (FIG. 9A) A*0201.

A panel of 116 predicted A*0201 binding peptides were generated using bioinformatics (Moutaftsi, et al. *Nat Biotechnol* 24:817 (2006)). Predicted HLA A*0201 binding peptides were combined into pools of 10 individual peptides and tested in an IFNγ ELISPOT assay using CD8+ T cells from HLA transgenic IFN-α/βR$^{-/-}$ and IFN-α/βR$^{+/+}$, S221 infected mice, respectively. Positive pools were deconvoluted and the individual peptides were tested in two independent experiments. Using this approach, a single peptide in the HLA*A0201 IFN-α/βR$^{+/+}$ mice was identified ($NS5_{3058}$-3066, FIG. 9A, white bars) whereas screening in IFN-α/βR$^{-/-}$ mice lead to identification of ten additional epitopes. (FIG. 9A, black bars.) These results demonstrate that the HLA A transgenic IFN-α/βR$^{-/-}$ has a stronger and broader T cell response.

Example 9

This example describes population coverage by additional HLA transgenic mice IFN-α/βR−/− strains.

To address whether similar observations could be made by assessing responses in other HLA-transgenic IFN-α/βR$^{-/-}$ and IFN-α/βR$^{+/+}$ mice, IFN-α/βR$^{-/-}$ mice were backcrossed with HLA A*0101, A*1101, and B*0702 transgenic mice. These alleles were chosen as representatives of three additional HLA class I supertypes (A1, A3 and B7, respectively).

Figure 9B:
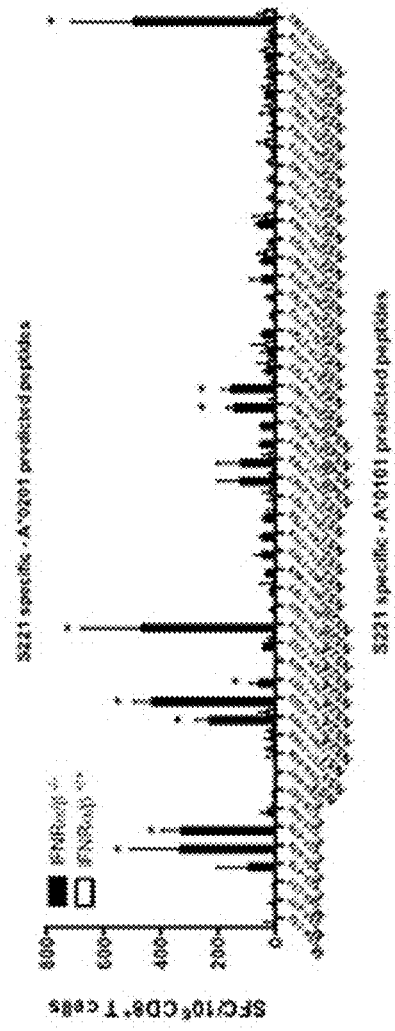
Figure 9C:
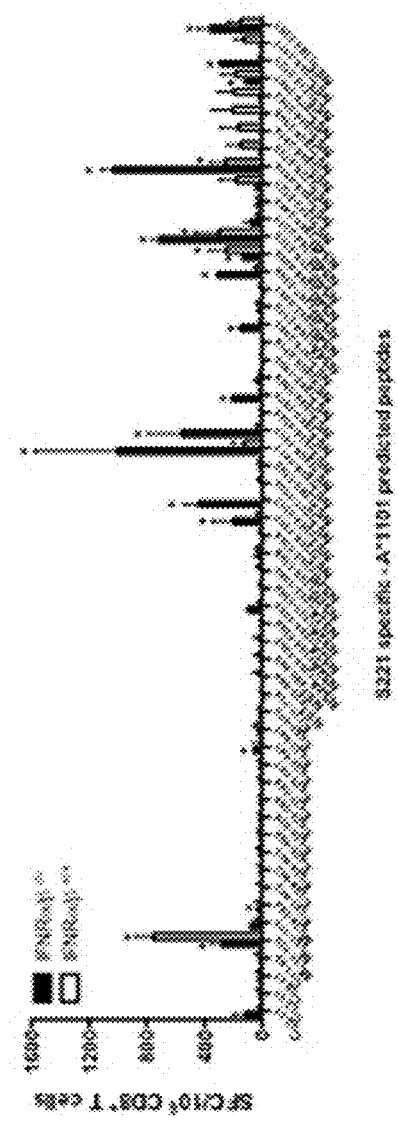

Screening in HLA A*0101 and A*1101 transgenic IFN-α/βR$^{-/-}$ mice revealed 9 HLA A*0101 restricted (FIG. 9B, black bars), and 16 A*1101 restricted epitopes (FIG. 9C, black bars), respectively. In case of the HLA A*0101 transgenic wildtype mice, no epitope could be detected, whereas the HLA A*1101 transgenic mice showed an overlap of 5 epitopes with the corresponding IFN-α/βR$^{-/-}$ strain ($M_{111-120}$, $NS3_{1608-1617}$, $NS4B_{2287-2296}$, $NS4B_{2315-2323}$ and $NS5_{3112-3121}$). Two of these epitopes were able to elicit a stronger response in the HLA A*1101 IFN-α/βR$^{+/+}$ mice compared to the IFN-α/βR$^{-/-}$ strain ($M_{111-120}$ and $NS4B_{2287-2296}$) All other responses observed were stronger in the IFN-α/βR$^{-/-}$ mice.

Figure 9D:
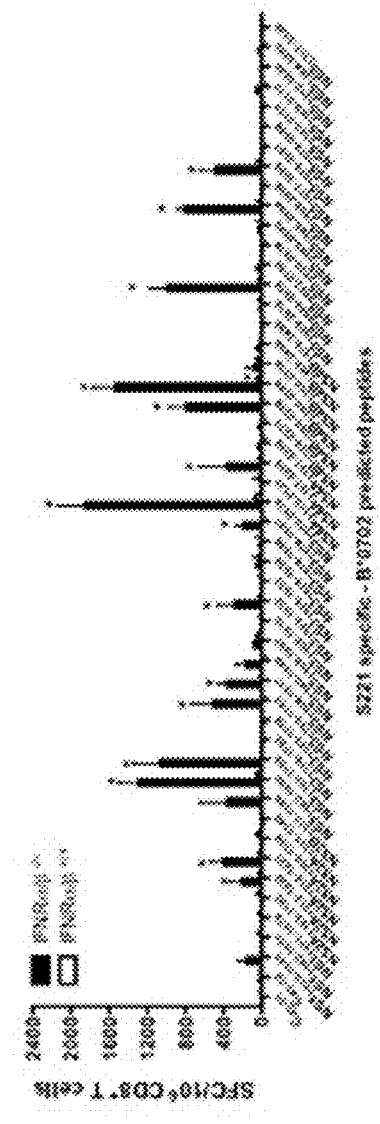

To extend the observations to mice transgenic for an HLA B allele HLA B*0702 transgenic IFN-α/βR$^{-/-}$ and IFN-α/βR$^{+/+}$ mice were infected and epitope recognition was compared between the two strains. 15 B*0702 restricted epitopes in the IFN-α/βR$^{-/-}$ strain (FIG. 9D, black bars) were identified. 1 of these has also been detected in the corresponding IFN-α/βR$^{+/+}$ mice (NS4B$_{2280-2289}$; FIG. 9D, white bars). Similar to the other HLA transgenic mouse strains, the responses observed in the HLA B*0702 transgenic IFN-α/βR$^{-/-}$ mice were not only broader but also more than ten-fold higher in magnitude. The one epitope recognized in the IFN-α/βR$^{+/+}$ strain elicited an IFNγ response of 50 SFC/10$^6$ CD8$^+$ T cells compared to an average of 857 SFC/10$^6$ CD8$^+$ T cells in the IFN-α/βR$^{-/-}$ mice.

Example 10

This example describes Dengue virus specific T cell responses in an MHC class II transgenic mouse model.

Figure 10:
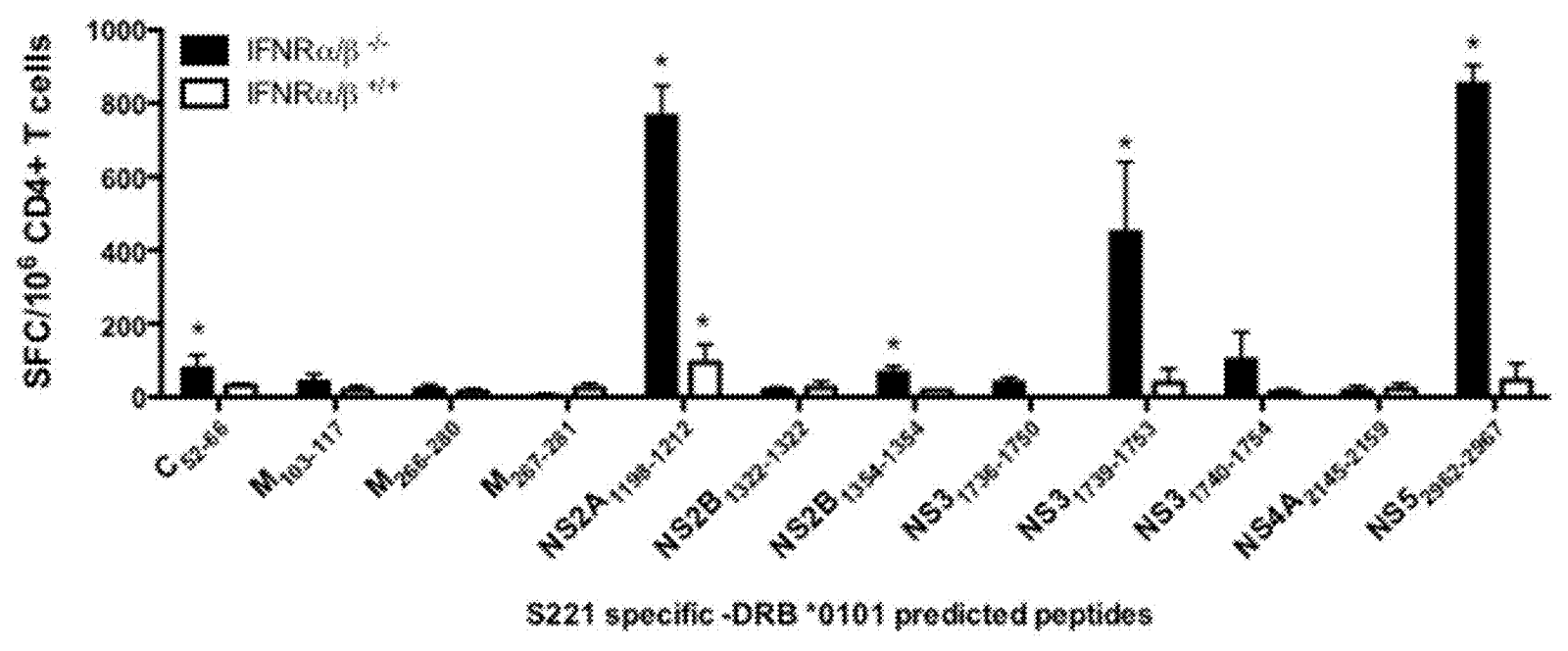

To determine if the observations made in the case of MHC class I transgenic mice were also applicable to MHC class II molecules, the antigenicity of HLA DRB1*0101 DENV predicted binding peptides in HLA DRB1*0101, IFN-α/βR$^{-/-}$ and IFN-α/βR$^{+/+}$ mice, respectively, was determined. Using the same study conditions described above for the MHC class I transgenic mice, HLA DRB1*0101, IFN-α/βR$^{-/-}$ and IFN-α/βR$^{+/+}$ mice were infected with DENV2 (S221), and CD4$^+$ T cells were isolated 7 days post infection. A panel of 12 predicted S221 specific peptides was then analyzed for IFNγ production by ELISPOT. Five epitopes in the DRB1*0101, IFN-α/βR$^{-/-}$ mice were identified from these assays which could elicit a significant IFNγ response in two independent experiments (FIG. 10; black bars). As seen above in the MHC class I transgenic mice, only one peptide could be detected in the corresponding DRB1*0101, IFN-α/βR$^{+/+}$ mice (NS2A$_{1199-1213}$; FIG. 10, white bars). This identified epitope in the IFN-α/βR$^{+/+}$ did not represent a novel epitope as it was also observed in the corresponding IFN-α/βR$^{-/-}$ mice. Similarly to the MHC class I transgenic mice all observed responses were stronger in the IFN-α/βR$^{-/-}$ mice.

In summary, a total of 55 epitopes were identified in the HLA transgenic IFN-α/βR$^{-/-}$ mice, whereas the same screen in HLA transgenic IFN-α/βR$^{+/+}$ mice only revealed 8 epitopes. All of these 8 epitopes have also been detected in the HLA transgenic IFN-α/βR$^{-/-}$ mice. The broader repertoire seen in IFN-α/βR$^{-/-}$ mice as well as the stronger and more robust IFNγ responses, suggest that HLA transgenic mice, backcrossed with IFN-α/βR$^{-/-}$ mice are a more suitable model to study T cell responses to DENV infection than HLA transgenic wildtype mice.

Example 11

This example is a description of mapping optimal epitopes with respect to peptide length, and further characterization of the identified epitopes.

Figure 11A:
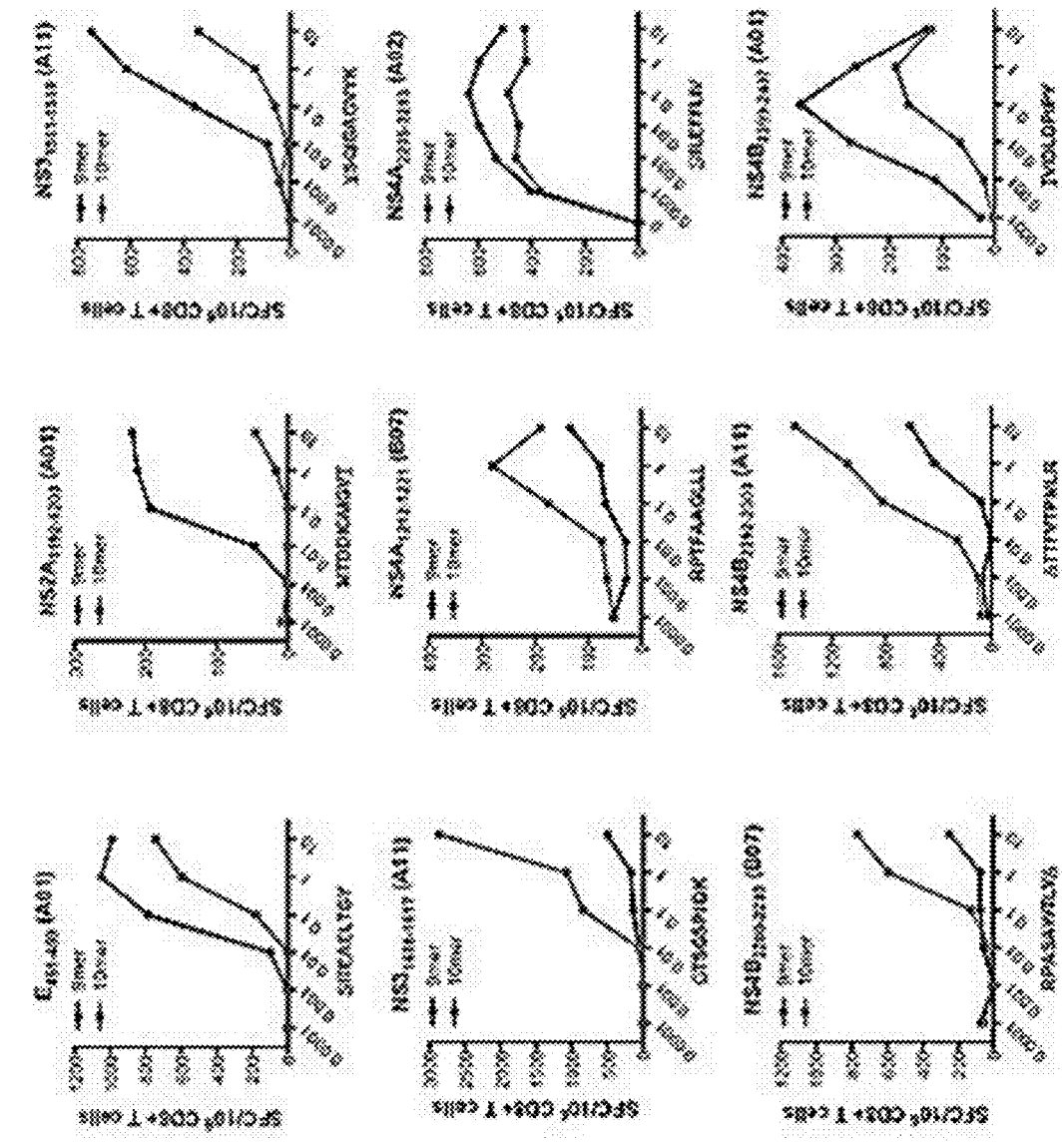
FIGS. 11A-11B show the determination of optimal epitope studies. To determine the dominant epitope, HLA-transgenic IFN-α/βR$^{-/-}$ mice were infected with 1×10$^{10}$ GE of DENV2 (S221) and spleens harvested 7 days post infection. CD8$^+$ T cells were purified and incubated for 24 hours with ascending concentrations of nested peptides.

For all HLA alleles tested in this study, class I 9- and 10-mer peptide predictions were performed using the consensus prediction tool as described in greater detail in Example 1. Within the 50 MHC class I restricted epitopes identified, 9 pairs of nested epitopes were identified, where the 9-mer as well as the 10-mer peptide was able to elicit an immune response. To determine which specific peptide within each nested epitope pair was the optimal epitope, peptide titration assays were employed (FIG. 11A). For one epitope (NS4A$_{2205-2213}$), both the 9- and the 10-mer displayed similar kinetics upon peptide titration (FIG. 11A).

Since the 9-mer was able to elicit slightly higher responses in all conditions tested, the 9-mer version of this epitope was used for further studies. In all other cases an optimal epitope length peptide could be unequivocally identified.

Figure 11B:
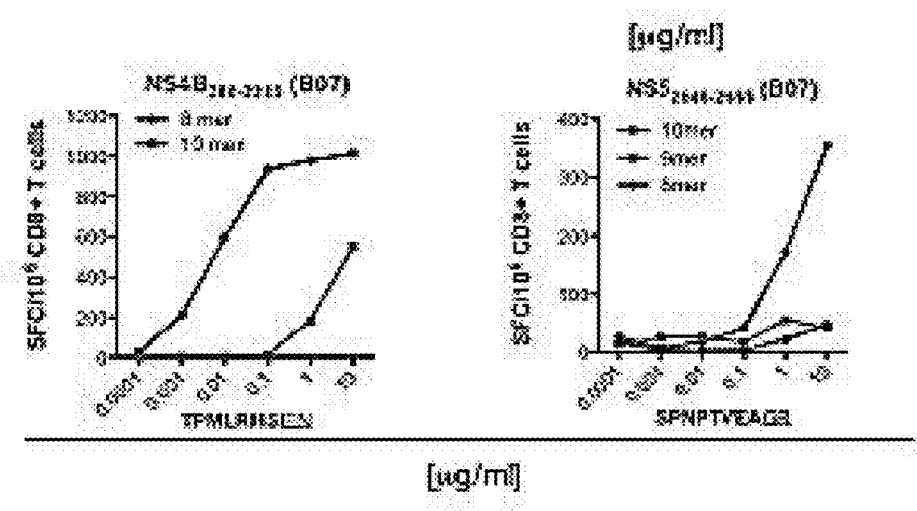

Similarly, for two of the identified B*0702 restricted epitopes (NS4B$_{2296-2305}$ and NS5$_{2646-2655}$) which showed low binding affinity (IC$_{50}$>1000 nM) 8-, and 9-mers carrying alternative dominant B7 motifs were synthesized and tested them for T cell recognition and binding affinity. In one case the corresponding 8-mer (NS4B$_{2296-2304}$) showed dominant IFNγ responses as well as higher binding affinity compared to the 9-mer. In the other case, the 10mer originally identified (NS5$_{2646-2655}$) was able to elicit higher responses than the newly synthesized 8- and 9-mer. In both cases the optimal epitope length could be identified and was considered further in the study, as shown in FIG. 11B.

Of all five HLA transgenic mouse strains analyzed, two strains, namely the A*0201 and the A*1101 transgenic strains, co-expressed murine MHC molecules together with the respective HLA molecule. Thus it was necessary to address that the observed responses were restricted by the human HLA class I molecule and not by murine Class I. Accordingly, purified T cells q were studied for their capacity to recognize the specific epitopes when pulsed on antigen presenting cells expressing only human HLA class and not any murine class I molecule. For this purpose, the tumor cell line 721.221 was utilized, which is negative for expression of any human or murine Class I molecule, and was transfected with either HLA A*0201 or HLA*1101.

Figure 12A:
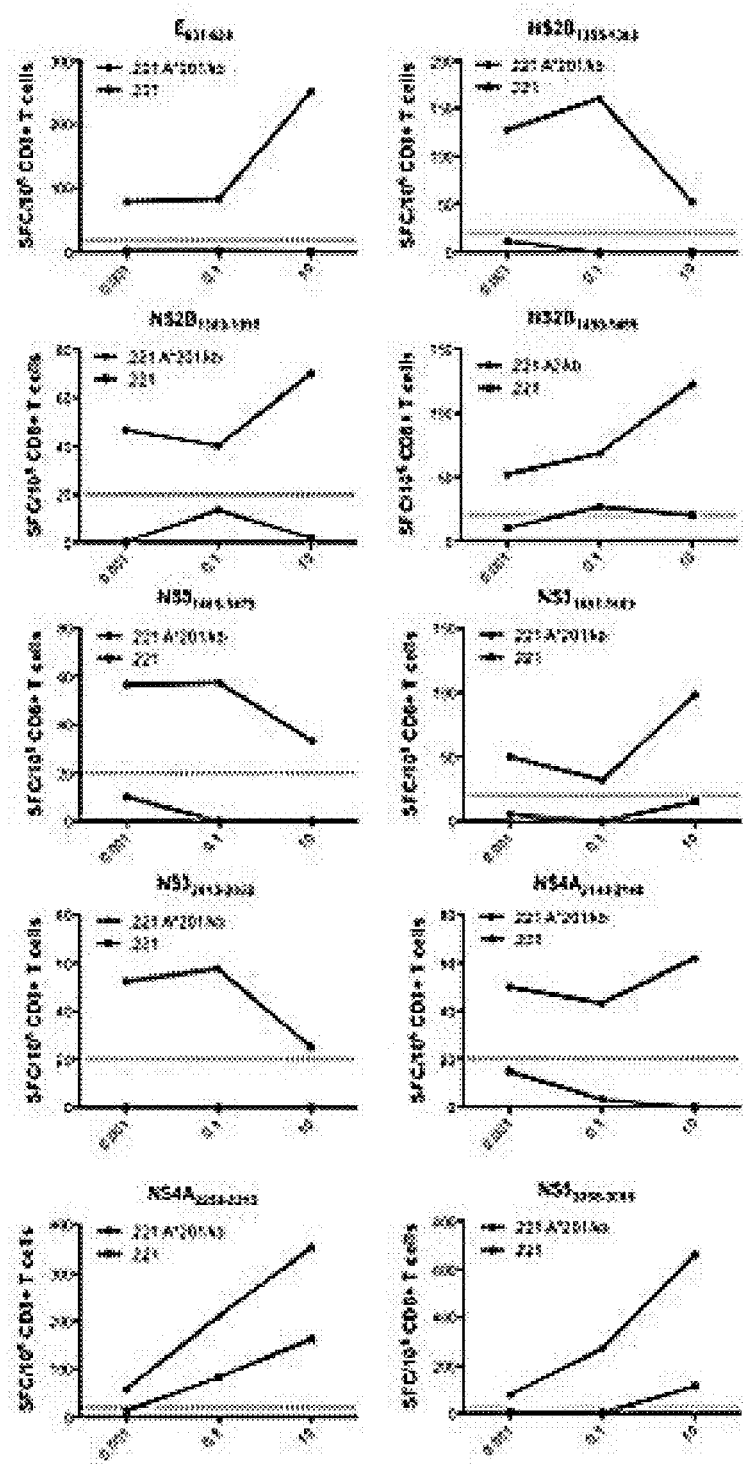
FIGS. 12A-12B show MHC-restriction of identified epitopes. HLA A*0201 (FIG. 12A) and HLA A*1101 (FIG. 12B) transfected 0.221 cells, as well as the non-transfected cell line as a control, were used as antigen presenting cells in titration experiments to determine MHC restriction. Purified CD8$^+$ T cells from DENV2 (S221) infected HLA A*A0201 and HLA A*110 IFN-α/βR$^{-/-}$ mice were incubated with increasing concentrations of peptides and tested for IFNγ production in an ELISPOT assay. Representative graphs of CD8$^+$ T cell responses are shown, when incubated with HLA transfected cell lines (A and B; black lines) and non-transfected cell lines (A and B, grey lines) are shown. The dotted line indicates the 25 net SFCs/10$^6$ cells threshold used to define positivity.
Figure 12B:
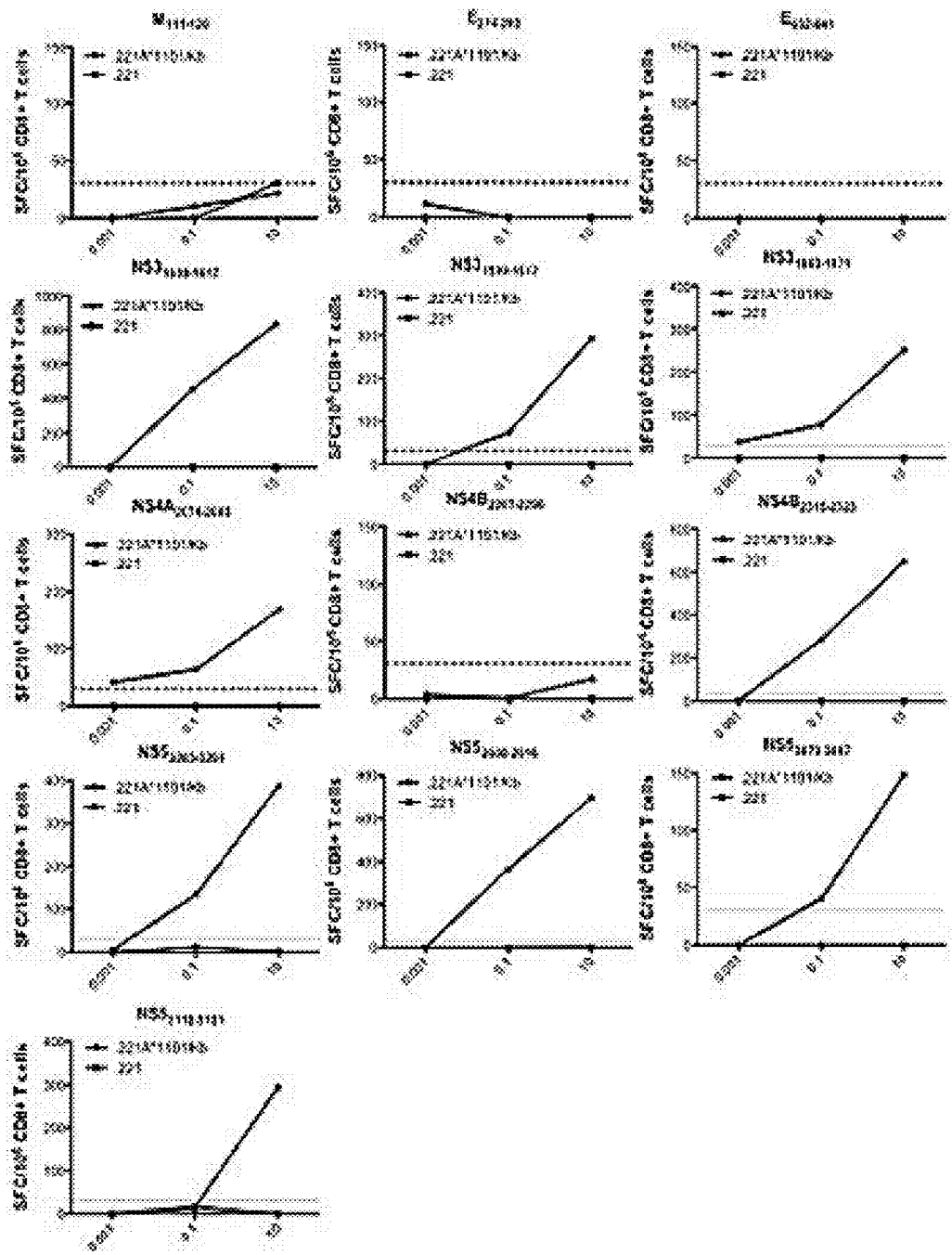

As shown in FIG. 12A, all ten HLA*A0201 restricted epitopes were recognized when presented by APC exclusively expressing HLA*A0201 molecules. Nine out of thirteen of the HLA*A1101 restricted epitopes identified did stimulate a CD8$^+$ T cell response when presented exclusively on HLA*1101 molecules (FIG. 12B). When the four remaining epitopes were tested in non-HLA transgenic IFN-α/βR$^{-/-}$ mice as described above, all elicited a significant T cell response. Furthermore, one of the epitopes has already been described to be recognized by T cells from DENV2 infected Balb/c mice (E$_{633-642}$ (Roehrig, et al. *J Virol* 66:3385 (1992))). These epitopes (M$_{111-120}$, E$_{274-282}$, E$_{633-642}$, NS4B$_{2287-2296}$) are therefore considered solely mouse MHC restricted, and were excluded from further study. Among those epitopes were also the two epitopes which elicited a stronger response in the HLA A*1101 IFN-α/βR$^{+/+}$ mice compared to the IFN-α/βR$^{-/-}$ strain (M$_{111-120}$ and NS4B$_{2287-2296}$).

To further confirm the MHC restriction of the identified epitopes, MHC-binding capacity to their predicted allelic molecule was measured using purified HLA molecules in an in vitro binding assay. The results of these assays are also shown in Table 2. 32 of the 42 tested peptides (67%) bound the corresponding predicted allele with high affinity as indicated by an IC$_{50}$<50 nM. 16 out of these even showed an IC$_{50}$<10 nM and can therefore be considered as very strong binders. Of the remaining peptides, 7 (17%) were able to bind the predicted allele with intermediate affinities as indicated by IC$_{50}$<150 nM. Only three of the identified epitopes (7%) bound with low affinity, showing an IC$_{50}$>500 nM. A summary of all epitopes identified, after conclusion of the studies and elimination of redundancies, is shown in Table 2 (SEQ ID NOs: 224-265).

TABLE 2

Identified DENV2 derived epitopes in HLA-transgenic IFN-α/βR$^{-/-}$ mice

| Epitope | Sequence (SEQ ID NOs: 224-265 in order of appearance). | Restriction | T cell responses [SFC] mouse | human | frequency in humans |
|---|---|---|---|---|---|
| E$_{451-459}$ | ITEAELTGY | A*0101 | 327 | 67 | 20% (1 out of 5) |
| NS1$_{1090-1099}$ | RSCTLPPLRY | | 228 | 104 | 20% (1 out of 5) |
| NS2A$_{1192-1200}$ | MTDDIGMGV | | 430 | 163 | 20% (1 out of 5) |
| NS2A$_{1251-1259}$ | LTDALALGM | | 465 | 143 | 40% (2 out of 5) |
| NS4B$_{2399-2407}$ | VIDLDPIPY | | 153 | 92 | 20% (1 out of 5) |
| NS5$_{3375-3383}$ | YTDYMPSMK | | 495 | 143 | 20% (1 out of 5) |
| E$_{631-639}$ | RLITVNPIV | A*0201 | 265 | 393 | 43% (3 out of 7) |
| NS2B$_{1355-1363}$ | IMAVGMVSI | | 503 | 417 | 43% (3 out of 7) |
| NS2B$_{1383-1391}$ | GLLTVCYVL | | 519 | 434 | 57% (4 out of 7) |
| NS2B$_{1450-1459}$ | LLVISGLFPV | | 361 | 588 | 43% (3 out of 7) |
| NS3$_{1465-1473}$ | AAAWYLWEV | | 207 | 495 | 57% (4 out of 7) |
| NS3$_{1681-1689}$ | YLPAIVREA | | 299 | 401 | 71% (5 out of 7) |
| NS3$_{2013-2022}$ | DLMRRGDLPV | | 417 | 312 | 71% (5 out of 7) |
| NS4A$_{2140-2148}$ | ALSELPETL | | 384 | 297 | 14% (1 out of 7) |
| NS4A$_{2205-2213}$ | IILEFFLIV | | 336 | 301 | 28% (2 out of 7) |
| NS5$_{3058-3066}$ | KLAEAIFKL | | 353 | 597 | 43% (3 out of 7) |
| NS3$_{1509-1517}$ | SQIGAGVYK | A*1101 | 436 | 0 | 0% (0 out of 5) |
| NS3$_{1608-1617}$ | GTSGSPIIDK | | 1003 | 880 | 20% (1 out of 5) |
| NS3$_{1863-1871}$ | KTFDSEYVK | | 208 | 0 | 0% (0 out of 5) |
| NS4A$_{2074-2083}$ | RIYSDPLALK | | 148 | 3087 | 20% (1 out of 5) |
| NS4B$_{2315-2323}$ | ATVLMGLGK | | 712 | 0 | 0% (0 out of 5) |
| NS5$_{2608-2616}$ | STYGWNLVR | | 1030 | 0 | 0% (0 out of 5) |
| NS5$_{3079-3087}$ | TVMDIISRR | | 105 | 0 | 0% (0 out of 5) |
| NS5$_{3112-3121}$ | RQMEGEGVFK | | 284 | 0 | 0% (0 out of 5) |
| NS5$_{3283-3291}$ | RTTWSIHAK | | 358 | 800 | 20% (1 out of 5) |
| NS2A$_{1212-1221}$ | RPTFAAGLLL | B*0702 | 400 | 335 | 20% (1 out of 5) |
| NS3$_{1682-1690}$ | LPAIVREAI | | 1293 | 207 | 20% (1 out of 5) |
| NS3$_{1700-1709}$ | APTRVVAAEM | | 1064 | 1426 | 40% (2 out of 5) |
| NS3$_{1753-1761}$ | VPNYNLIIM | | 509 | 410 | 20% (1 out of 5) |
| NS3$_{1808-1817}$ | APIMDEEREI | | 364 | 232 | 20% (1 out of 5) |
| NS3$_{1978-1987}$ | TPEGIIPSMF | | 194 | 1825 | 20% (1 out of 5) |
| NS3$_{2070-2078}$ | KPRWLDARI | | 1853 | 1633 | 40% (2 out of 5) |
| NS4B$_{2280-2289}$ | RPASAWTLYA | | 1539 | 0 | 0% (0 out of 5) |
| NS4B$_{2296-2304}$ | TPMLRHSI | | 1013 | 460 | 20% (1 out of 5) |
| NS5$_{2646-2655}$ | SPNPTVEAGR | | 994 | 0 | 0% (0 out of 5) |
| NS5$_{2885-2894}$ | TPRMCTREEF | | 811 | 1341 | 60% (3 out of 5) |
| NS5$_{3077-3085}$ | RPTPRGTVM | | 487 | 390 | 40% (2 out of 5) |
| C$_{53-67}$ | AFLRFLTIPPTAGIL | DRB1*0101 | 77 | 314 | 75% (3 out of 4) |
| NS2A$_{1199-1213}$ | GVTYLALLAAFKVRP | | 764 | 249 | 75% (3 out of 4) |
| NS2B$_{1356-1370}$ | MAVGMVSILASSLLK | | 65 | 279 | 75% (3 out of 4) |
| NS3$_{1742-1756}$ | TFTMRLLSPVRVPNY | | 448 | 336 | 75% (3 out of 4) |
| NS5$_{2966-2980}$ | SRAIWYMWLGARFLE | | 851 | 729 | 75% (3 out of 4) |

| Epitope | HLA binding [IC$_{50}$] | Conservancy within serotypes [%] DENV2 | DENV1 | DENV3 | DENV4 | References |
|---|---|---|---|---|---|---|
| E$_{451-459}$ | 25 | 85 | 0 | 0 | 0 | |
| NS1$_{1090-1099}$ | 5.9 | 100 | 0 | 100 | 0 | |
| NS2A$_{1192-1200}$ | 19 | 84 | 0 | 0 | 0 | |
| NS2A$_{1251-1259}$ | 129 | 91 | 0 | 0 | 0 | |
| NS4B$_{2399-2407}$ | 17 | 53 | 0 | 0 | 0 | |
| NS5$_{3375-3383}$ | 37 | 98 | 0 | 0 | 0 | |
| E$_{631-639}$ | 2.8 | 98 | 0 | 0 | 0 | |
| NS2B$_{1355-1363}$ | 1.9 | 92 | 0 | 0 | 0 | |
| NS2B$_{1383-1391}$ | 6.0 | 100 | 0 | 0 | 0 | |
| NS2B$_{1450-1459}$ | 26 | 50 | 0 | 0 | 0 | |
| NS3$_{1465-1473}$ | 0.39 | 92 | 0 | 0 | 0 | |
| NS3$_{1681-1689}$ | 18 | 99 | 0 | 0 | 0 | [76$^1$] |
| NS3$_{2013-2022}$ | 6.3 | 92 | 0 | 0 | 0 | |
| NS4A$_{2140-2148}$ | 61 | 99 | 0 | 0 | 0 | [77$^2$] |
| NS4A$_{2205-2213}$ | 18 | 99 | 0 | 0 | 0 | |
| NS5$_{3058-3066}$ | 2.2 | 95 | 0 | 0 | 0 | [77] |
| NS3$_{1509-1517}$ | 33 | 98 | 0 | 0 | 0 | |
| NS3$_{1608-1617}$ | 12 | 30 | 0 | 0 | 0 | [78$^3$] |

TABLE 2-continued

Identified DENV2 derived epitopes in HLA-transgenic IFN-α/βR$^{-/-}$ mice

| | | | | | | |
|---|---|---|---|---|---|---|
| NS3$_{1863-1871}$ | 140 | 75 | 0 | 0 | 0 | [76] |
| NS4A$_{2074-2083}$ | 51 | 89 | 0 | 0 | 0 | [76] |
| NS4B$_{2315-2323}$ | 16 | 98 | 0 | 0 | 0 | |
| NS5$_{2608-2616}$ | 22 | 100 | 0 | 0 | 0 | |
| NS5$_{3079-3087}$ | 71 | 91 | 0 | 0 | 0 | |
| NS5$_{3112-3121}$ | 118 | 43 | 0 | 0 | 0 | |
| NS5$_{3283-3291}$ | 83 | 65 | 0 | 0 | 0 | |
| NS2A$_{1212-1221}$ | 4.8 | 92 | 0 | 0 | 0 | |
| NS3$_{1682-1690}$ | 6.5 | 100 | 98 | 96 | 0 | [76] |
| NS3$_{1700-1709}$ | 4.6 | 99 | 0 | 100 | 100 | [76] |
| NS3$_{1753-1761}$ | 43 | 100 | 0 | 89 | 0 | [76] |
| NS3$_{1808-1817}$ | 572 | 77 | 0 | 0 | 0 | |
| NS3$_{1978-1987}$ | 589 | 99 | 0 | 0 | 0 | [76] |
| NS3$_{2070-2078}$ | 6.8 | 91 | 0 | 0 | 0 | [76] |
| NS4B$_{2280-2289}$ | 7.4 | 100 | 37 | 0 | 100 | |
| NS4B$_{2296-2304}$ | 1.1 | 100 | 0 | 0 | 0 | |
| NS5$_{2646-2655}$ | 1332 | 54 | 0 | 0 | 0 | |
| NS5$_{2885-2894}$ | 13 | 89 | 0 | 0 | 0 | |
| NS5$_{3077-3085}$ | 1.5 | 97 | 0 | 0 | 0 | |
| C$_{53-67}$ | 9.7 | 99 | 0 | 0 | 0 | [79$^4$] |
| NS2A$_{1199-1213}$ | 10 | 91 | 0 | 0 | 0 | |
| NS2B$_{1356-1370}$ | 34 | 100 | 0 | 0 | 0 | |
| NS3$_{1742-1756}$ | 1.5 | 70 | 100 | 99 | 0 | [76] |
| NS5$_{2966-2980}$ | 17 | 100 | 99 | 0 | 100 | |

$^1$[76] Simmons et al., J Virol 79: 5665 (2005)
$^2$[77] Appanna et al., Clin Vaccine Immunol 14: 969 (2007)
$^3$[78] Mongkolsapaya et al., 7 Immunol 176: 3821
$^4$[79] Wen et al., Virus Res 132: 42 (2008)

Example 12

This example includes a description of validation studies of the identified epitopes in human DENV seropositive donors.

To validate the epitopes identified in the HLA-transgenic IFN-α/βR$^{-/-}$ mice, the capacity of these epitopes to stimulate PBMC from human donors, previously exposed to DENV, was analyzed. Since the IFNγ response to these peptides was not detectable ex vivo, HLA-matched PBMC were re-stimulated for 7 days in presence of the respective peptides and IL2. As a control PBMC from donors which neither expressed the exact HLA-molecule nor one from the same supertype, as well as PBMC from DENV seronegative donors were re-stimulated. The average IFNγ response from these donors plus 3 times the standard deviation (SD) was set as a threshold of positivity.

Figure 13B:
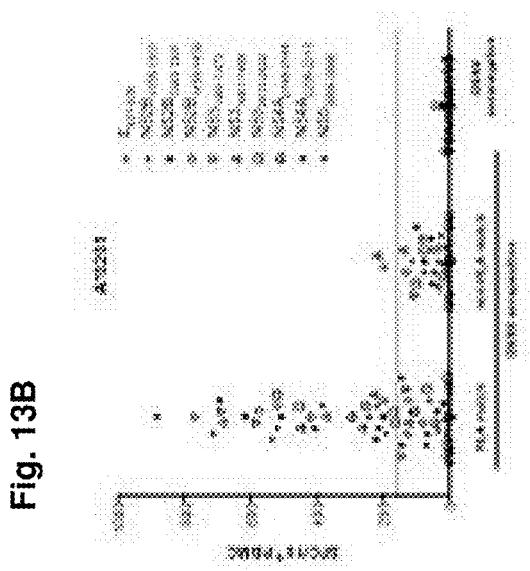
FIGS. 13A-13F show antigenicity of identified epitopes in human donors. Epitopes (1 µg/ml individual peptide for 7 days) identified in the HLA-transgenic IFN-α/βR$^{-/-}$ mice were validated by their capacity to stimulate PBMC (2×10$^6$ PBMC/ml) from human donors and then tested in an IFNγ ELISPOT assay.
Figure 13C:
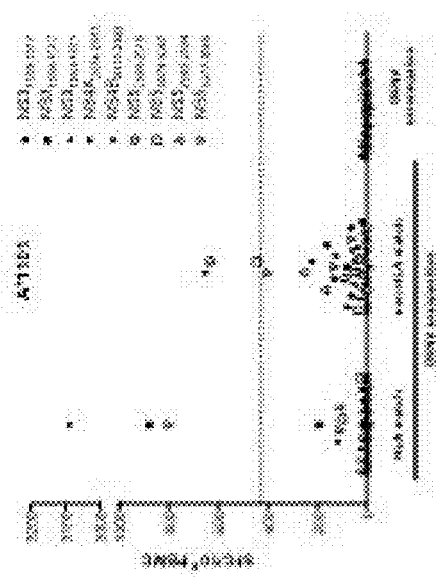
Figure 13A:
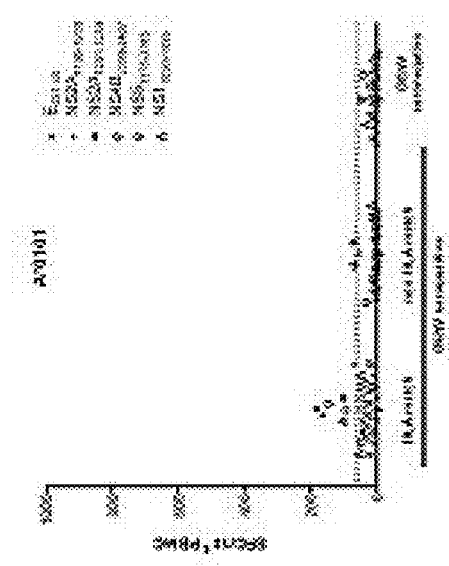
Figure 13E:
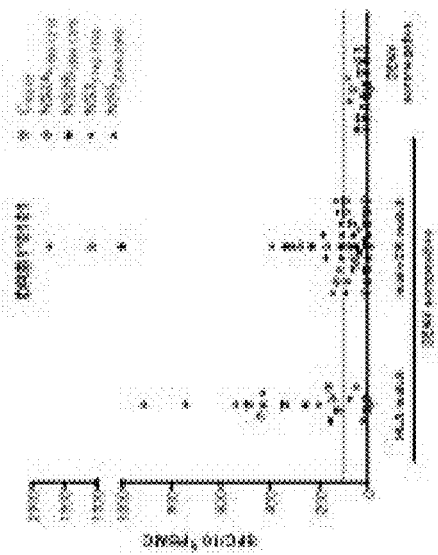
Figure 13D:
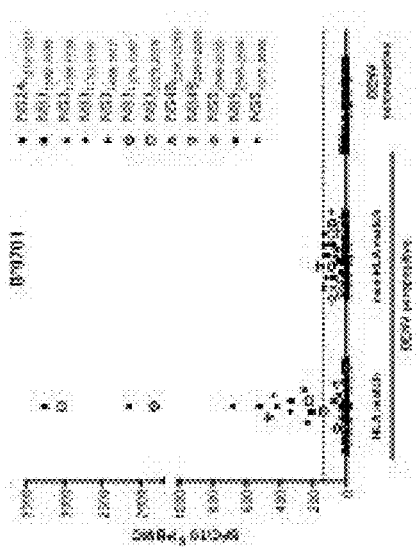

FIGS. 13A-13D (HLA A*0101, A*0201, A*1101, and B*0702) show the capacity of the identified epitopes to stimulate PBMC from the various donor categories. Each of the A*0101 and A*0201 epitopes was detected at least once in an HLA matched donor, although the magnitude as well as the frequency of responses was higher for the A*0201 restricted epitopes (FIGS. 13A-13B and Table 2). Out of the 9 A*1101 restricted epitopes, 3 have been detected once in HLA matched donors. These three epitopes though have been able to stimulate a robust IFNγ response, as indicated by net SFCs>800 (FIG. 13C). In case of the B*0702 restricted epitopes, 10 out of the 12 have been detected in one or more HLA matched donors as shown in FIG. 13D and Table 1. No significant responses could be detected in non-HLA matched donors studied, as shown for A1, A2, A3 and B7 molecules. In contrast, all four restricted DRB1*0101 epitopes have been detected in 3 out of 4 HLA matched donors tested and were also able to elicit significant IFNγ responses in non-HLA matched donors. This is in accordance with recent reports, demonstrating a high degree of repertoire sharing across MHC class II molecules (Greenbaum, et al. *Immunogenetics* 63:325 (2011)). Overall, responses to 34 of the 42 epitopes were detected in at least one donor, which corresponds to an overlap of 81% between the murine and human system. In addition to the experimental approach, an IEDB query was performed with the epitopes identified in the mouse model. Here, 13 of the 42 epitopes previously described to elicit an IFNγ in DENV seropositive individuals were identified, as indicated in Table 2 (SEQ ID NOs: 224-265). The 30% overlap with known epitopes contributes to the validation of our mouse model and shows on the other hand that 70% of the epitopes identified are novel, contributing to an extended knowledge of T cell mediated responses to DENV.

Example 13

This example includes studies showing dominance of B7 responses.

Figure 13F:
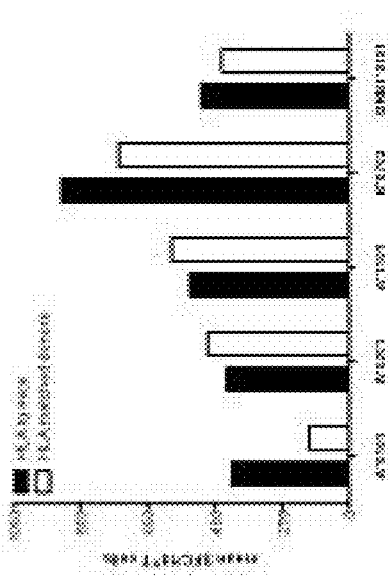

A notable observation here was that out of all HLA transgenic mouse strains tested the strongest CD8$^+$ T cell responses could be detected in the B*0702 transgenic IFN-α/βR$^{-/-}$ mice. Four B*0702 restricted epitopes were able to elicit an IFNγ response above a thousand SFC/10$^6$ CD8$^+$ T cells. On average B*0702 epitopes were able to elicit an IFNγ response of 857 SFC/10$^6$ CD8$^+$ T cells, compared to an average of 350, 365, and 476 SFC/10$^6$ CD8$^+$ T cells for the HLA A*0101, A*0201 and A*1101 restricted epitopes, respectively (FIG. 13F, black bars). Most interestingly, the exact same response pattern could be observed testing PBMC from HLA matched donors, previously exposed to DENV (FIG. 13F, white bars). As seen in mice, B*0702 restricted epitopes were able to elicit the strongest IFNγ responses, reaching an average of 688 SFC/10$^6$ CD8$^+$ T cells, followed by an average of 530, 423 and 119 SFC/10$^6$ CD8$^+$ T cells for HLA*1101, A*0202 and A*0101 restricted epitopes, respectively. The fact that the mouse model described herein reflects response patterns observed in humans makes it an especially suitable model to identify and study epitopes of human relevance to DENV infection.

Example 14

This example includes a description of studies showing the subprotein location of identified epitopes, and the conservancy of identified epitopes within the DENV2 serotype.

Figure 14:
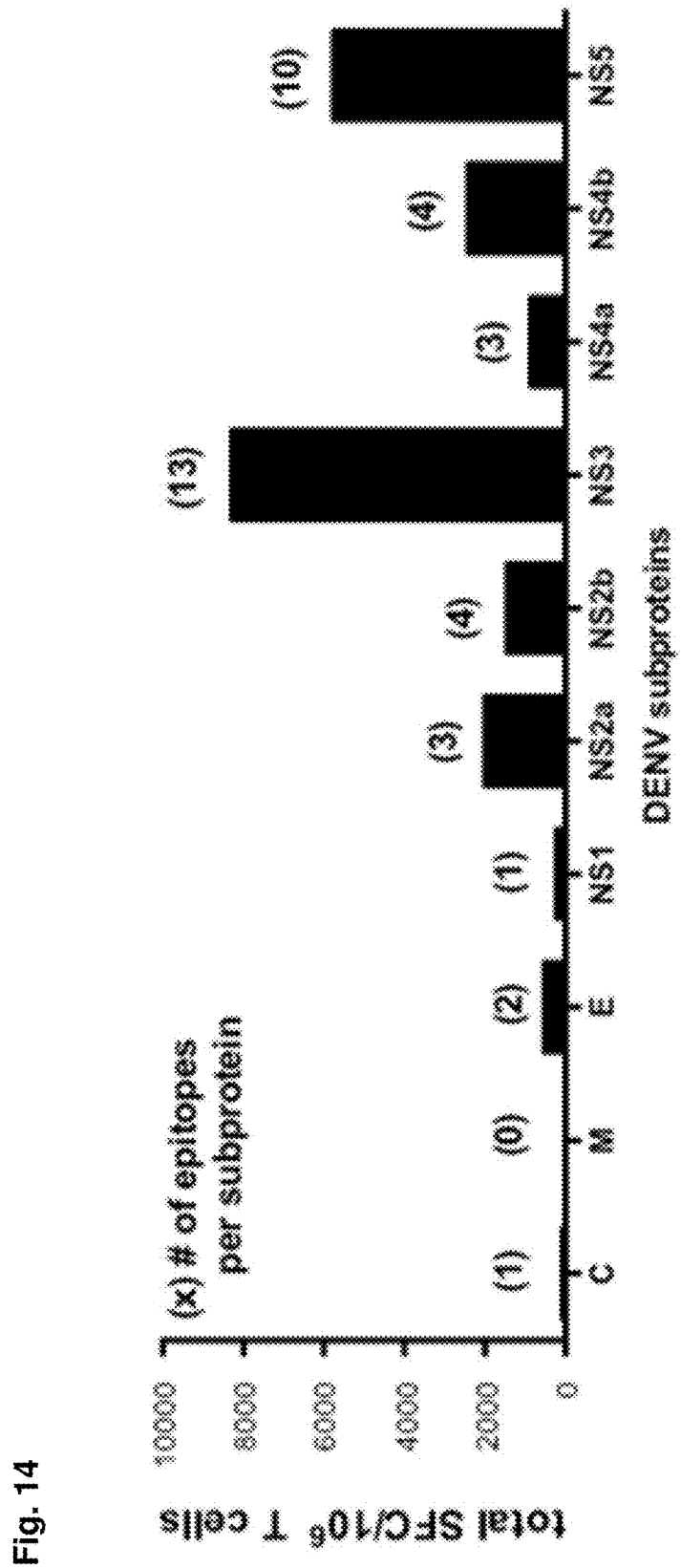
FIG. 14 shows subproteinlocation of identified epitopes from Table 2. All identified epitopes were grouped according to the DENV subprotein they are derived from. Black bars show the total IFNγ response all epitopes of a certain protein could elicit. Numbers in parenthesis indicate the number of epitopes that have been detected for this protein.

The identified epitopes are derived from 9 of the 10 DENV proteins, with the membrane protein being the only protein, no epitope could be detected (FIG. 14). The majority of epitopes are derived from the seven nonstructural proteins. 39 out of 42 of the identified epitopes (93%) originate from the nonstructural proteins, accounting for 97% of the total IFNγ response observed. Within the non-structural proteins, however, NS3 and NS5 alone account for 67% of the total response, representing a total number of 23 epitopes detected from these two proteins. NS5 is furthermore the only subprotein where at least one derived epitope has been identified in all five HLA transgenic mouse strains. These results are consistent with the immunodominance of NS3, but also identify NS5 as a major target of T cell responses.

Cross-reactivity of T cells is a well-described phenomenon in DENV infection (Mathew, et al. *Immunol Rev* 225:300 (2008))). To circumvent this issue, T cell reactivity was exclusively tested to S221 derived peptides, which was also used as infectious agent in this study. However, to asses the relevance for infections with other DENV2 strains, conservancy of these epitopes within the DENV2 serotype was analyzed. 171 full-length DENV2 polyprotein sequences from the NCBI Protein database were analyzed for conservancy. Of the epitopes identified, 30 out of the 42 epitopes were conserved in >90% of all DENV2 strains; 8 epitopes were even conserved in all 171 strains analyzed. Of the remaining 12 epitopes, 6 were conserved in >75% of all strains analyzed and the other half was found in the 30-65% range. This accounts for an average conservancy of 92% for the epitopes identified, which is significantly higher than the average conservancy of non-epitopes (73%; $p<0.001$).

To determine if the epitopes identified were also conserved in serotypes, other than DENV2, 162 DENV1, 169 DENV3 and 53 DENV4 sequences from the NCBI protein database were studied for conservancy. In contrast to a high degree of conservancy within the DENV2 serotype, 35 out of the 42 epitopes did not occur in any of the 384 DENV-1, 3 and 4 sequences tested and only 7 epitopes had sequence homologues in one or more of the other serotypes. Interestingly, most of the epitopes which show conservancy across serotypes have been identified in the B*0702 transgenic mice. 4 of the identified B*0702 restricted epitopes ($NS3_{1682-1690}$, $NS3_{1700-1709}$, $NS3_{1753-1761}$, $NS4B_{2280-2892}$) were additionally conserved in 89-100% of sequences derived from serotypes other than DENV2. The same has been observed for two DRB1*0101 restricted epitopes which were conserved across serotypes ($NS3_{1742-1756}$, $NS5_{2966-2980}$). Here, the epitopes were conserved in >99% of polyprotein sequences of two serotypes other than DENV2. Finally, one of the A*0101 restricted epitopes ($NS1_{1090-1099}$) is also conserved in 100% of DENV3 sequences. All results from this analysis are shown in Tables 2 and 3.

The DENV2 epitopes identified in Table 2 (SEQ ID NOs: 224-265) were analyzed for their respective homologues in DENV1, DENV3 and DENV4. 162 DENV1, 171 DENV2, 169 DENV3 and 53 DENV4 sequences from the NCBI Protein database were analyzed for conservancy. Table 3 shows the sequences of the epitopes identified after infection with DENV2 (bold letters). "Counts" indicate the number of strains in which the epitope is conserved within the respective serotype. Listed for each epitope are variants of the epitope in the DENV1, 3 and 4 serotypes and their respective counts. Epitopes are sorted according to their appearance in Table 2 (SEQ ID NOs: 224-265). These sequences help determine the cross-reactivity patterns of the identified epitopes.

TABLE 3

Conservancy and Variants of Epitopes Identified - CD8 Epitopes

| Epitope | Sequence (SEQ ID NOs: 266-300) in order of appearance | Serotype | Counts | Epitope | Sequence (SEQ ID NOs: 301-763) in order of appearance | Serotype | Counts |
|---|---|---|---|---|---|---|---|
| $E_{451-459}$ | ITEAELTGY | DENV2 | 146 | $NS2B_{1383-1391}$ | LLVISGLFPV | DENV2 | 85 |
| | STEIQLTDY | DENV1 | 5 | | LLAISGVYPL | DENV1 | 1 |
| | TTEIQLTDY | DENV1 | 37 | | LLAVSGMYPL | DENV1 | 5 |
| | TSEIQLIDY | DENV1 | 1 | | LLAVSGVYPL | DENV1 | 49 |
| | TSEIQLTDY | DENV1 | 119 | | LLVISGVYPM | DENV1 | 1 |
| | IAEAELTGY | DENV2 | 3 | | LLAVSGVYPI | DENV1 | 2 |
| | IAEAELTDY | DENV2 | 6 | | LLAASGVYPM | DENV1 | 1 |
| | ITDAELTGY | DENV2 | 2 | | LLAISGVYPM | DENV1 | 27 |
| | STEAELTGY | DENV2 | 2 | | LLAVSGVYPM | DENV1 | 76 |
| | TTEAELTGY | DENV2 | 10 | | LLVVSGLFPV | DENV2 | 1 |
| | ISEAELTDY | DENV2 | 2 | | LLVISGLFPA | DENV2 | 1 |
| | ITEAELTGY | DENV2 | 146 | | LLVISGLFPI | DENV2 | 15 |
| | TVEAVLLEY | DENV3 | 1 | | LLVISGVFPV | DENV2 | 69 |
| | TVEAVLPEY | DENV3 | 40 | | LLVISGLFPV | DENV2 | 85 |
| | TVEAILPEY | DENV3 | 44 | | LLIVSGIFPC | DENV3 | 1 |
| | TAEAILPEY | DENV3 | 4 | | LLIVSGIFPY | DENV3 | 151 |
| | THEALLPEY | DENV3 | 1 | | LLIVSGVFPY | DENV3 | 17 |
| | ITEAILPEY | DENV3 | 3 | | LITVSGLYPL | DENV4 | 53 |
| | TTEVILPEY | DENV3 | 1 | $NS3_{1465-1473}$ | AAAWYLWEV | DENV2 | 157 |
| | TTEAILPEY | DENV3 | 75 | | LFVWCFWQK | DENV1 | 1 |
| | SVEVELPDY | DENV4 | 2 | | LFLWYFWQK | DENV1 | 1 |
| | SVEVKLPDY | DENV4 | 51 | | LFVWHFWQK | DENV1 | 6 |

TABLE 3-continued Conservancy and Variants of Epitopes Identified - CD8 Epitopes

| Epitope | Sequence (SEQ ID NOs: 266-300) in order of appearance | Serotype | Counts | Epitope | Sequence (SEQ ID NOs: 301-763) in order of appearance | Serotype | Counts |
|---|---|---|---|---|---|---|---|
| NS1$_{1090-1099}$ | RSCTLPPLRY | DENV2 | 171 | | FFVWYFWQK | DENV1 | 1 |
| | RSCTLPPLRF | DENV1 | 162 | | PFVWYFWQK | DENV1 | 1 |
| | RSCTLPPLRY | DENV2 | 171 | | LFVWYFWQK | DENV1 | 152 |
| | RSCTLPPLRY | DENV3 | 169 | | AAAWYLWET | DENV2 | 13 |
| | RSCTMPPLRF | DENV4 | 53 | | AAAWYLWEA | DENV2 | 1 |
| NS2A$_{1192-1200}$ | MTDDIGMGV | DENV2 | 143 | | AAAWYLWEV | DENV2 | 157 |
| | ASDRMGMGM | DENV1 | 1 | | LLVWHAWQK | DENV3 | 1 |
| | ASDMMGMGT | DENV1 | 2 | | MLVWHTWQK | DENV3 | 1 |
| | ASDKMGMGT | DENV1 | 24 | | LLVWHTWQK | DENV3 | 167 |
| | ASDNMGMGT | DENV1 | 11 | | MALWYIWQV | DENV4 | 9 |
| | VSDRMGMGT | DENV1 | 6 | | MTLWYMWQV | DENV4 | 42 |
| | ASDRMGMGT | DENV1 | 118 | | MALWYMWQV | DENV4 | 2 |
| | MADDIGMGV | DENV2 | 12 | NS3$_{1681-1689}$ | YLPAIVREA | DENV2 | 170 |
| | MTDEMGMGV | DENV2 | 14 | | YLPAIIREA | DENV1 | 1 |
| | ITDDIGMGV | DENV2 | 2 | | YLPAIVREA | DENV1 | 158 |
| | MTDDIGMGV | DENV2 | 143 | | YLPAMVREA | DENV1 | 3 |
| | ASDRTGMGV | DENV3 | 1 | | SLPAIVREA | DENV2 | 1 |
| | ASDKMGMGV | DENV3 | 4 | | YLPAIVREA | DENV2 | 170 |
| | ATDRMGMGV | DENV3 | 1 | | YLPTIVREA | DENV3 | 2 |
| | ASDRMGMGV | DENV3 | 163 | | YLPAVVREA | DENV3 | 1 |
| NS2A$_{1251-1259}$ | LTDALALGM | DENV2 | 156 | | YLPAIVREA | DENV3 | 163 |
| | LGDGLAIGI | DENV1 | 1 | | YLPAIIREA | DENV3 | 3 |
| | LGDGFAMGI | DENV1 | 1 | | ILPSIVREA | DENV4 | 53 |
| | LGDGLAMGI | DENV1 | 160 | NS3$_{2013-2022}$ | DLMRRGDLPV | DENV2 | 157 |
| | LTDAIALGI | DENV2 | 13 | | DLLRRGDLPV | DENV1 | 1 |
| | LTDAWALGM | DENV2 | 1 | | ELMRRGDLPV | DENV1 | 161 |
| | LTDALALGI | DENV2 | 1 | | DLMKRGDLPV | DENV2 | 11 |
| | LTDALALGM | DENV2 | 156 | | ELMRRGDLPV | DENV2 | 3 |
| | MANGVALGL | DENV3 | 2 | | DLMRRGDLPV | DENV2 | 157 |
| | MANGIALGL | DENV3 | 167 | | ELMRRGHLPV | DENV3 | 2 |
| | LISGISLGL | DENV4 | 1 | | ELMRRGDLPV | DENV3 | 167 |
| | FIDGLSLGL | DENV4 | 1 | | ELMKRGDLPV | DENV4 | 2 |
| | LIDGISLGL | DENV4 | 45 | | ELMRRGDLPV | DENV4 | 51 |
| | LIDGISLGL | DENV4 | 1 | NS4A$_{2140-2148}$ | ALSELPETL | DENV2 | 169 |
| | FIDGISLGL | DENV4 | 5 | | ALEELPDTI | DENV1 | 5 |
| NS4B$_{2399-2407}$ | VIDLDPIPY | DENV2 | 90 | | AVEELPDTI | DENV1 | 1 |
| | TIDLDPVVY | DENV1 | 6 | | AMEELPDTI | DENV1 | 156 |
| | AIDLDPVVY | DENV1 | 156 | | ALSELAETL | DENV2 | 1 |
| | VIDLEPIPY | DENV2 | 81 | | ALGELPETL | DENV2 | 1 |
| | VIDLDPIPY | DENV2 | 90 | | ALSELPETL | DENV2 | 169 |
| | TIDLDSVIF | DENV3 | 1 | | AVEELPETM | DENV3 | 169 |
| | TIDLDPVIY | DENV3 | 167 | | ALNELTESL | DENV4 | 1 |
| | TIALDPVIY | DENV3 | 1 | | ALNELPESL | DENV4 | 52 |
| | VIDLEPISY | DENV4 | 53 | NS4A$_{2205-2213}$ | IILEFFLIV | DENV2 | 170 |
| NS5$_{3375-3383}$ | YTDYMPSMK | DENV2 | 168 | | IILKFFLMV | DENV1 | 1 |
| | YSDYMTSMK | DENV1 | 8 | | IILEFFLLMV | DENV1 | 1 |
| | YLDYMASMK | DENV1 | 1 | | IMLEFFLMV | DENV1 | 1 |
| | YIDYMTSMK | DENV1 | 1 | | IILEFFLMV | DENV1 | 159 |
| | YLDFMTSMK | DENV1 | 6 | | IILEFFLMV | DENV2 | 1 |
| | YLDYMTSMK | DENV1 | 143 | | IILEFFLIV | DENV2 | 170 |
| | YLDYMISMK | DENV1 | 2 | | IILEFFMMV | DENV3 | 1 |
| | YIDYMPSMK | DENV2 | 1 | | IVLEFFMMV | DENV3 | 168 |
| | YMDYMPSMK | DENV2 | 2 | | IILEFFLMV | DENV4 | 53 |
| | YTDYMPSMK | DENV2 | 168 | NS5$_{3058-3066}$ | KLAEAIFKL | DENV2 | 162 |
| | FLDYMPSMK | DENV3 | 169 | | LLAKAIFKL | DENV1 | 15 |
| | YADYMPVMK | DENV4 | 1 | | QLAKSIFKL | DENV1 | 1 |
| | YMDYMPVMK | DENV4 | 1 | | LLATSVFKL | DENV1 | 1 |
| | YVDYMPAMK | DENV4 | 5 | | LLAKSIFKL | DENV1 | 26 |
| | YVDYMPVMR | DENV4 | 2 | | LLATAIFKL | DENV1 | 1 |
| | YVDYMPVMK | DENV4 | 44 | | LLATSIFKL | DENV1 | 117 |
| E$_{631-639}$ | RLITVNPIV | DENV2 | 168 | | LLASSIFKL | DENV1 | 1 |
| | RVITANPIV | DENV1 | 7 | | KLAEAIFRL | DENV2 | 6 |
| | RLVTANPIV | DENV1 | 11 | | RLAEAIFKL | DENV2 | 2 |
| | RLITANPIV | DENV1 | 144 | | KLAEAVFKL | DENV2 | 1 |
| | RLITVNPVV | DENV2 | 1 | | KLAEAIFKL | DENV2 | 162 |
| | RLITVNPII | DENV2 | 1 | | QLASAIFKL | DENV3 | 6 |
| | RLITVNPIV | DENV2 | 168 | | LLANAIFKL | DENV3 | 1 |
| | RLTTVNPIV | DENV2 | 1 | | RLANAIFKL | DENV3 | 2 |
| | RLITANPIV | DENV3 | 11 | | QLANAIFKL | DENV3 | 160 |
| | RLITANPVV | DENV3 | 158 | | TLAKAIFKL | DENV4 | 9 |
| | RVISATPLA | DENV4 | 11 | | ILAKAIFKL | DENV4 | 44 |
| | RVISSTPLA | DENV4 | 15 | NS3$_{1509-1517}$ | SQIGAGVYK | DENV2 | 168 |

TABLE 3-continued

Conservancy and Variants of Epitopes Identified - CD8 Epitopes

| Epitope | Sequence (SEQ ID NOs: 266-300) in order of appearance | Serotype | Counts | Epitope | Sequence (SEQ ID NOs: 301-763) in order of appearance | Serotype | Counts |
|---|---|---|---|---|---|---|---|
| | RIISSTPLA | DENV4 | 9 | | SQVGVGVFQ | DENV1 | 162 |
| | RVISSTPFA | DENV4 | 1 | | SQIGAGVYR | DENV2 | 1 |
| | RIISSTPFA | DENV4 | 16 | | SQIGTGVYK | DENV2 | 1 |
| | RIISSIPFA | DENV4 | 1 | | SQIGVGVYK | DENV2 | 1 |
| NS2B$_{1355-1363}$ | IMAVGMVSI | DENV2 | 157 | | SQIGAGVYK | DENV2 | 168 |
| | IMAVGVVSI | DENV1 | 2 | | TQVGVGIQK | DENV3 | 3 |
| | VMAVGIVSI | DENV1 | 1 | | TQVGVGVHK | DENV3 | 2 |
| | IMAIGIVSI | DENV1 | 64 | | TQVGVGVQK | DENV3 | 164 |
| | IMAVGIVSI | DENV1 | 95 | | TQVGVGIHI | DENV4 | 4 |
| | VMAVGMVSI | DENV2 | 14 | | TQVGVGIHT | DENV4 | 1 |
| | IMAVGMVSI | DENV2 | 157 | | TQVGVGIHM | DENV4 | 47 |
| | VMAIGLVSI | DENV3 | 3 | | TQVGVGVHV | DENV4 | 1 |
| | VMAVGLVSI | DENV3 | 166 | NS3$_{1608-1617}$ | GTSGSPIIDK | DENV2 | 49 |
| | MMAVGLVSL | DENV4 | 1 | | GTSGSPIVSR | DENV1 | 1 |
| | IMAVGLVSL | DENV4 | 52 | | GTSGSPIVNR | DENV1 | 161 |
| NS2B$_{1383-1391}$ | GLLTVCYVL | DENV2 | 170 | | GTSGSPIIDK | DENV2 | 49 |
| | GMLITCYVI | DENV1 | 1 | | GTSGSPIADK | DENV2 | 1 |
| | GMLIACYVI | DENV1 | 161 | | GTSGSPIVDR | DENV2 | 75 |
| | GPLTVCYVL | DENV2 | 1 | | GTSGSPIVDK | DENV2 | 46 |
| | GLLTVCYVL | DENV2 | 170 | | GTSGSPIINK | DENV3 | 1 |
| | GMLIACYVI | DENV3 | 2 | | GTSGSPIINR | DENV3 | 168 |
| | GLLIACYVI | DENV3 | 167 | | GSSGSPIINR | DENV4 | 1 |
| | GLLLAAYMM | DENV4 | 1 | | GTSGSPIVNR | DENV4 | 1 |
| | GLLLAAYVM | DENV4 | 52 | | GTSGSPIINK | DENV4 | 13 |
| NS4A$_{2074-2083}$ | RIYSDPLALK | DENV2 | 153 | | GTSGSPIINR | DENV4 | 38 |
| | RTYSDPQALR | DENV1 | 1 | NS3$_{1863-1871}$ | KTFDSEYVK | DENV2 | 129 |
| | RTYSDPLALR | DENV1 | 161 | | KTFDTEYQK | DENV1 | 162 |
| | RTYSDPLALK | DENV2 | 13 | | KTFDTEYTK | DENV2 | 5 |
| | RIYSDPLTLK | DENV2 | 2 | | KTFDTEYIK | DENV2 | 7 |
| | KIYSDPLALK | DENV2 | 2 | | KTFDFEYIK | DENV2 | 1 |
| | RIYSEPRALK | DENV2 | 1 | | KTFDSEYIK | DENV2 | 26 |
| | RIYSDPLALK | DENV2 | 153 | | KTFDSEYAK | DENV2 | 3 |
| | RTYSDPLAPK | DENV3 | 1 | | KTFDSEYVK | DENV2 | 129 |
| | RTYSDPLALK | DENV3 | 167 | | KTFDTEYQR | DENV3 | 1 |
| | RIYSDPLALK | DENV3 | 1 | | KTFNTEYQK | DENV3 | 1 |
| | RVYADPMALQ | DENV4 | 1 | | KTFDTEYQK | DENV3 | 167 |
| | RVYADPMALK | DENV4 | 52 | | KTFDTEYPK | DENV4 | 53 |
| NS4B$_{2315-2323}$ | ATVLMGLGK | DENV2 | 168 | NS3$_{2070-2078}$ | KPRWLDARI | DENV2 | 155 |
| | AAILMGLDK | DENV1 | 162 | | KPRWLDART | DENV1 | 162 |
| | ATVLMGLGK | DENV2 | 168 | | KPRWLDART | DENV2 | 13 |
| | ATVLMGLGR | DENV2 | 3 | | KPRWLDAKI | DENV2 | 2 |
| | AVVLMGLNK | DENV3 | 1 | | KPRWLDPRI | DENV2 | 1 |
| | AVVLMGLDK | DENV3 | 168 | | KPRWLDARI | DENV2 | 155 |
| | AAVLMGLGK | DENV4 | 53 | | RPRWLDART | DENV3 | 168 |
| NS5$_{2608-2616}$ | STYGWNLVR | DENV2 | 171 | | RPRWLDARI | DENV3 | 1 |
| | AAYGWNLVK | DENV1 | 1 | | RPRWLDARV | DENV4 | 24 |
| | ATYGWNLVK | DENV1 | 161 | | RPKWLDARV | DENV4 | 29 |
| | STYGWNLVR | DENV2 | 171 | NS4B$_{2280-2289}$ | RPASAWTLYA | DENV2 | 171 |
| | STYGWNLVK | DENV3 | 3 | | HPASAWTLYA | DENV1 | 102 |
| | STYGWNVVK | DENV3 | 1 | | RPASAWTLYA | DENV1 | 60 |
| | STYGWNIVK | DENV3 | 165 | | RPASAWTLYA | DENV2 | 171 |
| | ATYGWNLVK | DENV4 | 53 | | HPASAWILYA | DENV3 | 1 |
| NS5$_{3079-3087}$ | TVMDIISRR | DENV2 | 155 | | HPASAWTLYA | DENV3 | 168 |
| | TVMDIISRR | DENV1 | 1 | | RPASAWTLYA | DENV4 | 53 |
| | TVMDVISRR | DENV1 | 161 | NS4B$_{2296-2303}$ | TPMLRHSI | DENV2 | 171 |
| | TVLDIISRR | DENV2 | 1 | | TPMLRHTI | DENV1 | 1 |
| | TVMDIISRK | DENV2 | 15 | | TPMMRHTI | DENV1 | 161 |
| | TVMDIISRR | DENV2 | 155 | | TPMLRHSI | DENV2 | 171 |
| | TVMDIISRK | DENV3 | 169 | | TPMLRHTI | DENV3 | 169 |
| | AVMDIISRK | DENV4 | 53 | | TPMLRHTI | DENV4 | 53 |
| NS5$_{3112-3291}$ | RQMEGEGVFK | DENV2 | 74 | NS5$_{2646-2655}$ | SPNPTVEAGR | DENV2 | 92 |
| | RQMESEEIFS | DENV1 | 1 | | SPNPTIEEGR | DENV1 | 162 |
| | RQMESEGIVS | DENV1 | 1 | | SPSPTVEAGR | DENV2 | 1 |
| | RQMESEGIFF | DENV1 | 5 | | SPNPTVDAGR | DENV2 | 1 |
| | RQMESEGIIL | DENV1 | 1 | | SPNPTVEAGP | DENV2 | 1 |
| | RQMESEGIFS | DENV1 | 87 | | SPNPTIEAGR | DENV2 | 76 |
| | RQMESEGIFL | DENV2 | 67 | | SPNPTVEAGR | DENV2 | 92 |
| | RQMEGEGVFR | DENV2 | 1 | | SPSPTVEEGR | DENV3 | 1 |
| | RQMEGEGIFR | DENV2 | 1 | | SPSLTVEESR | DENV3 | 1 |
| | RQMEGEGLFK | DENV2 | 13 | | SPSPIVEESR | DENV3 | 1 |
| | RQMEGEEVFK | DENV2 | 1 | | SPSPTVEESR | DENV3 | 166 |
| | RQMEGEGVFK | DENV2 | 74 | | SSNPTIEEGR | DENV4 | 53 |

TABLE 3-continued

Conservancy and Variants of Epitopes Identified - CD8 Epitopes

| Epitope | Sequence (SEQ ID NOs: 266-300) in order of appearance | Serotype | Counts | Epitope | Sequence (SEQ ID NOs: 301-763) in order of appearance | Serotype | Counts |
|---|---|---|---|---|---|---|---|
| | RQMEGEGIFK | DENV2 | 81 | NS5$_{2885-2894}$ | TPRMCTREEF | DENV2 | 152 |
| | RQMEGEGVLT | DENV3 | 12 | | KPRICTREEF | DENV1 | 162 |
| | RQMEGEGVLS | DENV3 | 155 | | RPRICTRAEF | DENV2 | 1 |
| | RQMEGEDVLS | DENV3 | 2 | | KPRICTRAEF | DENV2 | 12 |
| | RQMEAEGVIT | DENV4 | 53 | | TRRMCTREEF | DENV2 | 1 |
| NS5$_{3283-3291}$ | RTTWSIHAK | DENV2 | 111 | | TPRICTREEF | DENV2 | 3 |
| | RTTWSIHAH | DENV1 | 162 | | IPRMCTREEF | DENV2 | 2 |
| | RTTWSIHAR | DENV2 | 8 | | TPRMCTREEF | DENV2 | 152 |
| | RTTWSIHAT | DENV2 | 31 | | KPRLCPREEF | DENV3 | 1 |
| | RTTWSIHAS | DENV2 | 21 | | KPRLCTREEF | DENV3 | 88 |
| | RTTWSIHAK | DENV2 | 111 | | RPRLCTREEF | DENV3 | 80 |
| | RTTWSIHAH | DENV3 | 169 | | NPRLCTKEEF | DENV4 | 1 |
| | RTTWSIHAH | DENV4 | 53 | | SPRLCTREEF | DENV4 | 6 |
| NS2A$_{1212-1221}$ | RPTFAAGLLL | DENV2 | 158 | | TPRLCTREEF | DENV4 | 2 |
| | RPMLAVGLLF | DENV1 | 1 | | SPRLCTKEEF | DENV4 | 2 |
| | RPMFAMGLLF | DENV1 | 1 | | NPRLCTREEF | DENV4 | 41 |
| | RPMFAVGLLI | DENV1 | 4 | | KPRLCTREEF | DENV4 | 1 |
| | RPMFAVGLLF | DENV1 | 156 | NS5$_{3077-3085}$ | RPTPRGTVM | DENV2 | 166 |
| | RPTFAAGLFL | DENV2 | 1 | | RPVKNGTVM | DENV1 | 1 |
| | RPTFAVGLVL | DENV2 | 1 | | RPARNGTVM | DENV1 | 1 |
| | RPTFAVGLLL | DENV2 | 11 | | RPAKNGTVM | DENV1 | 147 |
| | RPTFAAGLLL | DENV2 | 158 | | RPAKSGTVM | DENV1 | 13 |
| | QPFLALGFFM | DENV3 | 1 | | RPTPRGTVL | DENV2 | 1 |
| | QPFLTLGFFL | DENV3 | 1 | | RPTPKGTVM | DENV2 | 2 |
| | QPFLALGFFL | DENV3 | 167 | | RPTPIGTVM | DENV2 | 2 |
| | SPRYVLGVFL | DENV4 | 1 | | RPTPRGTVM | DENV2 | 166 |
| | SPGYVLGVFL | DENV4 | 46 | | RPTPKGTVM | DENV3 | 89 |
| | SPGYVLGIFL | DENV4 | 6 | | RPTPTGTVM | DENV3 | 80 |
| NS3$_{1682-1690}$ | LPAIVREAI | DENV2 | 171 | | RPTPRGAVM | DENV4 | 35 |
| | LPAIIREAI | DENV1 | 1 | | RPTPKGAVM | DENV4 | 18 |
| | LPAIVREAI | DENV1 | 158 | C$_{53-67}$ | AFLRFLTIPPTAGIL | DENV2 | 169 |
| | LPAMVREAI | DENV1 | 3 | | AFLRFLAIPPTAGIV | DENV1 | 1 |
| | LPAIVREAI | DENV2 | 171 | | ALLRFLAIPPTAGIL | DENV2 | 2 |
| | LPTIVREAI | DENV3 | 2 | | AFLTFLAIPPTAGIL | DENV1 | 1 |
| | LPAVVREAI | DENV3 | 1 | | AFLRFLAIPPTAGIL | DENV1 | 158 |
| | LPAIVREAI | DENV3 | 163 | | AFLRFLTIPPTAGIL | DENV2 | 1 |
| | LPAIIREAI | DENV3 | 3 | | AFLRFLTIPPTVGIL | DENV2 | 1 |
| | LPSIVREAL | DENV4 | 53 | | AFLRFLTIPPTAGIL | DENV2 | 169 |
| NS3$_{1700-1709}$ | APTRVVAAEM | DENV2 | 170 | | AFLRFLAIPPTAGIL | DENV3 | 20 |
| | APTRVVASET | DENV1 | 1 | | AFLRFLAIPPTAGVL | DENV3 | 149 |
| | APTRVVAAEM | DENV1 | 1 | | TFLRVLSIPPTAGIL | DENV4 | 53 |
| | APTRVVASEM | DENV1 | 160 | NS2A$_{1199-1213}$ | GVTYLALLAAFKVRP | DENV2 | 156 |
| | APPRVVPAEM | DENV2 | 1 | | GTTYLALMATFRMRP | DENV1 | 27 |
| | APTRVVAAEM | DENV2 | 170 | | GMTYLALMATFKMRP | DENV1 | 1 |
| | APTRVVAAEM | DENV3 | 169 | | GTTYLALMATLKMRP | DENV1 | 1 |
| | APTRVVAAEM | DENV4 | 53 | | GTTHLALMATFKMRP | DENV1 | 2 |
| NS3$_{1753-1761}$ | VPNYNLIIM | DENV2 | 171 | | GTTYLALMATFKMRP | DENV1 | 131 |
| | VPNYNMIIV | DENV1 | 1 | | GVTYLALLATFKVRP | DENV2 | 1 |
| | VPNYNMIIM | DENV1 | 160 | | GVTYLALLAAYKVRP | DENV2 | 2 |
| | VPNYNMIVM | DENV1 | 1 | | GVTYLALLAAFRVRP | DENV2 | 12 |
| | VPNYNLIIM | DENV2 | 171 | | GVTYLALLAAFKVRP | DENV2 | 156 |
| | VPNYNLIVM | DENV3 | 11 | | GVTYLALIATFEIQP | DENV3 | 1 |
| | VPNYNLVVM | DENV3 | 1 | | GVTCLALIATFKIQP | DENV3 | 1 |
| | VPNYNLVIM | DENV3 | 6 | | GVTYLALIATFKVQP | DENV3 | 1 |
| | VSNYNLIIM | DENV3 | 1 | | GVTYLALIATFKIQP | DENV3 | 166 |
| | VPNYNLIIM | DENV3 | 150 | | GQTHLAIMAVFKMSP | DENV4 | 23 |
| | VPNYNLIVM | DENV4 | 53 | | GQIHLAIMAVFKMSP | DENV4 | 24 |
| NS3$_{1808-1817}$ | APIMDEEREI | DENV2 | 131 | | GQTHLAIMIVFKMSP | DENV4 | 2 |
| | AIIQDEERDI | DENV1 | 1 | | GQVHLAIMAVFKMSP | DENV4 | 3 |
| | AVIQDEEKDI | DENV1 | 13 | | GQIHLAIMTMFKMSP | DENV4 | 1 |
| | AAIQDEERDI | DENV1 | 3 | NS3$_{1356-1370}$ | MAVGMVSILASSLLK | DENV2 | 171 |
| | AVIQDEERDI | DENV1 | 145 | | MAVGVVSILLSSLLK | DENV1 | 2 |
| | APIMDDEREI | DENV2 | 1 | | MAIGIVSILLSSLLK | DENV1 | 64 |
| | APIIDEEREI | DENV2 | 30 | | MAVGIVSILLSSLLK | DENV1 | 96 |
| | APIVDEEREI | DENV2 | 9 | | MAVGMVSILASSLLK | DENV2 | 171 |
| | APIMDEEREI | DENV2 | 131 | | MAVGLVSILASSFLR | DENV3 | 11 |
| | APIQDEEKDI | DENV3 | 2 | | MAIGLVSILASSLLR | DENV3 | 3 |
| | SPIQDEERDI | DENV3 | 1 | | MAVGLVSILASSLLR | DENV3 | 155 |
| | APIQDEERDI | DENV3 | 164 | | MAVGLVSLLGSALLK | DENV4 | 53 |
| | APIQDKERDI | DENV3 | 2 | NS3$_{1742-1756}$ | TFTMRLLSPVRVPNY | DENV2 | 120 |
| | SPIEDIEREI | DENV4 | 53 | | TFTMRLLSPVRVPNY | DENV1 | 162 |

TABLE 3-continued

Conservancy and Variants of Epitopes Identified - CD8 Epitopes

| Epitope | Sequence (SEQ ID NOs: 266-300) in order of appearance | Serotype | Counts | Epitope | Sequence (SEQ ID NOs: 301-763) in order of appearance | Serotype | Counts |
|---|---|---|---|---|---|---|---|
| NS3₁₉₇₈₋₁₉₈₇ | TPEGIIPSMF | DENV2 | 170 | | PFTMRLLSPVRVPNY | DENV2 | 1 |
| | TPEGIIPALY | DENV1 | 1 | | TFTMRLLSPIRVPNY | DENV2 | 50 |
| | TPEGIIPALF | DENV1 | 161 | | TFTMRLLSPVRVPNY | DENV2 | 120 |
| | TPEGIIPSLF | DENV2 | 1 | | TFTMRLLSPVRVSNY | DENV3 | 1 |
| | TPEGIIPSMF | DENV2 | 170 | | PFTMRLLSPVRVPNY | DENV3 | 1 |
| | TPEGIIPALF | DENV3 | 169 | | TFTMRLLSPVRVPNY | DENV3 | 167 |
| | TPEGIIPTLF | DENV4 | 53 | | TFTFKLLSSTRVPNY | DENV4 | 1 |
| | | | | | TFTFALLSSTRVPNY | DENV4 | 52 |
| | | | | NS5₂₉₆₆₋₂₉₈₀ | SRAIWYMWLGARFLE | DENV2 | 171 |
| | | | | | SRAIWYVWLGARFLE | DENV1 | 1 |
| | | | | | SRAIWYMWLGAAFLE | DENV1 | 1 |
| | | | | | SRAIWYMWLGARFLE | DENV1 | 160 |
| | | | | | SRAIWYMWLGARFLE | DENV2 | 171 |
| | | | | | SRAIWYMWLGARFLE | DENV3 | 5 |
| | | | | | SRAIWYMWLGVRYLE | DENV3 | 1 |
| | | | | | SRAIWYMWLGARYLE | DENV3 | 163 |
| | | | | | SRAIWYMWLGARFLE | DENV4 | 53 |

Example 15

This example includes a discussion of the foregoing data and conclusions based upon the data.

Wild-type mice are resistant to DENV-induced disease, and therefore, development of mouse models for DENV infection to date has been challenging and has had to rely on infection of immunocompromised mice, non-physiologic routes of infection, and mouse-human chimeras (Yauch, et al. *Antiviral Res* 80:87 (2008)). Due to the importance of the IFN system in the host antiviral response, mice lacking the IFNR-α/β support a productive infection. A mouse-passaged DENV2 strain, S221, is highly immunogenic and also replicates to high levels in IFNR-α/β−/− mice, thus allowing the study of CD4+ and CD8+ T cell responses in DENV infection. In this murine model, vaccination with T cell epitopes prior to S221 infection provided significant protection (Yauch, et al. *J Immunol* 185:5405 (2010); Yauch, et al. *J Immunol* 182:4865 (2009)). While significant differences exist between human and murine TCR repertoires and processing pathways, HLA transgenic mice are fairly accurate models of human immune responses, especially when peptide immunizations are utilized. Numerous studies to date show that these mice develop T cell responses that mirror the HLA restricted responses observed in humans in context of various pathogens (Gianfrani, et al. *Hum Immunol* 61:438 (2000); Wentworth, et al. *Eur J Immunol* 26:97 (1996); Shirai, et al. *J Immunol* 154:2733 (1995); Ressing, et al. *J Immunol* 154:5934 (1995); Vitiello, et al. *J Exp Med* 173:1007 (1991); Diamond, et al. *Blood* 90:1751 (1997); Firat, et al. *Eur J Immunol* 29:3112 (1999); Le, et al. *J Immunol* 142:1366 (1989); Man, et al. *Int Immunol* 7:597 (1995)).

The data disclosed herein demonstrate that HLA transgenic IFNRα/β−/− mice are a valuable model to identify DENV epitopes recognized in humans. Not only were a number of HLA-restricted T cell responses identified, but the genome wide screen provided further insight into the subproteins targeted by T cells during DENV infection. The majority of DENV responses (97%) was derived from the nonstructural proteins; more than half of the epitopes identified originate from the NS3 and NS5 protein. The data show the immunodominant role of the highly conserved NS3 protein (Rothman *Adv Virus Res* 60:397 (2003); Duangchinda, et al. *Proc Natl Acad Sci USA* 107:16922 (2010)), and also suggest NS5 as a major target of T cell responses. Interestingly, proteins previously described as antibody targets (prM, E and NS1) (Rothman *J Clin Invest* 113:946 (2004)) accounted for less than 5% of all responses, with only 3 epitopes identified from these proteins. The observation that T cell and B cell epitopes after primary DENV infection are not derived from the same proteins may factor in vaccine design, since immunizing with NS3 and NS5 T cell epitopes would induce a robust T cell response without the risk of antibody-dependent-enhancement (ADE).

Another unique challenge in vaccine development is the high degree of sequence variation in a pathogen, characteristically associated with RNA viruses. This is of particular relevance in the case of DENV infections, where it is well documented that prior exposure to a different serotype may lead to more severe disease and immunopathology (Sangkawibha, et al. *Am J Epidemiol* 120:653 (1984)). The fact that there is also significant genetic variation within each serotype adds to the complexity of successful vaccinations (Twiddy, et al. *Virology* 298:63 (2002); Holmes, et al. *Trends Microbiol* 8:74 (2000)). It is hypothesized that in certain cases, peptide variants derived from the original antigen in the primary infection, with substitutions at particular residues, can induce a response that is qualitatively different from the response induced by the original antigen (for example inducing a different pattern of lymphokine production; Partial agonism), or even actively suppressing the response (TCR antagonism). Variants associated with this phenotype are often collectively referred to as Altered Peptide Ligands (APLs) (Yachi, et al. *Immunity* 25:203 (2006)). During secondary infections, the T cell response directed at the APL may lead to altered or aberrant patterns of lymphokine production, and TCR antagonist mediated inhibition of T cell responses (Kast, et al. *J Immunol* 152:3904 (1994)). Therefore, immunity to all four serotypes would provide an optimal DENV vaccine. It is generally recognized that conserved protein sequences represent important functional domains (Valdar *Proteins* 48:227

(2002)), thus mutations at these important protein sites could be detrimental to the survival of the virus. T cell epitopes that target highly conserved regions of a protein are therefore likely to target the majority of genetic variants of a pathogen (Khan, et al. *Cell Immunol* 244:141 (2006)). Most interestingly in this context was that epitopes that are highly conserved within the DENV2 serotype are the major target for T cells. This data suggests, that immunizations with peptides from a given serotype would protect from the majority of genotypes within this serotype. In contrast, the DENV2 derived epitopes identified are not conserved in other serotypes. These findings point to an immunization strategy with a collection of multiple non-crossreactive epitopes derived from each of the major DENV serotypes. The induction of separate non-crossreactive responses would avoid issues arising from incomplete crossreaction and APL/TCR antagonism effects.

In addition to sequence variation, HLA polymorphism adds to the complexity of studying T cell responses to DENV. MHC molecules are extremely polymorphic, with several hundred different variants known in humans (Klein, Natural History of the Major Histocompatibility Complex (1986); Hughes, et al. *Nature* 355:402 (1992)). Therefore, selecting multiple peptides matching different MHC binding specificities will increase coverage of the patient population for diagnostic and vaccine applications alike. However, different MHC types are expressed at dramatically different frequencies in different ethnicities. To address this issue, IFNR-α/β−/− mice were backcrossed with mice transgenic for HLA A*0101, A*0201, A*1101, B*0702 and DRB1*0101. These four MHC class I alleles were chosen as representatives of four supertypes (A1, A2, A3 and B7, respectively) and allow a combined coverage of approximately 90% of the worldwide human population (Sette, et al. *Immunogenetics* 50:201 (1999)), with more than 50% expressing the specific alleles. HLA supertypes are not limited to class I molecules. Several studies have demonstrated the existence of HLA class II supertypes (Doolan, et al. *J Immunol* 165:1123 (2000); Wilson, et al. *J Virol* 75:4195 (2001); Southwood, et al. *J Immunol* 160:3363 (1998)) and functional classification have revealed a surprising degree of repertoire sharing across supertypes (Greenbaum, et al. *Immunogenetics* 63:325 (2011)). This is in accordance with the data, since the DRB1*0101 restricted epitopes were identified in almost every donor, regardless if the donor was expressing the actual allele. Overall, the mouse model significantly reflects the response pattern observed in humans and that HLA B restricted responses seem to be dominant in B*0702 transgenic mice as well as in human donors, expressing the B*0702 allele (FIG. 13F).

The dominance of HLA B responses has been shown in context of several other viruses, such as HIV, EBV, CMV, and Influenza (Kiepiela, et al. *Nature* 432:769 (2004); Bihl, et al. *J Immunol* 176:4094 (2006); Boon, et al. *J Immunol* 172:4435 (2004); Lacey, et al. *Hum Immunol* 64:440 (2003)), suggesting that this observation is not limited to RNA viruses, and in fact, it has even been described for an intracellular bacterial pathogen, *Mycobacterium Tuberculosis* (Lewinsohn, et al. *PLoS Pathog* 3:1240 (2007); Axelsson-Robertson, et al. *Immunology* 129:496 (2010)). Furthermore, HLA B restricted T cell responses have been described to be of higher magnitude (Bihl, et al. *J Immunol* 176:4094 (2006)) and to influence infectious disease course and outcome. In case of DENV, one particular B07 epitope was reported to elicit higher responses in patients with DHF compared to patients suffering from DF only and could therefore be associated with disease outcome (Zivna, et al. *J Immunol* 168:5959 (2002)). Other reports suggest a role for HLA B44, B62, B76 and B77 alleles in protection against developing clinical disease after secondary DENV infection, whereas other alleles were associated with contribution to pathology (Stephens, et al. *Tissue Antigens* 60:309 (2002); Appanna, et al. *PLoS One* 5 (2010). Accordingly, HLA alleles appear to be associated with clinical outcome of exposure to dengue virus, in previously exposed and immunologically primed individuals. The fact that the stronger B*07 response occurs in our human samples as well as in our mouse model of DENV infection validates the relevance of this mouse model, since it even mimics patterns of immuno-dominance observed in humans.

Example 16

This example includes a description of studies showing the identification of T cell responses against additional DENV-derived peptides in human donors.

Peripheral blood samples were obtained from healthy adult blood donors from the National Blood Center in Colombo, Sri Lanka. DENV-seropositivity was determined by ELISA. Those samples that are positive for DENV-specific IgM or IgG are further examined by the FACS based neutralization assay to determine whether the donor may have been exposed to single or multiple DENV serotypes. For MHC class I binding predictions all 9- and 10-mer peptides were predicted for their binding affinity to their respective alleles. Binding predictions were performed using the command-line version of the consensus prediction tool available on the IEDB web site. Peptides were selected if they were in the top 1% of binders.

As HLA typing and ELISA results were available, donor samples were tested such that predicted peptides for all four serotypes were tested against all appropriate and available HLA types expressed by the donor. DENV specific T cell responses were detected directly ex vivo from our Sri Lankan donor cohort, as measured by an IFNγ ELISPOT assay. Epitopes that have been identified in one or more donors are listed in Table 4.

TABLE 4

Human Donor Table and DENV Epitopes

| # | Protein location Start position | Protein location End position | Sequence (SEQ ID NOs: 555-763) in order of appearance | Supertype | Allele | Length | Serotype | T cell response [SFC] | HLA-Binding [IC50] |
|---|---|---|---|---|---|---|---|---|---|
| 1 | 43 | 51 | GPMKLVMAF | B7 | B*0702 | 9 | DENV1 | 32 | 13 |
| 2 | 43 | 52 | GPMKLVMAFI | B7 | B*0702 | 10 | DENV1 | 62 | 86 |

TABLE 4-continued Human Donor Table and DENV Epitopes

| # | Protein location Start position | End position | Sequence (SEQ ID NOs: 555-763) in order of appearance | Supertype | Allele | Length | Serotype | T cell response [SFC] | HLA-Binding [IC50] |
|---|---|---|---|---|---|---|---|---|---|
| 3 | 49 | 57 | MAFIAFLRF | B7 | B*3501 | 9 | DENV1 | 82 | 3 |
| 4 | 75 | 83 | KSGAIKVLK | A3 | A*1101 | 9 | DENV3 | 823 | 151 |
| 5 | 104 | 113 | ITLLCLIPTV | A2 | A*0201 | 10 | DENV4 | 43 | 441 |
| 6 | 105 | 114 | CLMMMLPATL | A2 | A*0201 | 10 | DENV3 | 63 | 26 |
| 7 | 105 | 113 | TLLCLIPTV | A2 | A*0201 | 9 | DENV4 | 42 | 1 |
| 8 | 106 | 114 | LMMMLPATL | A2 | A*0201 | 9 | DENV3 | 78 | 22 |
| 9 | 106 | 115 | LMMMLPATLA | A2 | A*0201 | 10 | DENV3 | 50 | 14 |
| 10 | 107 | 115 | MMMLPATLA | A2 | A*0201 | 9 | DENV3 | 62 | 28 |
| 11 | 107 | 116 | MMMLPATLAF | B7 | B*3501 | 10 | DENV3 | 57 | 555 |
| 12 | 108 | 116 | MLIPTAMAF | B7 | B*3501 | 9 | DENV2 | 58 | 422 |
| 13 | 150 | 159 | TLMAMDLGEL | A2 | A*0201 | 10 | DENV2 | 67 | 15 |
| 14 | 164 | 172 | VTYECPLLV | A2 | A*0201 | 9 | DENV4 | 40 | 27 |
| 15 | 245 | 254 | HPGFTILALF | B7 | B*3501 | 10 | DENV3 | 63 | 118 |
| 16 | 248 | 257 | FTIMAAILAY | B7 | B*3501 | 10 | DENV2 | 53 | 4223 |
| 17 | 248 | 257 | FTILALFLAH | B7 | B*3501 | 10 | DENV3 | 32 | 24988 |
| 18 | 249 | 257 | TIMAAILAY | B7 | B*3501 | 9 | DENV2 | 123 | 82 |
| 19 | 274 | 282 | MLVTPSMTM | B7 | B*3501 | 9 | DENV3 | 115 | 3850 |
| 20 | 355 | 363 | CPTQGEATL | B7 | B*3501 | 9 | DENV1 | 143 | 26 |
| 21 | 355 | 363 | CPTQGEAVL | B7 | B*3501 | 9 | DENV3 | 135 | 19 |
| 22 | 363 | 371 | LPEEQDQNY | B7 | B*3501 | 9 | DENV3 | 28 | 1015 |
| 23 | 413 | 421 | YENLKYSVI | B44 | B*4402 | 9 | DENV1 | 37 | 90 |
| 24 | 537 | 545 | QEGAMHSAL | B44 | B*4001 | 9 | DENV4 | 22 | 16 |
| 25 | 537 | 545 | QEGAMHTAL | B44 | B*4001 | 9 | DENV1 | 120 | 5 |
| 26 | 578 | 586 | MSYTMCSGK | A3 | A*1101 | 9 | DENV4 | 48 | 27 |
| 27 | 578 | 587 | MSYSMCTGKF | B7 | B*3501 | 10 | DENV2 | 23 | 10625 |
| 28 | 612 | 621 | SPCKIPFEIM | B7 | B*3501 | 10 | DENV2 | 35 | 7486 |
| 29 | 616 | 625 | IPFEIMDLEK | B7 | B*3501 | 10 | DENV2 | 237 | 6012 |
| 30 | 664 | 673 | EPGQLKLNWF | B7 | B*3501 | 10 | DENV2 | 168 | 42066 |
| 31 | 721 | 729 | FGAIYGAAF | B7 | B*3501 | 9 | DENV2 | 28 | 7667 |
| 32 | 733 | 742 | SWMVRILIGF | A24 | A*2402 | 10 | DENV4 | 90 | 132 |
| 33 | 738 | 746 | IGIGILLTW | B58 | B*5801 | 9 | DENV1 | 23 | 3 |
| 34 | 814 | 823 | SPKRLATAIA | B7 | B*0702 | 10 | DENV3 | 102 | 34 |
| 35 | 845 | 853 | KQIANELNY | B62 | B*1501 | 9 | DENV3 | 22 | 9 |
| 36 | 950 | 959 | VYTQLCDHRL | A24 | A*2402 | 10 | DENV3 | 67 | 6 |
| 37 | 950 | 958 | VYTQLCDHR | A3 | A*3301 | 9 | DENV3 | 28 | 1902 |
| 38 | 968 | 977 | KAVHADMGYW | B58 | B*5801 | 10 | DENV1 | 85 | 1 |

TABLE 4-continued

Human Donor Table and DENV Epitopes

| # | Start position | End position | Sequence (SEQ ID NOs: 555-763) in order of appearance | Supertype | Allele | Length | Serotype | T cell response [SFC] | HLA-Binding [IC50] |
|---|---|---|---|---|---|---|---|---|---|
| 39 | 990 | 999 | RASFIEVKTC | B58 | B*5801 | 10 | DENV1 | 138 | 54 |
| 40 | 1023 | 1032 | FAGPVSQHNY | B7 | B*3501 | 10 | DENV2 | 190 | 38 |
| 41 | 1033 | 1041 | RPGYHTQTA | B7 | B*0702 | 9 | DENV2 | 177 | 10 |
| 42 | 1042 | 1051 | GPWHLGKLEL | B7 | B*0702 | 10 | DENV1 | 53 | 18 |
| 43 | 1042 | 1051 | GPWHLGKLEM | B7 | B*3501 | 10 | DENV2 | 25 | 6069 |
| 44 | 1098 | 1107 | RYMGEDGCWY | A24 | A*2402 | 10 | DENV3 | 182 | 829 |
| 45 | 1136 | 1145 | FTMGVLCLAI | A2 | A*0201 | 10 | DENV3 | 33 | 18 |
| 46 | 1176 | 1185 | MSFRDLGRVM | B7 | B*3501 | 10 | DENV2 | 35 | 469 |
| 47 | 1201 | 1209 | TYLALIATF | A24 | A*2402 | 9 | DENV3 | 82 | 7 |
| 48 | 1211 | 1219 | IQPFLALGF | A24 | A*2402 | 9 | DENV3 | 27 | 268 |
| 49 | 1218 | 1227 | GFFLRKLTSR | A3 | A*3301 | 10 | DENV3 | 230 | 59 |
| 50 | 1230 | 1238 | MMATIGIAL | B7 | B*3501 | 9 | DENV2 | 38 | 1117 |
| 51 | 1298 | 1306 | MALSIVSLF | B7 | B*5101 | 9 | DENV1 | 340 | 605 |
| 52 | 1356 | 1364 | MAVGMVSIL | B7 | B*3501 | 9 | DENV2 | 172 | 10 |
| 53 | 1373 | 1382 | IPMTGPLVAG | B7 | B*3501 | 10 | DENV2 | 182 | 129 |
| 54 | 1377 | 1385 | GPLVAGGLL | B7 | B*0702 | 9 | DENV2 | 35 | 67 |
| 55 | 1418 | 1427 | SPILSITISE | B7 | B*3501 | 10 | DENV2 | 158 | 4189 |
| 56 | 1457 | 1466 | FPVSIPITAA | B7 | B*3501 | 10 | DENV2 | 35 | 14 |
| 57 | 1461 | 1469 | IPITAAAWY | B7 | B*3501 | 9 | DENV2 | 70 | 6 |
| 58 | 1519 | 1527 | MEGVFHTMW | B44 | B*4403 | 9 | DENV4 | 68 | 3 |
| 59 | 1519 | 1528 | MEGVFHTMWH | B44 | B*4403 | 10 | DENV4 | 107 | 73 |
| 60 | 1608 | 1616 | KPGTSGSPI | B7 | B*0702 | 9 | DENV1 | 350 | 2 |
| 61 | 1608 | 1617 | KPGTSGSPII | B7 | B*0702 | 10 | DENV3 | 365 | 35 |
| 62 | 1610 | 1619 | GTSGSPIIDK | A3 | A*1101 | 10 | DENV2 | 32 | 12 |
| 63 | 1614 | 1623 | SPIINREGKV | B7 | B*0702 | 10 | DENV3 | 105 | 313 |
| 64 | 1653 | 1661 | NPEIEDDIF | B7 | B*3501 | 9 | DENV2 | 110 | 518 |
| 65 | 1672 | 1681 | HPGAGKTKRY | B7 | B*3501 | 10 | DENV2 | 108 | 680 |
| 66 | 1682 | 1690 | LPAIVREAI | B7 | B*0702 | 9 | DENV1 | 137 | 7 |
| 67 | 1700 | 1709 | APTRVVAAEM | B7 | B*3501 | 10 | DENV2 | 135 | 20 |
| 68 | 1700 | 1709 | APTRVVASEM | B7 | B*0702 | 10 | DENV1 | 153 | 8 |
| 69 | 1700 | 1709 | APTRVVAAEM | B7 | B*0702 | 10 | DENV2 | 113 | 5 |
| 70 | 1707 | 1716 | SEMAEALKGM | B44 | B*4001 | 10 | DENV1 | 120 | 613 |
| 71 | 1716 | 1724 | LPIRYQTPA | B7 | B*0702 | 9 | DENV2 | 180 | 19 |
| 72 | 1716 | 1725 | LPIRYQTPAI | B7 | B*3501 | 10 | DENV2 | 195 | 52 |
| 73 | 1768 | 1777 | DPASIAARGY | B7 | B*3501 | 10 | DENV1 | 183 | 5623 |
| 74 | 1769 | 1778 | PASIAARGYI | B58 | B*5801 | 10 | DENV1 | 140 | 263 |

TABLE 4-continued

Human Donor Table and DENV Epitopes

| # | Start position | End position | Sequence (SEQ ID NOs: 555-763) in order of appearance | Supertype | Allele | Length | Serotype | T cell response [SFC] | HLA-Binding [IC50] |
|---|---|---|---|---|---|---|---|---|---|
| 75 | 1795 | 1803 | TPPGSRDPF | B7 | B*3501 | 9 | DENV2 | 210 | 161 |
| 76 | 1803 | 1812 | FPQSNAPIMD | B7 | B*3501 | 10 | DENV2 | 107 | 1 |
| 77 | 1803 | 1811 | FPQSNAPIM | B7 | B*3501 | 9 | DENV2 | 127 | 13693 |
| 78 | 1813 | 1822 | EERDIPERSW | B44 | B*4403 | 10 | DENV1 | 190 | 410 |
| 79 | 1815 | 1824 | REIPERSWNT | B44 | B*4001 | 10 | DENV4 | 93 | 1488 |
| 80 | 1872 | 1881 | YPKTKLTDWD | B7 | B*3501 | 10 | DENV4 | 267 | 1317 |
| 81 | 1899 | 1908 | RVIDPRRCMK | A3 | A*1101 | 10 | DENV2 | 93 | 64 |
| 82 | 1899 | 1908 | RVIDPRRCLK | A3 | A*1101 | 10 | DENV1 | 117 | 58 |
| 83 | 1899 | 1908 | RVIDPRRCMK | A3 | A*3101 | 10 | DENV2 | 115 | 4 |
| 84 | 1899 | 1907 | RVIDPRRCL | B7 | B*0702 | 9 | DENV1 | 117 | 146 |
| 85 | 1899 | 1908 | RVIDPRRCMK | A3 | A*0301 | 10 | DENV2 | 160 | 13 |
| 86 | 1902 | 1910 | DPRRCLKPV | B7 | B*0702 | 9 | DENV1 | 115 | 225 |
| 87 | 1925 | 1933 | MPVTHSSAA | B7 | B*3501 | 9 | DENV2 | 60 | 73 |
| 88 | 1925 | 1934 | MPVTHSSAAQ | B7 | B*3501 | 10 | DENV2 | 25 | 933 |
| 89 | 1942 | 1950 | NPAQEDDQY | B7 | B*3501 | 9 | DENV4 | 118 | 136 |
| 90 | 1949 | 1957 | QYIFTGQPL | A24 | A*2402 | 9 | DENV3 | 78 | 271 |
| 91 | 1978 | 1986 | TPEGIIPSM | B7 | B*0702 | 9 | DENV2 | 108 | 254 |
| 92 | 1978 | 1987 | TPEGIIPSMF | B7 | B*0702 | 10 | DENV2 | 27 | 12953 |
| 93 | 1978 | 1986 | TPEGIIPAL | B7 | B*0702 | 9 | DENV1 | 57 | 1214 |
| 94 | 1978 | 1987 | TPEGIIPALF | B7 | B*0702 | 10 | DENV1 | 38 | 1392 |
| 95 | 1978 | 1986 | TPEGIIPSM | B7 | B*3501 | 9 | DENV2 | 295 | 8 |
| 96 | 1978 | 1987 | TPEGIIPSMF | B7 | B*3501 | 10 | DENV2 | 297 | 386 |
| 97 | 1978 | 1987 | TPEGIIPTLF | B7 | B*3501 | 10 | DENV4 | 90 | 94 |
| 98 | 1978 | 1987 | TPEGIIPALF | B7 | B*3501 | 10 | DENV1 | 20 | 160 |
| 99 | 1999 | 2008 | GEFRLRGEQR | B44 | B*4001 | 10 | DENV4 | 273 | 1407 |
| 100 | 2005 | 2014 | GEARKTFVEL | B44 | B*4001 | 10 | DENV1 | 95 | 7 |
| 101 | 2005 | 2014 | GEARKTFVDL | B44 | B*4001 | 10 | DENV2 | 87 | 5 |
| 102 | 2005 | 2014 | GESRKTFVEL | B44 | B*4001 | 10 | DENV3 | 92 | 4 |
| 103 | 2005 | 2014 | GEQRKTFVEL | B44 | B*4001 | 10 | DENV4 | 37 | 5 |
| 104 | 2013 | 2022 | ELMRRGDLPV | A2 | A*0201 | 10 | DENV1 | 28 | 22 |
| 105 | 2020 | 2029 | LPVWLAYKVA | B7 | B*3501 | 10 | DENV2 | 27 | 5097 |
| 106 | 2026 | 2035 | YKVASAGISY | B7 | B*3501 | 10 | DENV4 | 238 | 70 |
| 107 | 2038 | 2047 | REWCFTGERN | B44 | B*4001 | 10 | DENV4 | 48 | 502 |
| 108 | 2070 | 2078 | RPRWLDART | B7 | B*0702 | 9 | DENV1 | 113 | 2 |
| 109 | 2083 | 2091 | MALKDFKEF | B7 | B*3501 | 9 | DENV4 | 40 | 77 |
| 110 | 2087 | 2095 | EFKEFAAGR | A3 | A*3301 | 9 | DENV1 | 60 | 2 |

TABLE 4-continued

Human Donor Table and DENV Epitopes

| # | Start position | End position | Sequence (SEQ ID NOs: 555-763) in order of appearance | Supertype | Allele | Length | Serotype | T cell response [SFC] | HLA-Binding [IC50] |
|---|---|---|---|---|---|---|---|---|---|
| 111 | 2091 | 2100 | FASGRKSITL | B58 | B*5801 | 10 | DENV4 | 72 | 5541 |
| 112 | 2109 | 2118 | LPTFMTQKAR | B7 | B*3501 | 10 | DENV2 | 53 | 176 |
| 113 | 2113 | 2121 | MTQKARNAL | B7 | B*0702 | 9 | DENV2 | 263 | 16 |
| 114 | 2129 | 2137 | TAEAGGRAY | B7 | B*3501 | 9 | DENV2 | 230 | 46 |
| 115 | 2144 | 2153 | LPETLETLLL | B7 | B*3501 | 10 | DENV2 | 512 | 1693 |
| 116 | 2148 | 2156 | LETLMLVAL | B44 | B*4001 | 9 | DENV4 | 112 | 3 |
| 117 | 2148 | 2157 | LETLMLVALL | B44 | B*4001 | 10 | DENV4 | 185 | 127 |
| 118 | 2150 | 2159 | TLMLLALIAV | A2 | A*0201 | 10 | DENV1 | 50 | 8 |
| 119 | 2151 | 2160 | LMLLALIAVL | A2 | A*0201 | 10 | DENV1 | 63 | 95 |
| 120 | 2152 | 2160 | MLLALIAVL | A2 | A*0201 | 9 | DENV1 | 85 | 9 |
| 121 | 2163 | 2172 | GAMLFLISGK | A3 | A*1101 | 10 | DENV3 | 212 | 43 |
| 122 | 2204 | 2213 | SIILEFFLMV | A2 | A*0201 | 10 | DENV1 | 737 | 10 |
| 123 | 2205 | 2213 | IILEFFLMV | A2 | A*0201 | 9 | DENV1 | 232 | 75 |
| 124 | 2205 | 2214 | IILEFFLMVL | A2 | A*0201 | 10 | DENV1 | 152 | 96 |
| 125 | 2210 | 2219 | FLMVLLIPEP | A2 | A*0201 | 10 | DENV1 | 98 | 31 |
| 126 | 2224 | 2233 | TPQDNQLAYV | B7 | B*0702 | 10 | DENV1 | 100 | 331 |
| 127 | 2224 | 2232 | TPQDNQLTY | B7 | B*3501 | 9 | DENV2 | 22 | 11 |
| 128 | 2254 | 2263 | TTKRDLGMSK | A3 | A*1101 | 10 | DENV3 | 75 | 116 |
| 129 | 2266 | 2279 | TETTILDVDL | B44 | B*4001 | 10 | DENV4 | 852 | 11 |
| 130 | 2280 | 2288 | RPASAWTLY | B7 | B*0702 | 9 | DENV1 | 118 | 159 |
| 131 | 2280 | 2289 | RPASAWTLYA | B7 | B*0702 | 10 | DENV1 | 115 | 7 |
| 132 | 2280 | 2288 | HPASAWTLY | B7 | B*3501 | 9 | DENV1 | 38 | 6 |
| 133 | 2281 | 2290 | PASAWTLYAV | B58 | B*5801 | 10 | DENV1 | 90 | 704 |
| 134 | 2290 | 2298 | VATTFVTPM | B7 | B*3501 | 9 | DENV2 | 268 | 205 |
| 135 | 2295 | 2303 | ITPMLRHTI | A24 | A*2402 | 9 | DENV3 | 193 | 138 |
| 136 | 2296 | 2305 | TPMLRHTIEN | B7 | B*0702 | 10 | DENV3 | 90 | 1037 |
| 137 | 2315 | 2323 | IANQATVLM | B7 | B*3501 | 9 | DENV2 | 220 | 16 |
| 138 | 2338 | 2346 | VPLLAIGCY | B7 | B*3501 | 9 | DENV2 | 213 | 168 |
| 139 | 2350 | 2358 | NPLTLTAAV | B7 | B*0702 | 9 | DENV1 | 92 | 32 |
| 140 | 2353 | 2362 | TLTAAVLLLV | A2 | A*0201 | 10 | DENV3 | 43 | 179 |
| 141 | 2356 | 2365 | AAVLLLVTHY | B58 | B*5801 | 10 | DENV3 | 102 | 4148 |
| 142 | 2358 | 2367 | VLLLVTHYAI | A2 | A*0201 | 10 | DENV3 | 260 | 219 |
| 143 | 2403 | 2411 | DPIPYDPKF | B7 | B*3501 | 9 | DENV2 | 77 | 166 |
| 144 | 2419 | 2428 | MLLILCVTQV | A2 | A*0201 | 10 | DENV2 | 103 | 4 |
| 145 | 2444 | 2452 | ATGPLTTLW | B58 | B*5801 | 9 | DENV1 | 350 | 7 |
| 146 | 2444 | 2452 | ATGPISTLW | B58 | B*5801 | 9 | DENV2 | 163 | 1 |

TABLE 4-continued

Human Donor Table and DENV Epitopes

| # | Start position | End position | Sequence (SEQ ID NOs: 555-763) in order of appearance | Supertype | Allele | Length | Serotype | T cell response [SFC] | HLA-Binding [IC50] |
|---|---|---|---|---|---|---|---|---|---|
| 147 | 2444 | 2452 | ATGPITTLW | B58 | B*5801 | 9 | DENV3 | 110 | 5 |
| 148 | 2444 | 2452 | ATGPILTLW | B58 | B*5801 | 9 | DENV4 | 27 | 13 |
| 149 | 2444 | 2452 | ATGPVLTLW | B58 | B*5801 | 9 | DENV4 | 185 | 0 |
| 150 | 2451 | 2459 | LWEGSPGKF | A24 | A*2402 | 9 | DENV1 | 57 | 6165 |
| 151 | 2455 | 2464 | SPGKFWNTTI | B7 | B*0702 | 10 | DENV1 | 105 | 6 |
| 152 | 2464 | 2472 | IAVSMANIF | B7 | B*3501 | 9 | DENV1 | 118 | 143 |
| 153 | 2464 | 2472 | IAVSMANIF | B58 | B*5801 | 9 | DENV2 | 108 | 52 |
| 154 | 2464 | 2472 | IAVSTANIF | B58 | B*5801 | 9 | DENV4 | 135 | 196 |
| 155 | 2468 | 2476 | MANIFRGSY | B7 | B*3501 | 9 | DENV1 | 5982 | 553 |
| 156 | 2476 | 2484 | YLAGAGLAF | B7 | B*0702 | 9 | DENV1 | 72 | 98 |
| 157 | 2553 | 2562 | GSSKIRWIVE | B58 | B*5801 | 10 | DENV4 | 45 | 219 |
| 158 | 2602 | 2611 | GPGHEEPIPM | B7 | B*3501 | 10 | DENV1 | 53 | 1150 |
| 159 | 2609 | 2618 | IPMSTYGWNL | B7 | B*0702 | 10 | DENV2 | 203 | 59 |
| 160 | 2609 | 2618 | IPMATYGWNL | B7 | B*0702 | 10 | DENV1 | 450 | 20 |
| 161 | 2609 | 2618 | IPMSTYGWNL | B7 | B*3501 | 10 | DENV2 | 33 | 393 |
| 162 | 2611 | 2620 | MSTYGWNIVK | A3 | A*1101 | 10 | DENV3 | 30 | 146 |
| 163 | 2612 | 2620 | STYGWNIVK | A3 | A*1101 | 9 | DENV3 | 273 | 21 |
| 164 | 2622 | 2631 | QSGVDVFFTP | B58 | B*5801 | 10 | DENV2 | 387 | 2662 |
| 165 | 2658 | 2666 | RVLKMVEPW | B58 | B*5801 | 9 | DENV1 | 643 | 1 |
| 166 | 2676 | 2685 | KVLNPYMPSV | A2 | A*0201 | 10 | DENV2 | 48 | 8 |
| 167 | 2677 | 2685 | VLNPYMPSV | A2 | A*0201 | 9 | DENV2 | 987 | 1 |
| 168 | 2682 | 2691 | MPSVIEKMET | B7 | B*3501 | 10 | DENV2 | 1010 | 375 |
| 169 | 2724 | 2733 | VSSVNMVSRL | B58 | B*5801 | 10 | DENV3 | 820 | 95 |
| 170 | 2729 | 2737 | MVSRLLLNR | A3 | A*1101 | 9 | DENV3 | 992 | 50 |
| 171 | 2738 | 2747 | FTMRHKKATY | B7 | B*3501 | 10 | DENV2 | 103 | 7441 |
| 172 | 2787 | 2795 | WHYDQDHPY | B7 | B*3501 | 9 | DENV2 | 20 | 7598 |
| 173 | 2791 | 2800 | QENPYRTWAY | B44 | B*4001 | 10 | DENV4 | 992 | 1601 |
| 174 | 2798 | 2806 | WAYHGSYET | B7 | B*3501 | 9 | DENV2 | 265 | 873 |
| 175 | 2798 | 2806 | WAYHGSYEV | B7 | B*5101 | 9 | DENV1 | 97 | 11 |
| 176 | 2840 | 2848 | DTTPFGQQR | A3 | A*6801 | 9 | DENV1 | 40 | 91 |
| 177 | 2842 | 2850 | TPFGQQRVF | B7 | B*3501 | 9 | DENV1 | 48 | 47 |
| 178 | 2860 | 2869 | EPKEGTKKLM | B7 | B*3501 | 10 | DENV2 | 382 | 54438 |
| 179 | 2869 | 2877 | MEITAEWLW | B58 | B*5801 | 9 | DENV3 | 27 | 5 |
| 180 | 2885 | 2894 | KPRICTREEF | B7 | B*0702 | 10 | DENV1 | 133 | 72 |
| 181 | 2885 | 2894 | TPRMCTREEF | B7 | B*0702 | 10 | DENV2 | 60 | 13 |
| 182 | 2885 | 2894 | KPRLCTREEF | B7 | B*0702 | 10 | DENV3 | 48 | 13 |

TABLE 4-continued

Human Donor Table and DENV Epitopes

| # | Protein location Start position | End position | Sequence (SEQ ID NOs: 555-763) in order of appearance | Supertype | Allele | Length | Serotype | T cell response [SFC] | HLA-Binding [IC50] |
|---|---|---|---|---|---|---|---|---|---|
| 183 | 2885 | 2894 | NPRLCTREEF | B7 | B*0702 | 10 | DENV4 | 25 | 45 |
| 184 | 2885 | 2894 | RPRLCTREEF | B7 | B*0702 | 10 | DENV3 | 102 | 7 |
| 185 | 2885 | 2894 | TPRMCTREEF | B7 | B*3501 | 10 | DENV2 | 38 | 2576 |
| 186 | 2918 | 2926 | RAAVEDEEF | B58 | B*5801 | 9 | DENV3 | 87 | 866 |
| 187 | 2919 | 2928 | EAVEDSRFWE | B58 | B*5801 | 10 | DENV2 | 140 | 1714 |
| 188 | 2964 | 2973 | KGSRAIWYMW | B58 | B*5801 | 10 | DENV1 | 335 | 2 |
| 189 | 2977 | 2986 | RYLEFEALGF | A24 | A*2402 | 10 | DENV3 | 130 | 38 |
| 190 | 2977 | 2986 | RFLEFEALGF | A24 | A*2402 | 10 | DENV1 | 37 | 14 |
| 191 | 2993 | 3002 | FSRENSLSGV | B7 | B*5101 | 10 | DENV1 | 103 | 7587 |
| 192 | 3004 | 3012 | GEGLHKLGY | B44 | B*4403 | 9 | DENV1 | 248 | 281 |
| 193 | 3057 | 3065 | RQLANAIFK | A3 | A*1101 | 9 | DENV3 | 277 | 89 |
| 194 | 3079 | 3088 | TPRGTVMDII | B7 | B*0702 | 10 | DENV2 | 505 | 6 |
| 195 | 3079 | 3088 | TPKGAVMDII | B7 | B*0702 | 10 | DENV4 | 422 | 127 |
| 196 | 3116 | 3124 | RQMEGEGIF | B62 | B*1501 | 9 | DENV2 | 583 | 6 |
| 197 | 3116 | 3124 | RQMEGEGVL | B62 | B*1501 | 9 | DENV3 | 382 | 19 |
| 198 | 3182 | 3190 | KVRKDIQQW | B58 | B*5701 | 9 | DENV2 | 115 | 15 |
| 199 | 3254 | 3262 | YAQMWSLMY | B62 | B*1501 | 9 | DENV2 | 27 | 6 |
| 200 | 3254 | 3263 | YAQMWSLMYF | B7 | B*3501 | 10 | DENV2 | 625 | 177 |
| 201 | 3275 | 3283 | ICSAVPVHW | B58 | B*5801 | 9 | DENV3 | 305 | 6 |
| 202 | 3291 | 3299 | WSIHAHHQW | B58 | B*5801 | 9 | DENV1 | 45 | 1 |
| 203 | 3317 | 3326 | NPNMIDKTPV | B7 | B*0702 | 10 | DENV4 | 207 | 403 |
| 204 | 3317 | 3326 | NPWMEDKTPV | B7 | B*0702 | 10 | DENV2 | 137 | 56 |
| 205 | 3332 | 3341 | VPYLGKREDQ | B7 | B*0702 | 10 | DENV1 | 425 | 1251 |
| 206 | 3338 | 3346 | REDLWCGSL | B44 | B*4001 | 9 | DENV4 | 503 | 2 |
| 207 | 3338 | 3346 | REDQWCGSL | B44 | B*4001 | 9 | DENV1 | 150 | 2 |
| 208 | 3379 | 3388 | MPSMKRFRRE | B7 | B*3501 | 10 | DENV2 | 208 | 30905 |
| 209 | 3387 | 3395 | APFESEGVL | B7 | B*0702 | 9 | DENV4 | 77 | 38 |

Example 17

This example includes a description of studies showing a comprehensive approach to characterize Dengue virus T cell responses.

The role of CD8 T cells in DENV infection is not fully understood. A limitation of existing studies is that only a relatively small fraction of the epitopes derived from the four DENV serotypes and presented by common HLA Class I alleles expressed by populations in endemic areas have been defined, leading to a lack of comprehensiveness in the analyses feasible for investigators. Here the present inventors designed an approach to comprehensively characterize responses by, taking into account HLA polymorphism and the extensive sequence variability both between and amongst the four main DENV serotypes.

555 full-length unique DENV polyprotein sequences (162 DENV1, 171 DENV2, 169 DENV3 and 53 DENV4 sequences, respectively) available from the NCBI Protein database at the start of the study (2009) were retrieved. The number of sequences available varied drastically as a function of geographic locations. For example, in the case of DENV3 40% of the sequences were derived form Venezuela and Puerto Rico alone (Table 5). To ensure a balanced representation, the number of isolates by geographical region from any one country was limited to a maximum of 10. Table 5 illustrates the selection process for DENV3 sequences as an example.

Next, a panel of 16 HLA A and 11 HLA B alleles was selected, which it was estimated would account for 97% of HLA A and B allelic variants in most ethnicities (24). For all four serotypes, 9- and 10-mer sequences predicted to bind to each allelic molecule were generated as described herein. Peptides, which were predicted for two or more serotypes were placed in a "conserved peptides" group. Conversely, if two or more variant peptides at the same position were selected from one serotype, the less commonly encountered sequences were placed in a "variant" group. This resulted in a set of 8,088 peptides, subdivided in 162 different groups of 50 peptides on average (range from 25 to 72, Table 6).

TABLE 5

Selection of DENV3 specific polyprotein sequences

| Country | Count | Unique | Included |
|---|---|---|---|
| Anguilla | 1 | 1 | 1 |
| Bangladesh | 8 | 8 | 8 |
| Brazil | 19 | 18 | 10 |
| Cambodia | 23 | 22 | 10 |
| China | 3 | 2 | 2 |
| Colombia | 12 | 11 | 10 |
| Cook Islands | 1 | 1 | 1 |
| East Timor | 4 | 4 | 4 |
| Ecuador | 1 | 1 | 1 |
| French Polynesia | 9 | 9 | 9 |
| Guyana | 1 | 1 | 1 |
| India | 1 | 1 | 1 |
| Indonesia | 20 | 18 | 10 |
| Malaysia | 23 | 19 | 10 |
| Martinique | 2 | 1 | 1 |
| Mexico | 3 | 3 | 3 |
| Mozambique | 1 | 1 | 1 |
| Nicaragua | 17 | 15 | 10 |
| Peru | 1 | 1 | 1 |
| Philippines | 3 | 3 | 3 |
| Puerto Rico | 94 | 79 | 10 |
| Saint Lucia | 2 | 2 | 2 |
| Samoa | 1 | 1 | 1 |
| Singapore | 48 | 24 | 10 |
| Sri Lanka | 12 | 9 | 9 |
| Taiwan | 15 | 9 | 9 |
| Thailand | 28 | 19 | 10 |
| Trinidad and Tobago | 2 | 1 | 1 |
| Venezuela | 102 | 82 | 10 |
| Viet Nam | 36 | 33 | 10 |
| Total | 493 | 399 | 169 |

TABLE 6

Selection of HLA specific peptide sets

| Supertype | Allele | DENV 1 | DENV 2 | DENV 3 | DENV 4 | Variants | Conserved | Row total |
|---|---|---|---|---|---|---|---|---|
| HLA A | | | | | | | | |
| A*01 | A*01:01 | 57 | 59 | 47 | 69 | 39 | 31 | 302 |
| | A*26:01 | 58 | 65 | 60 | 64 | 31 | 26 | 304 |
| | A*30:02 | 51 | 59 | 49 | 60 | 33 | 30 | 282 |
| | A*32:01 | 58 | 65 | 56 | 65 | 46 | 25 | 315 |
| A*02 | A*02:01 | 62 | 72 | 59 | 66 | 46 | 27 | 332 |
| | A*02:03 | 64 | 68 | 58 | 70 | 46 | 23 | 329 |
| | A*02:06 | 62 | 66 | 55 | 64 | 43 | 27 | 317 |
| | A*68:02 | 58 | 68 | 56 | 70 | 36 | 30 | 318 |
| A*24 | A*23:01 | 51 | 45 | 50 | 53 | 36 | 40 | 275 |
| | A*24:01 | 51 | 51 | 55 | 58 | 34 | 36 | 285 |
| A*03 | A*03:01 | 58 | 67 | 52 | 59 | 34 | 30 | 300 |
| | A*11:01 | 57 | 71 | 53 | 60 | 29 | 30 | 300 |
| | A*30:01 | 60 | 67 | 59 | 64 | 26 | 26 | 302 |
| | A*31:01 | 55 | 61 | 46 | 57 | 37 | 33 | 289 |
| | A*33:01 | 56 | 58 | 47 | 57 | 28 | 34 | 280 |
| | A*68:01 | 54 | 58 | 54 | 63 | 24 | 30 | 283 |
| HLA B | | | | | | | | |
| B*44 | B*40:01 | 56 | 59 | 57 | 57 | 30 | 31 | 290 |
| | B*44:02 | 60 | 61 | 63 | 61 | 26 | 30 | 301 |
| | B*44:03 | 55 | 66 | 56 | 61 | 26 | 32 | 296 |
| B*57 | B*57:01 | 58 | 57 | 54 | 54 | 40 | 28 | 291 |
| | B*58:01 | 55 | 60 | 51 | 58 | 47 | 31 | 302 |
| B*15 | B*15:01 | 54 | 55 | 47 | 61 | 35 | 31 | 283 |
| B*07 | B*07:02 | 57 | 63 | 46 | 66 | 35 | 32 | 299 |
| | B*35:01 | 57 | 57 | 52 | 66 | 32 | 31 | 295 |
| | B*51:01 | 55 | 57 | 56 | 59 | 31 | 35 | 293 |
| | B*53:01 | 65 | 62 | 55 | 67 | 38 | 27 | 314 |
| B*08 | B*08:01 | 62 | 62 | 66 | 63 | 31 | 27 | 311 |
| Column total | | 1546 | 1659 | 1459 | 1672 | 939 | 813 | 8088 |

Example 18

Figure 15A:
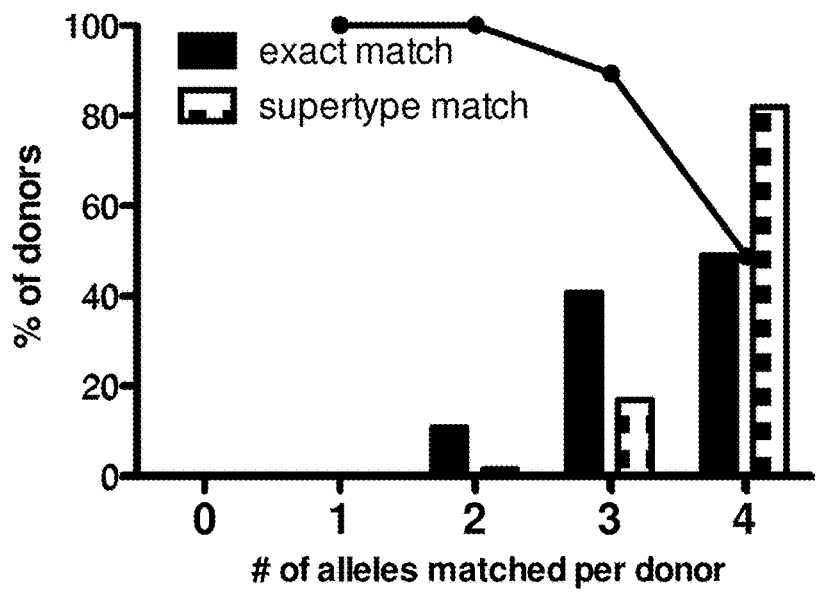
FIGS. 15A-15C show HLA coverage and serological characteristics of the study population.

This example includes a description of studies showing validation of the characterization of Dengue virus T cell responses in the general population from the Colombo endemic area Next, it was sought to validate the approach described herein in the donor population derived from the Colombo (Sri Lanka) region endemic area. In this region, levels of seropositivity for DENV approach 50% by the age of 16 (WHO, dengue bulletin). To capture the features of natural immunity in the general population, buffy coats form the National Blood Bank were obtained. PBMC from a total of 250 blood donors were collected HLA typed. The 27 alleles selected allowed to exactly match 3 out of 4 possible HLA A and B alleles expressed per donor in 41% of our cohort and for 4 out of 4 in 49% (FIG. 15A, black bars). Cumulatively, the number of donors matching at least 3 out of 4 possible HLA A and B alleles is than 90% (FIG. 15A, solid line). Considering closely related HLA alleles from the same supertype allowed to match at least three of four MHC class I alleles in 99% of the donors (FIG. 15A, white bars).

The assumption that this general donor population would be associated with high levels of previous DENV infection as evidenced by positivity in ELISA and neutralization assays was tested. When serum from all donors was tested for the presence of DENV specific IgG antibodies, 80% of the donors in the cohort were seropositive, (182 out of 227) and only 20% (n=45) were negative. To determine whether primary or secondary infection may have occurred, all 182 DENV positive samples were tested in a FACS-based neutralization assay, which showed that 55 donors had experienced primary infection and 127 donors experienced secondary infections.

Figure 15B:
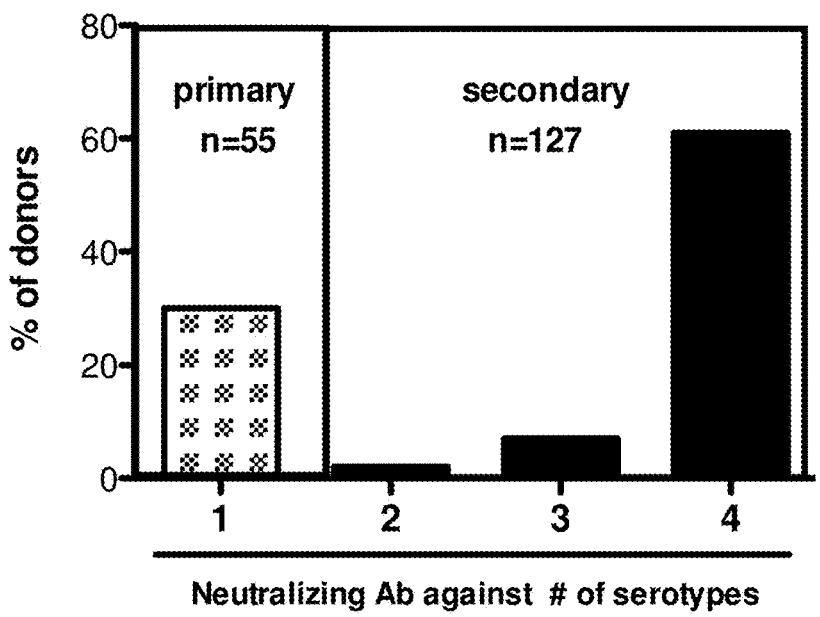
Figure 15C:
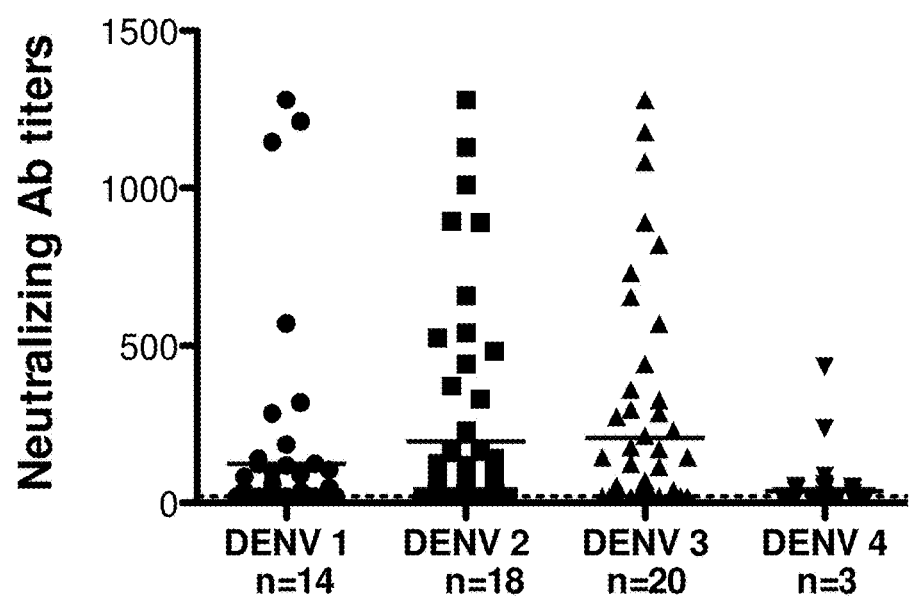

By definition, donors exposed to primary infection show neutralization antibodies to only one of the serotypes. Neutralization assays are however unable to distinguish which specific DENV serotypes were associated with secondary infections, and most donors had neutralizing antibodies to all four serotypes (FIG. 15B). Antibodies to all four serotypes were detected as infecting agents in our primary infection donors (14 DENV1, 18 DENV2, 20 DENV3 and 3 DENV4 donors; FIG. 15C) confirming a circulation of all four serotypes in Sri Lanka, as previously reported (25). The most frequently encountered primary titers were to DENV2 and DENV3, which have been reported to be the primary circulating serotypes in Sri Lanka (25, 26), followed by DENV1, for which an epidemic has been recently reported (27). Thus, as expected, the pattern of primary infection closely correlates with the DENV serotypes most prevalent in the recent years, close in time to the PBMC donations.

Example 18.1

This example includes a description of studies showing determination of T cell reactivity and correlation between T cell and Antibody responses Next, PBMCs from all donors were screened with HLA matched class I predicted peptide pools in ex vivo IFNγ ELISPOT assays. HLA matched peptide pools originated from all four serotypes. Responses against peptides were considered positive if the net spot-forming cells (SFC) per $10^6$ were ≥20, had a stimulation index of ≥2, and a p<0.05 in a t test comparing replicates with those from the negative control in two independent experiments. Positive pools were subsequently deconvoluted and a peptide was considered positive according to the criteria described above.

Overall, ex-vivo T cell reactivity was detected for 22% of primary and 43% of secondary infection donors. In total, 753 total donor/peptide responses were identified. These resulted in the identification of 408 unique CD8$^+$ T cell epitopes (Table 7). As a control all DENV negative donors (n=45) were screened and no significant responses were detected (data not shown).

It was also addressed whether the T cell reactivity correlated with IgG titers. Significantly higher titers in secondary infection compared to primary infection, were observed, no difference has been detected between responding and non-responding donors in either cohort (FIG. 20). A subset of 80 donor sera samples randomly selected and also tested for the presence of enhancing antibodies. In these samples, IgG titers, enhancement and neutralization titers showed only weak correlations with paired T cell responses (FIG. 20, B-D, respectively).

TABLE 7

Overall T cell responses in the study population

| DENV infection | n | mean response/donor [SFC] | frequency of responders [%] | mean epitopes/ donor |
|---|---|---|---|---|
| primary | 55 | 122 | 22 | 6 |
| secondary | 127 | 1004 | 43 | 11 |
| total T cell responses detected: | | | | 753 |
| total epitopes identified: | | | | 408 |
| total antigenic regions identified: | | | | 267 |

Example 19

Figure 16A:
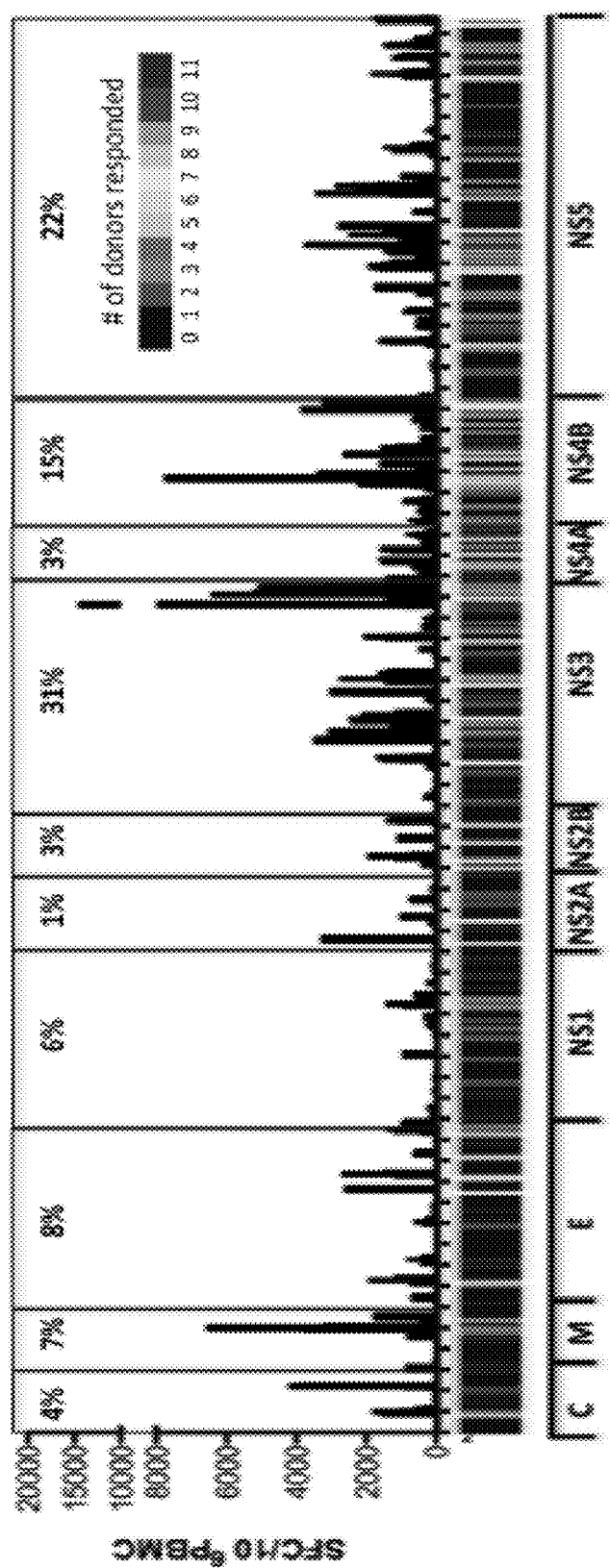
FIGS. 16A-16B show immunodominant regions of the dengue virus polyprotein.

This example includes a description of studies investigating the Immunodominant regions of the DENV polyprotein To investigate the relative immunodominance of different parts of the proteome, response magnitude (as SFC/$10^6$ PBMC values) and frequency of responding donors (as a heat map) were plotted as a function of the genomic position of DENV encoded proteins (FIG. 16a). NS3, NS4B and NS5 were the most vigorously and frequently recognized proteins within DENV and accounted for more than two thirds of the total response observed. Conversely, proteins known to be main antibody targets (such as NS1 and E) were less prominently recognized at the level of the T cell responses.

Figure 16B:
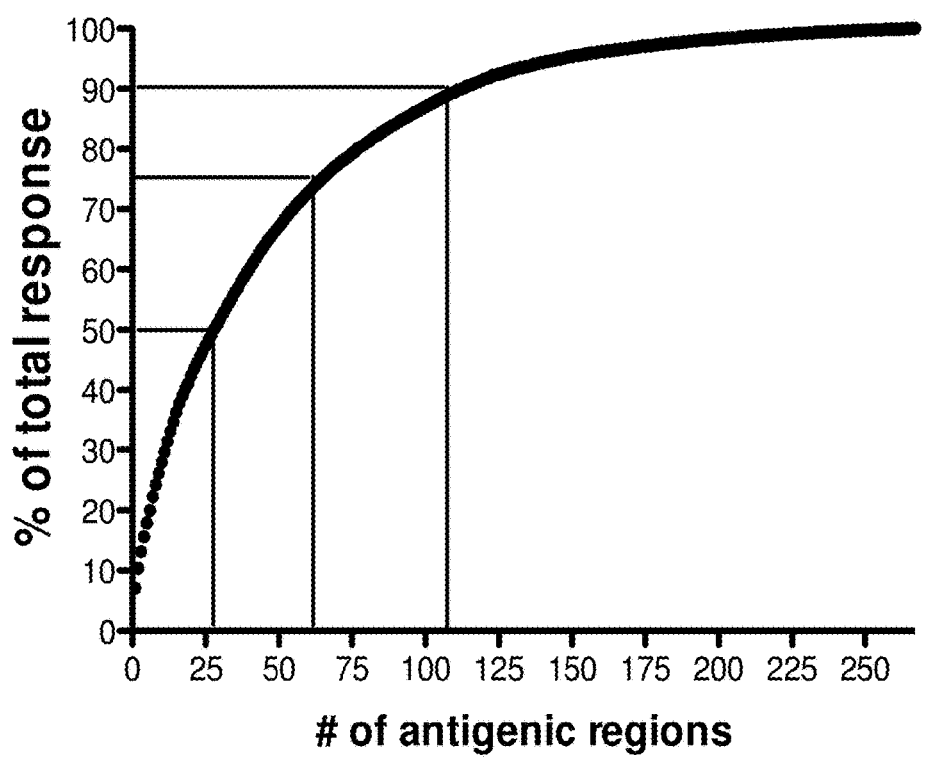

It was next noted that reactivity appeared to cluster in discrete regions of the polyprotein. The Epitope Cluster Analysis tool from the IEDB website was used to cluster epitopes that share more than 80% sequence homology, resulting in the definition of a total of 267 antigenic regions (Table 7). When these antigenic regions were plotted as a function of the percentage of the total response (FIG. 16B) it was found that about 25 regions account for half of the total response. Sequences, proteome location, serotype affiliation, HLA restriction as well as frequency and magnitude of responses of these 25 most immunodominant antigenic regions are shown in Table 8. Several immunodominant regions contain epitopes derived from multiple serotypes and also restricted by a variety of different alleles.

TABLE 8

Immunodominant regions of the DENV polyprotein

| Antigenic Region | Epitope (SEQ ID NOs: 764-812, 1106, 888 in order of appearance) | Proteome location | Serotype | HLA allele | # of responders | T cell response [SFC] | |
|---|---|---|---|---|---|---|---|
| 1 | TPFGIIPAL | 1978 | 1, 4 | B*0702 | 1 | 183 | 10671 |
|   | TPEGIIPALF | 1978 | 1, 4 | B*3501 | 9 | 2213 | |
|   | TPEGIIPSM | 1978 | 2 | B*3501, B*5301 | 5 | 2717 | |
|   | TPEGIIPSMF | 1978 | 2 | B*0702, B*3501 | 7 | 1772 | |
|   | TPEGIIPTLF | 1978 | 4 | B*3501, B*0702, B*5301 | 11 | 2914 | |
|   | YTPEGIIPTL | 1977 | 4 | A*0206 | 1 | 872 | |
| 2 | GEARKTFVDL | 2005 | 2 | B*4001 | 3 | 1405 | 5005 |
|   | GEARKTFVEL | 2005 | 1 | B*4001 | 3 | 1330 | |
|   | GEQRKTFVEL | 2005 | 4 | B*4001 | 2 | 1050 | |
|   | GESRKTFVEL | 2005 | 3 | B*4001 | 3 | 1220 | |
| 3 | LPVWLAHKVA | 2020 | 3 | B*3501 | 1 | 23 | 4157 |
|   | LPVWLAYKV | 2020 | 2 | B*5301, B*5101 | 2 | 923 | |
|   | LPVWLAYKVA | 2020 | 2 | B*3501 | 7 | 2427 | |
|   | LPVWLAYRVA | 2020 | 2 | B*5101 | 1 | 470 | |
|   | LPVWLSYKV | 2020 | 1 | B*5101 | 1 | 313 | |
| 4 | HPGAGKTKRY | 1672 | 2 | B*3501 | 10 | 3047 | 3047 |
| 5 | NPEIEDDIF | 1653 | 2 | B*3501 | 10 | 3390 | 3390 |
| 6 | DTTPFGQQR | 2840 | 1, 2, 3, 4 | A*6801, A*3301 | 8 | 3260 | 3260 |
| 7 | MSFRDLGRVM | 1176 | 2 | B*3501 | 8 | 3250 | 3250 |
| 8 | ATGPILTLW | 2444 | 4 | B*5801 | 2 | 938 | 3089 |
|   | ATGPISTLW | 2444 | 2 | B*5801 | 2 | 236 | |
|   | ATGPITTLW | 2444 | 3 | B*5801 | 1 | 505 | |
|   | ATGPLTTLW | 2444 | 1 | B*5801 | 1 | 275 | |
|   | ATGPVLTLW | 2444 | 4 | B*5801 | 2 | 390 | |
|   | LATGPVLTLW | 2443 | 4 | B*5301 | 1 | 745 | |
| 9 | CLIPTAMAF | 108 | 4 | B*1501 | 1 | 67 | 2815 |
|   | MLIPTAMAF | 108 | 2 | B*3501 | 7 | 2748 | |
| 10 | VATTFVTPM | 2290 | 2 | B*3501 | 8 | 2777 | 2777 |
| 11 | KPRICTREEF | 2885 | 1 | B*0702 | 1 | 340 | 2756 |
|   | KPRLCTREEF | 2885 | 3 | B*0702 | 1 | 350 | |
|   | NPRLCTREEF | 2885 | 4 | B*0702 | 1 | 365 | |
|   | RPRLCTREEF | 2885 | 3 | B*0702 | 4 | 501 | |
|   | TPRMCTREEF | 2885 | 2 | B*0702, B*3501 | 5 | 1200 | |
| 12 | VPLLAIGCY | 2338 | 2 | B*3501 | 7 | 1520 | 2603 |
|   | VPLLAMGCY | 2338 | 4 | B*3501 | 1 | 1083 | |
| 13 | MSYSMCTGKF | 578 | 2 | B*3501 | 6 | 2553 | 2553 |
| 14 | DPASIAARGY | 1768 | 1, 2, 3 | B*3501 | 9 | 2383 | 2383 |
| 15 | IANQATVLM | 2315 | 2 | B*3501 | 7 | 1518 | 1518 |
| 16 | APTRVVAAEM | 1700 | 2, 3, 4 | B*0702, B*3501 | 8 | 1623 | 2230 |
|   | APTRVVASEM | 1700 | 1 | B*0702 | 5 | 607 | |
| 17 | TPMLRHTIEN | 2296 | 3, 4 | B*0702 | 2 | 388 | 2123 |
| 18 | MLVTPSMTM | 274 | 3 | B*3501 | 8 | 1735 | 1735 |
| 19 | FTMRHKKATY | 2738 | 2 | B*3501 | 4 | 1723 | 1723 |
| 20 | FTILALFLAH | 248 | 3 | B*3501 | 8 | 1715 | 1715 |
| 21 | WHYDQDHPY | 2787 | 2 | B*3501 | 5 | 1628 | 1628 |
| 22 | MALKDFKEF | 2083 | 4 | B*3501 | 7 | 1497 | 1497 |

TABLE 8-continued

Immunodominant regions of the DENV polyprotein

| Antigenic Region | Epitope (SEQ ID NOs: 764-812, 1106, 888 in order of appearance) | Proteome location | Serotype | HLA allele | # of responders | T cell response [SFC] | |
|---|---|---|---|---|---|---|---|
| 23 | LMKITAEWLW | 2868 | 2 | B*5301 | 1 | 423 | 1417 |
|  | MEITAEWLW | 2869 | 3 | B*5801 | 1 | 583 |  |
|  | VMGITAEWLW | 2868 | 3 | B*5301 | 1 | 410 |  |
| 24 | TETTILDVDL | 2266 | 4 | B*4001 | 2 | 1413 | 1413 |
| 25 | GEFRLRGEQR | 1999 | 4 | B*4001 | 3 | 1373 | 1373 |

Example 20

This example includes a description of studies investigating differences between serotype specific responses.

Figure 17A:
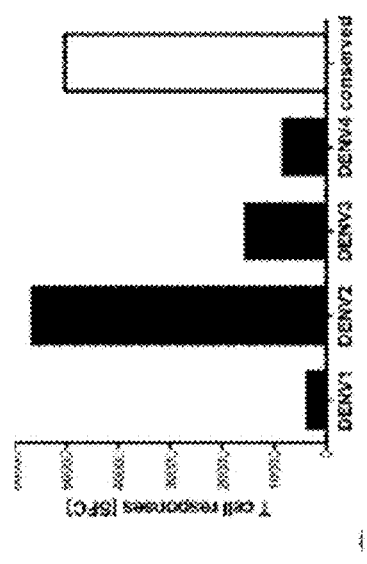
FIGS. 17A-17D show differences between serotype specific responses.

In the present section T cell reactivity was segregated as being directed against serotype specific sequences (found only in one serotype) or conserved/homologous sequences (sequences found in two or more serotypes, also allowing one residues substitutions to account for potential cross-reactivity of highly homologous sequences). Conserved sequences accounted for 37% of the overall responses (FIG. 17a). In terms of serotype specific responses, responses against DENV2 were by far most prevalent (42%), followed by DENV3 (12%), DENV4 (6%) and DENV1 (3%) (FIG. 17a).

Interestingly, the prominence of DENV2 responses is more marked at the level of T cell than at the level of antibodies (FIG. 15C). This may reflect that while DENV2 has historically been most prevalent in Sri Lanka, recent years have seen the appearance of new sub-strains of DEN3, and DENV1 has only recently appeared in this population.

Figure 17B:
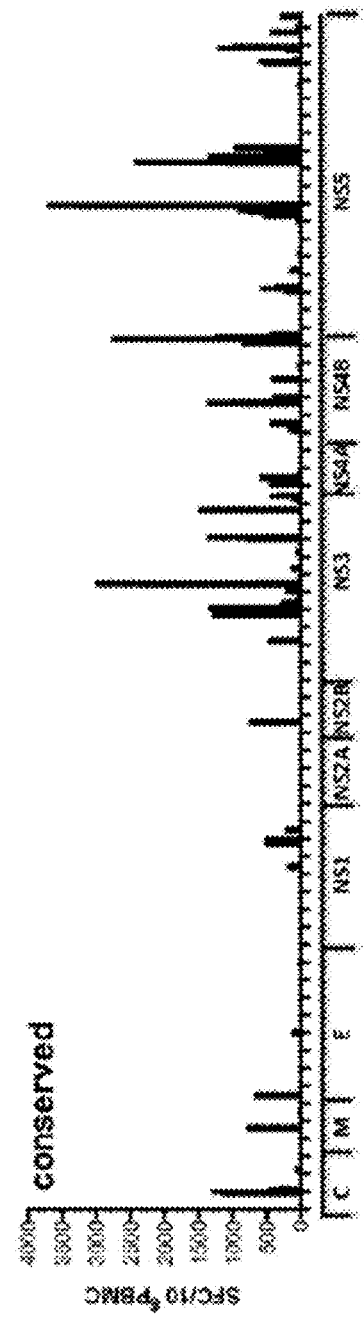
Figure 17C:
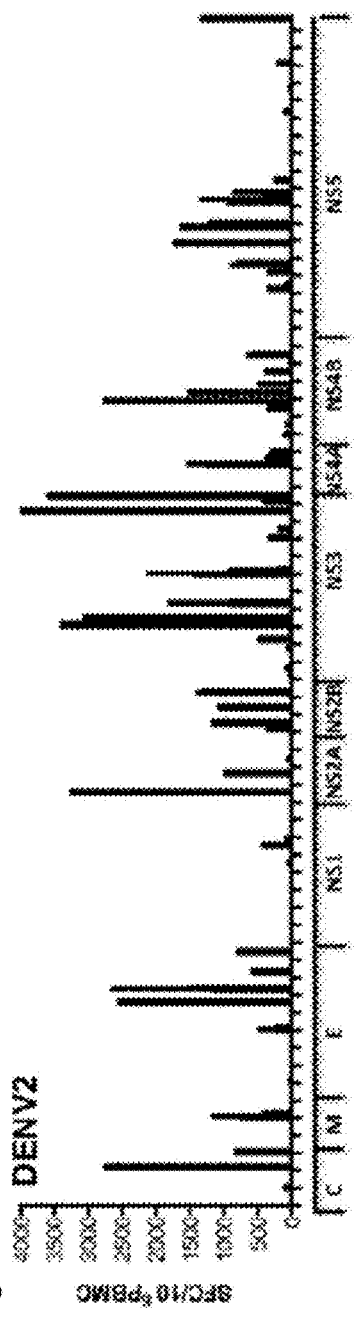
Figure 17D:
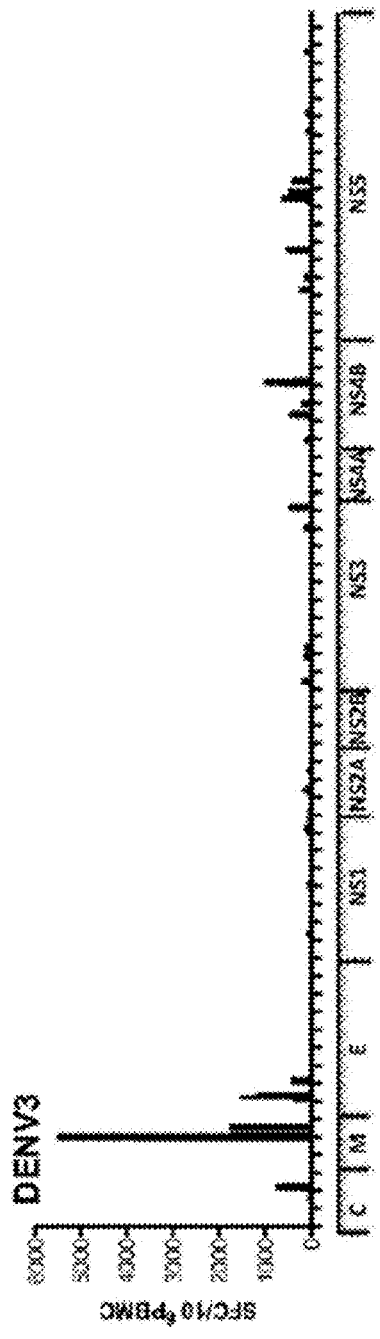

To further investigate the dominance of DENV2 in the cohort serotype specific responses were aligned along the dengue polyprotein. Epitopes conserved between serotypes (FIG. 17b) were mostly derived from the highly conserved NS proteins. Interestingly, DENV2 specific responses were more evenly distributed across the polyprotein (FIG. 17c) while DENV3 specific responses mostly targeted the structural proteins (FIG. 17d).

Example 21

This example includes a description of studies showing that Antigenic sin is not associated with differences in epitope avidity or multifunctionality.

The broad DENV2 and limited DENV3 specific response focused on surface proteins, might reflect lower immunogenicity of DENV3 as compared to DENV2. Alternatively, it might be that conserved epitopes dominate DENV3 responses, reflecting previous DENV2 infections and thus expansion of T cells recognizing conserved epitopes (antigenic sin).

To test this hypothesis, responses form donors either exhibiting responses against DENV3 (or DENV2) specific responses were compiled and used as an indicator of previous infection with either DENV2 (or DENV3). Overall, no difference in magnitude of responses was noted between the two groups if the total response to serotype specific and conserved epitopes per donor was compared. The average total response observed was 2819±1203 SFC for donors recognizing DENV2 specific epitopes and 2032±619 SFC for donors responding to DENV3 specific epitopes (p=0.61).

Figure 18A:
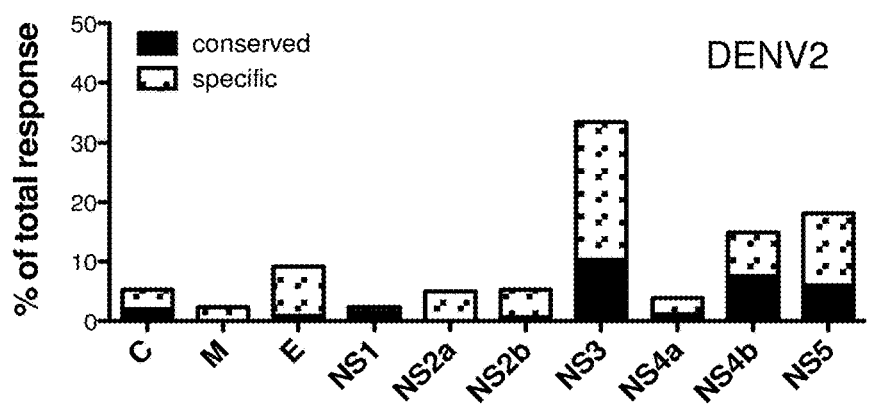
FIGS. 18A-18H show deciphering antigenic sin. Responses form donors either exhibiting responses against DENV2 (FIG. 18A) or DENV3 (FIG. 18B) specific epitopes are compiled. All responses observed in these donors were then plotted dependent on their origin from serotype specific (white bars) or conserved regions (black bars). Representative donors were incubated with donor-specific peptide pools [1 µg/ml] originated either from regions serotype specific for DENV3 (white circles) or regions conserved between two or more serotypes (black circles) for 6 hours in the presence of BFA. Cells were then stained with mAB against surface markers CD3, CD8, CD45RA, CD27, and mAB against intracellular C107a, IFNγ, TNFα and IL2. Magnitude of response (FIG. 18C), and phenotype of responding cell (FIG. 18D) of the individual donors (n=7) based on gating of the IFNγ producing cells is shown. The average CD45RA, CCR7, CD27 and CD107a expression for all responding cells is shown in panel (FIG. 18E). Multi-functional responses are shown for individual donors (FIG. 18F) and as average of all donors studied (FIG. 18G, n=6). Avidity of responding T cells was determined by incubating PBMC with ascending concentrations of peptide pools [0.001; 0.01; 0.1; 1; and 10 µg/ml]. The peptide concentration, which was necessary to induce 50% of the maximum responses (EC50) was calculated and compared between normalized samples (FIG. 18H).
Figure 18B:
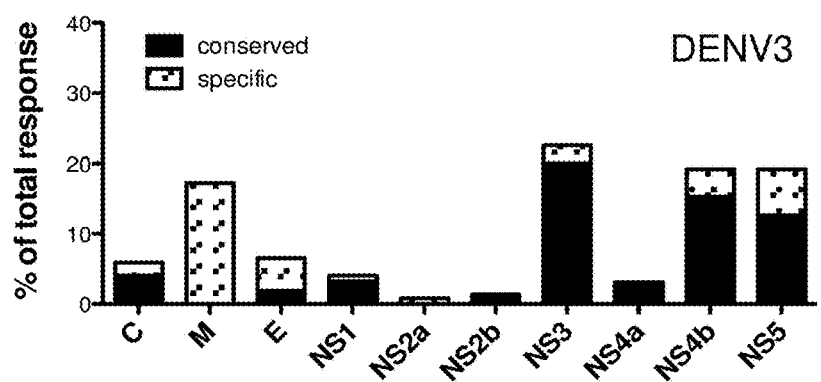
Figure 18C:
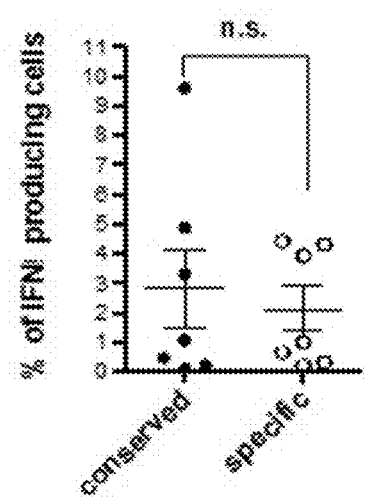
Figure 18D:
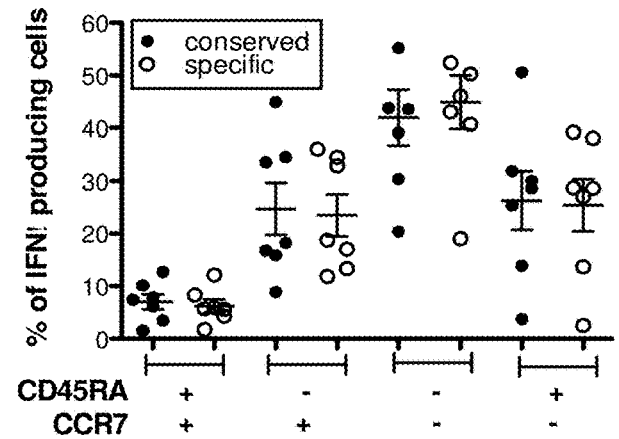
Figure 18E:
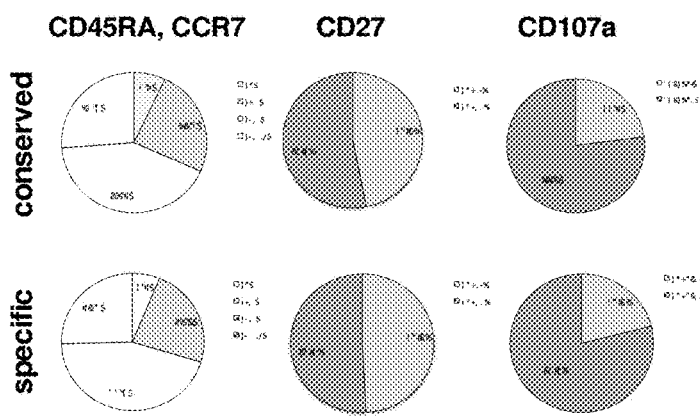
Figure 18F:
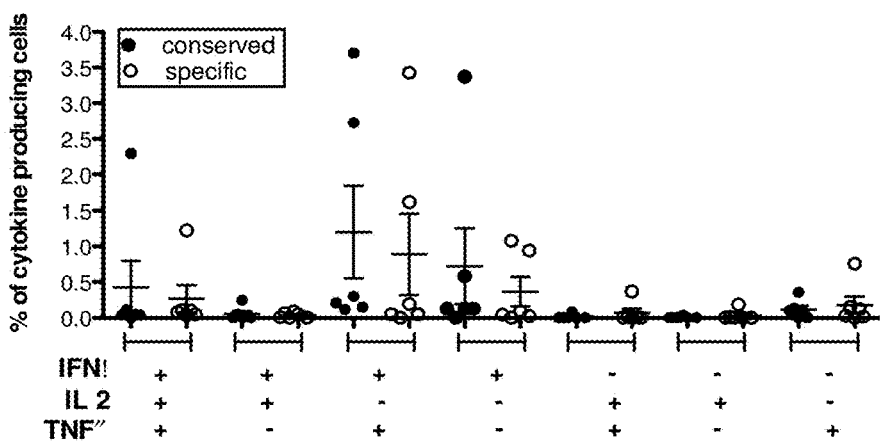
Figure 18G:
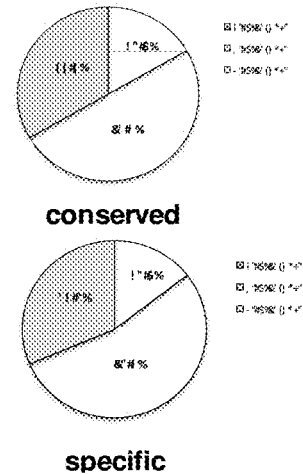
Figure 18H:
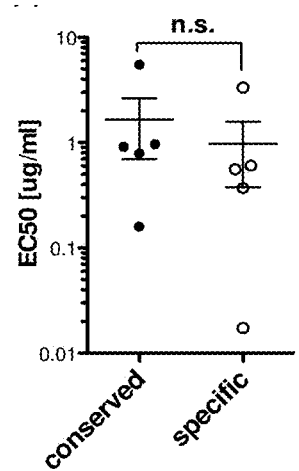

When responses were plotted as a function of the polyprotein position, consistent with the antigenic sin hypothesis it was noted that donors presumably infected by DENV2 responded utilizing both conserved and serotype-specific epitopes distributed along the entire sequence (FIG. 18A). In stark contrast, the lower serotype specific responses in donors presumably exposed to DENV3 were compensated by responses against conserved regions of the protein (FIG. 18B). These observations match the know historical prevalence of DENV serotypes circulating in Sri Lanka, and suggest that the differential focus of DENV2 versus DENV3 responses is the results of "antigenic sin".

These observations allowed testing whether antigenic sin is associated with differential quality of responses. Accordingly, pools of epitopes corresponding to either serotype specific or conserved epitopes were tested by ICS assays in several representative donors. There was no appreciable difference in the magnitude, phenotype, and pattern of multi-functionality or avidity of the T cell responses between serotype specific and conserved responses (FIG. 18C-H, respectively).

Example 22

This example includes a description of studies showing that low magnitude T cell responses are HLA-linked and associated with disease susceptibility.

Overall the results presented above suggest that antigenic sin does not significantly change or impair the quality of T cell responses in the general population of an endemic area. However, it possible that lower quality of responses might be present in the relatively few individuals that experience more severe clinical outcomes. Previous studies highlight that certain HLA alleles are associated with either increased or decreased risk of clinical manifestations. Those studies did not determine whether increased risk might be associated with a hyperactive T cell response, or rather a higher T cell response might have protective effects, leading to a decreased risk. In fact, since HLA class I restricted T cell responses have not been comprehensively mapped, it was unclear whether different HLA alleles were differentially associated with response frequency or magnitude.

Figure 19A:
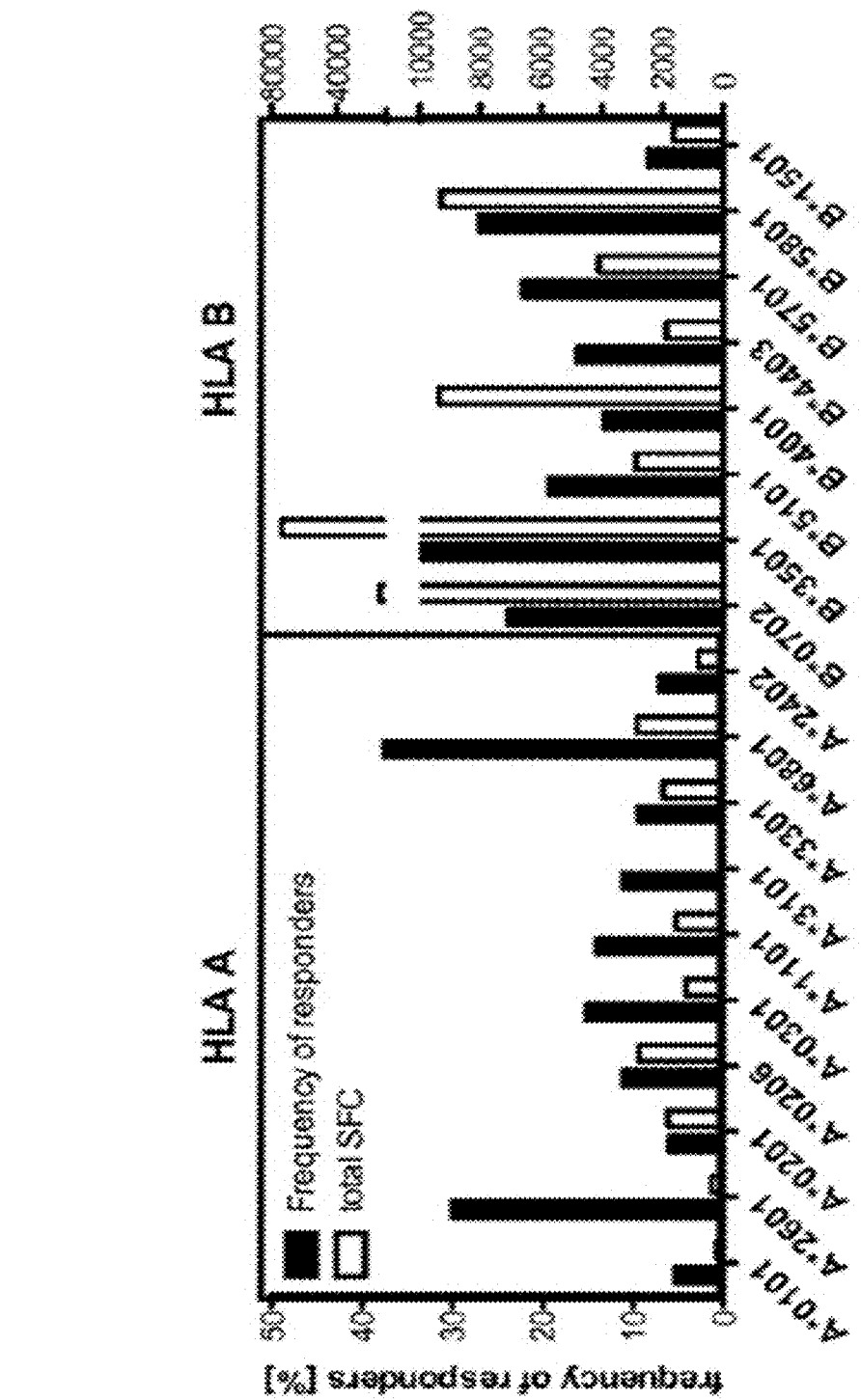
FIGS. 19A-19C show HLA linked T cell responses.

To address these points, HLA types expressed in our cohort were correlated with T cell responses. FIG. 19a shows the frequency (black bars) and the magnitude (white bars) of T cell responses sorted according to their restriction element. A wide variation in terms of frequency and magnitude was detected as a function of the different HLA alleles. Interestingly, certain alleles were associated with low response frequency and magnitude (A*0101, A*2401) while others were associated with high response frequency and magnitude (B*0702, B*3501). Still other alleles were associated with low frequency and high magnitude response (B*4001), while others were associated with high frequency and low magnitude response (A*2601). Overall HLA B restricted responses were of significantly higher magnitude but not frequency as compared to HLA A restricted responses.

To test whether T cell responses correlated with HLA associated disease susceptibility, all data available in the literature was compiled (15-21). For each of the studies, all investigated alleles were ranked according to their association with clinical manifestations (dengue fever [DF], dengue hemorrhagic fever [DHF] and dengue shock syndrome [DSS]; Table 9). A percentile ranking across all studies was calculated for the 18 alleles detected in significant frequencies in our own cohort and correlated the rankings with T cell responses (FIG. 19b).

Figure 19B:
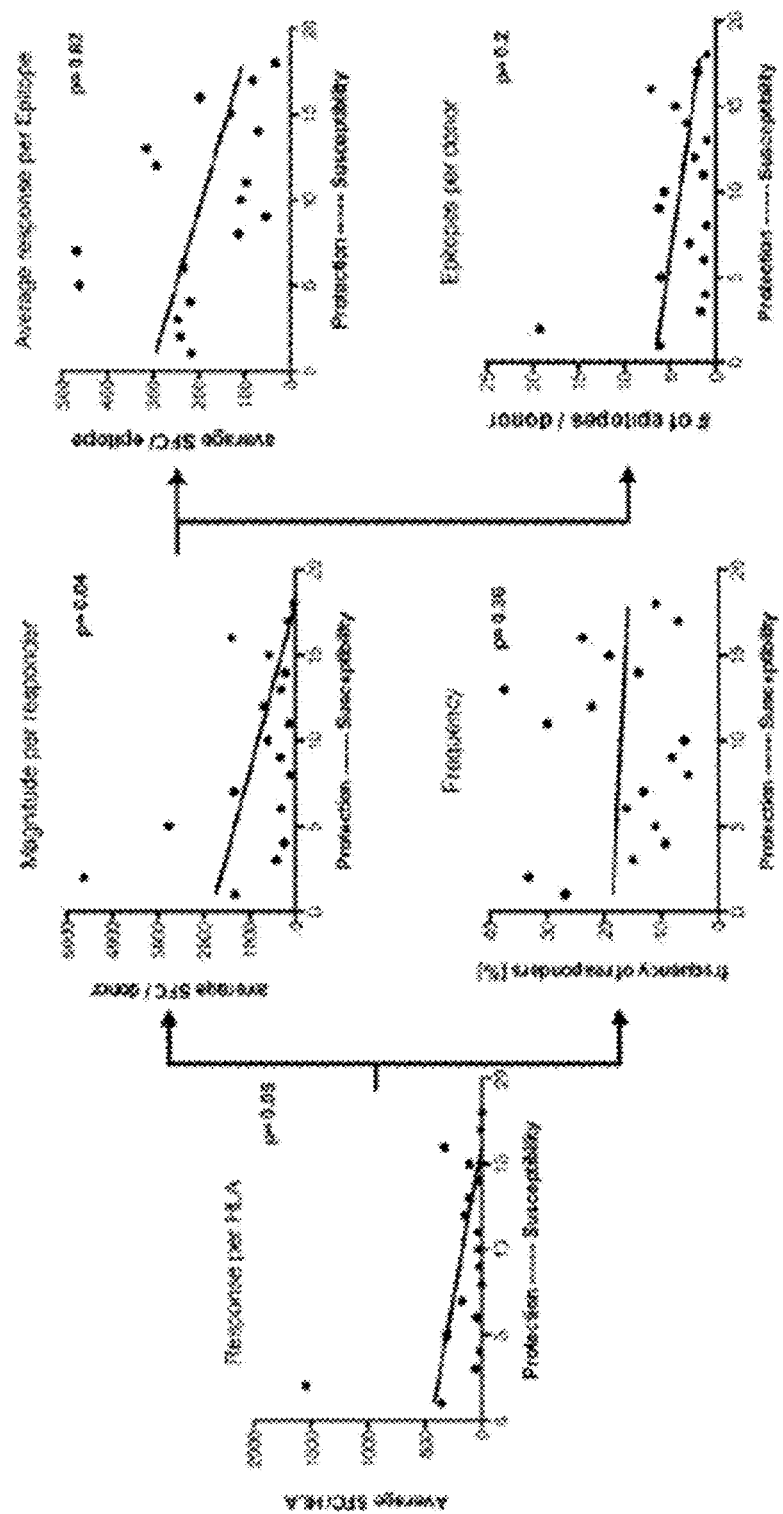

When average magnitudes of HLA restricted responses were compared with disease susceptibility, weak T cell responses correlated with disease susceptibility (FIG. 19b, left panel; $p=0.05$). This correlation was accounted for, by the response magnitude rather than their frequency (FIG. 19b, middle panel, $p=0.04$). Further analysis revealed that the magnitude per epitope rather than the breadth of responses correlated best with disease susceptibility (FIG. 19b, right panel, $p=0.02$) and that low T cell responses are associated with disease susceptibility.

TABLE 9

Ranking of reported HLA associations from the literature

| Study Ethnicity Parameter Allele | Malavige et al. Plos ONE 2011 | | | Stephens et al. Tissue Antigens 2002 | | | | Falcon et al Acta Tropica | | | Loke et al. J Infect Dis 2001 | Appanna et al. PloS ONE 2010 | | | | Lan et al. PloS NTDs 2008 | Sierra et al. Human Imm 2007 | Study Ethnicity Parameter Allele |
|---|---|---|---|---|---|---|---|---|---|---|---|---|---|---|---|---|---|---|
| | Sri Lankan Normal vs. acute DHF Rank | Sri Lankan Normal vs PD/SD Rank | Sri Lankan Normal vs DSS Rank | Thai Normal vs PD_DF Rank | Thai Normal vs PD_DHF Rank | Thai Normal vs SD_DF Rank | Thai Normal vs SD_DHF Rank | Mexican Normal vs DF/DHF Rank | Mest Normal vs DF Rank | Mest Normal vs DHF Rank | Vietnam Rank | total Normal vs DF/DHF Rank | Malay Normal vs DF/DHF Rank | Chinese Normal vs DF/DHF Rank | Indian Normal vs DF/DHF Rank | Vietnam Normal vs DHF/DSS Rank | Cuba Normal vs DENV2 Rank | |
| A*01 | 23 | 7 | 10 | 6 | 1 | 5 | 5 | 9 | 9 | 6 | | 9 | 18 | 1 | 14 | 1 | 17 | A*01 |
| A*02 | 11 | 4 | 8 | 21 | 20 | 24 | 23 | 9 | 9 | 6 | 2 | 14 | 19 | 15 | 13 | 1 | 30 | A*02 |
| A*03 | 21 | 3 | 9 | 2 | 1 | 4 | 3 | | | | | 3 | 5 | 1 | 12 | | 19 | A*03 |
| A*11 | 15 | | | 6 | 21 | 7 | 22 | | | | 4 | 16 | 8 | 21 | 25 | 1 | 2 | A*11 |
| A*23 | | | | | | | | | | | | | | | | | 12 | A*23 |
| A*24 | 22 | 12 | 3 | 21 | 5 | 8 | 8 | 9 | | 6 | 5 | 22 | 14 | 24 | 15 | 20 | 28 | A*24 |
| A*25 | | | | | | | | | | | | | | | | | 39 | A*25 |
| A*26 | 9 | 5 | 1 | | | | | | | | | 28 | | | | | 39 | A*26 |
| A*29 | | | | | | | | | | | 3 | | | | | | 19 | A*29 |
| A*30 | 5 | | | | | | | | | | | | | | 15 | 1 | 35 | A*30 |
| A*31 | 6 | | 13 | | | | | | | | | 33 | 23 | | 1 | | 40 | A*31 |
| A*32 | | | | | | | | | | | | 24 | | 8 | 29 | | 19 | A*32 |
| A*33 | 13 | 6 | 4 | 5 | 23 | 8 | 6 | | | | 1 | 11 | 16 | | 1 | | 10 | A*33 |
| A*34 | | | | | | | | | | | | 9 | 20 | 10 | 1 | | 30 | A*34 |
| A*36 | | | | | | | | | | | | 28 | | | | | 30 | A*36 |
| A*66 | | | | | | | | | | | | | | | | | 36 | A*66 |
| A*68 | 1 | | | | | | | | | | | 28 | | | 24 | | 2 | A*68 |
| A*74 | | | | | | | | | | | | | | | | | 19 | A*74 |
| B*07 | 16 | 2 | 2 | 8 | 7 | 9 | 9 | 9 | 17 | 6 | | 18 | 16 | 16 | 15 | 1 | 29 | B*07 |
| B*08 | 17 | | | | | | | | | | | | | | | 1 | 12 | B*08 |
| B*13 | 26 | | | 8 | 7 | 9 | 9 | 14 | | | | 28 | 26 | 12 | 27 | 1 | 1 | B*13 |
| B*14 | 14 | 11 | 11 | | | | | | 6 | 12 | | 11 | | 16 | | | 12 | B*14 |
| B*15 | 24 | | | 8 | 7 | 9 | 9 | | 5 | 2 | | 21 | 20 | 23 | 11 | | 7 | B*15 |
| B*18 | 8 | | | 8 | 7 | 9 | 9 | 6 | 14 | | | 1 | 1 | 16 | 1 | 1 | 37 | B*18 |
| B*27 | | | | | | | | | | | | 7 | | 25 | | | 19 | B*27 |
| B*35 | 25 | 10 | 7 | | | | | 2 | 1 | 1 | | 6 | 6 | 11 | 15 | | 2 | B*35 |
| B*37 | 20 | | | | | | | | | | | 26 | 9 | | | | 12 | B*37 |
| B*38 | 3 | | | 8 | 7 | 9 | 9 | 14 | 12 | 11 | | 19 | 23 | 6 | | 1 | 7 | B*38 |
| B*39 | | | | 8 | 7 | 9 | 9 | 4 | 4 | 4 | | 2 | 1 | 8 | 1 | | 19 | B*39 |
| B*40 | 7 | 8 | 5 | | | | | 18 | 18 | | | 14 | 15 | 14 | 15 | | 37 | B*40 |
| B*41 | | | | | | | | | | | | | | | | | 19 | B*41 |
| B*42 | | | | | | | | | | | | 1 | 1 | 1 | 1 | | 10 | B*42 |
| B*44 | 18 | 9 | | 4 | 22 | 6 | 3 | 3 | 3 | 4 | | 5 | 9 | 1 | 15 | | 19 | B*44 |
| B*45 | | | | | | | | | | | | | | | | | 17 | B*45 |
| B*46 | | | | | 21 | 24 | 23 | | | | | 19 | 20 | 16 | | 1 | 19 | B*46 |
| B*47 | | | | | | | | 15 | 6 | | | 11 | | 1 | | | 30 | B*47 |
| B*48 | | | | | | | | 6 | 13 | 13 | | 33 | 25 | | | | | B*48 |
| B*49 | | | | | | | | | | | | | | | | | 19 | B*49 |

TABLE 9-continued

Ranking of reported HLA associations from the literature

| | Malavige et al. Plos ONE 2011 | | | Stephens et al. Tissue Antigens 2002 | | | | Falcon et al Acta Tropica | | | Loke et al. J Infect Dis 2001 | Appanna et al. PloS ONE 2010 | | | | Lan et al. PloS NTDs 2008 | Sierra et al. Imm 2007 | |
|---|---|---|---|---|---|---|---|---|---|---|---|---|---|---|---|---|---|---|
| Study | Sri Lankan | Sri Lankan | Sri Lankan | Thai | Thai | Thai | Thai | Mest Mexican | Mexican | Mexican | Vietnam | total | Malay | Chinese | Indian | Vietnam | Cuba | Study |
| Ethnicity | Normal vs. acute DHF | Normal vs PD/SD | Normal vs DSS | Normal vs PD_DF | Normal vs PD_DHF | Normal vs SD_DF | Normal vs SD_DHF | Normal vs DF/DHF | Normal vs DF | Normal vs DHF | | Normal vs DF/DHF | Normal vs DF/DHF | Normal vs DF/DHF | Normal vs DF/DHF | Normal vs DHF/DSS | Normal vs DENV2 | Ethnicity |
| Parameter Allele | Rank | Rank | Rank | Rank | Rank | Rank | Rank | Rank | Rank | Rank | Rank | Rank | Rank | Rank | Rank | Rank | Rank | Parameter Allele |
| B*5 | | | | 25 | 25 | 25 | 25 | | | | | | | | | | | B*5 |
| B*50 | | | | | | | | | | | | | | | | | | B*50 |
| B*51 | 12 | 1 | | | | | | 1 | 17 | 2 | | 17 | 9 | 12 | 26 | 1 | 30 | B*51 |
| B*52 | 19 | | 12 | | | | | 19 | | | | 23 | 9 | | 23 | | 7 | B*52 |
| B*53 | | | | | | | | | | | | | | | | | | B*53 |
| B*54 | | | | | | | | | | | | 32 | | 22 | | | 12 | B*54 |
| B*55 | 4 | | | 8 | 7 | 9 | 9 | | | | | 7 | 9 | 16 | 1 | 1 | | B*55 |
| B*56 | | | | 8 | 7 | 9 | 9 | | | | | 24 | 1 | 1 | 15 | | | B*56 |
| B*57 | 10 | | | 8 | 7 | 9 | 9 | 16 | 15 | 15 | | 26 | | 7 | 27 | 1 | 30 | B*57 |
| B*58 | 2 | | | 8 | 7 | 9 | 9 | | | | | 4 | 7 | | 1 | 1 | 2 | B*58 |
| B*60 | | | | 8 | 7 | 9 | 9 | | | | | | | | | | | B*60 |
| B*62 | | | | 8 | 7 | 9 | 9 | | | | | | | | | | | B*62 |
| B*75 | | | | 1 | 1 | 1 | 1 | | | | | | | | | | | B*75 |
| B*76 | | | | 3 | 1 | 2 | 2 | | | | | | | | | | | B*76 |
| B*77 | | | | | | | 1 | | | | | | | | | | 1 | B*77 |
| B*78 | | | | | | | | | | | | | | | | | | B*78 |
| n = | 26 | 12 | 13 | 25 | 25 | 25 | 25 | 19 | 18 | 15 | 5 | 34 | 26 | 25 | 29 | 20 | 40 | |

Example 22.1

This example includes a description of studies showing that higher T cell responses are associated with multifunctional T cell responses.

Figure 19C:
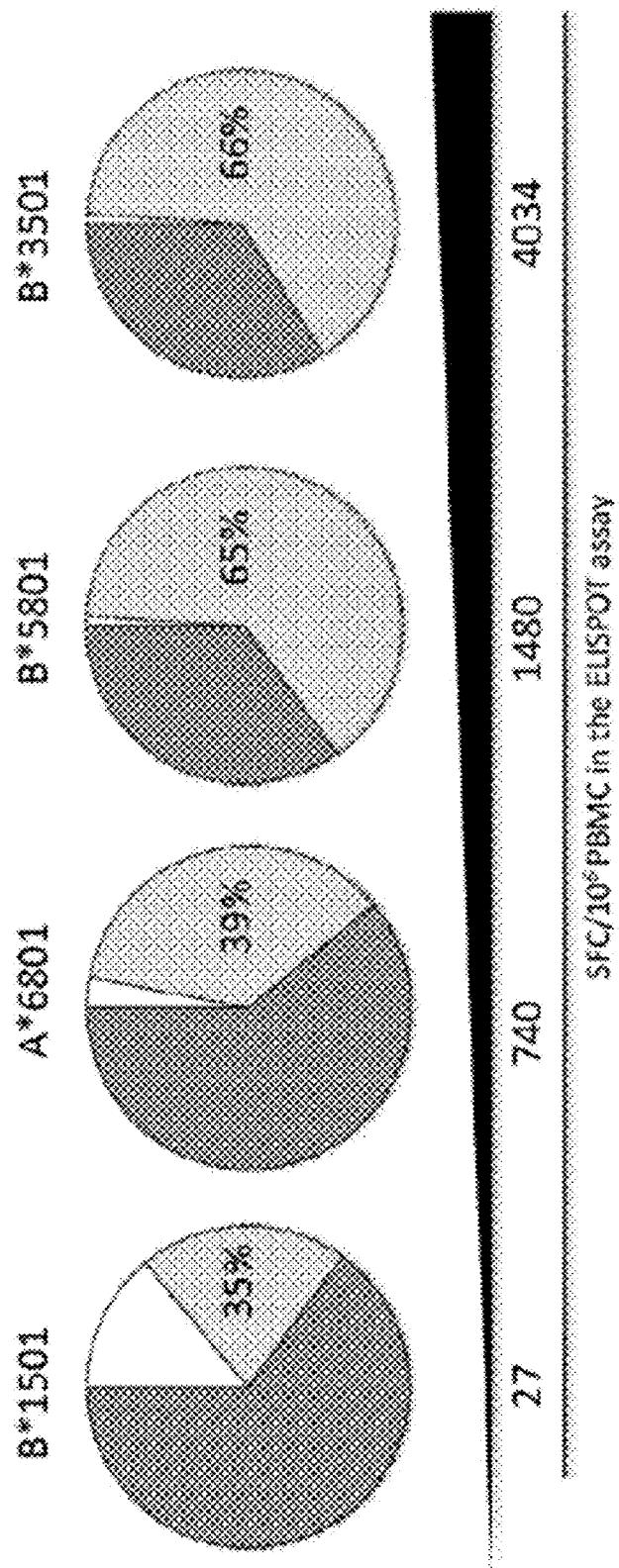
Figure 20A:
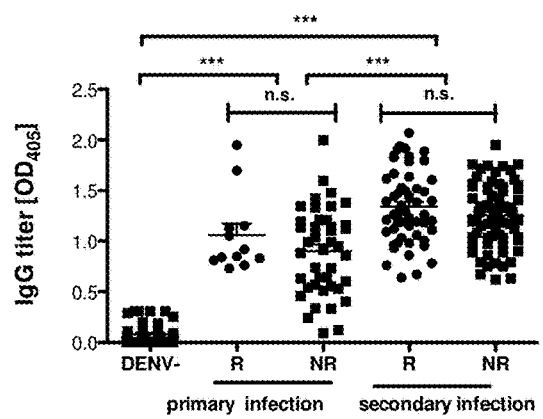
FIGS. 20A-20D show a correlation between T cell and antibody responses.
Figure 20B:
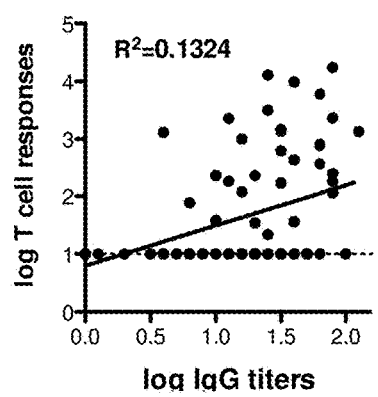
Figure 20C:
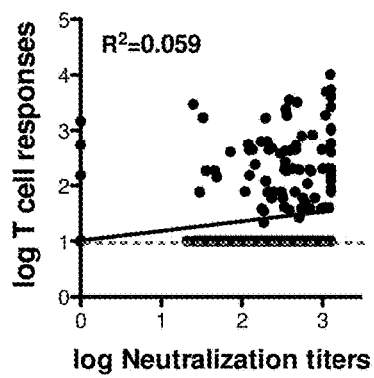
Figure 20D:
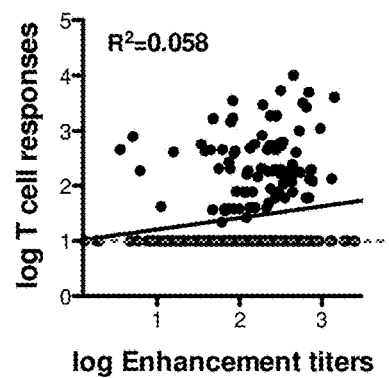
Figures 21A, 21B:
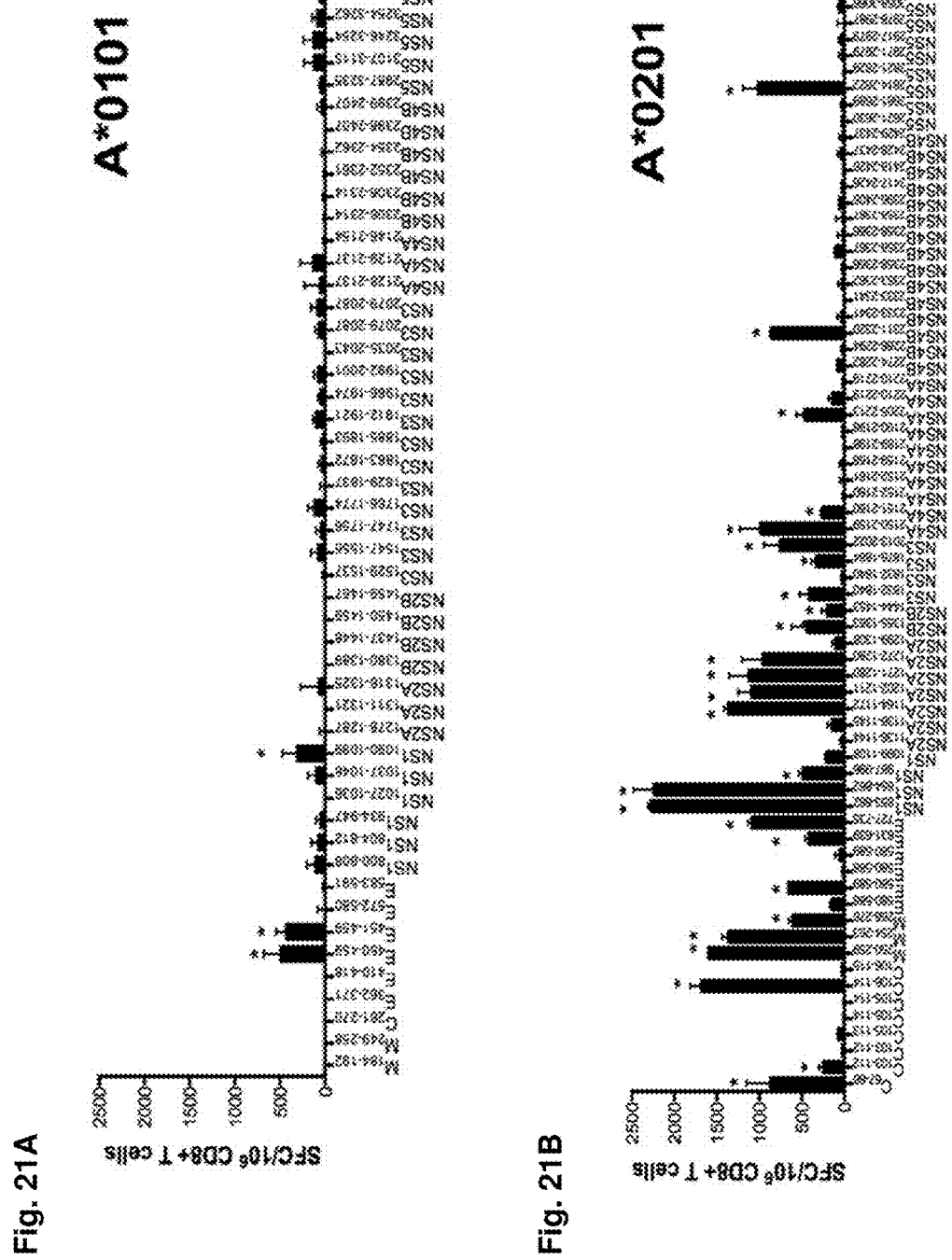
FIGS. 21A-21E show DENV 3 specific epitope identification in an HLA transgenic mouse model. DENV specific epitope identification was performed in five different HLA transgenic mouse strains: A*0101 (FIG. 21A); A*0201 (FIG. 21B); B*0702 (FIG. 21C); B*4001 (FIG. 21D) and DRB1*0101 (FIG. 21E). For all strains tested, IFNγ ELISPOT was performed using spleenic T cells isolated from HLA transgenic IFN-α/βR−/− mice (black bars). Mice were infected retro-orbitally with 1×1010 GE of DENV3. For all MHC class I mouse strains peptides were tested in pools of 10 peptides and subsequently deconvoluted if the pool was positive in two independent experiments. Shown are peptides from pools, which have been identified positive (5 A*0101 pools (FIG. 21A); 7 A*0201 pools (FIG. 21B); 7 B*0702 pools (FIG. 21C); 4 B*4001 pools (FIG. 21D)). MHC class II peptides were tested individually (FIG. 21E) Seven days post-infection, CD8+ (FIG. 21A-D) or CD4+ (FIG. 21E) T cells were purified and tested against a panel of DENV3 predicted peptides. The data are expressed as mean number of SFC/$10^6$ T cells of two independent experiments. Error bars represent SEM. Responses against peptides were considered positive if the stimulation index (SI) exceeded double the mean negative control wells (T cells plus APCs without peptide) and net spots were above the threshold of 20 SFCs/$10^6$ T cells in two independent experiments. Asterisks indicate peptides, which were able to elicit a significant IFNγ response in each individual experiment, according to the criteria described above.
Figure 21C:
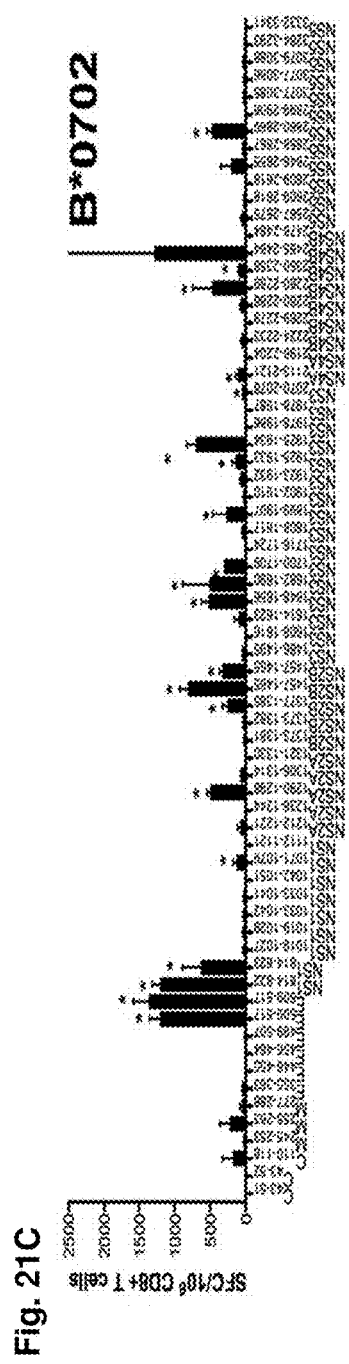
Figure 21D:
Figure 21E:
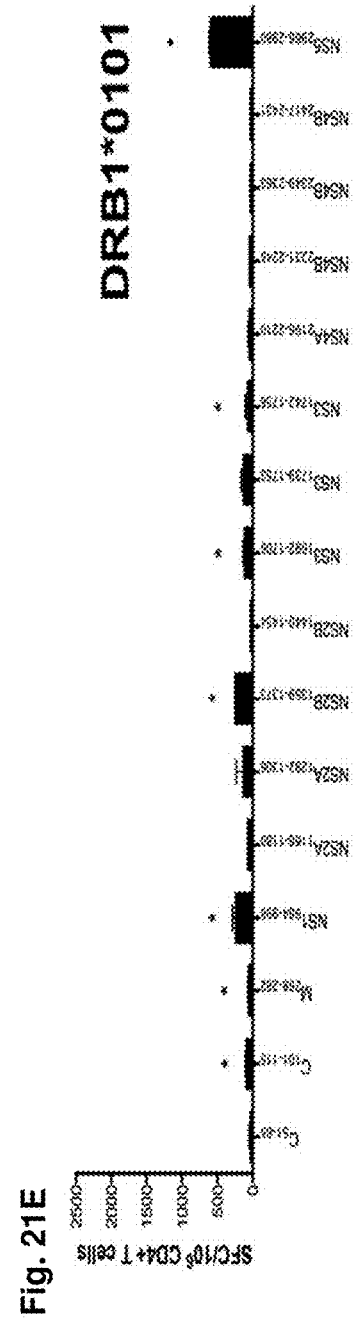

It was reasoned that a possible explanation for the observations above would be that certain alleles and epitopes are associated with higher magnitude responses, which are in turn associated with higher degrees of multi-functionality, and thus might be most beneficial in protecting from disease. A detailed analysis of cytokines produced by DENV specific T cells revealed indeed that stronger responses are associated with multifunctional T cell responses (FIG. 19c).

Example 23

This example includes a discussion of the foregoing data and conclusions based upon the data.

The role of $CD8^+$ T cells in dengue infection is not yet fully understood. Several reports highlight how $CD8^+$ T cell responses are detected in humans that have recovered from infection and disease. In animal models, $CD8^+$ T cells are associated with protection from infection and disease (28, 29). According to one hypothesis, however, T cells can also be detrimental, because of antigenic sin (30, 31). While definitions vary somewhat, antigenic sin is usually defined as the imprint of responses associated with infection of a given serotype, which shapes and biases responses following infection with a different serotype (32). Herein, it is shown that while "antigenic sin" can be detected in the general population from the Colombo (Sri Lanka) endemic region, its functional consequence is not generating a less functional response. Rather it results in honing responses towards recognition of conserved viral sequences, by highly multifunctional $CD8^+$ T cells.

It is further shown herein that different HLA alleles are associated with differential magnitude of anti DENV responses, and that HLA alleles known to be associated with increased risk of severe DENV disease (14, 32) are also associated with weaker $CD8^+$ responses. Finally, also in this case the higher magnitude responses are associated with more poly-functional $CD8^+$ T cells. Taken together, these data support a protective role for $CD8^+$ T cells, and dispel the notion that DENV associated pathogenicity is resulting from "antigenic sin".

A major obstacle to clearly elucidate the function of $CD8^+$ T cell responses in humans has been the somewhat anectodical evidence available to date. Only a handful of epitopes have been defined, and lack of knowledge of T cell epitopes presented by common MHC alleles expressed by populations in endemic areas allowed only a very episodical evaluation of responses. In this study, the present inventors report for the first time a comprehensive ex vivo characterization of HLA restricted DENV specific T cell memory in the general population of Sri Lanka, where dengue is endemic. A total of 250 different individuals were studied and in 90% of the donors 3 or more of the HLA molecules expressed by atypical heterozygous individual at the A and B locus, were addressed by the present approach. These efforts led to the identification of 408 unique $CD8^+$ T cell epitopes. The novelty and impact of these results can be appreciated by noting that previous studies, as compiled by the Immune Epitope Database (IEDB) (www.iedb.org) identified a total of 82 unique $CD8^+$ T cell epitopes. This reflects an almost 6 fold expansion in knowledge about DENV specific T cell epitopes.

The present results are consistent with previous studies that have emphasized NS3 as a major T cell target (30, 33). However a more complete and through characterization demonstrates that T cell epitopes originate from all of the ten dengue virus proteins (capsid (C), pre-membrane (prM/M), envelope (E), and the seven non-structural proteins NS1, NS2A, NS2B, NS3, NS4A, NS4B and NS5). Besides NS3, other non-structural proteins such as NS4B and NS5 were also highly immunogenic. These results have implication in terms of DENV vaccination strategies, and specifically suggest that inclusion of NS3, NS4, and NS5 will be necessary to replicate the natural $CD8^+$ adaptive immunity.

Likewise, to clearly monitor responses and study DENV-associated immunopathology, a broad set of epitopes and antigens is required. To map epitopes for the various MHC class I alleles, relatively large amounts of blood were necessary. The 408 epitopes identified herein provide a tool to further investigate the $CD8^+$ responses in smaller sample volumes available from acute fever patients and/or children experiencing dengue fever. This will allow further characterization of $CD8^+$ T cell responses in clinically defined cohorts.

Along those lines the present inventors have been able to demonstrate that reactivity clusters in specific regions of these proteins with some of them being recognized across serotypes and being restricted by multiple HLA alleles. This clustering of epitopes in small amino-acid stretches has also been shown in a previous smaller scale study conducted in Vietnamese adults for a certain region of the NS3 protein (34) suggesting that this phenomenon is not limited to a certain ethnicity. Clustering of about 50% of the response in about 25 main antigenic regions promises to simplify the development of reagents to be utilized for diagnostic purposes and for vaccine evaluations. A number of techniques are of potential interest, such as the use of epitopes pools in ICS assays, Q-dots and CyTOF (35, 36)

The epitopes were subdivided in those conserved or homologous amongst different serotypes, and those uniquely associated with one particular serotype, in that no identical or highly homologous sequence could be found in other serotypes. This allowed in turn identifying which donors in the general populations had been infected at some point in time by a given serotype. Consistent with the serological evidence derived from the same population, it was found that DENV2 and 3 were most prevalent, and that the magnitude of the responses did not differ appreciably between DENV 2 and DENV3 responses, defined for each individual as the sum total of responses directed against serotype specific and conserved/homologous epitopes.

According to the known epidemiologic history of DENV infection in Sri Lanka both DENV 2 and 3 are prevalent (25) and a new clade of DENV3 is associated with a more recent spread, associated with a recrudescence of severe DENV cases in Sri (26). Consistent with this data and with the antigenic sin notion, the present inventors see that while responses to both serotype specific and conserved epitopes are observed for DENV2, conserved epitopes dominate DENV3 responses, likely reflecting previous DENV2 infections and thus expansion of T cells recognizing conserved epitopes.

This observation provided a rare opportunity to test, at the level of a global population from an endemic region, whether antigenic sin was associated with a lower quality of responses. However no significant difference in the magnitude, phenotype, pattern of multi-functionality or avidity of the T cell responses between serotype specific and conserved/homologous responses. While to a certain extent a semantic issue, perhaps the term antigenic "sin" is misleading and because of an implicit negative connotation, inaccurate. The evidence revealed by the current study is more aptly described by maturation of the specificity of CD8+ T cell responses, induced by repeated stimulation with only partially cross-reactive antigens.

The present observations are in contrast to other studies that reported that humans who contract a secondary dengue infection may generate a CD8+ T cell response that reacts better with a previously encountered dengue serotype (31). This altered peptide ligand (APL) hypothesis is also in contrast with the observation that heterologous T cell responses are not needed to produce DHF in infants. Exactly the same severe vascular permeability clinical syndrome and the same concentrations of cytokines in blood are produced during primary dengue immune responses in infants, as are in children with secondary dengue infections (37). Another study has shown a temporal mismatch between the CD8+ T cell response and commencement of capillary leakage, suggesting that CD8+ T cells are not responsible for early triggering of capillary leakage in children with DHF (38). The present inventors were able to show that dengue specific T cells recognize a wide repertoire of epitopes. To explain the association with DHF and heterologous infection by the APLs hypothesis, would require that aberrant T cell responses would consistently occur across the whole dengue specific epitope repertoire in one donor, which seems unlikely. The present data relates to the feature of immunity present in the general population, and does not directly address the features present at the time of acute manifestations such as DHF and DHSS. While the present data demonstrates that secondary infection does not negatively affect the response at the level of the general population, without being limited to any particular theory it may be that it does so in the few individuals that develop DHF or DSS.

The present inventors next examined the responses associated with different HLA alleles present in the general population of Sri Lanka. Multiple HLA Class I alleles have been associated with either protection or susceptibility to dengue infection in several ethnicities so far (17, 18, 20, 21). The A*24 allele is associated with susceptibility to disease not only in secondary but also primary infections with dengue virus (17, 19) and a recent report associated the A*01 allele with susceptibility to DHF in the Brazilian population (39). In contrast the B*3501 allele was negatively associated with symptomatic disease in Mexican dengue fever patients (20) and one study reported that HLA A and not HLA B genes are associated with DHF (17). However, until now it was not clear whether this association reflected differences in the corresponding T cell responses. In the present study A*0101 and A*2402 restricted responses were amongst the lowest responses observed in terms of frequencies as well as magnitude, whereas B*3501 restricted responses were associated with high magnitude responses. More extensive correlations demonstrate that HLA class I responses are positively correlated with protection from severe disease. This data demonstrates that severe disease is not to be ascribed to an over-active CD8+ T cell response, and rather a strong HLA class I restricted response is a positive correlate of protection.

Regarding the mechanism that mediates the positive association of HLA class I with protection from severe disease, the present inventors found that the best correlate of protection is the magnitude of response associated with individual epitopes. In turn, strong responses were associated with multi-functionality, which has been shown to be a main predictor of immunity in other viral systems (40, 41). Higher frequencies of dengue virus specific IFNγ producing T cells are present in children who subsequently developed subclinical infection, compared with those who develop symptomatic secondary dengue virus infection (42). Furthermore, HIV specific HLA B*27 and HLA B*57 restricted T cell responses are not suppressed by regulatory T cells and thus maintain proliferative capacity over the course of chronic infection (43). It remains to be determined if similar mechanisms underlie the observed variations in HLA restricted responses against infection with dengue virus.

The data presented herein suggests a protective role of strong CD8+ T cell responses, and does not support a causative role in the induction of severe disease by heterologous infection. Thus, the mechanism underlying severe disease induction remains open. Without being limited to any particular theory, HLA class II responses might be linked to immunopathology. Serotype cross-reactive antibodies may exacerbate disease by antibody-dependent enhancement (ADE) of infection (11, 12). It is possible that ADE increases processing and presentation of structural proteins through the exogenous presentation pathway, which might increase CD4+ T cell responses and immunopathology associated with lymphokine production.

In conclusion, the present inventors present for the first time a comprehensive analysis of functional T cell memory against dengue virus and were able to correlate this with HLA alleles expressed in the very same donors. The results support a protective rather than pathogenetic role for DENV-specific, HLA class I restricted responses in humans.

Dengue T cell epitopes identified by the proteome-wide screen described herein are listed in Table 10.

TABLE 10

Dengue Antigenic Regions

| Cluster No. | Sequence (SEQ ID NOs: 813-1163, in order of appearance) | # donors responded | Super-typte | HLA allele | length | Serotype | Alignment start | Alignment end | Total Response per epitope | Total response per Cluster |
|---|---|---|---|---|---|---|---|---|---|---|
| 1 | AAVLLLVTHY | 2 | B58 | HLA-B-5801 | 10 | DENV3 | 2356 | 2365 | 393.3 | 393.3 |
| 2 | ALRGLPIRY | 2 | A3 | HLA-A-0301 | 9 | DENV2 | 1712 | 1720 | 918.3 | 918.3 |
| 3 | AMALSIVSLF | 1 | B62 | HLA-B-1501 | 10 | DENV1 | 1297 | 1306 | 68.3 | 116.7 |
| 3 | MALSIVSLF | 1 | B7 | HLA-B-5101 | 9 | DENV1 | 1298 | 1306 | 48.3 | |
| 4 | APFESEGVL | 2 | B7 | HLA-B-0702 | 9 | DENV4 | 3387 | 3395 | 401.7 | 401.7 |
| 5 | APIMDEEREI | 1 | B7 | HLA-B-5301 | 10 | DENV2 | 1808 | 1817 | 206.7 | 206.7 |

TABLE 10-continued

Dengue Antigenic Regions

| Cluster No. | Sequence (SEQ ID NOs: 813-1163, in order of appearance) | # donors responded | Super-type | HLA allele | length | Serotype | Alignment start | Alignment end | Total Response per epitope | Total response per Cluster |
|---|---|---|---|---|---|---|---|---|---|---|
| 6 | APTRVVAAEM | 8 | B7 | HLA-B-3501, B*0702 | 10 | DENV2,3,4 | 1700 | 1709 | 1623.3 | 2230.0 |
| 6 | APTRVVASEM | 5 | B7 | HLA-B-0702 | 10 | DENV1 | 1700 | 1709 | 606.7 | |
| 7 | ASSMVNGVVK | 1 | B58 | HLA-B-5801 | 10 | DENV1 | 2812 | 2821 | 116.7 | 523.3 |
| 7 | ASSMVNGVVR | 2 | B58 | HLA-B-5701 | 10 | DENV1,2 | 2812 | 2821 | 406.7 | |
| 8 | ASSVLLWMAS | 1 | B58 | HLA-B-5801 | 10 | DENV1 | 2186 | 2195 | 68.3 | 68.3 |
| 9 | ATGPILTLW | 2 | B58 | HLA-B-5801 | 9 | DENV4 | 2444 | 2452 | 938.3 | 3088.8 |
| 9 | ATGPISTLW | 2 | B58 | HLA-B-5801 | 9 | DENV2 | 2444 | 2452 | 235.5 | |
| 9 | ATGPITTLW | 1 | B58 | HLA-B-5801 | 9 | DENV3 | 2444 | 2452 | 505.0 | |
| 9 | ATGPLTTLW | 1 | B58 | HLA-B-5801 | 9 | DENV1 | 2444 | 2452 | 275.0 | |
| 9 | ATGPVLTLW | 2 | B58 | HLA-B-5801 | 9 | DENV4 | 2444 | 2452 | 390.0 | |
| 9 | LATGPVLTLW | 1 | B7 | HLA-B-5301 | 10 | DENV4 | 2443 | 2452 | 745.0 | |
| 10 | ATYGWNLVK | 1 | A3 | HLA-A-1101 | 9 | DENV1,4 | 2612 | 2620 | 28.3 | 291.7 |
| 10 | MATYGWNLVK | 1 | A3 | HLA-A-1101 | 10 | DENV1 | 2611 | 2620 | 26.7 | |
| 10 | MSTYGWNIVK | 1 | A3 | HLA-A-1101 | 10 | DENV3,1 | 2611 | 2620 | 236.7 | |
| 11 | AVQTKPGLFK | 1 | A3 | HLA-A-1101 | 10 | DENV2 | 1585 | 1594 | 63.3 | 63.3 |
| 12 | CLIPTAMAF | 1 | B62 | HLA-B-1501 | 9 | DENV4 | 108 | 116 | 66.7 | 2815.0 |
| 12 | MLIPTAMAF | 7 | B7 | HLA-B-3501 | 9 | DENV2 | 108 | 116 | 2748.3 | |
| 13 | CLMMMLPATL | 1 | A2 | HLA-A-0201 | 10 | DENV3 | 105 | 114 | 78.3 | 78.3 |
| 14 | CPTQGEATL | 1 | B7 | HLA-B-3501 | 9 | DENV1 | 355 | 363 | 295.0 | 680.0 |
| 14 | CPTQGEAVL | 2 | B7 | HLA-B-3501 | 9 | DENV3 | 355 | 363 | 385.0 | |
| 15 | CPTQGEPSL | 1 | B7 | HLA-B-5301 | 9 | DENV2 | 355 | 363 | 35.0 | 35.0 |
| 16 | DPASIAARGY | 9 | B7 | HLA-B-3501 | 10 | DENV1,2,3 | 1768 | 1777 | 2383.3 | 2383.3 |
| 17 | DPIPYDPKF | 1 | B7 | HLA-B-3501 | 9 | DENV2 | 2403 | 2411 | 38.3 | 38.3 |
| 18 | DPRRCLKPV | 2 | B7 | HLA-B-0702 | 9 | DENV1,3,4 | 1902 | 1910 | 556.7 | 556.7 |
| 19 | DTTPFGQQR | 8 | A3 | HLA-A-6801, A*3301 | 9 | DENV1,2,3,4 | 2840 | 2848 | 3260.0 | 3260.0 |
| 20 | DYMPSMKRFR | 1 | A3 | HLA-A-3301 | 10 | DENV2,3 | 3377 | 3386 | 285.0 | 285.0 |
| 21 | EAVEDSRFWE | 1 | B58 | HLA-B-5801 | 10 | DENV2 | 2919 | 2928 | 248.3 | 248.3 |
| 22 | EENMDVEIW | 1 | B44 | HLA-B-4403 | 9 | DENV1 | 2052 | 2060 | 448.3 | 448.3 |
| 23 | EERDIPERSW | 1 | B44 | HLA-B-4403 | 10 | DENV1,3 | 1813 | 1822 | 133.3 | 133.3 |
| 24 | EFKEFAAGR | 1 | A3 | HLA-A-3301 | 9 | DENV1 | 2087 | 2095 | 26.7 | 66.7 |
| 24 | EFKEFAAGRR | 1 | A3 | HLA-A-3301 | 10 | DENV1 | 2087 | 2096 | 40.0 | |
| 25 | ELMRRGDLPV | 1 | A2 | HLA-A-0201 | 10 | DENV1,3,4 | 2013 | 2022 | 123.3 | 123.3 |
| 26 | EPDYEVDEDI | 1 | B7 | HLA-B-5301 | 10 | DENV4 | 1651 | 1660 | 78.3 | 78.3 |
| 27 | EPGQLKLNWF | 5 | B7 | HLA-B-3501 | 10 | DENV2 | 664 | 673 | 581.7 | 581.7 |
| 28 | EPGVVSPTSY | 1 | B7 | HLA-B-3501 | 10 | DENV3 | 2264 | 2274 | 431.7 | 431.7 |
| 29 | EPIEGKVVQY | 1 | B7 | HLA-B-3501 | 10 | DENV3 | 404 | 413 | 403.3 | 403.3 |
| 30 | EPISYDPKF | 1 | B7 | HLA-B-5301 | 9 | DENV4 | 2403 | 2411 | 340.0 | 340.0 |
| 31 | EPKEGTKKLM | 3 | B7 | HLA-B-3501 | 10 | DENV2 | 2860 | 2869 | 928.3 | 928.3 |
| 32 | ESSSNPTIEE | 1 | B58 | HLA-B-5801 | 10 | DENV4 | 2644 | 2653 | 408.3 | 408.3 |
| 33 | ETACLGKAY | 3 | A1 | HLA-A-2601 | 9 | DENV3,4 | 3246 | 3254 | 240.0 | 771.6 |
| 33 | ETACLGKAYA | 1 | A1 | HLA-A-2601 | 10 | DENV3,4 | 3246 | 3255 | 73.3 | |
| 33 | ETACLGKSY | 4 | A1 | HLA-A-2601 | 9 | DENV1,2 | 3246 | 3254 | 321.7 | |

TABLE 10-continued

Dengue Antigenic Regions

| Cluster No. | Sequence (SEQ ID NOs: 813-1163, in order of appearance) | # donors responded | Super-typte | HLA allele | length | Serotype | Alignment start | Alignment end | Total Response per epitope | Total response per Cluster |
|---|---|---|---|---|---|---|---|---|---|---|
| 33 | KETACLGKSY | 1 | B44 | HLA-B-4403 | 10 | DENV2 | 3245 | 3254 | 23.3 | |
| 33 | RETACLGKAY | 1 | B44 | HLA-B-4403 | 10 | DENV3 | 3245 | 3254 | 60.0 | |
| 33 | RETACLGKSY | 1 | B44 | HLA-B-4403 | 10 | DENV1 | 3245 | 3254 | 53.3 | |
| 34 | ETTHHAVSR | 1 | A3 | HLA-A-6801 | 9 | DENV3 | 2544 | 2552 | 30.0 | 80.0 |
| 34 | ETTKHAVSR | 1 | A3 | HLA-A-3301 | 9 | DENV1 | 2544 | 2552 | 50.0 | |
| 35 | FAGPVSQHNY | 3 | B7 | HLA-B-3501 | 10 | DENV2 | 1023 | 1032 | 428.3 | 428.3 |
| 36 | FASGRKSITL | 1 | B58 | HLA-B-5801 | 10 | DENV4 | 2091 | 2100 | 26.7 | 26.7 |
| 37 | FGAIYGAAF | 3 | B7 | HLA-B-3501 | 9 | DENV2 | 721 | 729 | 798.3 | 798.3 |
| 38 | FLMVLLIPEP | 1 | A2 | HLA-A-0201 | 10 | DENV1,4 | 2210 | 2219 | 28.3 | 28.3 |
| 39 | FMALVAFLRF | 1 | B7 | HLA-B-3501 | 10 | DENV2 | 48 | 57 | 105.0 | 105.0 |
| 40 | FMKDGRSLVV | 1 | B7 | HLA-B-5101 | 10 | DENV4 | 3213 | 3222 | 66.7 | 66.7 |
| 41 | FPQSNAPIMD | 4 | B7 | HLA-B-3501 | 10 | DENV2 | 1803 | 1812 | 716.7 | 716.7 |
| 42 | FPVSIPITAA | 1 | B7 | HLA-B-3501 | 10 | DENV2 | 1457 | 1466 | 71.7 | 71.7 |
| 43 | FSRENSLSGV | 1 | B7 | HLA-B-5101 | 10 | DENV1,2 | 2993 | 3002 | 101.7 | 101.7 |
| 44 | FTILALFLAH | 8 | B7 | HLA-B-3501 | 10 | DENV3 | 248 | 257 | 1715.0 | 1715.0 |
| 45 | FTIMAAILAY | 2 | B7 | HLA-B-3501 | 10 | DENV2 | 248 | 257 | 675.0 | 738.3 |
| 45 | TIMAAILAY | 1 | B7 | HLA-B-3501 | 9 | DENV2 | 249 | 257 | 20.0 | |
| 45 | TLMAAILAY | 1 | B62 | HLA-B-1501 | 9 | DENV2 | 249 | 257 | 43.3 | |
| 46 | FTMGVLCLAI | 1 | A2 | HLA-A-0201 | 10 | DENV3 | 1136 | 1145 | 58.3 | 58.3 |
| 47 | FTMRHKKATY | 4 | B7 | HLA-B-3501 | 10 | DENV2 | 2738 | 2747 | 1723.3 | 1723.3 |
| 48 | FTNMEAQLVR | 1 | B7 | HLA-B-3501 | 10 | DENV3 | 3107 | 3116 | 88.3 | 88.3 |
| 49 | GAMLFLISGK | 1 | A3 | HLA-A-1101 | 10 | DENV3 | 2163 | 2172 | 23.3 | 23.3 |
| 50 | GASKRSWPLN | 1 | B58 | HLA-B-5801 | 10 | DENV4 | 1343 | 1352 | 51.7 | 51.7 |
| 51 | GEARKTFVDL | 3 | B44 | HLA-B-4001 | 10 | DENV2 | 2005 | 2014 | 1405.0 | 5005.0 |
| 51 | GEARKTFVEL | 3 | B44 | HLA-B-4001 | 10 | DENV1 | 2005 | 2014 | 1330.0 | |
| 51 | GEQRKTFVEL | 2 | B44 | HLA-B-4001 | 10 | DENV4 | 2005 | 2014 | 1050.0 | |
| 51 | GESRKTFVEL | 3 | B44 | HLA-B-4001 | 10 | DENV3 | 2005 | 2014 | 1220.0 | |
| 52 | GEFRLRGEQR | 3 | B44 | HLA-B-4001 | 10 | DENV4 | 1999 | 2008 | 1373.3 | 1373.3 |
| 53 | GEGLHKLGY | 2 | B44 | HLA-B-4403 | 9 | DENV1,3 | 3004 | 3012 | 413.3 | 413.3 |
| 54 | GEVGAIALDF | 1 | B44 | HLA-B-4403 | 10 | DENV1 | 1598 | 1607 | 101.7 | 101.7 |
| 55 | GFFLRKLTSR | 1 | A3 | HLA-A-3301 | 10 | DENV3 | 1218 | 1227 | 81.7 | 81.7 |
| 56 | GGWRLSAQW | 1 | B58 | HLA-B-5701 | 9 | DENV3 | 1558 | 1566 | 20.0 | 20.0 |
| 57 | GMGEAAAIF | 1 | B62 | HLA-B-1501 | 9 | DENV1 | 1783 | 1791 | 23.3 | 23.3 |
| 58 | GPGHEEPIPM | 3 | B7 | HLA-B-3501 | 10 | DENV1,2,4 | 2602 | 2611 | 235.0 | 235.0 |
| 59 | GPLVAGGLL | 3 | B7 | HLA-B-0702 HLA-B-0702 | 9 | DENV2,3 | 1377 | 1385 | 748.3 | 748.3 |
| 60 | GPMKLVMAF | 2 | B7 | HLA-B-5301 | 9 | DENV1,3 | 43 | 51 | 789.7 | 1148.0 |
| 60 | GPMKLVMAFI | 1 | B7 | HLA-B-0702 | 10 | DENV1,3 | 43 | 52 | 358.3 | |
| 61 | GPSLRTTTV | 1 | B7 | HLA-B-0702 | 9 | DENV1,3 | 1071 | 1079 | 213.3 | 213.3 |
| 62 | GPWHLGKLEL | 2 | B7 | HLA-B-0702 | 10 | DENV1,3 | 1042 | 1051 | 495.0 | 585.0 |
| 62 | GPWHLGKLEM | 3 | B7 | HLA-B-3501 | 10 | DENV2 | 1042 | 1051 | 90.0 | |
| 63 | GSSKIRWIVE | 2 | B58 | HLA-B-5801 | 10 | DENV4 | 2553 | 2562 | 111.7 | 111.7 |

TABLE 10-continued

Dengue Antigenic Regions

| Cluster No. | Sequence (SEQ ID NOs: 813-1163, in order of appearance) | # donors responded | Super-typte | HLA allele | length | Serotype | Alignment start | Alignment end | Total Response per epitope | Total response per Cluster |
|---|---|---|---|---|---|---|---|---|---|---|
| 64 | GTSGSPIIDK | 3 | A3 | HLA-A-1101 | 10 | DENV2 | 1610 | 1619 | 475.0 | 516.7 |
| 64 | TSGSPIIDK | 1 | A3 | HLA-A-1101 | 9 | DENV2 | 1611 | 1619 | 41.7 | |
| 65 | GTSGSPIVNR | 1 | B58 | HLA-B-5701 | 10 | DENV1 | 1610 | 1619 | 28.3 | 28.3 |
| 66 | HALLATSIF | 2 | B7 | HLA-B-3501 | 9 | DENV1 | 3056 | 3064 | 80.0 | 80.0 |
| 67 | HMIAGVLFTF | 1 | B62 | HLA-B-1501 | 10 | DENV3 | 1159 | 1168 | 45.0 | 45.0 |
| 68 | HPASAWTLY | 3 | B7 | HLA-B-3501 & HLA-B-5301 | 9 | DENV1,3 | 2280 | 2288 | 281.7 | 810.0 |
| 68 | RPASAWTLYA | 2 | B7 | HLA-B-0702 | 10 | DENV1,2,3 | 2280 | 2289 | 528.3 | |
| 69 | HPGAGKTKRY | 10 | B7 | HLA-B-3501 | 10 | DENV2 | 1672 | 1681 | 3046.7 | 3046.7 |
| 70 | HPGFTILALF | 9 | B7 A2 | HLA-B-3501 HLA-A-0206 | 10 | DENV3 | 245 | 254 | 3763.3 | 3763.3 |
| 71 | HQLWATLLSL | 2 | B62 | HLA-B-1501 | 10 | DENV1 | 1271 | 1280 | 601.7 | 601.7 |
| 72 | IAFLRFLAI | 1 | B7 | HLA-B-5101 | 9 | DENV1 | 52 | 60 | 318.3 | 318.3 |
| 73 | IANQAAILM | 1 | B7 | HLA-B-3501 | 9 | DENV1 | 2315 | 2323 | 58.3 | 58.3 |
| 74 | IANQATVLM | 7 | B7 B7 | HLA-B-3501 | 9 | DENV2 | 2315 | 2323 | 1518.3 | 1518.3 |
| 75 | IAVSMANIF | 6 | B58 | HLA-B-5801, HLA-B-3501 | 9 | DENV1,2,3 | 2464 | 2472 | 1966.7 | 2381.7 |
| 75 | IAVSTANIF | 2 | B58 | HLA-B-5801 | 9 | DENV4 | 2464 | 2472 | 415.0 | |
| 76 | ICSAVPVHW | 1 | B58 | HLA-B-5801 | 9 | DENV3 | 3275 | 3283 | 115.0 | 115.0 |
| 77 | IGIGILLTW | 1 | B58 | HLA-B-5801 | 9 | DENV1 | 738 | 746 | 525.0 | 903.3 |
| 77 | IGIGVLLTW | 1 | B58 | HLA-B-5801 | 9 | DENV1 | 738 | 746 | 378.3 | |
| 78 | IGLTSRATW | 1 | B58 | HLA-B-5801 | 9 | DENV2,3 | 3347 | 3355 | 50.0 | 50.0 |
| 79 | IILEFFLMV | 1 | A2 | HLA-A-0201 | 9 | DENV1,4 | 2205 | 2213 | 143.3 | 143.3 |
| 80 | IPFEIMDLEK | 5 | B7 | HLA-B-3501 | 10 | DENV2 | 616 | 625 | 1500.0 | 1500.0 |
| 81 | IPITAAAWY | 5 | B7 | HLA-B-3501 | 9 | DENV2 | 1461 | 1469 | 1001.7 | 1001.7 |
| 82 | IPKAYAGPF | 1 | B7 | HLA-B-3501 | 9 | DENV4 | 1019 | 1027 | 920.0 | 920.0 |
| 83 | IPMATYGWNL | 2 | B7 B7 | HLA-B-0702 HLA-B-0702 | 10 | DENV1,4 | 2609 | 2618 | 456.7 | 456.7 |
| 83 | IPMSTYGWNL | 3 | B7 | HLA-B-3501 | 10 | DENV2 | 2609 | 2618 | 320.0 | 320.0 |
| 84 | IPMTGPLVAG | 5 | B7 | HLA-B-3501 | 10 | DENV2 | 1373 | 1382 | 1160.0 | 1160.0 |
| 85 | IPQWEPSKGW | 1 | B7 | HLA-B-5301 | 10 | DENV1,4 | 3187 | 3196 | 26.7 | 26.7 |
| 86 | IPTVMAFHL | 1 | B7 | HLA-B-5301 | 9 | DENV2,4 | 110 | 118 | 70.0 | 70.0 |
| 87 | IQPFLALGF | 1 | A24 | HLA-A-2402 | 9 | DENV3 | 1211 | 1219 | 85.0 | 85.0 |
| 88 | ISSMLNIMNR | 1 | A3 | HLA-A-6801 | 10 | DENV1 | 89 | 98 | 30.0 | 30.0 |
| 89 | ITAAAWYLW | 1 | B7 | HLA-B-5301 | 9 | DENV2 | 1463 | 1471 | 310.0 | 310.0 |
| 90 | ITLLCLIPTV | 1 | A2 | HLA-A-0201 | 10 | DENV4 | 104 | 113 | 63.3 | 116.7 |
| 90 | TLLCLIPTV | 1 | A2 | HLA-A-0201 | 9 | DENV4 | 105 | 113 | 53.3 | |
| 91 | ITPMLRHTI | 1 | A24 | HLA-A-2402 | 9 | DENV3 | 2295 | 2303 | 190.0 | 190.0 |
| 92 | IVIGVGDSAL | 1 | B62 | HLA-B-1501 | 10 | DENV4 | 659 | 668 | 35.0 | 35.0 |
| 93 | KAKGSRAIW | 4 | B58 | HLA-B-5701 | 9 | DENV1,2,3 | 2962 | 2970 | 1070.0 | 1291.7 |
| 93 | RAKGSRAIW | 2 | B58 | HLA-B-5701 | 9 | DENV4 | 2962 | 2970 | 221.7 | |

TABLE 10-continued

Dengue Antigenic Regions

| Cluster No. | Sequence (SEQ ID NOs: 813-1163, in order of appearance) | # donors responded | Super-typte | HLA allele | length | Serotype | Alignment start | Alignment end | Total Response per epitope | Total response per Cluster |
|---|---|---|---|---|---|---|---|---|---|---|
| 94 | KATREAQKRA | 1 | B58 | HLA-B-5801 | 10 | DENV2 | 2375 | 2384 | 383.3 | 383.3 |
| 95 | KAVHADMGYW | 1 | B58 | HLA-B-5801 | 10 | DENV1,2 | 968 | 977 | 136.7 | 180.0 |
| 95 | RAVHADMGYW | 1 | B58 | HLA-B-5801 | 10 | DENV2 | 968 | 977 | 43.3 | |
| 96 | KAYAQMWSL | 2 | B58 | HLA-B-5801, B5701 | 9 | DENV3 | 3252 | 3260 | 116.7 | 116.7 |
| 97 | KEGVPHTMW | 1 | B44 | HLA-B-4403 | 9 | DENV3 | 1519 | 1527 | 178.3 | 178.3 |
| 98 | KGSRAIWYMW | 2 | B58 | HLA-B-5801, B5701 | 10 | DENV1,2,3,4 | 2964 | 2973 | 1345.0 | 1345.0 |
| 99 | KPGTSGSPI | 1 | B7 | HLA-B-0702 | 9 | DENV1,3,4 | 1608 | 1616 | 345.0 | 516.7 |
| 99 | KPGTSGSPII | 1 | B7 | HLA-B-0702 | 10 | DENV3,4 | 1608 | 1617 | 118.3 | |
| 99 | KPGTSGSPIV | 1 | B7 | HLA-B-0702 | 10 | DENV1 | 1608 | 1617 | 53.3 | |
| 100 | KPRICTREEF | 1 | B7 | HLA-B-0702 | 10 | DENV1 | 2885 | 2894 | 340.0 | 2756.3 |
| 100 | KPRLCTREEF | 1 | B7 | HLA-B-0702 | 10 | DENV3 | 2885 | 2894 | 350.0 | |
| 100 | NPRLCTREEF | 1 | B7 | HLA-B-0702 | 10 | DENV4 | 2885 | 2894 | 365.0 | |
| 100 | RPRLCTREEF | 4 | B7 | HLA-B-0702 | 10 | DENV3 | 2885 | 2894 | 501.3 | |
| 100 | TPRMCTREEF | 5 | B7 | HLA-B-0702, B-3501 | 10 | DENV2 | 2885 | 2894 | 1200.0 | |
| 101 | KPRWLDARI | 1 | B7 | HLA-B-0702 | 9 | DENV2 | 2070 | 2078 | 70.0 | 70.0 |
| 102 | KPTLDFELI | 1 | B7 | HLA-B-5301 | 9 | DENV2,4 | 319 | 327 | 670.0 | 670.0 |
| 103 | KPWDVIPMV | 3 | B7 | HLA-B-5101 | 9 | DENV1 | 2825 | 2833 | 746.7 | 1298.3 |
| 103 | KPWDVVPMV | 2 | B7 | HLA-B-5101 | 9 | DENV2 | 2825 | 2833 | 551.7 | |
| 104 | KQIANELNY | 1 | B62 | HLA-B-1501 | 9 | DENV3 | 845 | 853 | 26.7 | 53.3 |
| 104 | KQISNELNY | 1 | B62 | HLA-B-1501 | 9 | DENV1 | 845 | 853 | 26.7 | |
| 105 | KSGAIKVLK | 1 | A3 | HLA-A-1101 | 9 | DENV3 | 75 | 83 | 48.3 | 48.3 |
| 106 | KSYAQMWQL | 1 | B58 | HLA-B-5801 | 9 | DENV1 | 3252 | 3260 | 140.0 | 140.0 |
| 107 | KTDFGFYQV | 1 | A2 | HLA-A-0206 | 9 | DENV4 | 2256 | 2264 | 235.0 | 235.0 |
| 108 | KTFVDLMRR | 1 | A3 | HLA-A-1101 | 9 | DENV2 | 2009 | 2017 | 38.3 | 38.3 |
| 109 | KTWAYHGSY | 1 | B62 | HLA-B-1501 | 9 | DENV1 | 2796 | 2804 | 25.0 | 25.0 |
| 110 | KVIQLSRKTF | 1 | B62 | HLA-B-1501 | 10 | DENV2 | 1859 | 1868 | 51.7 | 51.7 |
| 111 | KVLNPYMPSV | 1 | A2 | HLA-A-0201 | 10 | DENV2 | 2676 | 2685 | 63.3 | 105.0 |
| 111 | VLNPYMPSV | 1 | A2 | HLA-A-0201 | 9 | DENV2 | 2677 | 2685 | 41.7 | |
| 112 | KVRKDIQQW | 1 | B58 | HLA-B-5701 | 9 | DENV2 | 3182 | 3190 | 38.3 | 38.3 |
| 113 | LAYTIGTTHF | 2 | B7 | HLA-B-3501 | 10 | DENV2 | 255 | 264 | 421.7 | 421.7 |
| 114 | LEFEALGFLN | 1 | B44 | HLA-B-4001 | 10 | DENV2 | 2979 | 2988 | 610.0 | 1166.7 |
| 114 | LEFEALGFMN | 1 | B44 | HLA-B-4001 | 10 | DENV1 | 2979 | 2988 | 556.7 | |
| 115 | LETLMLVAL | 1 | B44 | HLA-B-4001 | 9 | DENV4 | 2148 | 2156 | 103.3 | 103.3 |
| 116 | LGFLNEDHW | 1 | B58 | HLA-B-5701 | 9 | DENV2,3,4 | 2984 | 2992 | 546.7 | 546.7 |
| 117 | LIHQVFGTAY | 1 | B62 | HLA-B-1501 | 10 | DENV1 | 716 | 725 | 51.7 | 406.7 |
| 117 | LVHQIFGTAY | 1 | B62 | HLA-B-1501 | 10 | DENV1 | 716 | 725 | 355.0 | |
| 118 | LILCVTQVLM | 2 | B7 | HLA-B-3501 | 10 | DENV2 | 2421 | 2430 | 603.3 | 603.3 |
| 119 | LLMLVTPSM | 1 | B62 | HLA-B-1501 | 9 | DENV1 | 272 | 280 | 20.0 | 20.0 |
| 120 | LLSPVRVPNY | 1 | B62 | HLA-B-1501 | 10 | DENV1 | 1747 | 1756 | 36.7 | 36.7 |
| 121 | LMCHATFTM | 1 | B62 | HLA-B-1501 | 9 | DENV1 | 1737 | 1745 | 33.3 | 33.3 |

TABLE 10-continued

Dengue Antigenic Regions

| Cluster No. | Sequence (SEQ ID NOs: 813-1163, in order of appearance) | # donors responded | Super-typte | HLA allele | length | Serotype | Alignment start | Alignment end | Total Response per epitope | Total response per Cluster |
|---|---|---|---|---|---|---|---|---|---|---|
| 122 | LMKITAEWLW | 1 | B7 | HLA-B-5301 | 10 | DENV2 | 2868 | 2877 | 423.3 | 1416.7 |
| 122 | MEITAEWLW | 1 | B58 | HLA-B-5801 | 9 | DENV3 | 2869 | 2877 | 583.3 | |
| 122 | VMGITAEWLW | 1 | B7 | HLA-B-5301 | 10 | DENV3 | 2868 | 2877 | 410.0 | |
| 123 | LMMATIGIAL | 1 | B62 | HLA-B-1501 | 10 | DENV2 | 1229 | 1238 | 31.7 | 940.0 |
| 123 | MMATIGIAL | 6 | B7 | HLA-B-3501 | 9 | DENV2 | 1230 | 1238 | 908.3 | |
| 124 | LMMILPAAL | 1 | B62 | HLA-B-1501 | 9 | DENV3 | 106 | 114 | 46.7 | 46.7 |
| 125 | LMMMLPATLA | 1 | A2 | HLA-A-0201 | 10 | DENV3 | 106 | 115 | 61.7 | 61.7 |
| 126 | LMMTTIGVVL | 1 | B62 | HLA-B-1501 | 10 | DENV2 | 1229 | 1238 | 50.0 | 50.0 |
| 127 | LPAIVREAI | 3 | B7 | HLA-B-0702, B-5301 | 9 | DENV1,2,3 | 1682 | 1690 | 1280.0 | 1280.0 |
| 128 | LPEEQDQNY | 5 | B7 | HLA-B-3501 | 9 | DENV3 | 363 | 371 | 1166.7 | 1166.7 |
| 129 | LPESLETLM | 1 | B7 | HLA-B-3501 | 9 | DENV4 | 2144 | 2152 | 208.3 | 208.3 |
| 130 | LPETLETLLL | 4 | B7 | HLA-B-3501, B-5101 | 10 | DENV2 | 2144 | 2153 | 296.7 | 296.7 |
| 131 | LPGADTQGSN | 1 | B7 | HLA-B-3501 | 10 | DENV2 | 502 | 511 | 240.0 | 240.0 |
| 132 | LPIRYQTPA | 3 | B7 | HLA-B-0702, B-5101 | 9 | DENV2 | 1716 | 1724 | 270.0 | 1164.3 |
| 132 | LPIRYQTPAI | 5 | B7 | HLA-B-3501 | 10 | DENV2 | 1716 | 1725 | 894.3 | |
| 133 | LPLPWLPGAD | 1 | B7 | HLA-B-3501 | 10 | DENV2 | 497 | 506 | 238.3 | 238.3 |
| 134 | LPLPWTSGA | 1 | B7 | HLA-B-5101 | 9 | DENV1 | 497 | 505 | 111.7 | 111.7 |
| 135 | LPTFMTQKAR | 8 | B7 | HLA-B-3501 | 10 | DENV2 | 2109 | 2118 | 1263.3 | 1263.3 |
| 136 | LPTYLSSRAK | 1 | B7 | HLA-B-3501 | 10 | DENV4 | 2109 | 2118 | 26.7 | 26.7 |
| 137 | LPVWLAHKVA | 1 | B7 | HLA-B-3501 | 10 | DENV3 | 2020 | 2029 | 23.3 | 4156.7 |
| 137 | LPVWLAYKV | 2 | B7 | HLA-B-5301, B-5101 | 9 | DENV2 | 2020 | 2028 | 923.3 | |
| 137 | LPVWLAYKVA | 7 | B7 | HLA-B-3501 | 10 | DENV2 | 2020 | 2029 | 2426.7 | |
| 137 | LPVWLAYRVA | 1 | B7 | HLA-B-5101 | 10 | DENV2 | 2020 | 2029 | 470.0 | |
| 137 | LPVWLSYKV | 1 | B7 | HLA-B-5101 | 9 | DENV1 | 2020 | 2028 | 313.3 | |
| 138 | LRVLNLVENW | 1 | B7 | HLA-B-5301 | 10 | DENV2 | 2657 | 2666 | 351.7 | 351.7 |
| 139 | LSMGLITIAV | 1 | A2 | HLA-A-0206 | 10 | DENV4 | 2177 | 2186 | 571.7 | 571.7 |
| 140 | LSRNSTHEM | 1 | B62 | HLA-B-1501 | 9 | DENV1 | 2705 | 2713 | 26.7 | 26.7 |
| 141 | LTAAVLLLI | 1 | B58 | HLA-B-5801 | 9 | DENV3 | 2354 | 2362 | 545.0 | 611.7 |
| 141 | TLTAAVLLLV | 1 | A2 | HLA-A-0201 | 10 | DENV3 | 2353 | 2362 | 66.7 | |
| 142 | LWEGSPGKF | 1 | A24 | HLA-A-2402 | 9 | DENV1,3 | 2451 | 2459 | 25.0 | 25.0 |
| 143 | MAEIPLQWI | 1 | B7 B7 | HLA-B-5101 | 9 | DENV3 | 2193 | 2201 | 96.7 | 96.7 |
| 144 | MAFIAFLRF | 2 | B62 | HLA-B-3501, B-1501 | 9 | DENV1,3 | 49 | 57 | 146.7 | 146.7 |
| 145 | MAILGDTAW | 1 | B7 | HLA-B-3501 | 9 | DENV1,2,3 | 693 | 701 | 21.7 | 21.7 |
| 146 | MALKDFKEF | 7 | B7 | HLA-B-3501 | 9 | DENV4 | 2083 | 2091 | 1496.7 | 1496.7 |
| 147 | MAMTCIAVG | 1 | B7 | HLA-B-3501 | 9 | DENV4 | 756 | 764 | 123.3 | 123.3 |
| 148 | MANEMGFLEK | 1 | A3 | HLA-A-1101 | 10 | DENV2 | 2245 | 2254 | 21.7 | 21.7 |
| 149 | MANIFRGSY | 5 | B7 | HLA-B-3501 | 9 | DENV1,2,3 | 2468 | 2476 | 821.7 | 821.7 |
| 150 | MASSALLWMA | 1 | B58 | HLA-B-5801 | 10 | DENV1 | 2185 | 2194 | 45.0 | 45.0 |

TABLE 10-continued

Dengue Antigenic Regions

| Cluster No. | Sequence (SEQ ID NOs: 813-1163, in order of appearance) | # donors responded | Super-typte | HLA allele | length | Serotype | Alignment start | Alignment end | Total Response per epitope | Total response per Cluster |
|---|---|---|---|---|---|---|---|---|---|---|
| 151 | MAVGMVSIL | 5 | B7 | HLA-B-3501 | 9 | DENV2 | 1356 | 1364 | 361.7 | 361.7 |
| 152 | MGYWIESAL | 1 | B7 | HLA-B-3501 | 9 | DENV2 | 974 | 982 | 53.3 | 53.3 |
| 153 | MIDKTPVHSW | 1 | B7 | HLA-B-5301 | 10 | DENV4 | 3320 | 3329 | 720.0 | 720.0 |
| 154 | MLLALIAVL | 1 | A2 | HLA-A-0201 | 9 | DENV1 | 2152 | 2160 | 81.7 | 81.7 |
| 155 | MLLILCVTQV | 1 | A2 | HLA-A-0201 | 10 | DENV2 | 2419 | 2428 | 43.3 | 43.3 |
| 156 | MLVTPSMTM | 8 | B7 | HLA-B-3501 | 9 | DENV3 | 274 | 282 | 1735.0 | 1735.0 |
| 157 | MLWMAEIPL | 1 | B7 | HLA-B-3501 | 9 | DENV3 | 2190 | 2198 | 21.7 | 21.7 |
| 158 | MMLKLLTDF | 1 | B62 | HLA-B-1501 | 9 | DENV1 | 1260 | 1268 | 50.0 | 50.0 |
| 159 | MMLPATLAF | 1 | B7 | HLA-B-3501 | 9 | DENV3 | 108 | 116 | 80.0 | 80.0 |
| 159 | MMMLPATLAF | 2 | B7 | HLA-B-3501 | 10 | DENV3 | 107 | 116 | 473.3 | 473.3 |
| 160 | MPGTFQTTTG | 1 | B7 | HLA-B-3501 | 10 | DENV3 | 1589 | 1598 | 136.7 | 136.7 |
| 161 | MPGTRKVMGI | 1 | B7 | HLA-B-5101 | 10 | DENV3 | 2862 | 2871 | 60.0 | 85.0 |
| 161 | MPGTRRVMGI | 1 | B7 | HLA-B-5101 | 10 | DENV3 | 2862 | 2871 | 25.0 | |
| 162 | MPLVMAWRTI | 1 | B7 | HLA-B-5101 | 10 | DENV4 | 1287 | 1296 | 56.7 | 56.7 |
| 163 | MPSMKRFRRE | 5 | B7 | HLA-B-5301, B-3501 | 10 | DENV2 | 3379 | 3388 | 1336.7 | 1336.7 |
| 164 | MPSVIEKMET | 2 | B7 | HLA-B-3501, B-5301 | 10 | DENV2 | 2682 | 2691 | 783.3 | 783.3 |
| 165 | MPVMKRYSAP | 1 | B7 | HLA-B-5101 | 10 | DENV4 | 3379 | 3388 | 36.7 | 36.7 |
| 166 | MPVTHSSAAQ | 2 | B7 | HLA-B-3501 | 10 | DENV2 | 1925 | 1934 | 183.3 | 235.0 |
| 166 | MPVTVASAAQ | 1 | B7 | HLA-B-3501 | 10 | DENV1 | 1925 | 1934 | 51.7 | |
| 167 | MSFRDLGRVM | 8 | B7 | HLA-B-3501 | 10 | DENV2 | 1176 | 1185 | 3250.0 | 3250.0 |
| 168 | MSSEGAWKHA | 1 | B58 | HLA-B-5701 | 10 | DENV2,4 | 226 | 235 | 778.3 | 778.3 |
| 169 | MSYSMCTGKF | 6 | B7 | HLA-B-3501 | 10 | DENV2 | 578 | 587 | 2553.3 | 2553.3 |
| 170 | MSYTMCSGK | 1 | A3 | HLA-A-1101 | 9 | DENV4 | 578 | 586 | 23.3 | 23.3 |
| 171 | MTQKARNAL | 2 | B7 | HLA-B-0702 | 9 | DENV2 | 2113 | 2121 | 268.3 | 268.3 |
| 172 | MTTTANWLW | 1 | B7 | HLA-B-5301 | 9 | DENV4 | 2869 | 2877 | 40.0 | 40.0 |
| 173 | MVSRLLLNR | 1 | A3 | HLA-A-1101 | 9 | DENV3 | 2729 | 2737 | 28.3 | 28.3 |
| 174 | NPAQEDDQY | 2 | B7 | HLA-B-3501 | 9 | DENV4 | 1942 | 1950 | 176.7 | 176.7 |
| 175 | NPEIEDDIF | 10 | B7 | HLA-B-3501 | 9 | DENV2 | 1653 | 1661 | 3390.0 | 3390.0 |
| 176 | NPITLTAAL | 1 | B7 | HLA-B-0702 | 9 | DENV2 | 2350 | 2358 | 20.0 | 20.0 |
| 177 | NPLTLTAAV | 2 | B7 | HLA-B-0702 | 9 | DENV1,3 | 2350 | 2358 | 415.0 | 415.0 |
| 178 | NPNMIDKTPV | 2 | B7 | HLA-B-0702 | 10 | DENV4 | 3317 | 3326 | 376.7 | 675.0 |
| 178 | NPWMEDKTH | 1 | B7 | HLA-B-3501 | 9 | DENV1 | 3317 | 3325 | 106.7 | |
| 178 | NPWMEDKTPV | 2 | B7 | HLA-B-0702 | 10 | DENV2,3 | 3317 | 3326 | 191.7 | |
| 179 | NPTVDGITV | 1 | B7 | HLA-B-5101 | 9 | DENV2 | 2391 | 2399 | 30.0 | 30.0 |
| 180 | NQLIYVILTI | 1 | A2 | HLA-A-0206 | 10 | DENV4 | 2228 | 2237 | 381.7 | 381.7 |
| 181 | PASAWTLYAV | 1 | B58 | HLA-B-5801 | 10 | DENV1,2,3,4 | 2281 | 2290 | 503.3 | 503.3 |
| 182 | PASIAARGYI | 2 | B58 | HLA-B-5801 | 10 | DENV1,2,3 | 1769 | 1778 | 611.7 | 611.7 |

TABLE 10-continued

Dengue Antigenic Regions

| Cluster No. | Sequence (SEQ ID NOs: 813-1163, in order of appearance) | # donors responded | Super-type | HLA allele | length | Serotype | Alignment start | Alignment end | Total Response per epitope | Total response per Cluster |
|---|---|---|---|---|---|---|---|---|---|---|
| 183 | PTSRTTWSIH | 1 | B58 | HLA-B-5801 | 10 | DENV1 | 3285 | 3294 | 215.0 | 215.0 |
| 184 | QEGAMHSAL | 1 | B44 | HLA-B-4001 | 9 | DENV4 | 537 | 545 | 48.3 | 88.3 |
| 184 | QEGAMHTAL | 1 | B44 | HLA-B-4001 | 9 | DENV1,2,3 | 537 | 545 | 40.0 | |
| 185 | QENPYRTWAY | 1 | B44 | HLA-B-4001 | 10 | DENV4 | 2791 | 2800 | 265.0 | 265.0 |
| 186 | QIAMTDTTPF | 1 | B62 | HLA-B-1501 | 10 | DENV1 | 2835 | 2844 | 28.3 | 28.3 |
| 187 | QPESNILDI | 1 | B7 | HLA-B-5301 | 9 | DENV2 | 2268 | 2277 | 351.7 | 351.7 |
| 188 | QPHWIAASI | 1 | B7 | HLA-B-5101 | 9 | DENV2 | 2197 | 2205 | 71.7 | 71.7 |
| 189 | QSGVDVFFTP | 1 | B58 | HLA-B-5801 | 10 | DENV2 | 2622 | 2631 | 103.3 | 103.3 |
| 190 | QYIFTGQPL | 1 | A24 | HLA-A-2402 | 9 | DENV3 | 1949 | 1957 | 138.3 | 138.3 |
| 191 | QYSDRRWCF | 1 | A24 | HLA-A-2402 | 9 | DENV1 | 2034 | 2042 | 31.7 | 31.7 |
| 192 | RAAVEDEEF | 1 | B58 | HLA-B-5801 | 9 | DENV3 | 2918 | 2926 | 381.7 | 381.7 |
| 193 | RASFIEVKTC | 2 | B58 | HLA-B-5801 | 10 | DENV1 | 990 | 999 | 290.0 | 290.0 |
| 194 | REDLWCGSL | 1 | B44 | HLA-B-4001 | 9 | DENV4 | 3338 | 3346 | 96.7 | 145.0 |
| 194 | REDQWCGSL | 1 | B44 | HLA-B-4001 | 9 | DENV1,2,3 | 3338 | 3346 | 48.3 | |
| 195 | REIPERSWNT | 2 | B44 | HLA-B-4001 | 10 | DENV4 | 1815 | 1824 | 1278.3 | 1278.3 |
| 196 | REWCFTGERN | 2 | B44 | HLA-B-4001 | 10 | DENV4 | 2038 | 2047 | 1345.0 | 1345.0 |
| 197 | RFLEFEALGF | 1 | A24 | HLA-A-2402 | 10 | DENV1,2,4 | 2977 | 2986 | 181.7 | 358.3 |
| 197 | RYLEFEALGF | 1 | A24 | HLA-A-2402 | 10 | DENV3 | 2977 | 2986 | 176.7 | |
| 198 | RLRGEARKTF | 1 | B62 | HLA-B-1501 | 10 | DENV1 | 2002 | 2011 | 21.7 | 21.7 |
| 199 | RPGYHTQTA | 2 | B7 | HLA-B-0702 | 9 | DENV2,3 | 1033 | 1041 | 501.7 | 501.7 |
| 200 | RPISEKEENM | 1 | B7 | HLA-B-3501 | 10 | DENV3 | 1112 | 1121 | 101.7 | 101.7 |
| 201 | RPRWLDART | 2 | B7 | HLA-B-0702 | 9 | DENV1,3 | 2070 | 2078 | 585.0 | 585.0 |
| 202 | RPTPKGAVM | 1 | B7 | HLA-B-0702 | 9 | DENV4 | 3077 | 3085 | 191.7 | 223.3 |
| 202 | RPTPKGTVM | 1 | B7 | HLA-B-0702 | 9 | DENV3 | 3077 | 3085 | 31.7 | |
| 203 | RQLANAIFK | 1 | A3 | HLA-A-1101 | 9 | DENV3 | 3057 | 3065 | 90.0 | 90.0 |
| 204 | RQMEGEGIF | 1 | B62 | HLA-B-1501 | 9 | DENV2 | 3116 | 3124 | 108.3 | 108.3 |
| 205 | RQMEGEGVL | 1 | B62 | HLA-B-1501 | 9 | DENV3 | 3116 | 3124 | 56.7 | 56.7 |
| 206 | RVIDPRRCL | 2 | B7 | HLA-B-0702 | 9 | DENV1,3,4 | 1899 | 1907 | 541.7 | 1368.3 |
| 206 | RVIDPRRCLK | 3 | A3 | HLA-A-0301, A-1101 | 10 | DENV1 | 1899 | 1908 | 258.3 | |
| 206 | RVIDPRRCM | 1 | B7 | HLA-B-0702 | 9 | DENV2 | 1899 | 1907 | 88.3 | |
| 206 | RVIDPRRCMK | 6 | A3 | HLA-A-3101, A-1101, A-0301 | 10 | DENV2 | 1899 | 1908 | 480.0 | |
| 207 | RVLKMVEPW | 1 | B58 | HLA-B-5801 | 9 | DENV1,3,4 | 2658 | 2666 | 150.0 | 150.0 |
| 208 | RYMGEDGCWY | 1 | A24 | HLA-A-2402 | 10 | DENV3 | 1098 | 1107 | 66.7 | 66.7 |
| 209 | SEMAEALKGM | 1 | B44 | HLA-B-4001 | 10 | DENV1 | 1707 | 1716 | 30.0 | 30.0 |
| 210 | SPCKIPFEIM | 5 | B7 | HLA-B-3501 | 10 | DENV2 | 612 | 621 | 1156.0 | 1156.0 |
| 211 | SPGKFWNTTI | 3 | B7 | HLA-B-0702 | 10 | DENV1,2 | 2455 | 2464 | 826.7 | 826.7 |
| 212 | SPIINREGKV | 1 | B7 | HLA-B-0702 | 10 | DENV3 | 1614 | 1623 | 106.7 | 106.7 |
| 213 | SPILSITISE | 6 | B7 | HLA-B-3501 | 10 | DENV2 | 1418 | 1427 | 1068.3 | 1068.3 |
| 214 | SPKRLATAIA | 1 | B7 | HLA-B-0702 | 10 | DENV3 | 814 | 823 | 68.3 | 68.3 |

TABLE 10-continued

Dengue Antigenic Regions

| Cluster No. | Sequence (SEQ ID NOs: 813-1163, in order of appearance) | # donors responded | Super-type | HLA allele | length | Serotype | Alignment start | Alignment end | Total Response per epitope | Total response per Cluster |
|---|---|---|---|---|---|---|---|---|---|---|
| 215 | SPSPTVEESR | 1 | B7 | HLA-B-0702 | 10 | DENV3 | 2646 | 2655 | 118.3 | 118.3 |
| 216 | SPVRVPNYNL | 1 | B7 | HLA-B-0702 | 10 | DENV2,3 | 1749 | 1758 | 173.3 | 173.3 |
| 217 | SQIGAGVYK | 1 | A3 | HLA-A-1101 | 9 | DENV2 | 1511 | 1519 | 40.0 | 40.0 |
| 218 | STYGWNLVR | 1 | A3 | HLA-A-1101 | 9 | DENV2 | 2612 | 2620 | 28.3 | 28.3 |
| 219 | SWMVRILIGF | 1 | A24 | HLA-A-2402 | 10 | DENV4 | 733 | 742 | 53.3 | 53.3 |
| 220 | SYAQMWTLMY | 1 | A1 | HLA-A-0101 | 10 | DENV2 | 3253 | 3262 | 151.7 | 578.3 |
| 220 | YAQMWQLMYF | 1 | B7 | HLA-B-3501 | 10 | DENV1 | 3254 | 3263 | 135.0 | |
| 220 | YAQMWSLMY | 1 | B62 | HLA-B-1501 | 9 | DENV2,3,4 | 3254 | 3262 | 38.3 | |
| 220 | YAQMWSLMYF | 1 | B7 | HLA-B-3501 | 10 | DENV2,3,4 | 3254 | 3263 | 33.3 | |
| 220 | YAQMWTLMY | 2 | B62 | HLA-B-1501 | 9 | DENV2 | 3254 | 3262 | 175.0 | |
| 220 | YAQMWTLMYF | 1 | B62 | HLA-B-1501 | 10 | DENV2 | 3254 | 3263 | 45.0 | |
| 221 | TAAVLLLITH | 1 | B58 | HLA-B-5801 | 10 | DENV3 | 2355 | 2364 | 118.3 | 118.3 |
| 222 | TAEAGGRAY | 4 | B7 | HLA-B-3501 | 9 | DENV2 | 2129 | 2137 | 371.7 | 371.7 |
| 223 | IETTILDVDL | 2 | B44 | HLA-B-4001 | 10 | DENV4 | 2266 | 2279 | 1413.3 | 1413.3 |
| 224 | TFKVPHAKR | 1 | A3 | HLA-A-3301 | 9 | DENV4 | 520 | 528 | 78.3 | 78.3 |
| 225 | TLMAMDLGEL | 1 | A2 | HLA-A-0201 | 10 | DENV2 | 150 | 159 | 823.3 | 823.3 |
| 226 | TLMLLALIAV | 1 | A2 | HLA-A-0201 | 10 | DENV1 | 2150 | 2159 | 31.7 | 31.7 |
| 227 | TPEAKNSTF | 1 | B7 | HLA-B-3501 | 9 | DENV4 | 901 | 909 | 860.0 | 915.0 |
| 227 | TPEARNSTF | 1 | B7 | HLA-B-3501 | 9 | DENV4 | 901 | 909 | 55.0 | |
| 228 | TPEGIIPAL | 1 | B7 | HLA-B-0702 | 9 | DENV1,3 | 1978 | 1986 | 183.3 | 10671.0 |
| 228 | TPEGIIPALF | 9 | B7 | HLA-B-3501 | 10 | DENV1,3 | 1978 | 1987 | 2213.3 | |
| 228 | TPEGIIPSM | 5 | B7 | HLA-B-3501, B-5301 | 9 | DENV2 | 1978 | 1986 | 2716.7 | |
| 228 | TPEGIIPSMF | 7 | B7 | HLA-B-0702, B-3501 | 10 | DENV2 | 1978 | 1987 | 1771.7 | |
| 228 | TPEGIIPTLF | 11 | B7 | HLA-B-3501, B-0702, B-5301 | 10 | DENV4 | 1978 | 1987 | 2914.3 | |
| 228 | YTPEGIIPTL | 1 | A2 | HLA-A-0206 | 10 | DENV4 | 1977 | 1986 | 871.7 | |
| 229 | TPFGQQRVF | 3 | B7 | HLA-B-3501 | 9 | DENV1,2,3,4 | 2842 | 2850 | 438.3 | |
| 230 | TPKGAVMDII | 1 | B7 | HLA-B-0702 | 10 | DENV4 | 3079 | 3088 | 105.0 | 436.7 |
| 230 | TPRGTVMDII | 1 | B7 | HLA-B-0702 | 10 | DENV4 | 3079 | 3088 | 331.7 | |
| 231 | TPMLRHTIEN | 2 | B7 | HLA-B-0702 | 10 | DENV3,4 | 2296 | 2305 | 388.3 | 1805.0 |
| 232 | TPPGSRDPF | 7 | B7 | HLA-B-3501, B-0702 | 9 | DENV2 | 1795 | 1803 | 1416.7 | |
| 233 | TPQDNQLAY | 1 | B7 | HLA-B-3501 | 9 | DENV1,3 | 2224 | 2232 | 25.0 | 506.7 |
| 233 | TPQDNQLAYV | 2 | B7 | HLA-B-0702 | 10 | DENV1,3 | 2224 | 2233 | 406.7 | |
| 233 | TPQDNQLTY | 1 | B7 | HLA-B-3501 | 9 | DENV2 | 2224 | 2232 | 75.0 | |
| 234 | TPRSMPGTRR | 1 | B7 | HLA-B-0702 | 10 | DENV3 | 2858 | 2867 | 55.0 | 55.0 |
| 235 | TPVHSWEDI | 1 | B7 | HLA-B-5101 | 9 | DENV4 | 3324 | 3332 | 63.3 | 63.3 |
| 236 | TTFSLHYAW | 1 | B58 | HLA-B-5801 | 9 | DENV1 | 1285 | 1293 | 38.3 | 38.3 |
| 237 | TTKRDLGMSK | 1 | A3 | HLA-A-1101 | 10 | DENV3 | 2254 | 2263 | 35.0 | 35.0 |
| 238 | TYLALIATF | 1 | A24 | HLA-A-2402 | 9 | DENV3 | 1201 | 1209 | 28.3 | 28.3 |
| 239 | VASGLLWVAE | 1 | B58 | HLA-B-5801 | 10 | DENV4 | 2186 | 2195 | 53.3 | 53.3 |
| 240 | VATTFVTPM | 8 | B7 | HLA-B-3501 | 9 | DENV2 | 2290 | 2298 | 2776.7 | 2776.7 |
| 241 | VLLLVTHYAI | 1 | A2 | HLA-A-0201 | 10 | DENV3 | 2358 | 2367 | 40.0 | 40.0 |

TABLE 10-continued

Dengue Antigenic Regions

| Cluster No. | Sequence (SEQ ID NOs: 813-1163, in order of appearance) | # donors responded | Super-type | HLA allele | length | Serotype | Alignment start | Alignment end | Total Response per epitope | Total response per Cluster |
|---|---|---|---|---|---|---|---|---|---|---|
| 242 | VPLLAIGCY | 7 | B7 | HLA-B-3501 | 9 | DENV2 | 2338 | 2346 | 1520.0 | 2603.3 |
| 242 | VPLLAMGCY | 1 | B7 | HLA-B-3501 | 9 | DENV4 | 2338 | 2346 | 1083.3 | |
| 243 | VPMVTQMAM | 1 | B7 | HLA-B-0702 | 9 | DENV2,3 | 2830 | 2838 | 148.3 | 148.3 |
| 244 | VPNYNMIIM | 1 | B7 | HLA-B-5101 | 9 | DENV1 | 1753 | 1761 | 51.7 | 51.7 |
| 245 | VPYLGKREDQ | 2 | B7 | HLA-B-0702 | 10 | DENV1,2,3 | 3332 | 3341 | 423.3 | 423.3 |
| 246 | VQADMGCVV | 1 | A2 | HLA-A-0206 | 9 | DENV4 | 774 | 782 | 190.0 | 190.0 |
| 247 | VSSVNMVSRL | 1 | B58 | HLA-B-5801 | 10 | DENV3 | 2724 | 2733 | 421.7 | 421.7 |
| 248 | VTIDLDPVVY | 1 | B62 | HLA-B-1501 | 10 | DENV1 | 2398 | 2407 | 38.3 | 38.3 |
| 249 | VTRGAVLMHK | 1 | A3 | HLA-A-1101 | 10 | DENV2 | 1529 | 1538 | 81.7 | 81.7 |
| 250 | VTYECPLLV | 1 | A2 | HLA-A-0201 | 9 | DENV4 | 164 | 172 | 31.7 | 31.7 |
| 251 | VYTQLCDHR | 1 | A3 | HLA-A-3301 | 9 | DENV3 | 950 | 958 | 35.0 | 56.7 |
| 251 | VYTQLCDHRL | 1 | A24 | HLA-A-2402 | 10 | DENV3 | 950 | 959 | 21.7 | |
| 252 | WALCESITL | 1 | B7 | HLA-B-3501 | 9 | DENV1 | 2435 | 2443 | 23.3 | 23.3 |
| 253 | WAYHGSYET | 3 | B7 | HLA-B-3501 | 9 | DENV2 | 2798 | 2806 | 1220.0 | 1245.0 |
| 253 | WAYHGSYEV | 1 | B7 | HLA-B-5101 | 9 | DENV1,3 | 2798 | 2806 | 25.0 | |
| 254 | WHYDQDHPY | 5 | B7 | HLA-B-3501 | 9 | DENV2 | 2787 | 2795 | 1628.3 | 1628.3 |
| 255 | WSIHAHHQW | 3 | B58 | HLA-B-5801; B5701 | 9 | DENV1,3,4 | 3291 | 3299 | 950.0 | 950.0 |
| 256 | WVAEIQPQW | 1 | B58 | HLA-B-5801 | 9 | DENV4 | 2192 | 2200 | 30.0 | 30.0 |
| 257 | YAQIQPHWI | 1 | B7 | HLA-B-5101 | 9 | DENV2 | 2193 | 2201 | 48.3 | 48.3 |
| 258 | YENLKYSVI | 1 | B44 | HLA-B-4402 | 9 | DENV1 | 413 | 421 | 381.7 | 381.7 |
| 259 | YGGPISQHNY | 1 | B7 | HLA-B-3501 | 10 | DENV1 | 1023 | 1032 | 33.3 | 33.3 |
| 260 | YGVLFSGVSW | 1 | B7 | HLA-B-5301 | 10 | DENV1 | 725 | 734 | 166.7 | 166.7 |
| 262 | YLAGAGLAF | 3 | B7 B62 | HLA-B-0702, B-1501 | 9 | DENV1,3 | 2476 | 2484 | 340.0 | 340.0 |
| 263 | YPKTKLTDW | 1 | B7 | HLA-B-5301 | 9 | DENV4 | 1872 | 1880 | 320.0 | 430.0 |
| 263 | YPKTKLTDWD | 1 | B7 | HLA-B-3501 | 10 | DENV4 | 1872 | 1881 | 110.0 | |
| 264 | YQLAVTITAI | 1 | B62 | HLA-B-1501 | 10 | DENV2 | 1271 | 1280 | 63.3 | 63.3 |
| 265 | YQLWTALISL | 1 | B62 | HLA-B-1501 | 10 | DENV3 | 1271 | 1280 | 55.0 | 55.0 |
| 266 | YQNKVVKVLR | 1 | A3 | HLA-A-3301 | 10 | DENV4 | 3068 | 3077 | 895.0 | 1235.0 |
| 266 | YQNKVVKVQR | 1 | A3 | HLA-A-3301 | 10 | DENV3 | 3068 | 3077 | 340.0 | |
| 267 | YVSAIAQTEK | 1 | A3 | HLA-A-1101 | 10 | DENV2 | 1638 | 1647 | 36.7 | 36.7 |

REFERENCES

1. Fu, J., B. H. Tan, E. H. Yap, Y. C. Chan, and Y. H. Tan. 1992. Full-length cDNA sequence of dengue type 1 virus (Singapore strain S275/90). *Virology* 188:953-958.
2. Suaya, J. A., D. S. Shepard, J. B. Siqueira, C. T. Martelli, L. C. Lum, L. H. Tan, S. Kongsin, S. Jiamton, F. Garrido, R. Montoya, B. Armien, R. Huy, L. Castillo, M. Caram, B. K. Sah, R. Sughayyar, K. R. Tyo, and S. B. Halstead. 2009. Cost of dengue cases in eight countries in the Americas and Asia: a prospective study. *The American journal of tropical medicine and hygiene* 80:846-855.
3. Guzman, M. G., S. B. Halstead, H. Artsob, P. Buchy, J. Farrar, D. J. Gubler, E. Hunsperger, A. Kroeger, H. S. Margolis, E. Martinez, M. B. Nathan, J. L. Pelegrino, C. Simmons, S. Yoksan, and R. W. Peeling. 2010. Dengue: a continuing global threat. *Nature reviews. Microbiology* 8:S7-16.
4. Kyle, J. L., and E. Harris. 2008. Global spread and persistence of dengue. *Annual review of microbiology* 62:71-92.

5. Guzman, A., and R. E. Isturiz. 2010. Update on the global spread of dengue. *International journal of antimicrobial agents* 36 Suppl 1:S40-42.
6. Kyle, J. L., and E. Harris. 2008. Global spread and persistence of dengue. *Annu Rev Microbiol* 62:71-92.
7. Burke, D. S., A. Nisalak, D. E. Johnson, and R. M. Scott 1988. A prospective study of dengue infections in Bangkok. *The American journal of tropical medicine and hygiene* 38:172-180.
8. Sangkawibha, N., S. Rojanasuphot, S. Ahandrik, S. Viriyapongse, S. Jatanasen, V. Salitul, B. Phanthumachinda, and S. B. Halstead. 1984. Risk factors in dengue shock syndrome: a prospective epidemiologic study in Rayong, Thailand. I. The 1980 outbreak. *American journal of epidemiology* 120:653-669.
9. Halstead, S. B. 1988. Pathogenesis of dengue: challenges to molecular biology. *Science* 239:476-481.
10. Heinz, F. X, and K. Stiasny. 2012. Flaviviruses and flavivirus vaccines. *Vaccine* 30:4301-4306.
11. Morens, D. M. 1994. Antibody-dependent enhancement of infection and the pathogenesis of viral disease. *Clinical infectious diseases: an official publication of the Infectious Diseases Society of America* 19:500-512.
12. Halstead, S. B., S. Mahalingam, M. A. Marovich, S. Ubol, and D. M. Mosser. 2010. Intrinsic antibody-dependent enhancement of microbial infection in macrophages: disease regulation by immune complexes. *The Lancet infectious diseases* 10:712-722.
13. Halstead, S. B., S. Rojanasuphot, and N. Sangkawibha. 1983. Original antigenic sin in dengue. *The American journal of tropical medicine and hygiene* 32:154-156.
14. Lan, N. T., and K. Hirayama. 2011. Host genetic susceptibility to severe dengue infection. *Tropical medicine and health* 39:73-81.
15. Malavige, G. N., T. Rostron, L. T. Rohanachandra, S. D. Jayaratne, N. Fernando, A. D. De Silva, M. Liyanage, and G. Ogg. 2011. HLA class I and class II associations in dengue viral infections in a Sri Lankan population. *PLoS one* 6:e20581.
16. Stephens, H. A., R. Klaythong, M. Sirikong, D. W. Vaughn, S. Green, S. Kalayanarooj, T. P. Endy, D. H. Libraty, A. Nisalak, B. L. Innis, A. L. Rothman, F. A. Ennis, and D. Chandanayingyong. 2002. HLA-A and -B allele associations with secondary dengue virus infections correlate with disease severity and the infecting viral serotype in ethnic Thais. *Tissue antigens* 60:309-318.
17. Loke, H., D. B. Bethell, C. X. Phuong, M. Dung, J. Schneider, N. J. White, N. P. Day, J. Farrar, and A. V. Hill. 2001. Strong HLA class I-restricted T cell responses in dengue hemorrhagic fever: a double-edged sword? *The Journal of infectious diseases* 184:1369-1373.
18. Appanna, R., S. Ponnampalavanar, L. Lum Chai See, and S. D. Sekaran. 2010. Susceptible and protective HLA class 1 alleles against dengue fever and dengue hemorrhagic fever patients in a Malaysian population. *PLoS one* 5.
19. Nguyen, T. P., M. Kikuchi, T. Q. Vu, Q. H. Do, T. T. Tran, D. T. Vo, M. T. Ha, V. T. Vo, T. P. Cao, V. D. Tran, T. Oyama, K. Morita, M. Yasunami, and K. Hirayama. 2008. Protective and enhancing HLA alleles, HLA-DRB1*0901 and HLA-A*24, for severe forms of dengue virus infection, dengue hemorrhagic fever and dengue shock syndrome. *PLoS neglected tropical diseases* 2:e304.
20. Falcon-Lezama, J. A., C. Ramos, J. Zuniga, L. Juarez-Palma, H. Rangel-Flores, A. R. Garcia-Trejo, V. Acunha-Alonzo, J. Granados, and G. Vargas-Alarcon. 2009. HLA class I and II polymorphisms in Mexican Mestizo patients with dengue fever. *Acta tropica* 112:193-197.
21. Sierra, B., R. Alegre, A. B. Perez, G. Garcia, K. Sturn-Ramirez, O. Obasanjo, E. Aguirre, M. Alvarez, R. Rodriguez-Roche, L. Valdes, P. Kanki, and M. G. Guzman. 2007. HLA-A, -B, -C, and -DRB1 allele frequencies in Cuban individuals with antecedents of dengue 2 disease: advantages of the Cuban population for HLA studies of dengue virus infection. *Human immunology* 68:531-540.
22. Robinson, J., K. Mistry, H. McWilliam, R. Lopez, P. Parham, and S. G. Marsh. 2011. The IMGT/HLA database. *Nucleic acids research* 39:D1171-1176.
23. King, N. J., B. Shrestha, and A. M. Kesson. 2003. Immune modulation by flaviviruses. *Advances in virus research* 60:121-155.
24. Sette, A., and J. Sidney. 1999. Nine major HLA class I supertypes account for the vast preponderance of HLA-A and -B polymorphism. *Immunogenetics* 50:201-212.
25. Messer, W. B., U. T. Vitarana, K. Sivananthan, J. Elvtigala, L. D. Preethimala, R. Ramesh, N. Withana, D. J. Gubler, and A. M. De Silva. 2002. Epidemiology of dengue in Sri Lanka before and after the emergence of epidemic dengue hemorrhagic fever. *The American journal of tropical medicine and hygiene* 66:765-773.
26. Kanakaratne, N., W. M. Wahala, W. B. Messer, H. A. Tissera, A. Shahani, N. Abeysinghe, A. M. de-Silva, and M. Gunasekera. 2009. Severe dengue epidemics in Sri Lanka, 2003-2006. *Emerging infectious diseases* 15:192-199.
27. Tissera, H. A., E. E. Ooi, D. J. Gubler, Y. Tan, B. Logendra, W. M. Wahala, A. M. de Silva, M. R. Abeysinghe, P. Palihawadana, S. Gunasena, C. C. Tam, A. Amarasinghe, G. W. Letson, H. S. Margolis, and A. D. De Silva. 2011. New dengue virus type 1 genotype in Colombo, Sri Lanka. *Emerging infectious diseases* 17:2053-2055.
28. Yauch, L. E., R. M. Zellweger, M. F. Kotturi, A. Qutubuddin, J. Sidney, B. Peters, T. R. Prestwood, A. Sette, and S. Shresta. 2009. A protective role for dengue virus-specific CD8+ T cells. *Journal of immunology* 182:4865-4873.
29. Zompi, S., B. H. Santich, P. R. Beatty, and E. Harris. 2012. Protection from secondary dengue virus infection in a mouse model reveals the role of serotype cross-reactive B and T cells. *Journal of immunology* 188:404-416.
30. Duangchinda, T., W. Dejnirattisai, S. Vasanawathana, W. Limpitikul, N. Tangthawornchaikul, P. Malasit, J. Mongkolsapaya, and G. Screaton. 2010. Immunodominant T-cell responses to dengue virus NS3 are associated with DHF. *Proceedings of the National Academy of Sciences of the United States of America* 107:16922-16927.
31. Mongkolsapaya, J., W. Dejnirattisai, X. N. Xu, S. Vasanawathana, N. Tangthawornchaikul, A. Chairunsri, S. Sawasdivorn, T. Duangchinda, T. Dong, S. Rowland-Jones, P. T. Yenchitsomanus, A. McMichael, P. Malasit, and G. Screaton. 2003. Original antigenic sin and apoptosis in the pathogenesis of dengue hemorrhagic fever. *Nature medicine* 9:921-927.
32. Rothman, A. L. 2011. Immunity to dengue virus: a tale of original antigenic sin and tropical cytokine storms. *Nature reviews. Immunology* 11:532-543.
33. Mathew, A., I. Kurane, A. L. Rothman, L. L. Zeng, M. A. Brinton, and F. A. Ennis. 1996. Dominant recognition by human CD8+ cytotoxic T lymphocytes of dengue virus nonstructural proteins NS3 and NS1.2a. *The Journal of clinical investigation* 98:1684-1691.

34. Simmons, C. P., T. Dong, N. V. Chau, N. T. Dung, T. N. Chau, T. T. Thao le, T. T. Hien, S. Rowland-Jones, and J. Farrar. 2005. Early T-cell responses to dengue virus epitopes in Vietnamese adults with secondary dengue virus infections. *Journal of virology* 79:5665-5675.
35. Hsieh, Y. H., S. J. Liu, H. W. Chen, Y. K. Lin, K. S. Liang, and L. J. Lai. 2010. Highly sensitive rare cell detection based on quantum dot probe fluorescence analysis. *Analytical and bioanalytical chemistry* 396:1135-1141.
36. Newell, E. W., N. Sigal, S. C. Bendall, G. P. Nolan, and M. M. Davis. 2012. Cytometry by time-of-flight shows combinatorial cytokine expression and virus-specific cell niches within a continuum of CD8+ T cell phenotypes. *Immunity* 36:142-152.
37. Nguyen, T. H., H. Y. Lei, T. L. Nguyen, Y. S. Lin, K. J. Huang, B. L. Le, C. F. Lin, T. M. Yeh, Q. H. Do, T. Q. Vu, L. C. Chen, J. H. Huang, T. M. Lam, C. C. Liu, and S. B. Halstead. 2004. Dengue hemorrhagic fever in infants: a study of clinical and cytokine profiles. *The Journal of infectious diseases* 189:221-232.
38. Dung, N. T., H. T. Duyen, N. T. Thuy, T. V. Ngoc, N. V. Chau, T. T. Hien, S. L. Rowland-Jones, T. Dong, J. Farrar, B. Wills, and C. P. Simmons. 2010. Timing of CD8+ T cell responses in relation to commencement of capillary leakage in children with dengue. *Journal of immunology* 184:7281-7287.
39. Monteiro, S. P., P. E. do Brasil, G. M. Cabello, R. V. de Souza, P. Brasil, I. Georg, P. H. Cabello, and L. De Castro. 2012. HLA-A*01 allele: a risk factor for dengue haemorrhagic fever in Brazil's population. *Memorias do Instituto Oswaldo Cruz* 107:224-230.
40. Almeida, J. R., D. Sauce, D. A. Price, L. Papagno, S. Y. Shin, A. Moris, M. Larsen, G. Pancino, D. C. Douek, B. Autran, A. Saez-Cirion, and V. Appay. 2009. Antigen sensitivity is a major determinant of CD8+ T-cell polyfunctionality and HIV-suppressive activity. *Blood* 113: 6351-6360.
41. Park, S. H., E. C. Shin, S. Capone, L. Caggiari, V. De Re, A. Nicosia, A. Folgori, and B. Rehermann. 2012. Successful Vaccination Induces Multifunctional Memory T-Cell Precursors Associated with Early Control of Hepatitis C Virus. *Gastroenterology*.
42. Hatch, S., T. P. Endy, S. Thomas, A. Mathew, J. Potts, P. Pazoles, D. H. Libraty, R. Gibbons, and A. L. Rothman. 2011. Intracellular cytokine production by dengue virus-specific T cells correlates with subclinical secondary infection. *The Journal of infectious diseases* 203:1282-1291.
43. Elahi, S., W. L. Dinges, N. Lejarcegui, K. J. Laing, A. C. Collier, D. M. Koelle, M. J. McElrath, and H. Horton. 2011. Protective HIV-specific CD8+ T cells evade Treg cell suppression. *Nature medicine* 17:989-995.
44. Barrett, J. H., M. M. Iles, M. Harland, J. C. Taylor, J. F. Aitken, P. A. Andresen, L. A. Akslen, B. K. Armstrong, M. F. Avril, E. Azizi, B. Bakker, W. Bergman, G. Bianchi-Scarra, B. Bressac-de Paillerets, D. Calista, L. A. Cannon-Albright, E. Corda, A. E. Cust, T. Debniak, D. Duffy, A. M. Dunning, D. F. Easton, E. Friedman, P. Galan, P. Ghiorzo, G. G. Giles, J. Hansson, M. Hocevar, V. Hoiom, J. L. Hopper, C. Ingvar, B. Janssen, M. A. Jenkins, G. Jonsson, R. F. Kefford, G. Landi, M. T. Landi, J. Lang, J. Lubinski, R. Mackie, J. Malvehy, N. G. Martin, A. Molven, G. W. Montgomery, F. A. van Nieuwpoort, S. Novakovic, H. Olsson, L. Pastorino, S. Puig, J. A. Puig-Butille, J. Randerson-Moor, H. Snowden, R. Tuominen, P. Van Belle, N. van der Stoep, D. C. Whiteman, D. Zelenika, J. Han, S. Fang, J. E. Lee, Q. Wei, G. M. Lathrop, E. M. Gillanders, K. M. Brown, A. M. Goldstein, P. A. Kanetsky, G. J. Mann, S. Macgregor, D. E. Elder, C. I. Amos, N. K. Hayward, N. A. Gruis, F. Demenais, J. A. Bishop, and D. T. Bishop. 2011. Genome-wide association study identifies three new melanoma susceptibility loci. *Nature genetics* 43:1108-1113.
45. Kim, Y., J. Ponomarenko, Z. Zhu, D. Tamang, P. Wang, J. Greenbaum, C. Lundegaard, A. Sette, O. Lund, P. E. Bourne, M. Nielsen, and B. Peters. 2012. Immune epitope database analysis resource. *Nucleic acids research*.
46. Kraus, A. A., W. Messer, L. B. Haymore, and A. M. de Silva. 2007. Comparison of plaque- and flow cytometry-based methods for measuring dengue virus neutralization. *J Clin Microbiol* 45:3777-3780.

Example 24

Materials and Methods

Ethics Statement

All murine experiments in this study were performed according to the National Institutes of Health Guide for Care and Use of Experimental Animals and following Institutional Animal Care and Use Committee-approved animal protocols.

Viral Stocks

The mouse adapted DENV3 strain D3S5CX was derived from the clinical isolate UNC3001, obtained from Aravinda de Silva (UNC School of Medicine). Passaging of UNC3001 through the serum of IFN-α/βR−/−, IFN-γR−/−, mice 5 times, followed by passaging through the spleens of Cardif−/− mice 10 times has resulted in strain D3S5CX that replicates more efficiently in IFN-α/βR−/−, mice than the parental strain. S221 is a plaque-purified DENV2 strain which was derived from the clinical isolate PL046 by passaging through IFN-α/βR−/−, IFN-γR−/−, and mosquito cells, as previously described. Viral stocks were amplified in C6/36 mosquito cells, also as previously described. Infectious doses were determined based on genomic equivalents (GE), which were quantified by RT-PCR.

Mice and Infections

HLA A*0101, A*0201/Kb, B*0702, B*4001 and DRB1*0101 transgenic mice were bred and back-crossed with IFN-α/βR−/− mice on the C57BL/6 background at the La Jolla Institute for Allergy and Immunology facility (La Jolla, Calif.). Mice were used between 6 and 10 weeks of age. For all experiments mice were infected i.v (retro-orbitally) with $10^{10}$ GE of DENV in 100 μl PBS. On day 7 post-infection, the mice were sacrificed and splenic CD8+ or CD4+ T cells were used in mouse IFNγ ELISPOT assays. For secondary infection experiments, B*0702 IFN-α/βR−/− mice were infected 28 days after primary DENV3 infection with either DENV3 (homologous) or DENV2 (heterologous). 7 days post secondary infection, mice were sacrificed and splenic CD8+ T cells were used in mouse IFNγ ELISPOT assays. All mouse experiments were performed following Institutional Animal Care and Use Committee-approved animal protocols.

Bioinformatic Analyses and Peptide Synthesis

The HLA A*0201, A*0101, B*0702 and B*4001 binding capacity of all 9 and 10mer peptides encoded in the D3S5CX proteome was predicted using the command-line version of the MHC class I consensus prediction tool available on the IEDB web site. Peptides were selected if they scored in the top 1% of all peptides for any of the 4 alleles. For the MHC class II DRB1*0101 allele binding predictions were performed for all 15mer peptides from the same proteome using the consensus approach. The top 2% of predicted DRB1*0101 binders was selected for synthesis. In total, 365 9-mer and 10-mer peptides were identified by MHC class I predictions, and 29 15-mers by the DRB1*0101 predictions. All peptides were synthesized by Mimotopes (Victoria, Australia) as crude material on a 1 mg scale. For screening studies, the class I peptides were combined into pools of approximately 10 individual peptides, according to their predicted HLA restriction. MHC class II peptides were tested individually.

MHC Peptide-Binding and Restriction Assays

Purification of HLA A*0201, A*0101, B*0702, B*4001 and DRB1*0101 MHC molecules and the performance of quantitative competition assays to measure the binding affinity of peptides to purified MHC were performed. To determine restriction for A*0201 and B*4001 epitopes, CD8+ T cells from DENV3-infected HLA A*A0201 and HLA B*4001 transgenic IFN-α/βR−/− mice were incubated with APC pulsed with ascending concentrations of peptides and tested for IFN-γ production in an ELISPOT assay. The tumor cell line 721.221, which lacks expression of HLA-A, -B and C class I genes, was transfected with the HLA-A*0201/Kb chimeric genes, and used as antigen-presenting cells (APC) in the A*0201 restriction assays. The non-transfected cell line was used as a negative control. An Epstein-Barr virus (EBV)-transformed B cell line expressing the B*4001 molecule (SVEIG) was utilized as APC in the B*4001 restriction assay. The LG2 cell line was used as a negative control.

IFNγ ELISPOT Assay

For all murine experiments, splenic CD4+ or CD8+ T cells were isolated by magnetic bead positive selection (Miltenyi Biotec, Bergisch Gladbach, Germany) 7 days after infection with DENV. $2 \times 10^5$ T cells were stimulated with $1 \times 10^5$ uninfected splenocytes as APCs and pools of 10 individual DENV peptides in 96-well flat-bottom plates (Immobilon-P; Millipore, Bedford, Mass.) coated with anti-IFNγ mAb (clone AN18; Mabtech, Stockholm, Sweden). Positive pools were deconvoluted and the individual peptides responsible for the reactivity were determined Responses were considered positive if the net spot-forming cells (SFC) per $10^6$ were ≥20, had a stimulation index of ≥2, and a p<0.05 in a t test comparing replicates with those from the negative control.

Example 25

DENV3 Peptide Specific Responses in an HLA Transgenic Mouse Model

To determine the DENV3 specific T cell response the mouse adapted DENV3 strain D3S5CX was used to infect HLA A*0101-, A*0201-, B*0702-, B*4001- and DRB1*0101-transgenic IFN-α/βR−/− mice. In the case of class I, the HLA A and B alleles studied were chosen as representative of the HLA A1, A2, B7, and B44 class I supertypes, respectively. Together, these class I supertypes are estimated to provide coverage of over 90% of the general population. DRB1*0101 was chosen as representative of the main HLA DR class II supertype. Given the high degree of repertoire overlap between HLA class II molecules, the main DR supertype is expected to be represented in over 90% of individuals. Using bioinformatics-based algorithms panels of D3S5CX-derived peptides were generated predicted to bind HLA A*0101-, A*0201-, B*0702-, B*4001- or DRB1*0101 molecules.

For each allele the corresponding predicted peptides were combined into pools of 10 peptides each and tested in IFNγ ELISPOT assays using splenic T cells from HLA transgenic IFN-α/βR−/− mice 7 days post infection. Positive pools were deconvoluted and the individual peptides responsible for the reactivity were determined Using this approach a total of 59 responses were identified, considering all HLA transgenic IFN-α/βR−/− mice mouse strains tested. More specifically, these experiments revealed 3 A*0101-, 26 A*0201-, 19 B*0702-, 4 B*4001- and 7 DRB1*0101-restricted epitopes (FIG. 21A-E).

Example 26

Further Characterization of the DENV3 Epitopes

Figures 25A, 25B:
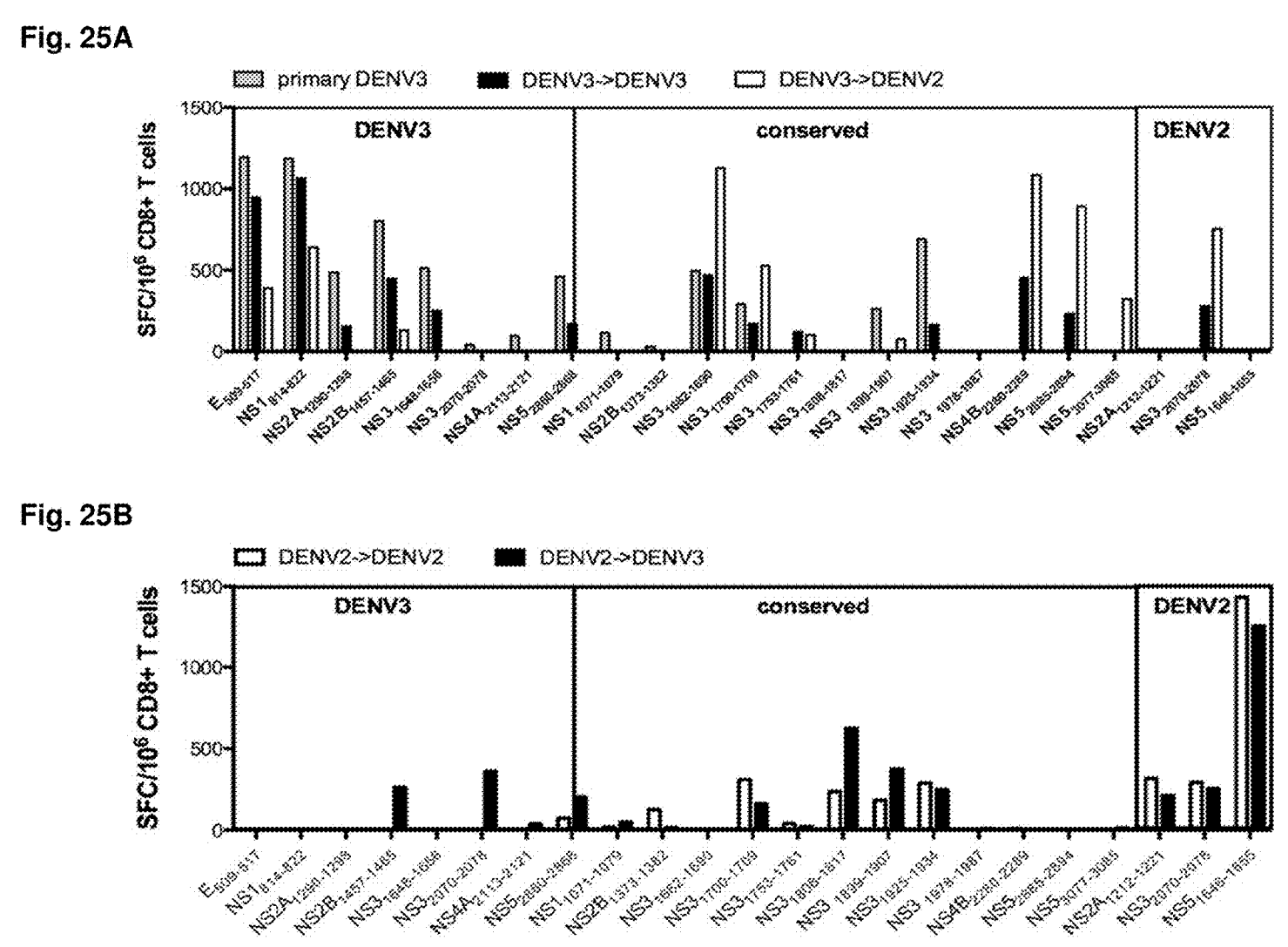
Figure 25C:
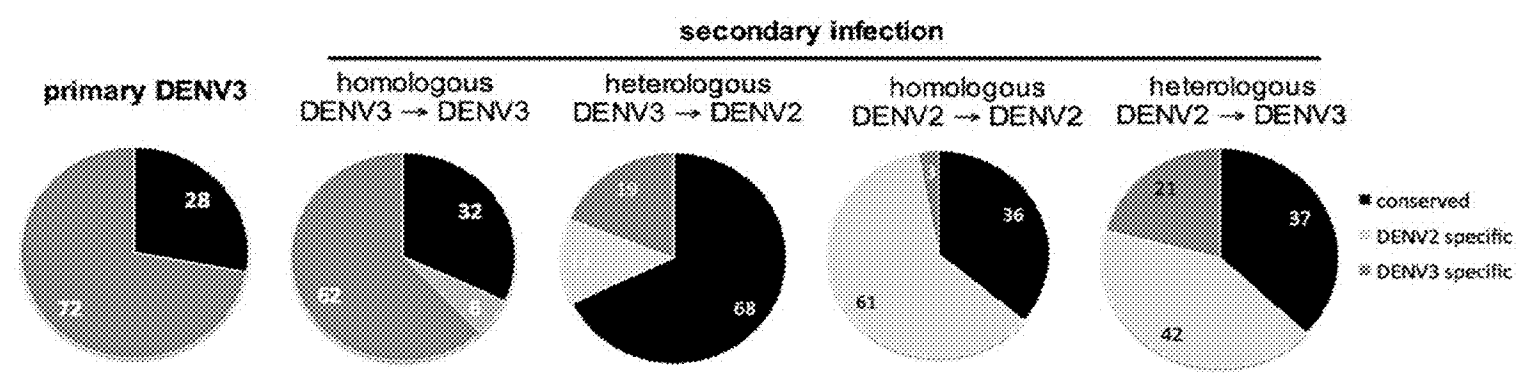

The A*0101, A*0201 and B*0702 epitopes identified included 9 pairs of nested epitopes, where a 10-mer as well as a nested 9-mer peptide were able to elicit immune responses (FIGS. 21 A-C). To determine which peptide was the optimal epitope, each nested peptide pair was further titrated, as shown in FIG. 25A. In eight out of nine cases the optimal epitope could be unequivocally identified and therefore utilized in all further studies. In the case of one A*0201 epitope (NS2A1164-1172, FIG. 25) the 9-mer and the 10-mer showed equivalent dose response curves. In this case the 10-mer was selected for use in further experiments, since it also fully contains the 9-mer sequence.

Of the five HLA transgenic mouse strains tested, the A*0201 and the B*4001 mice co-express murine MHC molecules. To confirm that the observed responses were restricted by the transfected human class I molecule and not the co-expressed murine class I, purified T cells were tested for their capacity to recognize the specific epitopes when pulsed on antigen presenting cells expressing only human class I. Accordingly, for the A*0201 epitopes HLA A*0201 transfected 721.221 cells were utilized, which are negative for expression of murine class I molecules. All 23 of the HLA*A0201 restricted epitopes stimulated a CD8+ T cell response when presented exclusively on HLA*0201 molecules (FIG. 25B). Similarly, all four B*4001 restricted epitopes were recognized when presented by corresponding cell lines expressing HLA B*4001 molecules (FIG. 25C) but no murine class I. As an additional control, all A*0201 and B*4001 epitopes were tested for their reactivity in non-HLA transgenic IFN-α/βR−/− mice and were found to not elicit CD8+ T cell responses in IFNγ ELISPOT assays (data not shown).

To further characterize the MHC restriction of the identified epitopes their binding capacity was measured for their putative restricting HLA allelic molecule in in-vitro binding assays using purified MHC molecules (Table 11). Forty of the 50 peptides (80%) bound the corresponding predicted allele with high affinity, as indicated by an IC50<50 nM, including 26 peptides that bound with an affinity of 10 nM, or better. Of the remaining 10 peptides, 9 (18%) bound the corresponding allele with intermediate affinity, with IC50s in the 50-500 nM range, and one (2%) bound with low affinity (IC50>1000 nM).

Taken together, the data in this and the preceding section have defined a total of 50 unique DENV3-derived, HLA-restricted, T cell epitopes. As summarized in Table 11, 2 are restricted by A*0101, 23 by A*0201, 14 by B*0702, 4 by B*4001 and 7 by DRB1*0101.

Example 27

DENV Epitopes Identified in the Transgenic Mouse Model Reflect the T Cell Repertoire in Humans Following Natural Exposure To investigate if the epitopes identified in the HLA transgenic mouse model are also recognized in context of natural infection in humans, a search of the Immune Epitope Database was performed (IEDB; iedb.org). It was found that 34 (68%) of the 50 DENV3 epitopes detected in this study were independently described to elicit a T cell response in humans exposed to dengue virus. At the same time, a similar analysis of the DENV2 epitopes identified in the HLA transgenic mouse system was performed and found that 32 (76%) of the 42 epitopes have also been described in humans. The overall high concordance of 72% (66 out of 92 epitopes) confirms that the HLA transgenic IFN-α/βR−/− mice are a reliable model of T cell responses relevant to human infection with DENV.

Example 28

DENV2 and DENV 3 Responses are Serotype Specific and Largely Non-Overlapping The degree of overlap was analysed between the repertoires of HLA transgenic mice infected with the two different DENV strains. Table 11 indicates for each of the DENV3 specific epitopes whether they are also conserved in the DENV2 strain S221. Four of the 50 DENV3 epitopes share 100% sequence identity with the DENV2 S221 strain (NS11090-1099 A*0101, NS31682-1690 and NS31700-1709 B*0702, NS31742-1756 DRB1*0101). All 4 of these epitopes were also independently identified after infection with DENV2. None of the remaining 46 DENV3 specific epitopes, or variants thereof, were identified after infection with DENV2. These results demonstrate that the T cell repertoires for DENV2 and DENV3 are largely non-overlapping, and suggest that the primary T cell response is serotype specific.

Example 29

Differential Pattern of Immunogenicity after Infection with DENV3 as Compared to DENV2

Figure 22A:
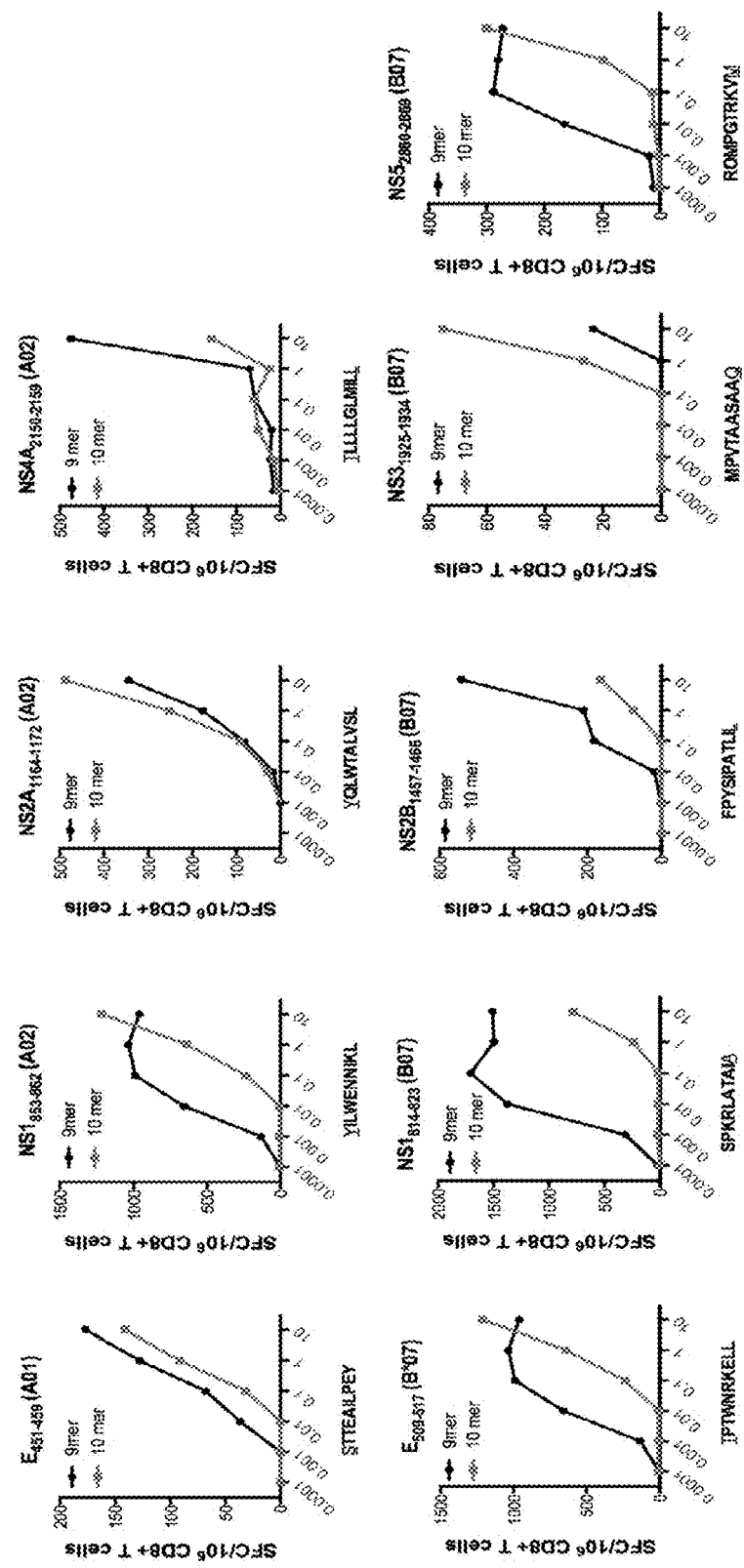
FIGS. 22A-22C show further characterization of DENV3 epitopes.
Figure 22B:
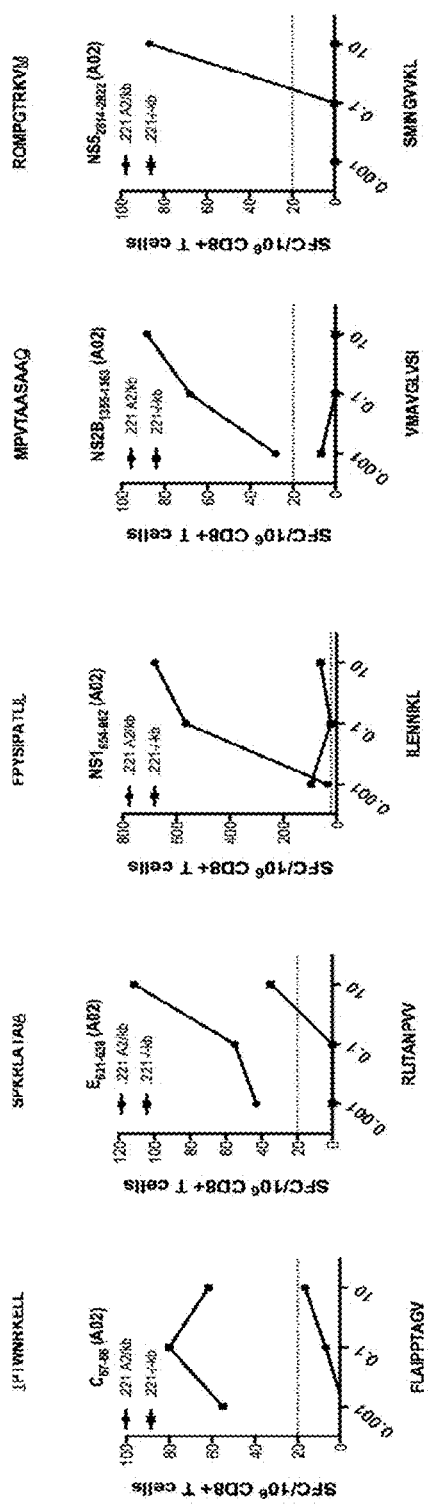
Figure 22C:
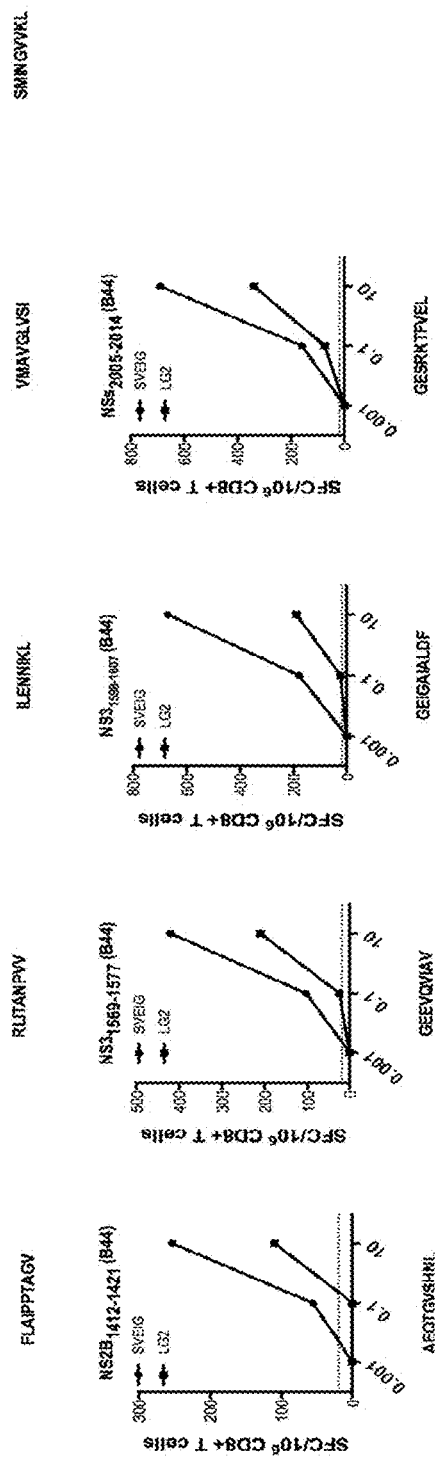
Figure 23A:
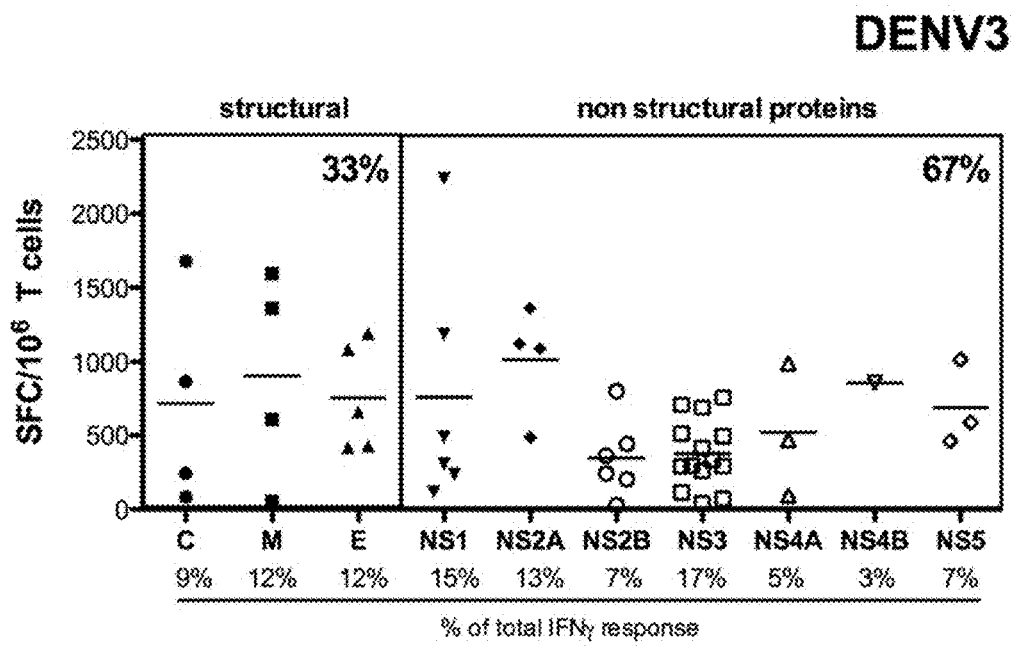
FIGS. 23A-23B show differential pattern of immunogenicity after infection with DENV3 as compared to DENV2. All identified DENV3 (FIG. 23A) and DENV2 (FIG. 23B) specific epitopes were grouped according to the protein of provenance. IFNγ responses of individual epitopes derived from the three structural (capsid (C), pre-membrane (prM/M), envelope (E)) and seven non-structural (NS1, NS2A, NS2B, NS3, NS4A, NS4B and NS5) proteins are shown. Numbers below the protein indicate the relative (% of total) response against the corresponding protein. Numbers in the upper right corner of the boxes represent the relative responses either targeted against structural proteins (left box) or non-structural proteins (right box).
Figure 23B:
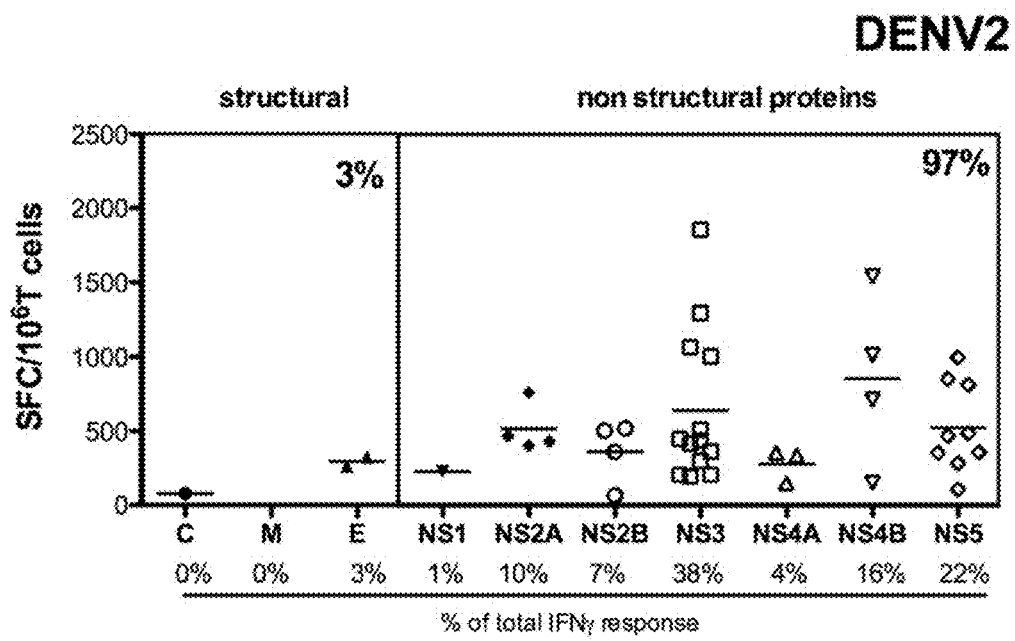

The specificity of the DENV3 immune response at the antigen level was determined. The relative strength of recognition of the 10 DENV proteins was analyzed, namely the three structural proteins (Capsid (C), Membrane (M), and Envelope (E)), and the seven non-structural proteins (NS1, NS2A, NS2B, NS3, NS4A, NS4B and NS5). As shown in FIG. 22A, the immune response against DENV3 was broad, and epitopes originating from all 10 proteins were recognized. The majority (37 out of 50; 74%) of the epitopes were derived from the seven nonstructural proteins, and accounted for two thirds (67%) of the total IFNγ response observed. Within the seven nonstructural proteins, NS3 and NS1 were the most dominantly targeted, accounting for 17% and 15% of the total IFNγ response, respectively. 13 of the 50 (26%) epitopes were derived from the three structural proteins, and accounted for one third (33%) of the total IFNγ response observed. This is in contrast to infection with DENV2 where 3% of the responses were directed against structural proteins (p=0.0001 in Fisher's exact test), and also shown in FIG. 22B for comparison purposes. The remaining 97% of the total response were derived from the nonstructural proteins, and accounted for 39 out of 42 (93%) of the epitopes detected. NS3 alone accounted for 38% of the total response, whereas only one epitope had been observed against the NS1 protein. These results point to a different hierarchy of immune dominance associated with the different DENV proteins, as a function of the infecting serotype.

Example 30

Threshold for Cross-Reactive Epitope Recognition

B*0702 transgenic IFN-α/βR−/− mouse strain was selected as representative for additional, and more in-depth, analysis of the observed immunodominance differences associated with DENV2 and DENV3 primary infection and the effects of preexisting immunity and heterologous infection on T cell recognition. To enable these studies a homology threshold associated with cross-reactivity was experimentally defined at the T cell level. The phenomenon of T cell mediated cross-reactivity between various serotypes has been the subject of much discussion in the context of dengue but a definition of the threshold for cross-reactivity, broadly applicable to large number of epitopes, has not been experimentally addressed.

For these analyses, a panel of 137 peptides was synthesized, corresponding to naturally occurring DENV variants with various degrees of sequence homology to the D3S5CX strain. This panel was then tested for T cell reactivity following infection of B*0702 transgenic IFN-α/βR−/− mice with this strain. As shown in FIG. 23, the majority of responses, in terms of both frequency (15 of 63 peptides; 24%) and magnitude, were detected in peptides with 100% sequence identity to the infecting strain. Another roughly 20% of the total response (5 out of 45 peptides) observed was elicited by variants with just one or two amino acid variations, corresponding to ≥78%, or ≥80%, sequence identity in case of 9-mer, and 10-mer peptides, respectively. No response was observed in variants with 3 or more amino acid differences, compared to the corresponding D3S5CX strain. These results thus identify a sequence homology threshold that discriminates conserved or cross-reactive recognition and non-cross-reactive (and hence serotype-specific) immune responses.

Example 31

Effect of Heterologous Infection on the T Cell Repertoire

The results shown above demonstrate remarkable differences in the immunodominance pattern of responses to DENV3, as compared to DENV2. A significant fraction of the DENV3 primary response is directed against structural proteins that are associated with higher sequence variability. As a result, a majority of the DENV3 response is directed against serotype specific epitopes. By contrast, in the case of DENV2 a greater fraction of the response is directed against the more conserved NS proteins.

This observation prompted a test whether pre-immunization with one serotype would interfere with development of immunity to a second serotype, because the pattern of response imprinted by the original infection would be preserved in the heterologous infection. Accordingly, B*0702 transgenic IFN-α/βR−/− mice were infected with DENV3 and subsequently with DENV2 (heterologous secondary infection). According to the threshold established as described above, the B*0702 epitopes were divided into DENV3 specific (sequence identity D3S5CX≥80%, S221<80%), conserved (D3S5CX≥80%, S221≥80%) and DENV2 specific (D3S5CX<80%, S221≥80%) subsets.

Figure 24:
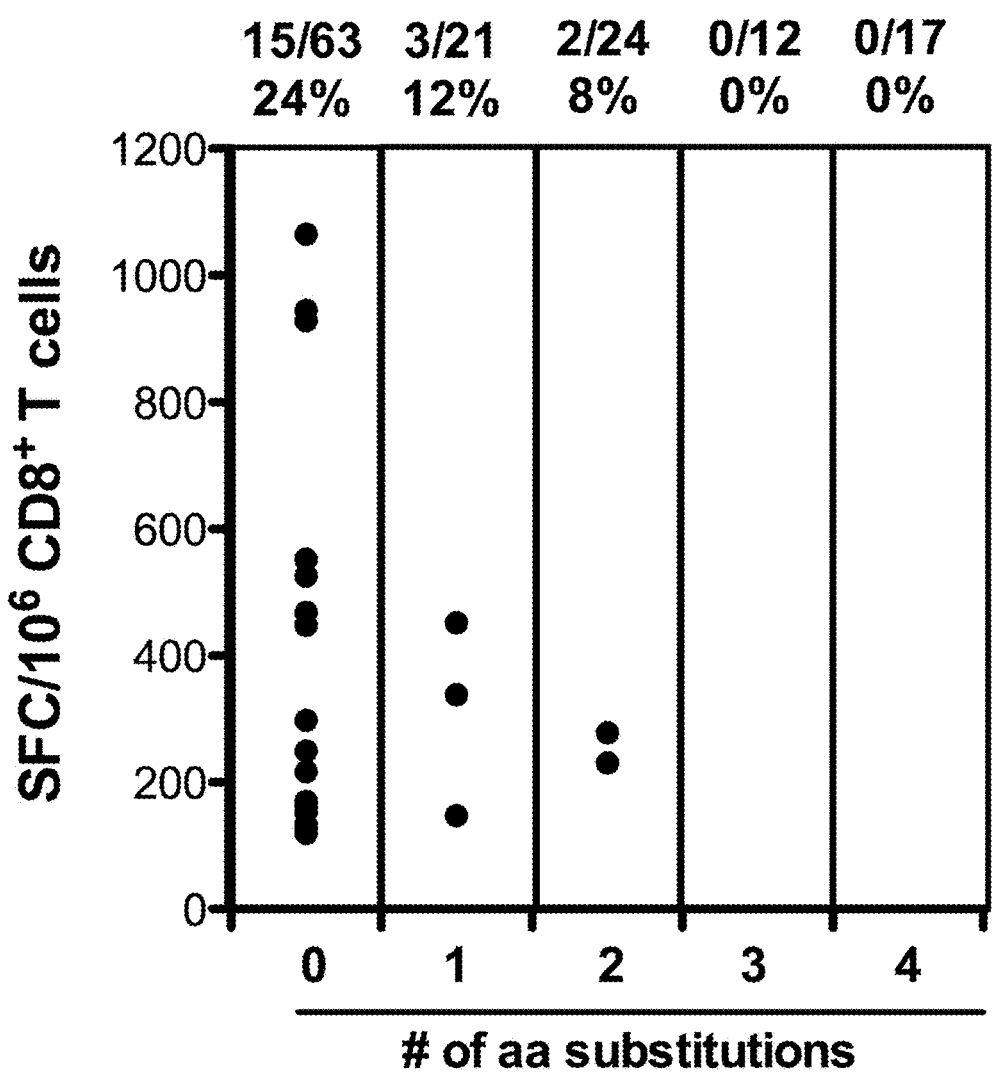
FIG. 24 shows threshold for cross-reactive epitope recognition. A panel of 137 peptides corresponding to naturally occurring DENV variants of a set of B*0702 epitopes, with various degrees of sequence homology to the DENV3 strain D3S5CX, was synthesized and tested for T cell reactivity after infection of B*0702 transgenic IFN-α/βR−/− mice with D3S5CX. The data are expressed as mean number of SFC/10⁶ CD8+ T cells of two independent experiments. Responses against peptides were considered positive if the stimulation index (SI) exceeded double the mean negative control wells (T cells plus APCs without peptide) and net spots were above the threshold of 20 SFCs/10⁶ CD8+ T cells in two independent experiments.

FIG. 24B shows the patterns of response elicited by the individual epitopes after either primary DENV3 infection (white bars) or heterologous secondary infection with DENV2 (black bars). While primary infection elicited responses prevalently directed towards DENV3 specific epitopes (72%, FIG. 24B, dark grey pie), the heterologous infection elicited responses predominantly targeting epitopes conserved between the two serotypes (69%, FIG. 24B, black pie). The overall response magnitude after either primary or secondary infection was comparable (FIG. 24C). Primary DENV3 infection followed by homologous secondary infection with the same DENV serotype did not shift the responses towards these conserved epitopes but kept the focus on the DENV3 serotype specific epitopes (data not shown). In conclusion, the controlled experimental conditions enabled by the HLA transgenic mice system allowed a demonstration that the pattern of dominance in primary infection is not preserved following heterologous secondary infection, and that heterologous infection is associated with predominant recognition of conserved/cross-reactive epitopes.

TABLE 11

DENV3 specific epitopes identified

| Epitope | Sequence (SEQ. ID Nos: 1164-1213, in order of appearance) | Restriction | T cell response [SFC] | HLA binding [IC$_{50}$] | Conservancy within serotypes [%] | |
|---|---|---|---|---|---|---|
| | | | | | S221 | D3S5CX |
| E$_{451-459}$ | TTLAILPEY 76 | A*0101 | 429 | 31 | 56 | 100 |
| NS1$_{1090-1099}$ | RSCTLPPLRY 15 | | 305 | 5.9 | 100 | 100 |
| C$_{57-66}$ | FLAIPPTAGV new | A*0201 | 868 | 3.6 | 80 | 100 |
| C$_{103-112}$ | SLCLMMILPA new | | 244 | 5.7 | 50 | 100 |
| C$_{106-114}$ | LMMILPAAL | | 1679 | 6.6 | 56 | 100 |
| M$_{250-259}$ | ILALFLAHYI | | 1595 | 6.3 | 50 | 100 |
| M$_{254-263}$ | FLAHYIGTSL | | 1363 | 4.8 | 50 | 100 |
| M$_{268-276}$ | VIFILLMLV | | 607 | 375 | 67 | 100 |
| E$_{580-589}$ | YAMCTNTFVL | | 658 | 33 | 50 | 100 |
| E$_{631-639}$ | RLITANPVV | | 418 | 20 | 78 | 100 |
| E$_{727-735}$ | ALFSGVSWV | | 1086 | 20 | 78 | 100 |
| NS1$_{854-862}$ | ILWENNIKL | | 2238 | 2.7 | 67 | 100 |
| NS1$_{987-996}$ | KLEKASLIEV | | 488 | 77 | 80 | 100 |
| NS2A$_{1164-1172}$ | VLFTFVLLL | | 1363 | 10 | 45 | 100 |
| NS2A$_{1202-1211}$ | YLALIATFKI | | 1089 | 10 | 70 | 100 |
| NS2A$_{1271-1280}$ | YQLWTALVSL | | 1122 | 1.7 | 40 | 100 |
| NS2B$_{1355-1363}$ | VMAVGLVSI | | 442 | 21 | 78 | 100 |
| NS2B$_{1444-1453}$ | VLLKTALLIV | | 203 | 23 | 50 | 100 |
| NS3$_{1832-1840}$ | FAGKTVWFV | | 415 | 11 | 89 | 100 |
| NS3$_{1876-1884}$ | KLNDWDFVV | | 333 | 1.8 | 78 | 100 |
| NS3$_{2013-2022}$ | ELMRRGDLPV | | 757 | 22 | 90 | 100 |
| NS4A$_{2150-2159}$ | TLLLLGLMIL | | 990 | 52 | 60 | 100 |
| NS4A$_{2205-2213}$ | IVLEFFMMV | | 469 | 11 | 67 | 100 |
| NS4B$_{2311-2320}$ | SLAAIANQAV | | 858 | 6.7 | 80 | 100 |
| NS5$_{2814-2822}$ | SMINGVVKL | | 1016 | 14 | 78 | 100 |
| E$_{509-517}$ | TPTWNRKEL | B*0702 | 1193 | 2.8 | 56 | 100 |
| NS1$_{814-822}$ | SPKRLATAI | | 1186 | 1.5 | 67 | 100 |
| NS1$_{1071-1079}$ | GPSLRTTTV | | 115 | 2.2 | 89 | 100 |

TABLE 11-continued

DENV3 specific epitopes identified

| Epitope | Sequence (SEQ. ID Nos: 1164-1213, in order of appearance) | T cell Restriction | T cell response [SFC] | HLA binding [IC$_{50}$] | Conservancy within serotypes [%] S221 | Conservancy within serotypes [%] D3S5CX |
|---|---|---|---|---|---|---|
| NS2A$_{1290-1298}$ | TVAWRTATL | | 486 | 3.6 | 56 | 100 |
| NS2B$_{1373-1382}$ | VPMAGPLVAG | | 28 | 115 | 80 | 100 |
| NS2B$_{1457-1465}$ | FPYSIPATL | | 802 | 1.0 | 67 | 100 |
| NS3$_{1648-1656}$ | EPDGPTPEL | | 512 | 299 | 44 | 100 |
| NS3$_{1682-1690}$ | LPAIVREAI | | 494 | 6.5 | 100 | 100 |
| NS3$_{1700-1709}$ | APTRVVAAEM | | 291 | 4.6 | 100 | 100 |
| NS3$_{1899-1907}$ | RVIDPRRCL | | 260 | 146 | 89 | 100 |
| NS3$_{1925-1934}$ | MPVTAASAAQ | | 690 | 1072 | 80 | 100 |
| NS3$_{2070-2078}$ | RPRWLDART | | 40 | 2.1 | 78 | 100 |
| NS4A$_{2113-2121}$ | LAHRTRNAL | | 95 | 3.3 | 56 | 100 |
| NS5$_{2860-2868}$ | RPMPGTRKV | | 461 | 2.7 | 44 | 100 |
| NS2B$_{1412-1421}$ | AEQTGVSHNL | B*4001 | 362 | 67 | 50 | 100 |
| NS3$_{1569-1577}$ | GEEVQVIAV | | 293 | 12 | 78 | 100 |
| NS3$_{1598-1607}$ | GEIGAIALDF | | 289 | 40 | 70 | 100 |
| NS3$_{2005-2014}$ | GESRKTFVEL | | 708 | 3.5 | 80 | 100 |
| C$_{101-115}$ | KTSLCLMMILPAALA new? | DRB1*0101 | 82 | 12 | 40 | 100 |
| M$_{268-282}$ | VIFILLMLVTPSMTM | | 53 | 53 | 73 | 100 |
| NS1$_{984-998}$ | GSWKLEKASLIEVKT | | 236 | 56 | 67 | 100 |
| NS2B$_{1359-1373}$ | GLVSILASSLLRNDV | | 241 | 2.1 | 80 | 100 |
| NS3$_{1692-1706}$ | RRLRTLILAPTRVVA | | 113 | 5.3 | 93 | 100 |
| NS3$_{1742-1756}$ | TFTMRLLSPVRVPNY | | 70 | 1.5 | 100 | 100 |
| NS5$_{2967-2981}$ | RAIWYMWLGARYLEF | | 586 | 48 | 93 | 100 |

Example 32

Discussion

The study of DENV infection in humans and immune correlates associated with protection on one hand, and immunopathology on the other, is fraught with considerable complexities. One of the issues contributing to this complexity is that individuals in endemic areas, in general, and those affected by the more severe forms of disease, in particular, are typically afflicted by multiple heterologous infections. As a result, the patterns of reactivity associated with primary DENV infection are relatively less well defined. Furthermore, it has been suggested that heterologous infection leads to the preferential recognition of sequences cross-reactive between the two (or more) infecting viruses, but that this cross-reactive response is of lower efficacy in controlling viral disease. This possibility has been described as the original antigenic sin hypothesis. In most cases, however, the exact infecting serotypes and the corresponding order and times of infection are unknown, highlighting the need for a more controlled experimental model system to study the evolution of HLA restricted T cell responses to dengue. Here it was shown that while DENV3 primary infection is dominated by serotype specific responses, heterologous infection results in dominating responses targeting cross-reactive or conserved epitopes.

The primary immune response against DENV3 was broad and targeted all 10 DENV proteins. One third of the responses identified were elicited by T cell epitopes derived from the three structural proteins (C, M, E). This is in contrast to the T cell targets observed after infection with DENV2, where the vast majority of responses (97%) were targeted towards epitopes derived from the nonstructural and not the structural protein. This differential targeting of proteins could have direct implications in vaccine design. The most advanced dengue vaccine to date consists of live-attenuated tetravalent chimeric dengue-yellow fever vaccine strains, which present DENV serotype specific membrane (M) and envelope (E) proteins in a Yellow fever 17D backbone. Results from a recent clinical trial demonstrated partial (60-80%) protection towards 3 of the 4 DENV serotypes, but no protection against DENV2 infection. In humans the majority of the DENV2 specific T cell responses are directed against the non-structural proteins, which are absent in the tetravalent vaccine. This deficiency could explain the lack of protective immunity against DENV2. Similarly, the data in HLA transgenic mice demonstrates that while only 3% of the DENV2 specific immune response is focused on the structural proteins, almost 25% of the DENV3 specific response is directed against the prM and E structural proteins, both of which are present in the vaccine. These substantial serotype specific differences could provide an explanation as to why the live-attenuated tetravalent chimeric vaccine was able to partially protect against 3 of the 4 dengue serotypes, but not DENV2.

Another protein dominantly targeted after infection with DENV3, but not following DENV2 infection, is the NS1 protein. Unlike other nonstructural proteins, NS1 can also be secreted, and detection of early concentrations of NS1 in blood is positively associated with disease severity. It has been suggested that NS1 from dengue-infected cells contributes to the dengue shock syndrome by forming complexes with pro-thrombin. Formation of such complexes may result in a prolongation of activated partial thromboplastin times, values that have been shown to be the strongest correlate of vascular permeability in patients with dengue infection. 15% of all DENV3 specific reactivity was targeted against the NS1 protein, whereas NS1 reactivity was basically absent after primary DENV2 infection. Furthermore, DENV3 specific NS1 reactivity was not restricted to certain alleles, since at least one NS1 epitope was identified in 4 out of 5 HLA class I alleles tested. Thus, the DENV3 specific response against NS1 could contribute to protection while this immune response is absent in infection with DENV2, which has in fact been reported as a risk factor for severe disease.

The observation that T cell epitopes targeted following primary DENV infection with different serotypes are not derived from the same proteins may factor in future vaccine design strategies. With this consideration, NS3 has been the most dominantly targeted protein after infection with both DENV2 and DENV3 serotypes, albeit with a somewhat variable level of dominance Immunizing with antigens containing the NS3 epitopes would induce a robust T cell response against both DENV serotypes without the risk of antibody-dependent-enhancement.

In conclusion, different DENV strains are associated with different and unique hierarchies in terms of the specific antigens that are immunodominant for cellular immunity. These findings have potential relevance for both vaccine design and DENV immunopathogenesis. Furthermore, the results clearly demonstrate how the pattern of responses observed following a primary infection does not dominate the T cell response observed following a secondary heterologous infection, which is associated with the immunodominance of cross-reactive/conserved sequences.

Example 33

Materials and Methods

Ethics Statement

Clinical data and serum samples for this study were derived from separate phase I clinical trials, performed at the University of Vermont (UVM) Vaccine Testing Center and the Center of Immunization Research at the Johns Hopkins School of Public Health (JHSPH). Clinical trials are described at Clincaltrials.gov: NCT01084291, NCT01073306, NCT00831012, NCT00473135, NCT00920517, NCT00831012 and NCT01072786. Study design and clinical protocols were approved by the Committees for Human Research (UVM) and the Western Institutional Review Board (JHSPH).

Study Populations

Healthy adult male and nonpregnant female volunteers 18-50 years of age were enrolled and vaccinated with either one of the four monovalent or the tetravalent vaccine formulation. All individuals were seronegative to all DENV serotypes, yellow fever virus, West Nile virus, St. Louis encephalitis virus, Hepatitis B and C and human immunodeficiency virus (HIV). Study participants were recalled 6-18 months after vaccination, to donate a full unit of blood. Blood samples from donors experiencing natural infection have been obtained from healthy adult blood donors from the National Blood Center, Ministry of Health, Colombo, Sri Lanka. Blood processing and HLA typing of both study population was performed as previously described.

Vaccines

Attenuation of the different dengue viruses has been achieved by deleting one (rDEN1Δ30, rDENV4Δ30) or two regions (DEN3Δ30,31) from the 3' untranslated region (UTR). DEN2/4 Δ30 is a chimeric virus in which the DENV2 prM and E genes replaced those of the DEN4Δ30 vaccine candidate. For the tetravalent vaccination used in this study (TV003) the four monovalent vaccines were combined into tetravalent admixtures prior to vaccination.

MHC Class I Binding Predictions and Peptide Selection

Sets of 9 and 10mer peptides encoded in proteome of the vaccine strains and predicted to bind a set 27 MHC class I alleles, selected to account for 97% of HLA A and B allelic variants in most ethnicities, were synthesized (Mimotopes, Victoria, Australia). Peptides combined into pools of 10 individual peptides, according to their predicted HLA restriction.

Conservancy Analysis

For the conservancy analysis full-length DENV polyprotein sequences were retrieved for each serotype from the NCBI Protein database using the following query: txid11053 AND 3000:5000[slen]. The number of isolates from any one country was limited to 10 to eliminate geographical bias. Sequences were considered unique if they varied by at least 1 amino acid from all other sequences. In summary 162 DENV1, 171 DENV2, 169 DENV3 and 53 DENV4 sequences were retrieved from the NCBI Protein database and investigated the conservancy of the identified epitopes within the sequences of the respective serotypes.

Ex Vivo IFNγ ELISPOT Assay $2 \times 10^5$ PBMC were incubated in triplicates with 0.1 ml complete RPMI 1640 in the presence of HLA-matched peptide pools [2 µg/ml]. Following a 20 h incubation at 37° C., the cells were incubated with biotinylated IFNγ mAb (mAb 7-B6-1 Mabtech, Stockholm, Sweden) for 2 h and developed. Pools positive in two individual experiments were subsequently deconvoluted to identify the individual responding epitopes.

Flow Cytometry and Intracellular Cytokine Staining (ICS)

The following monoclonal antibodies were used in this study: BD Biosciences: anti-CD8a V500 (clone RPA-T8), anti-CD3 Alexa Flour 700 (clone UCHT1). eBioscience: anti-CD45RA eFlour 450 (clone H100), anti-IFNγ FITC (clone 4S.B3), anti-IL-2 PE (clone MQ1-17H12), anti-TNFα APC (clone MAb11), anti-CD107a PE (clone ebioH4A3). Biolegend: anti-CD197 (CCR7) PerCP-CY5.5 (clone G043H7). PBMC were cultured in the presence of

Example 34

DENV Specific T Cell Responses are Readily Detected Ex Vivo after Vaccination with Monovalent Live Attenuated DENV Vaccines To perform a comprehensive analysis of the T cell response after monovalent vaccination responses were examined from 41 recipients (11 DENV1, 10 DENV2, 11 DENV3 and 9 DENV4) of experimental live attenuated dengue vaccines (DLAV). PBMC from all study participants were screened in IFNγ ELISPOT assays with pools of HLA matched predicted class I binder peptides, also corresponding to the specific DLAV serotypes they had been vaccinated with. As shown in Table 12 ex-vivo reactivity was detected for 50% of DENV1, 70% of DENV2, 55% of DENV3 and 60% of all DENV4 monovalent vaccine recipients studied. In total, 191 donor/peptide responses were identified, corresponding to 94 unique CD8+ T cell epitopes. A complete list is available on the Immune Epitope Database. Responses to the different monovalent DLAVs were comparable both in average magnitude (mean of 95 SFC/$10^6$ PBMC, range 76 to 123) and breadth of repertoires (mean of 6, range 3 to 8). The fact that responses can be readily detected ex vivo is remarkable, as compared to the level of reactivity seen in endemic areas as discussed below. Furthermore it allows evaluating vaccine-induced response avoiding the potential artifacts introduced by in vitro restimulation of the cells.

Figure 26A:
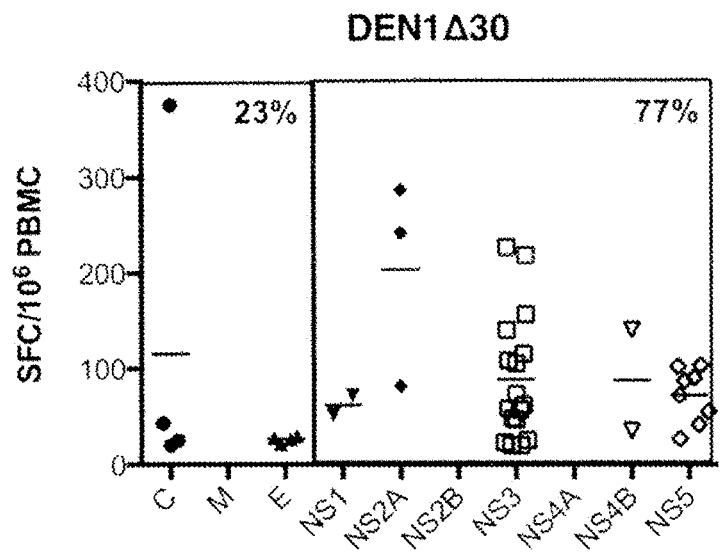
FIGS. 26A-26D show protein location of epitopes varies as a function of the DENV serotype. Shown are responses detected in study participants vaccinated with DENV1 (FIG. 26A), DENV2 (FIG. 26B), DENV3 (FIG. 26C) or DENV4 (FIG. 26D) live attenuated monovalent dengue vaccine. Responses are expressed as the number of IFNγ secreting cells per 10⁶ PBMC and considered positive if the magnitude of response to the test peptide is significantly different as compared with a negative control peptide (p<0.05, Student's t-test) and the stimulation index (S.I.=ratio test SFCs/control SFCs) is greater than 2.0.
Figure 26B:
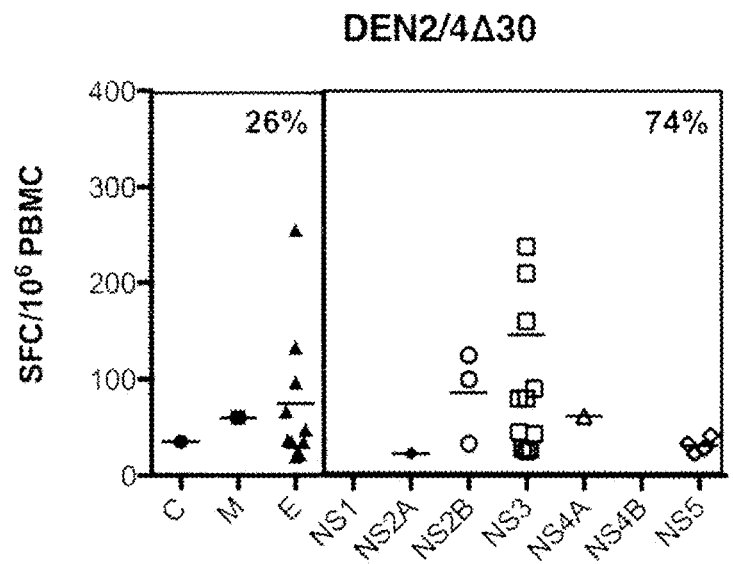
Figure 26C:
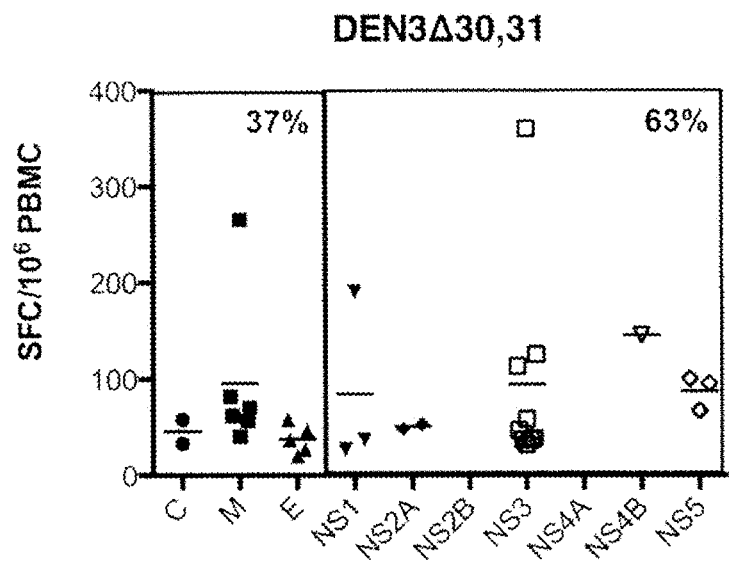
Figure 26D:
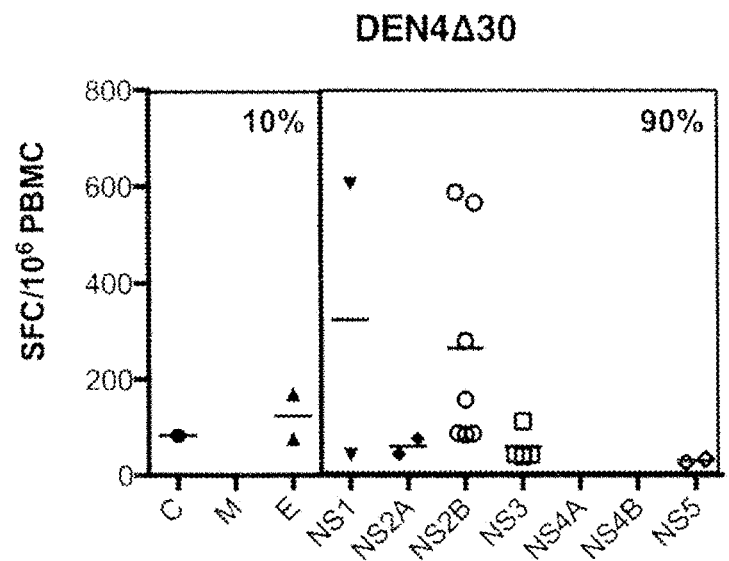

Next, the specificity of the vaccine specific immune response was investigated at the antigen level. The relative strength of recognition was analysed of the three structural proteins (Capsid (C), Membrane (M), and Envelope (E)), and the seven NS proteins (NS1, NS2A, NS2B, NS3, NS4A, NS4B and NS5). As shown in FIG. 26, epitopes were identified from all of the 10 DENV proteins. Interestingly, the antigenic dominance seemed to differ depending on the serotype used in the vaccine. On one extreme, in case of the DENV4 vaccine the majority of the responses were derived from the seven NS proteins, and accounted for 90%, of the total IFNγ response observed (FIG. 26D). In contrast, in the case of DENV3 all three of the structural proteins were targeted accounting for 37% of the total response observed (FIG. 26C). Within the seven nonstructural proteins, NS1, NS3 and NS5 were dominant, regardless of the vaccination serotype. In contrast, only vaccination with DENV4 elicited a strong response against NS2B. These results point to a differential immunodominance hierarchy as a function of the infecting serotype.

Example 35

The Immune Response Induced by Tetravalent Vaccination is Targeted Against Highly Conserved Epitopes and Displays a Multifunctional Effector Memory Phenotype Next, the T cell response was examined in 11 recipients of a live attenuated tetravalent (LATV) dengue vaccine, consisting of a mixture of all the individual monovalent vaccines, each represented in the same dose used for monovalent vaccination. Following the same methodology as described above, PBMC from all study participants were screened with pools of predicted HLA matched class I binding peptides covering all four serotypes in IFNγ ELISPOT assays. Ex-vivo reactivity was detected in 73% of vaccine recipients with an average magnitude of 235 SFC/PBMC and an average repertoire breadth of 8 epitopes per donor (Table 12). When the results of DLAV monovalent and tetravalent vaccination were compared with the levels of natural immunity observed following secondary infection, comparable levels of CD8+ reactivity were observed (Table 13).

Figure 27A:
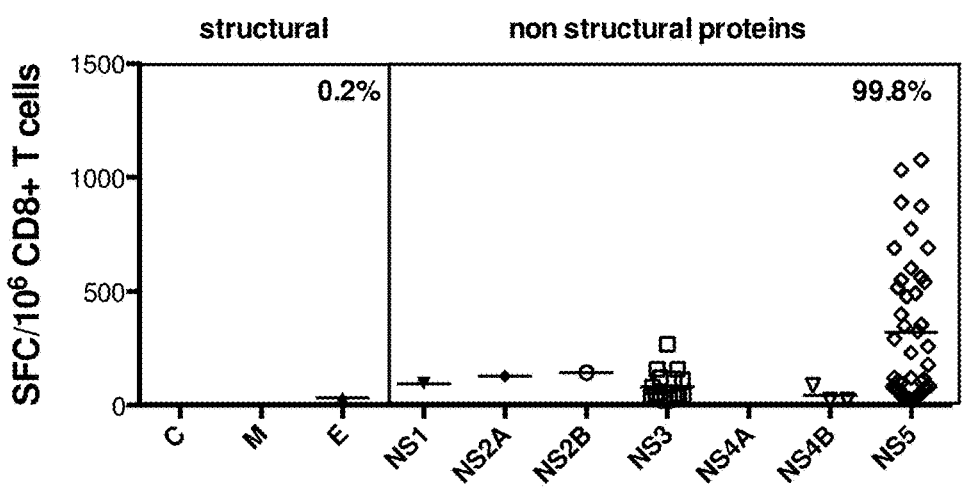
FIGS. 27A-27E show the immune response induced by tetravalent vaccination is targeted against highly conserved proteins and displays a multifunctional effector memory phenotype.
Figure 27B:
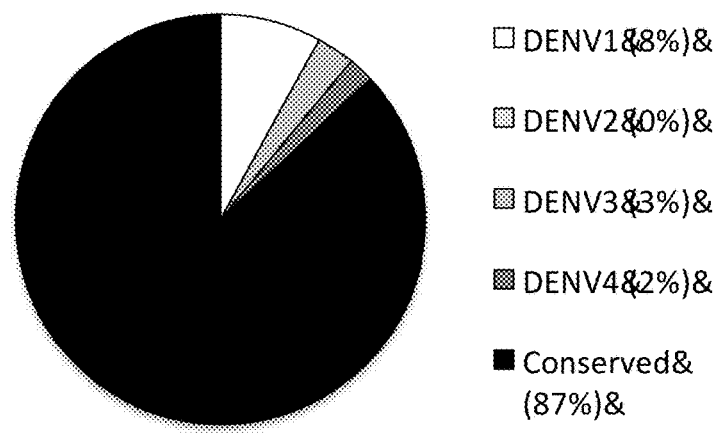

Further analysis of the protein location revealed a highly focused response against the nonstructural proteins accounting for 99.8% of the response observed (FIG. 27A). While responses to 6 out of the 7 nonstructural proteins have been detected, NS3 and NS5 were the most dominantly targeted, together accounting for 97% of the response. T cell reactivity was categorized on the basis of whether it was directed against serotype specific sequences (found only in one serotype), or against conserved/homologous sequences (sequences found in two or more serotypes, allowing a single residue substitution to account for potential cross-reactivity of highly homologous sequences). Strikingly, conserved sequences accounted for 87% of the overall responses (FIG. 27B) suggesting that the responses induced by the tetravalent vaccine should be able to recognize epitopes from all four serotypes.

Figure 27C:
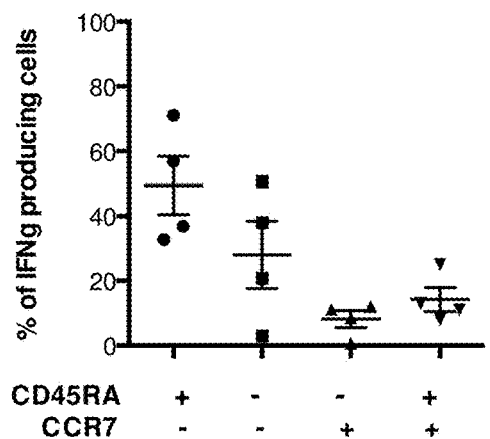
Figure 27D:
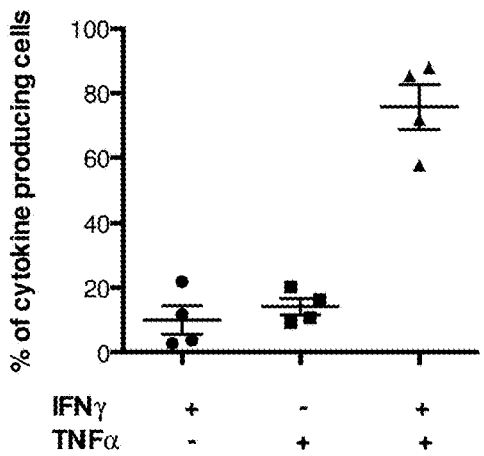
Figure 27E:
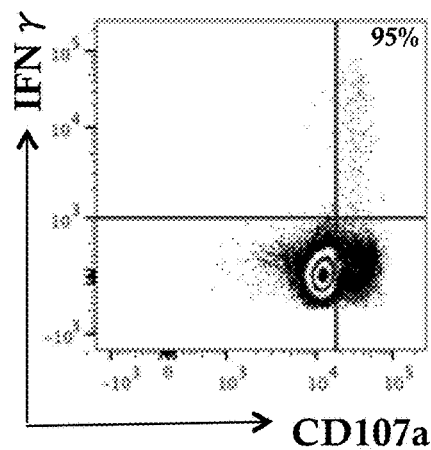

The phenotype and cytokine profile of the responding T cells was also analyzed. As shown in FIG. 27C the majority of responses elicited by the tetravalent vaccine were produced by T cells displaying a effector memory phenotype (mean 49% TEMRA and 28% TEM). In terms of cytokine expression patterns, on average 76% of cells responding to vaccine-specific pools were double positive for IFNγ, TNFα followed by cells positive for only one cytokine (10% and 14% for IFNγ and TNFα, respectively; FIG. 27D). The expression level of the marker for cytotoxicity CD107a was >95% in all donors tested (FIG. 27E), indicating that the responding cells exhibit a phenotype compatible with elimination of virus infected cells.

Example 36

Figure 28A:
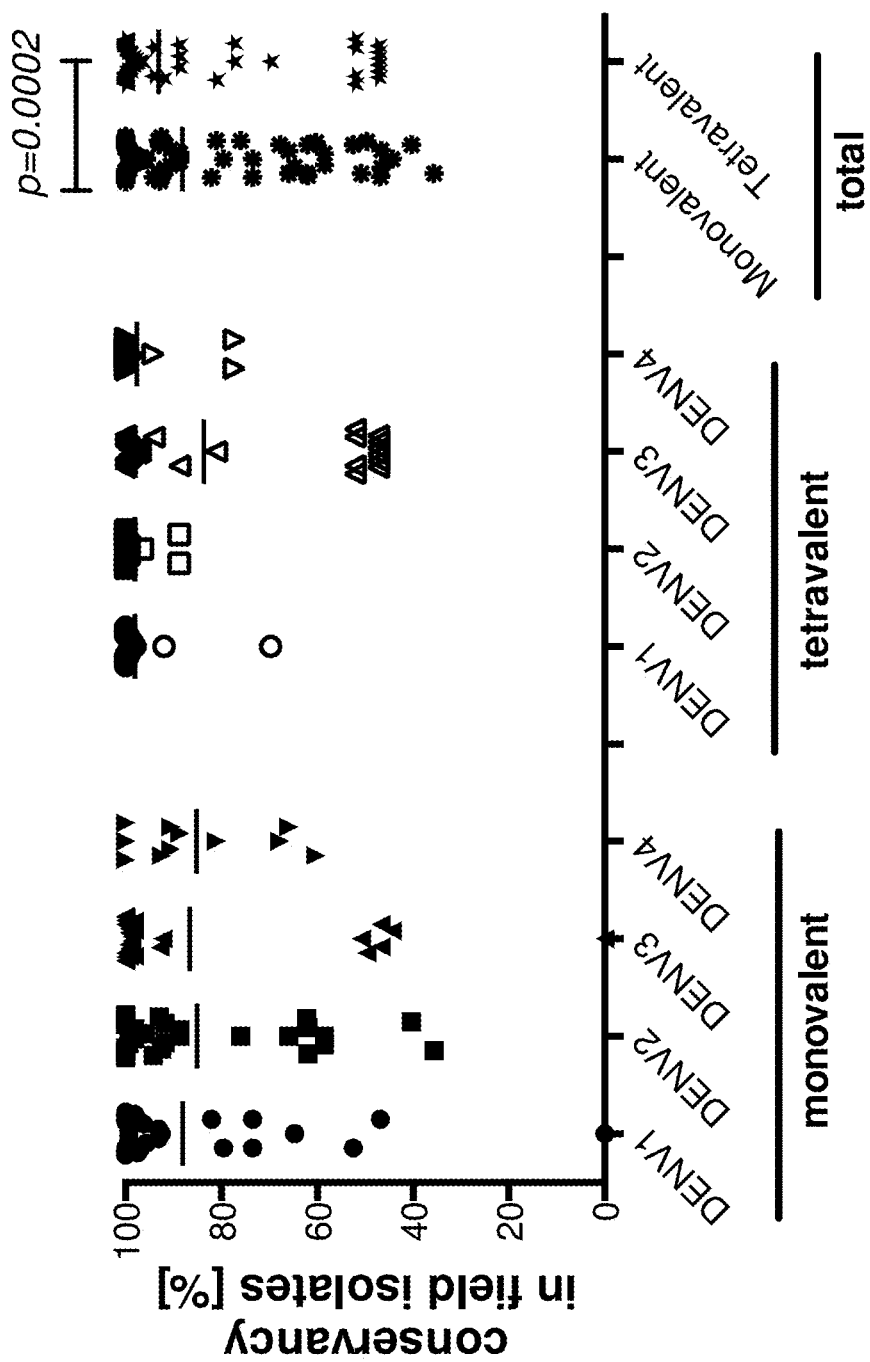
FIGS. 28A-28C shows epitopes induced by DLAV are highly conserved in field isolates of DENV and recognized by donors exposed to natural infection with DENV.

Epitopes Induced by DLAV are Highly Conserved in Field Isolates of DENV and Recognized by Donors Exposed to Natural Infection with DENV To further assess the relevance of vaccine-induced epitopes in the context of natural infections the conservancy of the vaccine-derived epitopes was investigated within 555 field isolates from all four DENV serotypes (FIG. 28A). A high degree of conservancy was found after monovalent vaccination for all of the serotypes. Vaccine-specific epitopes were conserved in 88% of DENV1, 85% of DENV2, 87% of DENV3 and 86% of DENV4 corresponding field isolates (FIG. 28A left panel). It was further found that the epitopes recognized after tetravalent vaccination were 98% conserved within DENV1, 2 and 4 field isolates and 84% of all DENV3 field isolates (FIG. 28A middle panel). When all epitope reactivity is combined, and monovalent and tetravalent vaccination is compared, it was found that administration of tetravalent vaccination shifted the response to even more intra-serotype conserved regions (p=0.002; FIG. 28A, right panel) indicating that vaccine induced responses should be able to recognize a vast variety of natural occurring DENV strains occurring in endemic areas around the world.

Figure 28B:
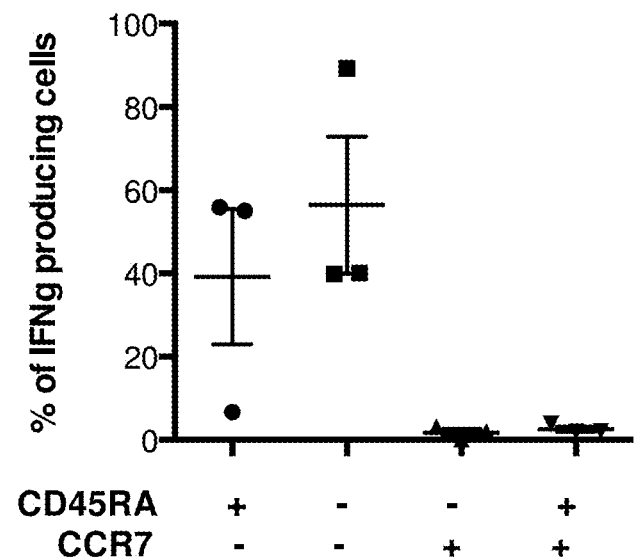
Figure 28C:
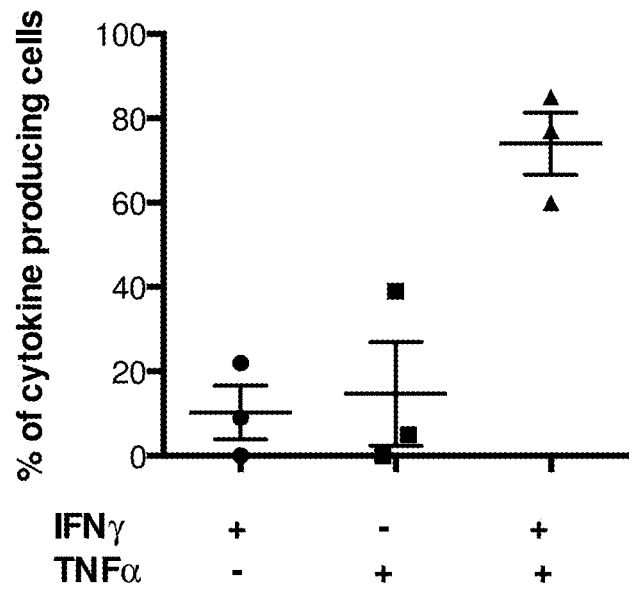

The epitopes induced by vaccination in donors were evaluated from the DENV endemic area Sri Lanka, who have previously experienced natural infection with DENV. Responses were readily detected, and were associated with similar phenotype and cytokine profile (FIGS. 28B and C) in vaccines and naturally exposed Sri Lankan donors. This underlines the relevance of vaccine induced T cell immunity in the context of natural infection.

Example 37

Discussion

The development of effective vaccination against DENV infection and associated disease is tasks of high societal value and significance, and at the same time a challenge of significant complexity. The immune correlates of vaccine efficacy are poorly understood. Recent data suggest that neutralizing antibody titers might be insufficient to predict vaccine efficacy, and that CD8+ responses might be an important component of natural protection. A comprehensive ex vivo characterization of HLA restricted T cell memory responses in recipients of dengue live attenuated vaccines has been reported here. It was demonstrated that vaccine-specific CD8+ T cell responses are similar in magnitude and frequency to those observed in the context of naturally immune populations, as detected ex vivo in donors exposed to both experimental and natural infection with DENV. The kinetics of IFNγ and TNFα production by CD4+ T cells has been previously investigated up to 6 weeks post vaccination with the monovalent DENV1 vaccine. The fact that ex vivo T cell responses are still robust 6-18 months post vaccination points to the induction of a long lasting memory response, one of the desirable attributes of a vaccine candidate. In this context, it is important to point out that the average time between DENV infections in the Sri Lanka endemic area is estimated to be of about seven years. This difference might explain why the magnitude and frequency of the ex vivo responses to the DLAV vaccines, despite their attenuation, seem to be comparable and even exceed those observed in Sri Lankans associated with primary and secondary infection.

Following monovalent vaccination, DLAVs of different serotypes elicited responses with somewhat different immunodominance hierarchy. Following tetravalent vaccination the induction of responses dominantly targeting the non-structural proteins NS3 and NS5 was observed, which are also dominantly targeted by natural DENV immunity. This has potential relevance in the context of the insufficient protection against all four serotypes by the most advanced tetravalent dengue-yellow fever chimeric virus vaccine, in which these proteins are absent.

Still the remarkable focus of responses towards conserved epitopes was somewhat unexpected. In the tetravalent vaccination setting sequences of all four serotypes are administered at once and thus differ from secondary infection were the different serotypes are usually encountered sequentially. It is possible that the 4-fold greater representation of conserved sequences over serotype specific ones also influenced their immune dominance. Indeed, a protective role was found for CD8+ T cells focusing on conserved regions of the DENV polyprotein upon secondary heterologous infection. The evolution of secondary T cell responses towards conserved regions could contribute to heightened protection and less disease severity observed in tertiary heterotypic DENV infections.

Influenza virus is another RNA virus associated with a high degree of sequence variation. It has been shown that cross-reactive cytotoxic T cells recognizing conserved epitopes across viral subtypes contribute to heterotypic immunity against different strains of Influenza. Furthermore, a CD8+ T cell subset specific for highly conserved epitopes from core proteins has been recently reported as correlate of protection against symptomatic infection with influenza. The fact that the epitopes elicited by the tetravalent vaccine are highly conserved across a huge variety of field isolated supports the notion that T cells will also respond to infection with a virus different from the vaccine strain. This is highly relevant for a global vaccine since the circulating viruses show annual variation and vary as a function of geographic location.

Finally, the phenotype of the cells induced by tetravalent vaccination is also of note. These cells were found to be multi-specific, expressing the cytotoxicity marker CD107, and mostly contained in TEM and TEMRA subsets. Since these features have been associated with protective capacity form viral infections in different systems, these data provide impetus for further testing of DLAV tetravalent vaccination to prevent DENV infection and disease.

TABLE 12

T cell reactivity after DLAV vaccination

| Vaccine | Frequency of responders [%] | Average response per donor [a] | Average # of epitopes per donor |
|---|---|---|---|
| DEN1Δ30 | 50 | 83 | 8 |
| DEN2/4 Δ30 | 70 | 76 | 5 |
| DEN3Δ30,31 | 55 | 98 | 6 |
| DEN4Δ30 | 60 | 123 | 3 |
| TV003 | 73 | 235 | 8 |

[a] expressed as IFNγ SFC/10[6] PBMC

TABLE 13

Comparison of T cell reactivity after vaccination and natural infection

| Parameter | Vaccine Recipients (NIH) | | Naturally infected donors (Sri Lanka) [c] | |
|---|---|---|---|---|
| | mono-valent [b] | tetra-valent | primary | secondary |
| Frequency of responders [%] | 59 | 73 | 22 | 43 |
| Average response per donor [a] | 6 | 8 | 6 | 11 |
| Average # of epitopes per donor | 95 | 235 | 96 | 220 |
| n = | 41 | 11 | 55 | 127 |

[a] expressed as IFNγ SFC/10[6] PBMC

[b] shown is the average response observed in vaccinees with any of the four monovalent vaccines

[c] previously reported in Weiskopf et al. 2013 [9]

TABLE 14

T Cell Epitope Reactivity

Reactive T Cell Epitopes

| (begins with SEQ. ID. NO. 1214 in left to right order of appearance) FNMLKRARNR | ILIGVIITW | GTSGSPIINK | MANIFRGSY |
|---|---|---|---|
| MLKRERNRV | HTWTEQYKF | KPGTSGSPI | IMKSVGTGK |
| GPMKLVMAFI | PPASDLKYSW | GLYGNGVVTK | ATYGWNLVK |
| MVLALITFL | IEKASLIEV | NPEIEDDIF | ASSMVNGVVR |
| KEISSMLNIM | RPGYHTQTA | AIKRKLRTL | IPMVTQIAM |
| ITLLCLIPTV | GPWHLGKLEL | IKRKLRTLIL | TPFGQQRVF |
| VTYECPLLV | RSCTLPPLRY | APTRVVAAEM | KPRICTREEF |
| HPGFTILALF | RPINEKEENM | VPNYNLIVM | NPRLCTREEF |
| FTILALFLAH | LAILFEEVM | DPASIAARGY | RPRLCTREEF |
| MLVTPSMTM | MIAGVFFTF | EERDIPERSW | TPRMCTREEF |
| TEVTNPAVL | FRRLTSREVL | DISEMGANF | RSNAAIGAVF |
| EAKQPATLR | IPHDLMELI | RVIDPRRCMK | VEDERFWDL |
| PTSEIQLTDY | LTDFQSHQL | DPRRCLKPV | KLGEFGRAK |
| LPEYGTLGLE | ALPVYLMTL | TPEGIIPALF | KAKGSRAIW |
| LTDYGALTL | LPVYLMTLMK | TPEGIIPSM | RFLEFEALGF |
| LPWTSGATT | GPLVAGGLL | EFRLRGEQR | TVMDVISRR |
| IQKETLVTF | IEETNMITL | LEENMEVEIW | ALLALNDMGK |
| NYKERMVTF | YPLAIPVTM | GERKKLKPRW | KVRKDIPQW |
| IQMSSGNLLF | ALWYVWQVK | RPRWLDART | REIVVPCRNQ |
| MSYAMCTNTF | ALSEGVYRI | YSDPLALRE | ETACLGKSYA |
| SYSMCTGKF | VLDDGIYRI | AGRRSVSGDL | LGKSYAQMW |
| YAMCTNTFVL | IYRILQRGLL | IAVASGLLW | YAQMWSLMYF |
| MVHQIFGSAY | GLFGKTQVGV | NPLTLTAAV | TWSIHAHHQW |
| MVHQIFGSAY | MEGVFHTMWH | SPGKFWNTTI | TTWEDVPYL |
| GAAFSGVSW | GEIGAVTLDF | IAVSMANIF (ends with SEQ. ID. NO. 1312 in left to right order of appearance) | |

TABLE 15

Novel T Cell Epitopes

| Novel T Cell Epitopes (begins with SEQ. ID. NO. 1313 in left to right order of appearance) FLAHYIGTSL | MLKRERNRV | MVHQIFGSAY | IEETNMITL | YSDPLALRE |
|---|---|---|---|---|
| VIFILLMLV | MVLALITFL | MVHQIFGSAY | YPLAIPVTM | AGRRSVSGDL |
| YAMCTNTFVL | | KEISSMLNIM | GAAFSGVSW | ALWYVWQVK | IAVASGLLW |

TABLE 15-continued

Novel T Cell Epitopes

| | | | | |
|---|---|---|---|---|
| ILWENNIKL | TEVTNPAVL | ILIGVIITW | ALSEGVYRI | IMKSVGTGK |
| VLFTFVLLL | EAKQPATLR | HTWTEQYKF | VLDDGIYRI | IPMVTQIAM |
| IVLEFFMMV | PTSEIQLTDY | PPASDLKYSW | IYRILQRGLL | RSNAAIGAVF |
| SLAAIANQAV | LPEYGTLGLE | IEKASLIEV | GLFGKTQVGV | VEDERFWDL |
| TPTWNRKEL | LTDYGALTL | RPINEKEENM | GEIGAVTLDF | KLGEFGRAK |
| TVAWRTATL | LPWTSGATT | LAILFEEVM | GLYGNGVVTK | ALLALNDMGK |
| FPYSIPATL | IQKETLVTF | MIAGVFFTF | AIKRKLRTL | KVRKDIPQW |
| EPDGPTPEL | NYKERMVTF | FRRLTSREVL | IKRKLRTLIL | REIVVPCRNQ |
| LAHRTRNAL | IQMSSGNLLF | IPHDLMELI | DISEMGANF | ETACLGKSYA |
| AEQTGVSHNL | MSYAMCTNTF | LTDFQSHQL | EFRLRGEQR | LGKSYAQMW |
| GLVSILASSLLRNDV | SYSMCTGKF | ALPVYLMTL | LEENMEVEIW | TWSIHAHHQW |
| FNMLKRARNR | YAMCTNTFVL | LPVYLMTLMK | GERKKLKPRW | TTWEDVPYL (ends with SEQ. ID. NO. 1387 in left to right order of appearance) |

SUPPLEMENT LIST OF REFERENCES

Bouri N, Sell T K, Franco C, Adalja A A, Henderson D A, et al. (2012) Return of epidemic dengue in the United States: implications for the public health practitioner. Public health reports 127: 259-266.

Frank C, Hohle M, Stark K, Lawrence J (2013) More reasons to dread rain on vacation? Dengue fever in 42 German and United Kingdom Madeira tourists during autumn 2012. Euro surveillance: bulletin Europeen sur les maladies transmissibles=European communicable disease bulletin 18: 20446.

Bhatt S, Gething P W, Brady O J, Messina J P, Farlow A W, et al. (2013) The global distribution and burden of dengue. Nature 496: 504-507.

Fu J, Tan B H, Yap E H, Chan Y C, Tan Y H (1992) Full-length cDNA sequence of dengue type 1 virus (Singapore strain S275/90). Virology 188: 953-958.

Suaya J A, Shepard D S, Siqueira J B, Martelli C T, Lum L C, et al. (2009) Cost of dengue cases in eight countries in the Americas and Asia: a prospective study. The American journal of tropical medicine and hygiene 80: 846-855.

Kurane I (2007) Dengue hemorrhagic fever with special emphasis on immunopathogenesis. Comparative immunology, microbiology and infectious diseases 30: 329-340.

Halstead S B (1988) Pathogenesis of dengue: challenges to molecular biology. Science 239: 476-481.

Rothman A L (2011) Immunity to dengue virus: a tale of original antigenic sin and tropical cytokine storms. Nature reviews Immunology 11: 532-543.

Mongkolsapaya J, Dejnirattisai W, Xu X N, Vasanawathana S, Tangthawornchaikul N, et al. (2003) Original antigenic sin and apoptosis in the pathogenesis of dengue hemorrhagic fever. Nat Med 9: 921-927.

Halstead S B, Rojanasuphot S, Sangkawibha N (1983) Original antigenic sin in dengue. Am J Trop Med Hyg 32: 154-156.

Nguyen T H, Lei H Y, Nguyen T L, Lin Y S, Huang K J, et al. (2004) Dengue hemorrhagic fever in infants: a study of clinical and cytokine profiles. The Journal of infectious diseases 189: 221-232.

Dung N T, Duyen H T, Thuy N T, Ngoc T V, Chau N V, et al. (2010) Timing of CD8+ T cell responses in relation to commencement of capillary leakage in children with dengue. Journal of immunology 184: 7281-7287.

Weiskopf D, Angelo M A, de Azeredo E L, Sidney J, Greenbaum J A, et al. (2013) Comprehensive analysis of dengue virus-specific responses supports an HLA-linked protective role for CD8+ T cells. Proceedings of the National Academy of Sciences of the United States of America 110: E2046-2053.

Kotturi M F, Botten J, Maybeno M, Sidney J, Glenn J, et al. (2010) Polyfunctional CD4+ T cell responses to a set of pathogenic arenaviruses provide broad population coverage Immunome Res 6: 4.

Kotturi M F, Assarsson E, Peters B, Grey H, Oseroff C, et al. (2009) Of mice and humans: how good are HLA transgenic mice as a model of human immune responses? Immunome Res 5: 3.

Pasquetto V, Bui H H, Giannino R, Banh C, Mirza F, et al. (2005) HLA-A*0201, HLA-A*1101, and HLA-B*0702 transgenic mice recognize numerous poxvirus determinants from a wide variety of viral gene products. J Immunol 175: 5504-5515.

Yauch L E, Prestwood T R, May M M, Morar M M, Zellweger R M, et al. (2010) CD4+ T cells are not required for the induction of dengue virus-specific CD8+ T cell or antibody responses but contribute to protection after vaccination. J Immunol 185: 5405-5416.

Yauch L E, Zellweger R M, Kotturi M F, Qutubuddin A, Sidney J, et al. (2009) A protective role for dengue virus-specific CD8+ T cells. J Immunol 182: 4865-4873.

Shresta S, Kyle J L, Snider H M, Basavapatna M, Beatty P R, et al. (2004) Interferon-dependent immunity is essential for resistance to primary dengue virus infection in mice, whereas T- and B-cell-dependent immunity are less critical. J Virol 78: 2701-2710.

Weiskopf D, Yauch L E, Angelo M A, John D V, Greenbaum J A, et al. (2011) Insights into HLA-restricted T cell responses in a novel mouse model of dengue virus infection point toward new implications for vaccine design. Journal of immunology 187: 4268-4279.

Lin Y L, Liao C L, Chen L K, Yeh C T, Liu C I, et al. (1998) Study of Dengue virus infection in SCID mice engrafted with human K562 cells. J Virol 72: 9729-9737.

Perry S T, Prestwood T R, Lada S M, Benedict C A, Shresta S (2009) Cardif-mediated signaling controls the initial innate response to dengue virus in vivo. J Virol 83: 8276-8281.

Prestwood T R, Prigozhin D M, Sharar K L, Zellweger R M, Shresta S (2008) A mouse-passaged dengue virus strain with reduced affinity for heparan sulfate causes severe disease in mice by establishing increased systemic viral loads. J Virol 82: 8411-8421.

Kim Y, Ponomarenko J, Zhu Z, Tamang D, Wang P, et al. (2012) Immune epitope database analysis resource. Nucleic acids research 40: W525-530.

Wang P, Sidney J, Dow C, Mothe B, Sette A, et al. (2008) A systematic assessment of MHC class II peptide binding predictions and evaluation of a consensus approach. PLoS Comput Biol 4: e1000048.

Sidney J, Southwood S, Moore C, Oseroff C, Pinilla C, et al. (2013) Measurement of MHC/peptide interactions by gel filtration or monoclonal antibody capture. Current protocols in immunology/edited by John E Coligan [et al] Chapter 18: Unit 18 13.

Shimizu Y, DeMars R (1989) Production of human cells expressing individual transferred HLA-A,-B,-C genes using an HLA-A,-B,-C null human cell line. J Immunol 142: 3320-3328.

Sette A, Sidney J (1999) Nine major HLA class I supertypes account for the vast preponderance of HLA-A and -B polymorphism. Immunogenetics 50: 201-212.

Southwood S, Sidney J, Kondo A, del Guercio M F, Appella E, et al. (1998) Several common HLA-D R types share largely overlapping peptide binding repertoires. Journal of immunology 160: 3363-3373.

Greenbaum J, Sidney J, Chung J, Brander C, Peters B, et al. (2011) Functional classification of class II human leukocyte antigen (HLA) molecules reveals seven different supertypes and a surprising degree of repertoire sharing across supertypes. Immunogenetics 63: 325-335.

Vita R, Zarebski L, Greenbaum J A, Emami H, Hoof I, et al. (2010) The immune epitope database 2.0. Nucleic acids research 38: D854-862.

Bashyam H S, Green S, Rothman A L (2006) Dengue virus-reactive CD8+ T cells display quantitative and qualitative differences in their response to variant epitopes of heterologous viral serotypes. Journal of immunology 176: 2817-2824.

Friberg H, Burns L, Woda M, Kalayanarooj S, Endy T P, et al. (2011) Memory CD8+ T cells from naturally acquired primary dengue virus infection are highly cross-reactive. Immunology and cell biology 89: 122-129.

Beaumier C M, Mathew A, Bashyam H S, Rothman A L (2008) Cross-reactive memory CD8(+) T cells alter the immune response to heterologous secondary dengue virus infections in mice in a sequence-specific manner. The Journal of infectious diseases 197: 608-617.

Appanna R, Huat T L, See L L, Tan P L, Vadivelu J, et al. (2007) Cross-reactive T-cell responses to the nonstructural regions of dengue viruses among dengue fever and dengue hemorrhagic fever patients in Malaysia. Clinical and vaccine immunology: CVI 14: 969-977.

Mongkolsapaya J, Duangchinda T, Dejnirattisai W, Vasanawathana S, Avirutnan P, et al. (2006) T cell responses in dengue hemorrhagic fever: are cross-reactive T cells suboptimal? Journal of immunology 176: 3821-3829.

Mongkolsapaya J, Dejnirattisai W, Xu X N, Vasanawathana S, Tangthawornchaikul N, et al. (2003) Original antigenic sin and apoptosis in the pathogenesis of dengue hemorrhagic fever. Nature medicine 9: 921-927.

Sabchareon A, Wallace D, Sirivichayakul C, Limkittikul K, Chanthavanich P, et al. (2012) Protective efficacy of the recombinant, live-attenuated, CYD tetravalent dengue vaccine in Thai schoolchildren: a randomised, controlled phase 2b trial. Lancet 380: 1559-1567.

Libraty D H, Young P R, Pickering D, Endy T P, Kalayanarooj S, et al. (2002) High circulating levels of the dengue virus nonstructural protein NS1 early in dengue illness correlate with the development of dengue hemorrhagic fever. The Journal of infectious diseases 186: 1165-1168.

Wills B, Tran V N, Nguyen T H, Truong T T, Tran T N, et al. (2009) Hemostatic changes in Vietnamese children with mild dengue correlate with the severity of vascular leakage rather than bleeding. The American journal of tropical medicine and hygiene 81: 638-644.

Halstead S B (2013) Dengue vascular permeability syndrome: what, no T cells? Clinical infectious diseases: an official publication of the Infectious Diseases Society of America 56: 900-901.

Vaughn D W, Green S, Kalayanarooj S, Innis B L, Nimmannitya S, et al. (2000) Dengue viremia titer, antibody response pattern, and virus serotype correlate with disease severity. The Journal of infectious diseases 181: 2-9.

Friberg H, Bashyam H, Toyosaki-Maeda T, Potts J A, Greenough T, et al. (2011) Cross-reactivity and expansion of dengue-specific T cells during acute primary and secondary infections in humans. Scientific reports 1: 51.

Imrie A, Meeks J, Gurary A, Sukhbataar M, Kitsutani P, et al. (2007) Differential functional avidity of dengue virus-specific T-cell clones for variant peptides representing heterologous and previously encountered serotypes. Journal of virology 81: 10081-10091.

Malavige G N, McGowan S, Atukorale V, Salimi M, Peelawatta M, et al. (2012) Identification of serotype-specific T cell responses to highly conserved regions of the dengue viruses. Clinical and experimental immunology 168: 215-223.

Mangada M M, Rothman A L (2005) Altered cytokine responses of dengue-specific CD4+ T cells to heterologous serotypes. Journal of immunology 175: 2676-2683.

Mathew A, Kurane I, Rothman A L, Zeng L L, Brinton M A, et al. (1996) Dominant recognition by human CD8+ cytotoxic T lymphocytes of dengue virus nonstructural proteins NS3 and NS1.2a. The Journal of clinical investigation 98: 1684-1691.

Simmons C P, Dong T, Chau N V, Dung N T, Chau T N, et al. (2005) Early T-cell responses to dengue virus epitopes in Vietnamese adults with secondary dengue virus infections. Journal of virology 79: 5665-5675.

Wen J, Duan Z, Jiang L (2010) Identification of a dengue virus-specific HLA-A*0201-restricted CD8+ T cell epitope. Journal of medical virology 82: 642-648.

Zeng L, Kurane I, Okamoto Y, Ennis F A, Brinton M A (1996) Identification of amino acids involved in recognition by dengue virus NS3-specific, HLA-DR15-restricted cytotoxic CD4+ T-cell clones. Journal of virology 70: 3108-3117.

Zivna I, Green S, Vaughn D W, Kalayanarooj S, Stephens H A, et al. (2002) T cell responses to an HLA-B*07-restricted epitope on the dengue NS3 protein correlate with disease severity. Journal of immunology 168: 5959-5965.

Rivino L, Kumaran E A, Jovanovic V, Nadua K, Teo E W, et al. (2013) Differential targeting of viral components by CD4+ versus CD8+ T lymphocytes in dengue virus infection. Journal of virology 87: 2693-2706.

Bhatt S, Gething P W, Brady O J, et al. The global distribution and burden of dengue. Nature 2013; 496(7446): 504-7.

Stahl H C, Butenschoen V M, Tran H T, et al. Cost of dengue outbreaks: literature review and country case studies. BMC Public Health 2013; 13: 1048.

Sabin A B. Research on dengue during World War II. Am J Trop Med Hyg 1952; 1(1): 30-50.

Zellweger R M, Prestwood T R, Shresta S. Enhanced infection of liver sinusoidal endothelial cells in a mouse model of antibody-induced severe dengue disease. Cell Host Microbe 2010; 7(2): 128-39.

Balsitis S J, Williams K L, Lachica R, et al. Lethal antibody enhancement of dengue disease in mice is prevented by Fc modification. PLoS Pathog 2010; 6(2): e1000790.

Mongkolsapaya J, Dejnirattisai W, Xu X N, et al. Original antigenic sin and apoptosis in the pathogenesis of dengue hemorrhagic fever. Nat Med 2003; 9(7): 921-7.

Sabchareon A, Wallace D, Sirivichayakul C, et al. Protective efficacy of the recombinant, live-attenuated, CYD tetravalent dengue vaccine in Thai schoolchildren: a randomised, controlled phase 2b trial. Lancet 2012; 380(9853): 1559-67.

Durbin A P, Kirkpatrick B D, Pierce K K, et al. A single dose of any of four different live attenuated tetravalent dengue vaccines is safe and immunogenic in flavivirus-naive adults: a randomized, double-blind clinical trial. J Infect Dis 2013; 207(6): 957-65.

Weiskopf D, Angelo M A, de Azeredo E L, et al. Comprehensive analysis of dengue virus-specific responses supports an HLA-linked protective role for CD8+ T cells. Proc Natl Acad Sci USA 2013; 110(22): E2046-53.

Duangchinda T, Dejnirattisai W, Vasanawathana S, et al Immunodominant T-cell responses to dengue virus NS3 are associated with DHF. Proc Natl Acad Sci USA 2010; 107(39): 16922-7.

Rivino L, Kumaran E A, Jovanovic V, et al. Differential targeting of viral components by CD4+ versus CD8+ T lymphocytes in dengue virus infection. J Virol 2013; 87(5): 2693-706.

Lindow J C, Durbin A P, Whitehead S S, Pierce K K, Carmolli M P, Kirkpatrick B D. Vaccination of volunteers with low-dose, live-attenuated, dengue viruses leads to serotype-specific immunologic and virologic profiles. Vaccine 2013; 31(33): 3347-52.

Durbin A P, Kirkpatrick B D, Pierce K K, et al. A single dose of any of four different live attenuated tetravalent dengue vaccines is safe and immunogenic in flavivirus-naive adults: a randomized, double-blind clinical trial. J Infect Dis 2013; 207(6): 957-65.

Sabchareon A, Wallace D, Lang J, Bouckenooghe A, Moureau A. Efficacy of tetravalent dengue vaccine in Thai schoolchildren—Authors' reply. Lancet 2013; 381(9872): 1094-5.

Lindow J C, Borochoff-Porte N, Durbin A P, et al. Primary vaccination with low dose live dengue 1 virus generates a proinflammatory, multifunctional T cell response in humans. PLoS Negl Trop Dis 2012; 6(7): e1742.

Tam C C, Tissera H, de Silva A M, De Silva A D, Margolis H S, Amarasinge A. Estimates of dengue force of infection in children in Colombo, Sri Lanka. PLoS Negl Trop Dis 2013; 7(6): e2259.

Guy B, Barrere B, Malinowski C, Saville M, Teyssou R, Lang J. From research to phase III: preclinical, industrial and clinical development of the Sanofi Pasteur tetravalent dengue vaccine. Vaccine 2011; 29(42): 7229-41.

Gordon A, Kuan G, Mercado J C, et al. The Nicaraguan pediatric dengue cohort study: incidence of inapparent and symptomatic dengue virus infections, 2004-2010. PLoS Negl Trop Dis 2013; 7(9): e2462.

Wikramaratna P S, Simmons C P, Gupta S, Recker M. The effects of tertiary and quaternary infections on the epidemiology of dengue. PLoS One 2010; 5(8): e12347.

Gras S, Kedzierski L, Valkenburg S A, et al. Cross-reactive CD8+ T-cell immunity between the pandemic H1N1-2009 and H1N1-1918 influenza A viruses. Proc Natl Acad Sci USA 2010; 107(28): 12599-604.

Sridhar S, Begom S, Bermingham A, et al. Cellular immune correlates of protection against symptomatic pandemic influenza. Nat Med 2013; 19(10): 1305-12.

Holmes E C, Twiddy S S. The origin, emergence and evolutionary genetics of dengue virus. Infect Genet Evol 2003; 3(1): 19-28.

Akondy R S, Monson N D, Miller J D, et al. The yellow fever virus vaccine induces a broad and polyfunctional human memory CD8+ T cell response. J Immunol 2009; 183(12): 7919-30.

What is claimed:

1. A pharmaceutical composition comprising a pharmaceutically acceptable carrier or excipient, an adjuvant and a peptide consisting of a sequence 9-25 amino acids in length wherein 9 contiguous amino acids are identical to VAT-TFVTPM (SEQ ID NO:134), wherein the peptide elicits, stimulates, induces, promotes, increases, or enhances an anti-DV CD8+ T cell response or an anti-DV CD4+ T cell response, wherein the adjuvant is present in an amount that increases immunogenicity of the peptide.

2. The pharmaceutical composition of claim 1, wherein the peptide is isolated or purified.

3. The pharmaceutical composition of claim 1, wherein said anti-DV CD8+ T cell response comprises increased IFN-gamma, TNF-alpha, IL-1alpha, IL-6 or IL-8 production by CD8+ T cells in the presence of the peptide.

4. The pharmaceutical composition of claim 1, wherein the CD4+ T cells produce IFN-gamma, TNF, IL-2, or CD40L in the presence of the peptide, or kill peptide-pulsed target cells.

5. The pharmaceutical composition of claim 1, wherein the adjuvant comprises Freund's complete adjuvant (CFA), Freund's incomplete adjuvant (IFA), metal or metallic salts, aluminum or aluminum salts, aluminum phosphate, aluminum hydroxide, alum, hydrated potassium aluminum sulfate, bacterially derived compounds, Monophosphoryllipid A and derivatives thereof, enterobacteriallipopolysaccharides (LPS), plant derived saponins and derivatives thereof, Quil A and fragments thereof, soya lecithin or oleic acid surfactants, sorbitan trioleate, polyvinylpyrrolidone, CpG oligonucleotides, polyriboA and polyriboU, block copolymers, GM-CSF, IL-1, or Muramyl tripeptide (MTP).

6. A method of stimulating, inducing, promoting, increasing, or enhancing an immune response against Dengue virus serotype 2 (DENV-2) in a subject, comprising administering to a subject an amount of the pharmaceutical composition of claim 1 sufficient to stimulate, induce, promote, increase, or enhance an immune response against DENV-2 in the subject.

7. The method of claim 6, wherein the Dengue virus (DV) infection is acute.

8. The pharmaceutical composition of claim 1, wherein the composition is sterile.

* * * * *

SEQUENCE LISTING

```
<160> NUMBER OF SEQ ID NOS: 763

<210> SEQ ID NO 1
<211> LENGTH: 9
<212> TYPE: PRT
<213> ORGANISM: Dengue virus

<400> SEQUENCE: 1

Gly Pro Met Lys Leu Val Met Ala Phe
1               5

<210> SEQ ID NO 2
<211> LENGTH: 10
```

<210> SEQ ID NO 2
<211> LENGTH: 10
<212> TYPE: PRT
<213> ORGANISM: Dengue virus

<400> SEQUENCE: 2

Gly Pro Met Lys Leu Val Met Ala Phe Ile
1               5                   10

<210> SEQ ID NO 3
<211> LENGTH: 9
<212> TYPE: PRT
<213> ORGANISM: Dengue virus

<400> SEQUENCE: 3

Met Ala Phe Ile Ala Phe Leu Arg Phe
1               5

<210> SEQ ID NO 4
<211> LENGTH: 9
<212> TYPE: PRT
<213> ORGANISM: Dengue virus

<400> SEQUENCE: 4

Lys Ser Gly Ala Ile Lys Val Leu Lys
1               5

<210> SEQ ID NO 5
<211> LENGTH: 10
<212> TYPE: PRT
<213> ORGANISM: Dengue virus

<400> SEQUENCE: 5

Ile Thr Leu Leu Cys Leu Ile Pro Thr Val
1               5                   10

<210> SEQ ID NO 6
<211> LENGTH: 10
<212> TYPE: PRT
<213> ORGANISM: Dengue virus

<400> SEQUENCE: 6

Cys Leu Met Met Met Leu Pro Ala Thr Leu
1               5                   10

<210> SEQ ID NO 7
<211> LENGTH: 9
<212> TYPE: PRT
<213> ORGANISM: Dengue virus

<400> SEQUENCE: 7

Thr Leu Leu Cys Leu Ile Pro Thr Val
1               5

<210> SEQ ID NO 8
<211> LENGTH: 9
<212> TYPE: PRT
<213> ORGANISM: Dengue virus

<400> SEQUENCE: 8

Leu Met Met Met Leu Pro Ala Thr Leu
1               5

<210> SEQ ID NO 9
<211> LENGTH: 10
<212> TYPE: PRT
<213> ORGANISM: Dengue virus

```
<400> SEQUENCE: 9

Leu Met Met Met Leu Pro Ala Thr Leu Ala
1               5                   10

<210> SEQ ID NO 10
<211> LENGTH: 9
<212> TYPE: PRT
<213> ORGANISM: Dengue virus

<400> SEQUENCE: 10

Met Met Met Leu Pro Ala Thr Leu Ala
1               5

<210> SEQ ID NO 11
<211> LENGTH: 10
<212> TYPE: PRT
<213> ORGANISM: Dengue virus

<400> SEQUENCE: 11

Met Met Met Leu Pro Ala Thr Leu Ala Phe
1               5                   10

<210> SEQ ID NO 12
<211> LENGTH: 9
<212> TYPE: PRT
<213> ORGANISM: Dengue virus

<400> SEQUENCE: 12

Met Leu Ile Pro Thr Ala Met Ala Phe
1               5

<210> SEQ ID NO 13
<211> LENGTH: 10
<212> TYPE: PRT
<213> ORGANISM: Dengue virus

<400> SEQUENCE: 13

Thr Leu Met Ala Met Asp Leu Gly Glu Leu
1               5                   10

<210> SEQ ID NO 14
<211> LENGTH: 9
<212> TYPE: PRT
<213> ORGANISM: Dengue virus

<400> SEQUENCE: 14

Val Thr Tyr Glu Cys Pro Leu Leu Val
1               5

<210> SEQ ID NO 15
<211> LENGTH: 10
<212> TYPE: PRT
<213> ORGANISM: Dengue virus

<400> SEQUENCE: 15

His Pro Gly Phe Thr Ile Leu Ala Leu Phe
1               5                   10

<210> SEQ ID NO 16
<211> LENGTH: 10
<212> TYPE: PRT
<213> ORGANISM: Dengue virus

<400> SEQUENCE: 16
```

```
Phe Thr Ile Met Ala Ala Ile Leu Ala Tyr
1               5                   10

<210> SEQ ID NO 17
<211> LENGTH: 10
<212> TYPE: PRT
<213> ORGANISM: Dengue virus

<400> SEQUENCE: 17

Phe Thr Ile Leu Ala Leu Phe Leu Ala His
1               5                   10

<210> SEQ ID NO 18
<211> LENGTH: 9
<212> TYPE: PRT
<213> ORGANISM: Dengue virus

<400> SEQUENCE: 18

Thr Ile Met Ala Ala Ile Leu Ala Tyr
1               5

<210> SEQ ID NO 19
<211> LENGTH: 9
<212> TYPE: PRT
<213> ORGANISM: Dengue virus

<400> SEQUENCE: 19

Met Leu Val Thr Pro Ser Met Thr Met
1               5

<210> SEQ ID NO 20
<211> LENGTH: 9
<212> TYPE: PRT
<213> ORGANISM: Dengue virus

<400> SEQUENCE: 20

Cys Pro Thr Gln Gly Glu Ala Thr Leu
1               5

<210> SEQ ID NO 21
<211> LENGTH: 9
<212> TYPE: PRT
<213> ORGANISM: Dengue virus

<400> SEQUENCE: 21

Cys Pro Thr Gln Gly Glu Ala Val Leu
1               5

<210> SEQ ID NO 22
<211> LENGTH: 9
<212> TYPE: PRT
<213> ORGANISM: Dengue virus

<400> SEQUENCE: 22

Leu Pro Glu Glu Gln Asp Gln Asn Tyr
1               5

<210> SEQ ID NO 23
<211> LENGTH: 9
<212> TYPE: PRT
<213> ORGANISM: Dengue virus

<400> SEQUENCE: 23

Tyr Glu Asn Leu Lys Tyr Ser Val Ile
```

```
<210> SEQ ID NO 24
<211> LENGTH: 9
<212> TYPE: PRT
<213> ORGANISM: Dengue virus

<400> SEQUENCE: 24

Gln Glu Gly Ala Met His Ser Ala Leu
1               5

<210> SEQ ID NO 25
<211> LENGTH: 9
<212> TYPE: PRT
<213> ORGANISM: Dengue virus

<400> SEQUENCE: 25

Gln Glu Gly Ala Met His Thr Ala Leu
1               5

<210> SEQ ID NO 26
<211> LENGTH: 9
<212> TYPE: PRT
<213> ORGANISM: Dengue virus

<400> SEQUENCE: 26

Met Ser Tyr Thr Met Cys Ser Gly Lys
1               5

<210> SEQ ID NO 27
<211> LENGTH: 10
<212> TYPE: PRT
<213> ORGANISM: Dengue virus

<400> SEQUENCE: 27

Met Ser Tyr Ser Met Cys Thr Gly Lys Phe
1               5                   10

<210> SEQ ID NO 28
<211> LENGTH: 10
<212> TYPE: PRT
<213> ORGANISM: Dengue virus

<400> SEQUENCE: 28

Ser Pro Cys Lys Ile Pro Phe Glu Ile Met
1               5                   10

<210> SEQ ID NO 29
<211> LENGTH: 10
<212> TYPE: PRT
<213> ORGANISM: Dengue virus

<400> SEQUENCE: 29

Ile Pro Phe Glu Ile Met Asp Leu Glu Lys
1               5                   10

<210> SEQ ID NO 30
<211> LENGTH: 10
<212> TYPE: PRT
<213> ORGANISM: Dengue virus

<400> SEQUENCE: 30

Glu Pro Gly Gln Leu Lys Leu Asn Trp Phe
1               5                   10
```

```
<210> SEQ ID NO 31
<211> LENGTH: 9
<212> TYPE: PRT
<213> ORGANISM: Dengue virus

<400> SEQUENCE: 31

Phe Gly Ala Ile Tyr G

<211> LENGTH: 10
<212> TYPE: PRT
<213> ORGANISM: Dengue virus

<400> SEQUENCE: 38

Lys Ala Val His Ala Asp Met Gly Tyr Trp
1 5 10

<210> SEQ ID NO 39
<211> LENGTH: 10
<212> TYPE: PRT
<213> ORGANISM: Dengue virus

<400> SEQUENCE: 39

Arg Ala Ser Phe Ile Glu Val Lys Thr Cys
1 5 10

<210> SEQ ID NO 40
<211> LENGTH: 10
<212> TYPE: PRT
<213> ORGANISM: Dengue virus

<400> SEQUENCE: 40

Phe Ala Gly Pro Val Ser Gln His Asn Tyr
1 5 10

<210> SEQ ID NO 41
<211> LENGTH: 9
<212> TYPE: PRT
<213> ORGANISM: Dengue virus

<400> SEQUENCE: 41

Arg Pro Gly Tyr His Thr Gln Thr Ala
1 5

<210> SEQ ID NO 42
<211> LENGTH: 10
<212> TYPE: PRT
<213> ORGANISM: Dengue virus

<400> SEQUENCE: 42

Gly Pro Trp His Leu Gly Lys Leu Glu Leu
1 5 10

<210> SEQ ID NO 43
<211> LENGTH: 10
<212> TYPE: PRT
<213> ORGANISM: Dengue virus

<400> SEQUENCE: 43

Gly Pro Trp His Leu Gly Lys Leu Glu Met
1 5 10

<210> SEQ ID NO 44
<211> LENGTH: 10
<212> TYPE: PRT
<213> ORGANISM: Dengue virus

<400> SEQUENCE: 44

Arg Tyr Met Gly Glu Asp Gly Cys Trp Tyr
1 5 10

<210> SEQ ID NO 45
<211> LENGTH: 10
<212> TYPE: PRT

<213> ORGANISM: Dengue virus

<400> SEQUENCE: 45

Phe Thr Met Gly Val Leu Cys Leu Ala Ile
1 5 10

<210> SEQ ID NO 46
<211> LENGTH: 10
<212> TYPE: PRT
<213> ORGANISM: Dengue virus

<400> SEQUENCE: 46

Met Ser Phe Arg Asp Leu Gly Arg Val Met
1 5 10

<210> SEQ ID NO 47
<211> LENGTH: 9
<212> TYPE: PRT
<213> ORGANISM: Dengue virus

<400> SEQUENCE: 47

Thr Tyr Leu Ala Leu Ile Ala Thr Phe
1 5

<210> SEQ ID NO 48
<211> LENGTH: 9
<212> TYPE: PRT
<213> ORGANISM: Dengue virus

<400> SEQUENCE: 48

Ile Gln Pro Phe Leu Ala Leu Gly Phe
1 5

<210> SEQ ID NO 49
<211> LENGTH: 10
<212> TYPE: PRT
<213> ORGANISM: Dengue virus

<400> SEQUENCE: 49

Gly Phe Phe Leu Arg Lys Leu Thr Ser Arg
1 5 10

<210> SEQ ID NO 50
<211> LENGTH: 9
<212> TYPE: PRT
<213> ORGANISM: Dengue virus

<400> SEQUENCE: 50

Met Met Ala Thr Ile Gly Ile Ala Leu
1 5

<210> SEQ ID NO 51
<211> LENGTH: 9
<212> TYPE: PRT
<213> ORGANISM: Dengue virus

<400> SEQUENCE: 51

Met Ala Leu Ser Ile Val Ser Leu Phe
1 5

<210> SEQ ID NO 52
<211> LENGTH: 9
<212> TYPE: PRT
<213> ORGANISM: Dengue virus

```
<400> SEQUENCE: 52

Met Ala Val Gly Met Val Ser Ile Leu
1               5

<210> SEQ ID NO 53
<211> LENGTH: 10
<212> TYPE: PRT
<213> ORGANISM: Dengue virus

<400> SEQUENCE: 53

Ile Pro Met Thr Gly Pro Leu Val Ala Gly
1               5                   10

<210> SEQ ID NO 54
<211> LENGTH: 9
<212> TYPE: PRT
<213> ORGANISM: Dengue virus

<400> SEQUENCE: 54

Gly Pro Leu Val Ala Gly Gly Leu Leu
1               5

<210> SEQ ID NO 55
<211> LENGTH: 10
<212> TYPE: PRT
<213> ORGANISM: Dengue virus

<400> SEQUENCE: 55

Ser Pro Ile Leu Ser Ile Thr Ile Ser Glu
1               5                   10

<210> SEQ ID NO 56
<211> LENGTH: 10
<212> TYPE: PRT
<213> ORGANISM: Dengue virus

<400> SEQUENCE: 56

Phe Pro Val Ser Ile Pro Ile Thr Ala Ala
1               5                   10

<210> SEQ ID NO 57
<211> LENGTH: 9
<212> TYPE: PRT
<213> ORGANISM: Dengue virus

<400> SEQUENCE: 57

Ile Pro Ile Thr Ala Ala Ala Trp Tyr
1               5

<210> SEQ ID NO 58
<211> LENGTH: 9
<212> TYPE: PRT
<213> ORGANISM: Dengue virus

<400> SEQUENCE: 58

Met Glu Gly Val Phe His Thr Met Trp
1               5

<210> SEQ ID NO 59
<211> LENGTH: 10
<212> TYPE: PRT
<213> ORGANISM: Dengue virus

<400> SEQUENCE: 59
```

```
Met Glu Gly Val Phe His Thr Met Trp His
1               5                   10

<210> SEQ ID NO 60
<211> LENGTH: 9
<212> TYPE: PRT
<213> ORGANISM: Dengue virus

<400> SEQUENCE: 60

Lys Pro Gly Thr Ser Gly Ser Pro Ile
1               5

<210> SEQ ID NO 61
<211> LENGTH: 10
<212> TYPE: PRT
<213> ORGANISM: Dengue virus

<400> SEQUENCE: 61

Lys Pro Gly Thr Ser Gly Ser Pro Ile Ile
1               5                   10

<210> SEQ ID NO 62
<211> LENGTH: 10
<212> TYPE: PRT
<213> ORGANISM: Dengue virus

<400> SEQUENCE: 62

Gly Thr Ser Gly Ser Pro Ile Ile Asp Lys
1               5                   10

<210> SEQ ID NO 63
<211> LENGTH: 10
<212> TYPE: PRT
<213> ORGANISM: Dengue virus

<400> SEQUENCE: 63

Ser Pro Ile Ile Asn Arg Glu Gly Lys Val
1               5                   10

<210> SEQ ID NO 64
<211> LENGTH: 9
<212> TYPE: PRT
<213> ORGANISM: Dengue virus

<400> SEQUENCE: 64

Asn Pro Glu Ile Glu Asp Asp Ile Phe
1               5

<210> SEQ ID NO 65
<211> LENGTH: 10
<212> TYPE: PRT
<213> ORGANISM: Dengue virus

<400> SEQUENCE: 65

His Pro Gly Ala Gly Lys Thr Lys Arg Tyr
1               5                   10

<210> SEQ ID NO 66
<211> LENGTH: 9
<212> TYPE: PRT
<213> ORGANISM: Dengue virus

<400> SEQUENCE: 66

Leu Pro Ala Ile Val Arg Glu Ala Ile
1               5
```

<210> SEQ ID NO 67
<211> LENGTH: 10
<212> TYPE: PRT
<213> ORGANISM: Dengue virus

<400> SEQUENCE: 67

Ala Pro Thr Arg Val Val Ala Ala Glu Met
1               5                   10

<210> SEQ ID NO 68
<211> LENGTH: 10
<212> TYPE: PRT
<213> ORGANISM: Dengue virus

<400> SEQUENCE: 68

Ala Pro Thr Arg Val Val Ala Ser Glu Met
1               5                   10

<210> SEQ ID NO 69
<211> LENGTH: 10
<212> TYPE: PRT
<213> ORGANISM: Dengue virus

<400> SEQUENCE: 69

Ala Pro Thr Arg Val Val Ala Ala Glu Met
1               5                   10

<210> SEQ ID NO 70
<211> LENGTH: 10
<212> TYPE: PRT
<213> ORGANISM: Dengue virus

<400> SEQUENCE: 70

Ser Glu Met Ala Glu Ala Leu Lys Gly Met
1               5                   10

<210> SEQ ID NO 71
<211> LENGTH: 9
<212> TYPE: PRT
<213> ORGANISM: Dengue virus

<400> SEQUENCE: 71

Leu Pro Ile Arg Tyr Gln Thr Pro Ala
1               5

<210> SEQ ID NO 72
<211> LENGTH: 10
<212> TYPE: PRT
<213> ORGANISM: Dengue virus

<400> SEQUENCE: 72

Leu Pro Ile Arg Tyr Gln Thr Pro Ala Ile
1               5                   10

<210> SEQ ID NO 73
<211> LENGTH: 10
<212> TYPE: PRT
<213> ORGANISM: Dengue virus

<400> SEQUENCE: 73

Asp Pro Ala Ser Ile Ala Ala Arg Gly Tyr
1               5                   10

```
<210> SEQ ID NO 74
<211> LENGTH: 10
<212> TYPE: PRT
<213> ORGANISM: Dengue virus

<400> SEQUENCE: 74

Pro Ala Ser Ile Ala Ala Arg Gly Tyr Ile
1               5                   10

<210> SEQ ID NO 75
<211> LENGTH: 9
<212> TYPE: PRT
<213> ORGANISM: Dengue virus

<400> SEQUENCE: 75

Thr Pro Pro Gly Ser Arg Asp Pro Phe
1               5

<210> SEQ ID NO 76
<211> LENGTH: 10
<212> TYPE: PRT
<213> ORGANISM: Dengue virus

<400> SEQUENCE: 76

Phe Pro Gln Ser Asn Ala Pro Ile Met Asp
1               5                   10

<210> SEQ ID NO 77
<211> LENGTH: 9
<212> TYPE: PRT
<213> ORGANISM: Dengue virus

<400> SEQUENCE: 77

Phe Pro Gln Ser Asn Ala Pro Ile Met
1               5

<210> SEQ ID NO 78
<211> LENGTH: 10
<212> TYPE: PRT
<213> ORGANISM: Dengue virus

<400> SEQUENCE: 78

Glu Glu Arg Asp Ile Pro Glu Arg Ser Trp
1               5                   10

<210> SEQ ID NO 79
<211> LENGTH: 10
<212> TYPE: PRT
<213> ORGANISM: Dengue virus

<400> SEQUENCE: 79

Arg Glu Ile Pro Glu Arg Ser Trp Asn Thr
1               5                   10

<210> SEQ ID NO 80
<211> LENGTH: 10
<212> TYPE: PRT
<213> ORGANISM: Dengue virus

<400> SEQUENCE: 80

Tyr Pro Lys Thr Lys Leu Thr Asp Trp Asp
1               5                   10

<210> SEQ ID NO 81
<211> LENGTH: 10
```

<212> TYPE: PRT
<213> ORGANISM: Dengue virus

<400> SEQUENCE: 81

Arg Val Ile Asp Pro Arg Arg Cys Met Lys
1 5 10

<210> SEQ ID NO 82
<211> LENGTH: 10
<212> TYPE: PRT
<213> ORGANISM: Dengue virus

<400> SEQUENCE: 82

Arg Val Ile Asp Pro Arg Arg Cys Leu Lys
1 5 10

<210> SEQ ID NO 83
<211> LENGTH: 10
<212> TYPE: PRT
<213> ORGANISM: Dengue virus

<400> SEQUENCE: 83

Arg Val Ile Asp Pro Arg Arg Cys Met Lys
1 5 10

<210> SEQ ID NO 84
<211> LENGTH: 9
<212> TYPE: PRT
<213> ORGANISM: Dengue virus

<400> SEQUENCE: 84

Arg Val Ile Asp Pro Arg Arg Cys Leu
1 5

<210> SEQ ID NO 85
<211> LENGTH: 10
<212> TYPE: PRT
<213> ORGANISM: Dengue virus

<400> SEQUENCE: 85

Arg Val Ile Asp Pro Arg Arg Cys Met Lys
1 5 10

<210> SEQ ID NO 86
<211> LENGTH: 9
<212> TYPE: PRT
<213> ORGANISM: Dengue virus

<400> SEQUENCE: 86

Asp Pro Arg Arg Cys Leu Lys Pro Val
1 5

<210> SEQ ID NO 87
<211> LENGTH: 9
<212> TYPE: PRT
<213> ORGANISM: Dengue virus

<400> SEQUENCE: 87

Met Pro Val Thr His Ser Ser Ala Ala
1 5

<210> SEQ ID NO 88
<211> LENGTH: 10
<212> TYPE: PRT
<213> ORGANISM: Dengue virus

```
<400> SEQUENCE: 88

Met Pro Val Thr His Ser Ser Ala Ala Gln
1               5                   10

<210> SEQ ID NO 89
<211> LEN

```
Thr Pro Glu Gly Ile Ile Pro Ser Met
1               5

<210> SEQ ID NO 96
<211> LENGTH: 10
<212> TYPE: PRT
<213> ORGANISM: Dengue virus

<400> SEQUENCE: 96

Thr Pro Glu Gly Ile Ile Pro Ser Met Phe
1               5                   10

<210> SEQ ID NO 97
<211> LENGTH: 10
<212> TYPE: PRT
<213> ORGANISM: Dengue virus

<400> SEQUENCE: 97

Thr Pro Glu Gly Ile Ile Pro Thr Leu Phe
1               5                   10

<210> SEQ ID NO 98
<211> LENGTH: 10
<212> TYPE: PRT
<213> ORGANISM: Dengue virus

<400> SEQUENCE: 98

Thr Pro Glu Gly Ile Ile Pro Ala Leu Phe
1               5                   10

<210> SEQ ID NO 99
<211> LENGTH: 10
<212> TYPE: PRT
<213> ORGANISM: Dengue virus

<400> SEQUENCE: 99

Gly Glu Phe Arg Leu Arg Gly Glu Gln Arg
1               5                   10

<210> SEQ ID NO 100
<211> LENGTH: 10
<212> TYPE: PRT
<213> ORGANISM: Dengue virus

<400> SEQUENCE: 100

Gly Glu Ala Arg Lys Thr Phe Val Glu Leu
1               5                   10

<210> SEQ ID NO 101
<211> LENGTH: 10
<212> TYPE: PRT
<213> ORGANISM: Dengue virus

<400> SEQUENCE: 101

Gly Glu Ala Arg Lys Thr Phe Val Asp Leu
1               5                   10

<210> SEQ ID NO 102
<211> LENGTH: 10
<212> TYPE: PRT
<213> ORGANISM: Dengue virus

<400> SEQUENCE: 102

Gly Glu Ser Arg Lys Thr Phe Val Glu Leu
```

<210> SEQ ID NO 103
<211> LENGTH: 10
<212> TYPE: PRT
<213> ORGANISM: Dengue virus

<400> SEQUENCE: 103

Gly Glu Gln Arg Lys Thr Phe Val Glu Leu
1               5                   10

<210> SEQ ID NO 104
<211> LENGTH: 10
<212> TYPE: PRT
<213> ORGANISM: Dengue virus

<400> SEQUENCE: 104

Glu Leu Met Arg Arg Gly Asp Leu Pro Val
1               5                   10

<210> SEQ ID NO 105
<211> LENGTH: 10
<212> TYPE: PRT
<213> ORGANISM: Dengue virus

<400> SEQUENCE: 105

Leu Pro Val Trp Leu Ala Tyr Lys Val Ala
1               5                   10

<210> SEQ ID NO 106
<211> LENGTH: 10
<212> TYPE: PRT
<213> ORGANISM: Dengue virus

<400> SEQUENCE: 106

Tyr Lys Val Ala Ser Ala Gly Ile Ser Tyr
1               5                   10

<210> SEQ ID NO 107
<211> LENGTH: 10
<212> TYPE: PRT
<213> ORGANISM: Dengue virus

<400> SEQUENCE: 107

Arg Glu Trp Cys Phe Thr Gly Glu Arg Asn
1               5                   10

<210> SEQ ID NO 108
<211> LENGTH: 9
<212> TYPE: PRT
<213> ORGANISM: Dengue virus

<400> SEQUENCE: 108

Arg Pro Arg Trp Leu Asp Ala Arg Thr
1               5

<210> SEQ ID NO 109
<211> LENGTH: 9
<212> TYPE: PRT
<213> ORGANISM: Dengue virus

<400> SEQUENCE: 109

Met Ala Leu Lys Asp Phe Lys Glu Phe
1               5

<210> SEQ ID NO 110
<211> LENGTH: 9
<212> TYPE: PRT
<213> ORGANISM: Dengue virus

<400> SEQUENCE: 110

Glu Phe Lys Glu Phe Ala Ala Gly Arg
1               5

<210> SEQ ID NO 111
<211> LENGTH: 10
<212> TYPE: PRT
<213> ORGANISM: Dengue virus

<400> SEQUENCE: 111

Phe Ala Ser Gly Arg Lys Ser Ile Thr Leu
1               5                   10

<210> SEQ ID NO 112
<211> LENGTH: 10
<212> TYPE: PRT
<213> ORGANISM: Dengue virus

<400> SEQUENCE: 112

Leu Pro Thr Phe Met Thr Gln Lys Ala Arg
1               5                   10

<210> SEQ ID NO 113
<211> LENGTH: 9
<212> TYPE: PRT
<213> ORGANISM: Dengue virus

<400> SEQUENCE: 113

Met Thr Gln Lys Ala Arg Asn Ala Leu
1               5

<210> SEQ ID NO 114
<211> LENGTH: 9
<212> TYPE: PRT
<213> ORGANISM: Dengue virus

<400> SEQUENCE: 114

Thr Ala Glu Ala Gly Gly Arg Ala Tyr
1               5

<210> SEQ ID NO 115
<211> LENGTH: 10
<212> TYPE: PRT
<213> ORGANISM: Dengue virus

<400> SEQUENCE: 115

Leu Pro Glu Thr Leu Glu Thr Leu Leu Leu
1               5                   10

<210> SEQ ID NO 116
<211> LENGTH: 9
<212> TYPE: PRT
<213> ORGANISM: Dengue virus

<400> SEQUENCE: 116

Leu Glu Thr Leu Met Leu Val Ala Leu
1               5

<210> SEQ ID NO 117

```
<211> LENGTH: 10
<212> TYPE: PRT
<213> ORGANISM: Dengue virus

<400> SEQUENCE: 117

Leu Glu Thr Leu Met Leu Val Ala Leu Leu
1               5                   10

<210> SEQ ID NO 118
<211> LENGTH: 10
<212> TYPE: PRT
<213> ORGANISM: Dengue virus

<400> SEQUENCE: 118

Thr Leu Met Leu Leu Ala Leu Ile Ala Val
1               5                   10

<210> SEQ ID NO 119
<211> LENGTH: 10
<212> TYPE: PRT
<213> ORGANISM: Dengue virus

<400> SEQUENCE: 119

Leu Met Leu Leu Ala Leu Ile Ala Val Leu
1               5                   10

<210> SEQ ID NO 120
<211> LENGTH: 9
<212> TYPE: PRT
<213> ORGANISM: Dengue virus

<400> SEQUENCE: 120

Met Leu Leu Ala Leu Ile Ala Val Leu
1               5

<210> SEQ ID NO 121
<211> LENGTH: 10
<212> TYPE: PRT
<213> ORGANISM: Dengue virus

<400> SEQUENCE: 121

Gly Ala Met Leu Phe Leu Ile Ser Gly Lys
1               5                   10

<210> SEQ ID NO 122
<211> LENGTH: 10
<212> TYPE: PRT
<213> ORGANISM: Dengue virus

<400> SEQUENCE: 122

Ser Ile Ile Leu Glu Phe Phe Leu Met Val
1               5                   10

<210> SEQ ID NO 123
<211> LENGTH: 9
<212> TYPE: PRT
<213> ORGANISM: Dengue virus

<400> SEQUENCE: 123

Ile Ile Leu Glu Phe Phe Leu Met Val
1               5

<210> SEQ ID NO 124
<211> LENGTH: 10
<212> TYPE: PRT
```

<213> ORGANISM: Dengue virus

<400> SEQUENCE: 124

Ile Ile Leu Glu Phe Phe Leu Met Val Leu
1 5 10

<210> SEQ ID NO 125
<211> LENGTH: 10
<212> TYPE: PRT
<213> ORGANISM: Dengue virus

<400> SEQUENCE: 125

Phe Leu Met Val Leu Leu Ile Pro Glu Pro
1 5 10

<210> SEQ ID NO 126
<211> LENGTH: 10
<212> TYPE: PRT
<213> ORGANISM: Dengue virus

<400> SEQUENCE: 126

Thr Pro Gln Asp Asn Gln Leu Ala Tyr Val
1 5 10

<210> SEQ ID NO 127
<211> LENGTH: 9
<212> TYPE: PRT
<213> ORGANISM: Dengue virus

<400> SEQUENCE: 127

Thr Pro Gln Asp Asn Gln Leu Thr Tyr
1 5

<210> SEQ ID NO 128
<211> LENGTH: 10
<212> TYPE: PRT
<213> ORGANISM: Dengue virus

<400> SEQUENCE: 128

Thr Thr Lys Arg Asp Leu Gly Met Ser Lys
1 5 10

<210> SEQ ID NO 129
<211> LENGTH: 10
<212> TYPE: PRT
<213> ORGANISM: Dengue virus

<400> SEQUENCE: 129

Thr Glu Thr Thr Ile Leu Asp Val Asp Leu
1 5 10

<210> SEQ ID NO 130
<211> LENGTH: 9
<212> TYPE: PRT
<213> ORGANISM: Dengue virus

<400> SEQUENCE: 130

Arg Pro Ala Ser Ala Trp Thr Leu Tyr
1 5

<210> SEQ ID NO 131
<211> LENGTH: 10
<212> TYPE: PRT
<213> ORGANISM: Dengue virus

```
<400> SEQUENCE: 131

Arg Pro Ala Ser Ala Trp Thr Leu Tyr Ala
1               5                   10

<210> SEQ ID NO 132
<211> LENGTH: 9
<212> TYPE: PRT
<213> ORGANISM: Dengue virus

<400> SEQUENCE: 132

His Pro Ala Ser Ala Trp Thr Leu Tyr
1               5

<210> SEQ ID NO 133
<211> LENGTH: 10
<212> TYPE: PRT
<213> ORGANISM: Dengue virus

<400> SEQUENCE: 133

Pro Ala Ser Ala Trp Thr Leu Tyr Ala Val
1               5                   10

<210> SEQ ID NO 134
<211> LENGTH: 9
<212> TYPE: PRT
<213> ORGANISM: Dengue virus

<400> SEQUENCE: 134

Val Ala Thr Thr Phe Val Thr Pro Met
1               5

<210> SEQ ID NO 135
<211> LENGTH: 9
<212> TYPE: PRT
<213> ORGANISM: Dengue virus

<400> SEQUENCE: 135

Ile Thr Pro Met Leu Arg His Thr Ile
1               5

<210> SEQ ID NO 136
<211> LENGTH: 10
<212> TYPE: PRT
<213> ORGANISM: Dengue virus

<400> SEQUENCE: 136

Thr Pro Met Leu Arg His Thr Ile Glu Asn
1               5                   10

<210> SEQ ID NO 137
<211> LENGTH: 9
<212> TYPE: PRT
<213> ORGANISM: Dengue virus

<400> SEQUENCE: 137

Ile Ala Asn Gln Ala Thr Val Leu Met
1               5

<210> SEQ ID NO 138
<211> LENGTH: 9
<212> TYPE: PRT
<213> ORGANISM: Dengue virus

<400> SEQUENCE: 138
```

Val Pro Leu Leu Ala Ile Gly Cys Tyr
1               5

<210> SEQ ID NO 139
<211> LENGTH: 9
<212> TYPE: PRT
<213> ORGANISM: Dengue virus

<400> SEQUENCE: 139

Asn Pro Leu Thr Leu Thr Ala Ala Val
1               5

<210> SEQ ID NO 140
<211> LENGTH: 10
<212> TYPE: PRT
<213> ORGANISM: Dengue virus

<400> SEQUENCE: 140

Thr Leu Thr Ala Ala Val Leu Leu Leu Val
1               5                   10

<210> SEQ ID NO 141
<211> LENGTH: 10
<212> TYPE: PRT
<213> ORGANISM: Dengue virus

<400> SEQUENCE: 141

Ala Ala Val Leu Leu Leu Val Thr His Tyr
1               5                   10

<210> SEQ ID NO 142
<211> LENGTH: 10
<212> TYPE: PRT
<213> ORGANISM: Dengue virus

<400> SEQUENCE: 142

Val Leu Leu Leu Val Thr His Tyr Ala Ile
1               5                   10

<210> SEQ ID NO 143
<211> LENGTH: 9
<212> TYPE: PRT
<213> ORGANISM: Dengue virus

<400> SEQUENCE: 143

Asp Pro Ile Pro Tyr Asp Pro Lys Phe
1               5

<210> SEQ ID NO 144
<211> LENGTH: 10
<212> TYPE: PRT
<213> ORGANISM: Dengue virus

<400> SEQUENCE: 144

Met Leu Leu Ile Leu Cys Val Thr Gln Val
1               5                   10

<210> SEQ ID NO 145
<211> LENGTH: 9
<212> TYPE: PRT
<213> ORGANISM: Dengue virus

<400> SEQUENCE: 145

Ala Thr Gly Pro Leu Thr Thr Leu Trp
1               5

<210> SEQ ID NO 146
<211> LENGTH: 9
<212> TYPE: PRT
<213> ORGANISM: Dengue virus

<400> SEQUENCE: 146

Ala Thr Gly Pro Ile Ser Thr Leu Trp
1               5

<210> SEQ ID NO 147
<211> LENGTH: 9
<212> TYPE: PRT
<213> ORGANISM: Dengue virus

<400> SEQUENCE: 147

Ala Thr Gly Pro Ile Thr Thr Leu Trp
1               5

<210> SEQ ID NO 148
<211> LENGTH: 9
<212> TYPE: PRT
<213> ORGANISM: Dengue virus

<400> SEQUENCE: 148

Ala Thr Gly Pro Ile Leu Thr Leu Trp
1               5

<210> SEQ ID NO 149
<211> LENGTH: 9
<212> TYPE: PRT
<213> ORGANISM: Dengue virus

<400> SEQUENCE: 149

Ala Thr Gly Pro Val Leu Thr Leu Trp
1               5

<210> SEQ ID NO 150
<211> LENGTH: 9
<212> TYPE: PRT
<213> ORGANISM: Dengue virus

<400> SEQUENCE: 150

Leu Trp Glu Gly Ser Pro Gly Lys Phe
1               5

<210> SEQ ID NO 151
<211> LENGTH: 10
<212> TYPE: PRT
<213> ORGANISM: Dengue virus

<400> SEQUENCE: 151

Ser Pro Gly Lys Phe Trp Asn Thr Thr Ile
1               5                   10

<210> SEQ ID NO 152
<211> LENGTH: 9
<212> TYPE: PRT
<213> ORGANISM: Dengue virus

<400> SEQUENCE: 152

Ile Ala Val Ser Met Ala Asn Ile Phe
1               5

<210> SEQ ID NO 153
<211> LENGTH: 9
<212> TYPE: PRT
<213> ORGANISM: Dengue virus

<400> SEQUENCE: 153

Ile Ala Val Ser Met Ala Asn Ile Phe
1               5

<210> SEQ ID NO 154
<211> LENGTH: 9
<212> TYPE: PRT
<213> ORGANISM: Dengue virus

<400> SEQUENCE: 154

Ile Ala Val Ser Thr Ala Asn Ile Phe
1               5

<210> SEQ ID NO 155
<211> LENGTH: 9
<212> TYPE: PRT
<213> ORGANISM: Dengue virus

<400> SEQUENCE: 155

Met Ala Asn Ile Phe Arg Gly Ser Tyr
1               5

<210> SEQ ID NO 156
<211> LENGTH: 9
<212> TYPE: PRT
<213> ORGANISM: Dengue virus

<400> SEQUENCE: 156

Tyr Leu Ala Gly Ala Gly Leu Ala Phe
1               5

<210> SEQ ID NO 157
<211> LENGTH: 10
<212> TYPE: PRT
<213> ORGANISM: Dengue virus

<400> SEQUENCE: 157

Gly Ser Ser Lys Ile Arg Trp Ile Val Glu
1               5                   10

<210> SEQ ID NO 158
<211> LENGTH: 10
<212> TYPE: PRT
<213> ORGANISM: Dengue virus

<400> SEQUENCE: 158

Gly Pro Gly His Glu Glu Pro Ile Pro Met
1               5                   10

<210> SEQ ID NO 159
<211> LENGTH: 10
<212> TYPE: PRT
<213> ORGANISM: Dengue virus

<400> SEQUENCE: 159

Ile Pro Met Ser Thr Tyr Gly Trp Asn Leu
1               5                   10

<210> SEQ ID NO 160
<211> LENGTH: 10

<212> TYPE: PRT
<213> ORGANISM: Dengue virus

<400> SEQUENCE: 160

Ile Pro Met Ala Thr Tyr Gly Trp Asn Leu
1 5 10

<210> SEQ ID NO 161
<211> LENGTH: 10
<212> TYPE: PRT
<213> ORGANISM: Dengue virus

<400> SEQUENCE: 161

Ile Pro Met Ser Thr Tyr Gly Trp Asn Leu
1 5 10

<210> SEQ ID NO 162
<211> LENGTH: 10
<212> TYPE: PRT
<213> ORGANISM: Dengue virus

<400> SEQUENCE: 162

Met Ser Thr Tyr Gly Trp Asn Ile Val Lys
1 5 10

<210> SEQ ID NO 163
<211> LENGTH: 9
<212> TYPE: PRT
<213> ORGANISM: Dengue virus

<400> SEQUENCE: 163

Ser Thr Tyr Gly Trp Asn Ile Val Lys
1 5

<210> SEQ ID NO 164
<211> LENGTH: 10
<212> TYPE: PRT
<213> ORGANISM: Dengue virus

<400> SEQUENCE: 164

Gln Ser Gly Val Asp Val Phe Phe Thr Pro
1 5 10

<210> SEQ ID NO 165
<211> LENGTH: 9
<212> TYPE: PRT
<213> ORGANISM: Dengue virus

<400> SEQUENCE: 165

Arg Val Leu Lys Met Val Glu Pro Trp
1 5

<210> SEQ ID NO 166
<211> LENGTH: 10
<212> TYPE: PRT
<213> ORGANISM: Dengue virus

<400> SEQUENCE: 166

Lys Val Leu Asn Pro Tyr Met Pro Ser Val
1 5 10

<210> SEQ ID NO 167
<211> LENGTH: 9
<212> TYPE: PRT
<213> ORGANISM: Dengue virus

<400> SEQUENCE: 167

Val Leu Asn Pro Tyr Met Pro Ser Val
1               5

<210> SEQ ID NO 168
<211> LENGTH: 10
<212> TYPE: PRT
<213> ORGANISM: Dengue virus

<400> SEQUENCE: 168

Met Pro Ser Val Ile Glu Lys Met Glu Thr
1               5                   10

<210> SEQ ID NO 169
<211> LENGTH: 10
<212> TYPE: PRT
<213> ORGANISM: Dengue virus

<400> SEQUENCE: 169

Val Ser Ser Val Asn Met Val Ser Arg Leu
1               5                   10

<210> SEQ ID NO 170
<211> LENGTH: 9
<212> TYPE: PRT
<213> ORGANISM: Dengue virus

<400> SEQUENCE: 170

Met Val Ser Arg Leu Leu Leu Asn Arg
1               5

<210> SEQ ID NO 171
<211> LENGTH: 10
<212> TYPE: PRT
<213> ORGANISM: Dengue virus

<400> SEQUENCE: 171

Phe Thr Met Arg His Lys Lys Ala Thr Tyr
1               5                   10

<210> SEQ ID NO 172
<211> LENGTH: 9
<212> TYPE: PRT
<213> ORGANISM: Dengue virus

<400> SEQUENCE: 172

Trp His Tyr Asp Gln Asp His Pro Tyr
1               5

<210> SEQ ID NO 173
<211> LENGTH: 10
<212> TYPE: PRT
<213> ORGANISM: Dengue virus

<400> SEQUENCE: 173

Gln Glu Asn Pro Tyr Arg Thr Trp Ala Tyr
1               5                   10

<210> SEQ ID NO 174
<211> LENGTH: 9
<212> TYPE: PRT
<213> ORGANISM: Dengue virus

<400> SEQUENCE: 174

```
Trp Ala Tyr His Gly Ser Tyr Glu Thr
1               5
```

<210> SEQ ID NO 175
<211> LENGTH: 9
<212> TYPE: PRT
<213> ORGANISM: Dengue virus

<400> SEQUENCE: 175

```
Trp Ala Tyr His Gly Ser Tyr Glu Val
1               5
```

<210> SEQ ID NO 176
<211> LENGTH: 9
<212> TYPE: PRT
<213> ORGANISM: Dengue virus

<400> SEQUENCE: 176

```
Asp Thr Thr Pro Phe Gly Gln Gln Arg
1               5
```

<210> SEQ ID NO 177
<211> LENGTH: 9
<212> TYPE: PRT
<213> ORGANISM: Dengue virus

<400> SEQUENCE: 177

```
Thr Pro Phe Gly Gln Gln Arg Val Phe
1               5
```

<210> SEQ ID NO 178
<211> LENGTH: 10
<212> TYPE: PRT
<213> ORGANISM: Dengue virus

<400> SEQUENCE: 178

```
Glu Pro Lys Glu Gly Thr Lys Lys Leu Met
1               5                   10
```

<210> SEQ ID NO 179
<211> LENGTH: 9
<212> TYPE: PRT
<213> ORGANISM: Dengue virus

<400> SEQUENCE: 179

```
Met Glu Ile Thr Ala Glu Trp Leu Trp
1               5
```

<210> SEQ ID NO 180
<211> LENGTH: 10
<212> TYPE: PRT
<213> ORGANISM: Dengue virus

<400> SEQUENCE: 180

```
Lys Pro Arg Ile Cys Thr Arg Glu Glu Phe
1               5                   10
```

<210> SEQ ID NO 181
<211> LENGTH: 10
<212> TYPE: PRT
<213> ORGANISM: Dengue virus

<400> SEQUENCE: 181

```
Thr Pro Arg Met Cys Thr Arg Glu Glu Phe
```

-continued

```
1               5                   10

<210> SEQ ID NO 182
<211> LENGTH:

-continued

<210> SEQ ID NO 189
<211> LENGTH: 10
<212> TYPE: PRT
<213> ORGANISM: Dengue virus

<400> SEQUENCE: 189

Arg Tyr Leu Glu Phe Glu Ala Leu Gly Phe
1               5                   10

<210> SEQ ID NO 190
<211> LENGTH: 10
<212> TYPE: PRT
<213> ORGANISM: Dengue virus

<400> SEQUENCE: 190

Arg Phe Leu Glu Phe Glu Ala Leu Gly Phe
1               5                   10

<210> SEQ ID NO 191
<211> LENGTH: 10
<212> TYPE: PRT
<213> ORGANISM: Dengue virus

<400> SEQUENCE: 191

Phe Ser Arg Glu Asn Ser Leu Ser Gly Val
1               5                   10

<210> SEQ ID NO 192
<211> LENGTH: 9
<212> TYPE: PRT
<213> ORGANISM: Dengue virus

<400> SEQUENCE: 192

Gly Glu Gly Leu His Lys Leu Gly Tyr
1               5

<210> SEQ ID NO 193
<211> LENGTH: 9
<212> TYPE: PRT
<213> ORGANISM: Dengue virus

<400> SEQUENCE: 193

Arg Gln Leu Ala Asn Ala Ile Phe Lys
1               5

<210> SEQ ID NO 194
<211> LENGTH: 10
<212> TYPE: PRT
<213> ORGANISM: Dengue virus

<400> SEQUENCE: 194

Thr Pro Arg Gly Thr Val Met Asp Ile Ile
1               5                   10

<210> SEQ ID NO 195
<211> LENGTH: 10
<212> TYPE: PRT
<213> ORGANISM: Dengue virus

<400> SEQUENCE: 195

Thr Pro Lys Gly Ala Val Met Asp Ile Ile
1               5                   10

<210> SEQ ID NO 196

-continued

<211> LENGTH: 9
<212> TYPE: PRT
<213> ORGANISM: Dengue virus

<400> SEQUENCE: 196

Arg Gln Met Glu Gly Glu Gly Ile Phe
1 5

<210> SEQ ID NO 197
<211> LENGTH: 9
<212> TYPE: PRT
<213> ORGANISM: Dengue virus

<400> SEQUENCE: 197

Arg Gln Met Glu Gly Glu Gly Val Leu
1 5

<210> SEQ ID NO 198
<211> LENGTH: 9
<212> TYPE: PRT
<213> ORGANISM: Dengue virus

<400> SEQUENCE: 198

Lys Val Arg Lys Asp Ile Gln Gln Trp
1 5

<210> SEQ ID NO 199
<211> LENGTH: 9
<212> TYPE: PRT
<213> ORGANISM: Dengue virus

<400> SEQUENCE: 199

Tyr Ala Gln Met Trp Ser Leu Met Tyr
1 5

<210> SEQ ID NO 200
<211> LENGTH: 10
<212> TYPE: PRT
<213> ORGANISM: Dengue virus

<400> SEQUENCE: 200

Tyr Ala Gln Met Trp Ser Leu Met Tyr Phe
1 5 10

<210> SEQ ID NO 201
<211> LENGTH: 9
<212> TYPE: PRT
<213> ORGANISM: Dengue virus

<400> SEQUENCE: 201

Ile Cys Ser Ala Val Pro Val His Trp
1 5

<210> SEQ ID NO 202
<211> LENGTH: 9
<212> TYPE: PRT
<213> ORGANISM: Dengue virus

<400> SEQUENCE: 202

Trp Ser Ile His Ala His His Gln Trp
1 5

<210> SEQ ID NO 203
<211> LENGTH: 10
<212> TYPE: PRT

<213> ORGANISM: Dengue virus

<400> SEQUENCE: 203

Asn Pro Asn Met Ile Asp Lys Thr Pro Val
1 5 10

<210> SEQ ID NO 204
<211> LENGTH: 10
<212> TYPE: PRT
<213> ORGANISM: Dengue virus

<400> SEQUENCE: 204

Asn Pro Trp Met Glu Asp Lys Thr Pro Val
1 5 10

<210> SEQ ID NO 205
<211> LENGTH: 10
<212> TYPE: PRT
<213> ORGANISM: Dengue virus

<400> SEQUENCE: 205

Val Pro Tyr Leu Gly Lys Arg Glu Asp Gln
1 5 10

<210> SEQ ID NO 206
<211> LENGTH: 9
<212> TYPE: PRT
<213> ORGANISM: Dengue virus

<400> SEQUENCE: 206

Arg Glu Asp Leu Trp Cys Gly Ser Leu
1 5

<210> SEQ ID NO 207
<211> LENGTH: 9
<212> TYPE: PRT
<213> ORGANISM: Dengue virus

<400> SEQUENCE: 207

Arg Glu Asp Gln Trp Cys Gly Ser Leu
1 5

<210> SEQ ID NO 208
<211> LENGTH: 10
<212> TYPE: PRT
<213> ORGANISM: Dengue virus

<400> SEQUENCE: 208

Met Pro Ser Met Lys Arg Phe Arg Arg Glu
1 5 10

<210> SEQ ID NO 209
<211> LENGTH: 9
<212> TYPE: PRT
<213> ORGANISM: Dengue virus

<400> SEQUENCE: 209

Ala Pro Phe Glu Ser Glu Gly Val Leu
1 5

<210> SEQ ID NO 210
<211> LENGTH: 114
<212> TYPE: PRT
<213> ORGANISM: Dengue virus

<400> SEQUENCE: 210

Met Asn Asn Gln Arg Lys Lys Ala Arg Asn Thr Pro Phe Asn Met Leu
1               5                   10                  15

Lys Arg Glu Arg Asn Arg Val Ser Thr Val Gln Gln Leu Thr Lys Arg
            20                  25                  30

Phe Ser Leu Gly Met Leu Gln Gly Arg Gly Pro Leu Lys Leu Phe Met
        35                  40                  45

Ala Leu Val Ala Phe Leu Arg Phe Leu Thr Ile Pro Pro Thr Ala Gly
    50                  55                  60

Ile Leu Lys Arg Trp Gly Thr Ile Lys Ser Lys Ala Ile Asn Val
65                  70                  75                  80

Leu Arg Gly Phe Arg Lys Glu Ile Gly Arg Met Leu Asn Ile Leu Asn
                85                  90                  95

Arg Arg Arg Arg Thr Ala Gly Met Ile Ile Met Leu Ile Pro Thr Val
            100                 105                 110

Met Ala

<210> SEQ ID NO 211
<211> LENGTH: 166
<212> TYPE: PRT
<213> ORGANISM: Dengue virus

<400> SEQUENCE: 211

Phe His Leu Thr Thr Arg Asn Gly Glu Pro His Met Ile Val Ser Arg
1               5                   10                  15

Gln Glu Lys Gly Lys Ser Leu Leu Phe Lys Thr Gly Asp Gly Val Asn
            20                  25                  30

Met Cys Thr Leu Met Ala Met Asp Leu Gly Glu Leu Cys Glu Asp Thr
        35                  40                  45

Ile Thr Tyr Lys Cys Pro Leu Leu Arg Gln Asn Glu Pro Glu Asp Ile
    50                  55                  60

Asp Cys Trp Cys Asn Ser Thr Ser Thr Trp Val Thr Tyr Gly Thr Cys
65                  70                  75                  80

Thr Thr Thr Gly Glu His Arg Arg Glu Lys Arg Ser Val Ala Leu Val
                85                  90                  95

Pro His Val Gly Met Gly Leu Glu Thr Arg Thr Glu Thr Trp Met Ser
            100                 105                 110

Ser Glu Gly Ala Trp Lys His Ala Gln Arg Ile Glu Thr Trp Ile Leu
        115                 120                 125

Arg His Pro Gly Phe Thr Ile Met Ala Ala Ile Leu Ala Tyr Thr Ile
    130                 135                 140

Gly Thr Thr His Phe Gln Arg Ala Leu Ile Phe Ile Leu Leu Thr Ala
145                 150                 155                 160

Val Ala Pro Ser Met Thr
                165

<210> SEQ ID NO 212
<211> LENGTH: 495
<212> TYPE: PRT
<213> ORGANISM: Dengue virus

<400> SEQUENCE: 212

Met Arg Cys Ile Gly Ile Ser Asn Arg Asp Phe Val Glu Gly Val Ser
1 5 10 15

Gly Gly Ser Trp Val Asp Ile Val Leu Glu His Gly Ser Cys Val Thr
20 25 30

Thr Met Ala Lys Asn Lys Pro Thr Leu Asp Phe Glu Leu Ile Lys Thr
            35                  40                  45

Glu Ala Lys Gln Ser Ala Thr Leu Arg Lys Tyr Cys Ile Glu Ala Lys
    50                  55                  60

Leu Thr Asn Thr Thr Thr Glu Ser Arg Cys Pro Thr Gln Gly Glu Pro
65                  70                  75                  80

Ser Leu Asn Glu Glu Gln Asp Lys Arg Phe Val Cys Lys His Ser Met
                85                  90                  95

Val Asp Arg Gly Trp Gly Asn Gly Cys Gly Leu Phe Gly Lys Gly Gly
                100                 105                 110

Ile Val Thr Cys Ala Met Phe Thr Cys Lys Lys Asn Met Lys Gly Lys
                115                 120                 125

Val Val Gln Pro Glu Asn Leu Glu Tyr Thr Ile Val Ile Thr Pro His
                130                 135                 140

Ser Gly Glu Glu His Ala Val Gly Asn Asp Thr Gly Lys His Gly Lys
145                 150                 155                 160

Glu Ile Lys Ile Thr Pro Gln Ser Ser Ile Thr Glu Ala Glu Leu Thr
                165                 170                 175

Gly Tyr Gly Thr Val Thr Met Glu Cys Ser Pro Arg Thr Gly Leu Asp
                180                 185                 190

Phe Asn Glu Met Val Leu Leu Gln Met Glu Asn Lys Ala Trp Leu Val
                195                 200                 205

His Arg Gln Trp Phe Leu Asp Leu Pro Leu Pro Trp Leu Pro Gly Ala
                210                 215                 220

Asp Thr Gln Gly Ser Asn Trp Ile Gln Lys Glu Thr Leu Val Thr Phe
225                 230                 235                 240

Lys Asn Pro His Ala Lys Lys Gln Asp Val Val Val Leu Gly Ser Gln
                245                 250                 255

Glu Gly Ala Met His Thr Ala Leu Thr Gly Ala Thr Glu Ile Gln Met
                260                 265                 270

Ser Ser Gly Asn Leu Leu Phe Thr Gly His Leu Lys Cys Arg Leu Arg
                275                 280                 285

Met Asp Lys Leu Gln Leu Lys Gly Met Ser Tyr Ser Met Cys Thr Gly
                290                 295                 300

Lys Phe Lys Val Val Lys Glu Ile Ala Glu Thr Gln His Gly Thr Ile
305                 310                 315                 320

Val Ile Arg Val Gln Tyr Glu Gly Asp Gly Ser Pro Cys Lys Ile Pro
                325                 330                 335

Phe Glu Ile Met Asp Leu Glu Lys Arg His Val Leu Gly Arg Leu Ile
                340                 345                 350

Thr Val Asn Pro Ile Val Thr Glu Lys Asp Ser Pro Val Asn Ile Glu
                355                 360                 365

Ala Glu Pro Pro Phe Gly Asp Ser Tyr Ile Ile Ile Gly Val Glu Pro
                370                 375                 380

Gly Gln Leu Lys Leu Asn Trp Phe Lys Lys Gly Ser Ser Ile Gly Gln
385                 390                 395                 400

Met Leu Glu Thr Thr Met Arg Gly Ala Lys Arg Met Ala Ile Leu Gly
                405                 410                 415

Asp Thr Ala Trp Asp Phe Gly Ser Leu Gly Gly Val Phe Thr Ser Ile
                420                 425                 430

Gly Lys Ala Leu His Gln Val Phe Gly Ala Ile Tyr Gly Ala Ala Phe
                435                 440                 445

```
Ser Gly Val Ser Trp Thr Met Lys Ile Leu Ile Gly Val Ile Ile Thr
        450                 455                 460
Trp Ile Gly Met Asn Ser Arg Ser Thr Ser Leu Ser Val Ser Leu Val
465                 470                 475                 480
Leu Val Gly Val Val Thr Leu Tyr Leu Gly Val Met Val Gln Ala
                485                 490                 495

<210> SEQ ID NO 213
<211> LENGTH: 353
<212> TYPE: PRT
<213> ORGANISM: Dengue virus

<400> SEQUENCE: 213

Ala Asp Ser Gly Cys Val Val Ser Trp Lys Asn Lys Glu Leu Lys Cys
1               5                   10                  15
Gly Ser Gly Ile Phe Ile Thr Asp Asn Val His Thr Trp Thr Glu Gln
            20                  25                  30
Tyr Lys Phe Gln Pro Glu Ser Pro Ser Lys Leu Ala Ser Ala Ile Gln
        35                  40                  45
Lys Ala His Glu Glu Gly Ile Cys Gly Ile Arg Ser Val Thr Arg Leu
    50                  55                  60
Glu Asn Leu Met Trp Lys Gln Ile Thr Pro Glu Leu Asn His Ile Leu
65                  70                  75                  80
Ser Glu Asn Glu Val Lys Leu Thr Ile Met Thr Gly Asp Ile Lys Gly
                85                  90                  95
Ile Met Gln Ala Gly Lys Arg Ser Leu Arg Pro Gln Pro Thr Glu Leu
            100                 105                 110
Lys Tyr Ser Trp Lys Thr Trp Gly Lys Ala Lys Met Leu Ser Thr Glu
        115                 120                 125
Ser His Asn Gln Thr Phe Leu Ile Asp Gly Pro Glu Thr Ala Glu Cys
    130                 135                 140
Pro Asn Thr Asn Arg Ala Trp Asn Ser Leu Glu Val Glu Asp Tyr Gly
145                 150                 155                 160
Phe Gly Val Phe Thr Thr Asn Ile Trp Leu Lys Leu Arg Glu Lys Gln
                165                 170                 175
Asp Val Phe Cys Asp Ser Lys Leu Met Ser Ala Ala Ile Lys Asp Asn
            180                 185                 190
Arg Ala Val His Ala Asp Met Gly Tyr Trp Ile Glu Ser Ala Leu Asn
        195                 200                 205
Asp Thr Trp Lys Ile Glu Lys Ala Ser Phe Ile Glu Val Lys Ser Cys
    210                 215                 220
His Trp Pro Lys Ser His Thr Leu Trp Ser Asn Glu Val Leu Glu Ser
225                 230                 235                 240
Glu Met Ile Ile Pro Lys Asn Phe Ala Gly Pro Val Ser Gln His Asn
                245                 250                 255
Tyr Arg Pro Gly Tyr His Thr Gln Thr Ala Gly Pro Trp His Leu Gly
            260                 265                 270
Lys Leu Glu Met Asp Phe Asp Phe Cys Glu Gly Thr Thr Val Val Val
        275                 280                 285
Thr Glu Asp Cys Gly Asn Arg Gly Pro Ser Leu Arg Thr Thr Thr Ala
    290                 295                 300
Ser Gly Lys Leu Ile Thr Glu Trp Cys Cys Arg Ser Cys Thr Leu Pro
305                 310                 315                 320
Pro Leu Arg Tyr Arg Gly Glu Asp Gly Cys Trp Tyr Gly Met Glu Ile
                325                 330                 335
```

```
Arg Pro Leu Lys Glu Lys Glu Asn Leu Val Asn Ser Leu Val Thr
                340                 345                 350
Ala

<210> SEQ ID NO 214
<211> LENGTH: 218
<212> TYPE: PRT
<213> ORGANISM: Dengue virus

<400> SEQUENCE: 214

Gly His Gly Gln Ile Asp Asn Phe Ser Leu Gly Val Leu Gly Met Ala
1               5                   10                  15

Leu Phe Leu Glu Glu Met Leu Arg Thr Arg Val Gly Thr Lys His Ala
            20                  25                  30

Ile Leu Leu Val Ala Val Ser Phe Val Thr Leu Ile Thr Gly Asn Met
        35                  40                  45

Ser Phe Arg Asp Leu Gly Arg Val Met Val Met Val Gly Ala Thr Met
    50                  55                  60

Thr Asp Asp Ile Gly Met Gly Val Thr Tyr Leu Ala Leu Leu Ala Ala
65                  70                  75                  80

Phe Lys Val Arg Pro Thr Phe Ala Ala Gly Leu Leu Leu Arg Lys Leu
                85                  90                  95

Thr Ser Lys Glu Leu Met Met Thr Thr Ile Gly Ile Val Leu Leu Ser
            100                 105                 110

Gln Ser Thr Ile Pro Glu Thr Ile Leu Glu Leu Thr Asp Ala Leu Ala
        115                 120                 125

Leu Gly Met Met Val Leu Lys Met Val Arg Lys Met Glu Lys Tyr Gln
130                 135                 140

Leu Ala Val Thr Ile Met Ala Ile Leu Cys Val Pro Asn Ala Val Ile
145                 150                 155                 160

Leu Gln Asn Ala Trp Lys Val Ser Cys Thr Ile Leu Ala Val Val Ser
                165                 170                 175

Val Ser Pro Leu Phe Leu Thr Ser Ser Gln Gln Lys Ala Asp Trp Ile
            180                 185                 190

Pro Leu Ala Leu Thr Ile Lys Gly Leu Asn Pro Thr Ala Ile Phe Leu
        195                 200                 205

Thr Thr Leu Ser Arg Thr Asn Lys Lys Arg
    210                 215

<210> SEQ ID NO 215
<211> LENGTH: 130
<212> TYPE: PRT
<213> ORGANISM: Dengue virus

<400> SEQUENCE: 215

Ser Trp Pro Leu Asn Glu Ala Ile Met Ala Val Gly Met Val Ser Ile
1               5                   10                  15

Leu Ala Ser Ser Leu Leu Lys Asn Asp Ile Pro Met Thr Gly Pro Leu
            20                  25                  30

Val Ala Gly Gly Leu Leu Thr Val Cys Tyr Val Leu Thr Gly Arg Ser
        35                  40                  45

Ala Asp Leu Glu Leu Glu Arg Ala Ala Asp Val Lys Trp Glu Asp Gln
    50                  55                  60

Ala Glu Ile Ser Gly Ser Ser Pro Ile Leu Ser Ile Thr Ile Ser Glu
65                  70                  75                  80
```

```
Asp Gly Ser Met Ser Ile Lys Asn Glu Glu Glu Gln Thr Leu Thr
                85                  90                  95

Ile Leu Ile Arg Thr Gly Leu Leu Val Ile Ser Gly Leu Phe Pro Val
            100                 105                 110

Ser Leu Pro Ile Thr Ala Ala Ala Trp Tyr Leu Trp Glu Val Lys Lys
        115                 120                 125

Gln Arg
    130

<210> SEQ ID NO 216
<211> LENGTH: 618
<212> TYPE: PRT
<213> ORGANISM: Dengue virus

<400> SEQUENCE: 216

Ala Gly Val Leu Trp Asp Val Pro Ser Pro Pro Val Gly Lys Ala
1               5                   10                  15

Glu Leu Glu Asp Gly Ala Tyr Arg Ile Lys Gln Lys Gly Ile Leu Gly
            20                  25                  30

Tyr Ser Gln Ile Gly Ala Gly Val Tyr Lys Glu Gly Thr Phe His Thr
        35                  40                  45

Met Trp His Val Thr Arg Gly Ala Val Leu Met His Lys Gly Lys Arg
    50                  55                  60

Ile Glu Pro Ser Trp Ala Asp Val Lys Lys Asp Leu Ile Ser Tyr Gly
65                  70                  75                  80

Gly Gly Trp Lys Leu Glu Gly Glu Trp Lys Glu Gly Glu Glu Val Gln
                85                  90                  95

Val Leu Ala Leu Glu Pro Gly Lys Asn Pro Arg Ala Val Gln Thr Lys
            100                 105                 110

Pro Gly Leu Phe Lys Thr Asn Ala Gly Thr Ile Gly Ala Val Ser Leu
        115                 120                 125

Asp Phe Ser Pro Gly Thr Ser Gly Ser Pro Ile Ile Asp Lys Lys Gly
    130                 135                 140

Lys Val Val Gly Leu Tyr Gly Asn Gly Val Val Thr Arg Ser Gly Ala
145                 150                 155                 160

Tyr Val Ser Ala Ile Ala Gln Thr Glu Lys Ser Ile Glu Asp Asn Pro
                165                 170                 175

Glu Ile Glu Asp Asp Ile Phe Arg Lys Arg Lys Leu Thr Ile Met Asp
            180                 185                 190

Leu His Pro Gly Ala Gly Lys Thr Lys Arg Tyr Leu Pro Ala Ile Val
        195                 200                 205

Arg Glu Ala Ile Lys Arg Gly Leu Arg Thr Leu Ile Leu Ala Pro Thr
    210                 215                 220

Arg Val Val Ala Ala Glu Met Glu Glu Ala Leu Arg Gly Leu Pro Ile
225                 230                 235                 240

Arg Tyr Gln Thr Pro Ala Ile Arg Ala Glu His Thr Gly Arg Glu Ile
                245                 250                 255

Val Asp Leu Met Cys His Ala Thr Phe Thr Met Arg Leu Leu Ser Pro
            260                 265                 270

Val Arg Val Pro Asn Tyr Asn Leu Ile Ile Met Asp Glu Ala His Phe
        275                 280                 285

Thr Asp Pro Ala Ser Ile Ala Ala Arg Gly Tyr Ile Ser Thr Arg Val
    290                 295                 300

Glu Met Gly Glu Ala Ala Gly Ile Phe Met Thr Ala Thr Pro Pro Gly
305                 310                 315                 320
```

Ser Arg Asp Pro Phe Pro Gln Ser Asn Ala Pro Ile Met Asp Glu Glu
                325                 330                 335

Arg Glu Ile Pro Glu Arg Ser Trp Ser Ser Gly His Glu Trp Val Thr
            340                 345                 350

Asp Phe Lys Gly Lys Thr Val Trp Phe Val Pro Ser Ile Lys Ala Gly
        355                 360                 365

Asn Asp Ile Ala Ala Cys Leu Arg Lys Asn Gly Lys Lys Val Ile Gln
    370                 375                 380

Leu Ser Arg Lys Thr Phe Asp Ser Glu Tyr Val Lys Thr Arg Thr Asn
385                 390                 395                 400

Asp Trp Asp Phe Val Val Thr Thr Asp Ile Ser Glu Met Gly Ala Asn
                405                 410                 415

Phe Lys Ala Glu Arg Val Ile Asp Pro Arg Arg Cys Met Lys Pro Val
            420                 425                 430

Ile Leu Thr Asp Gly Glu Glu Arg Val Ile Leu Ala Gly Pro Met Pro
        435                 440                 445

Val Thr His Ser Ser Ala Ala Gln Arg Arg Gly Arg Ile Gly Arg Asn
    450                 455                 460

Pro Lys Asn Glu Asn Asp Gln Tyr Ile Tyr Met Gly Glu Pro Leu Glu
465                 470                 475                 480

Asn Asp Glu Asp Cys Ala His Trp Lys Glu Ala Lys Met Leu Leu Asp
                485                 490                 495

Asn Ile Asn Thr Pro Glu Gly Ile Ile Pro Ser Met Phe Glu Pro Glu
            500                 505                 510

Arg Glu Lys Val Asp Ala Ile Asp Gly Glu Tyr Arg Leu Arg Gly Glu
        515                 520                 525

Ala Arg Lys Thr Phe Val Asp Leu Met Arg Arg Gly Asp Leu Pro Val
    530                 535                 540

Trp Leu Ala Tyr Arg Val Ala Ala Glu Gly Ile Asn Tyr Ala Asp Arg
545                 550                 555                 560

Arg Trp Cys Phe Asp Gly Ile Lys Asn Asn Gln Ile Leu Glu Glu Asn
                565                 570                 575

Val Glu Val Glu Ile Trp Thr Lys Glu Gly Glu Arg Lys Lys Leu Lys
            580                 585                 590

Pro Arg Trp Leu Asp Ala Arg Ile Tyr Ser Asp Pro Leu Ala Leu Lys
        595                 600                 605

Glu Phe Lys Glu Phe Ala Ala Gly Arg Lys
        610                 615

<210> SEQ ID NO 217
<211> LENGTH: 150
<212> TYPE: PRT
<213> ORGANISM: Dengue virus

<400> SEQUENCE: 217

Ser Leu Thr Leu Ser Leu Ile Thr Glu Met Gly Arg Leu Pro Thr Phe
1               5                   10                  15

Met Thr Gln Lys Ala Arg Asp Ala Leu Asp Asn Leu Ala Val Leu His
            20                  25                  30

Thr Ala Glu Ala Gly Gly Arg Ala Tyr Asn His Ala Leu Ser Glu Leu
        35                  40                  45

Pro Glu Thr Leu Glu Thr Leu Leu Leu Thr Leu Leu Ala Thr Val
    50                  55                  60

Thr Gly Gly Ile Phe Leu Phe Leu Met Ser Gly Arg Gly Ile Gly Lys

```
             65                  70                  75                  80
Met Thr Leu Gly Met Cys Cys Ile Ile Thr Ala Ser Ile Leu Leu Trp
                     85                  90                  95

Tyr Ala Gln Ile Gln Pro His Trp Ile Ala Ala Ser Ile Ile Leu Glu
            100                 105                 110

Phe Phe Leu Ile Val Leu Leu Ile Pro Glu Pro Glu Lys Gln Arg Thr
        115                 120                 125

Pro Gln Asp Asn Gln Leu Thr Tyr Val Val Ile Ala Ile Leu Thr Val
    130                 135                 140

Val Ala Ala Thr Met Ala
145                 150

<210> SEQ ID NO 218
<211> LENGTH: 248
<212> TYPE: PRT
<213> ORGANISM: Dengue virus

<400> SEQUENCE: 218

Asn Glu Met Gly Phe Leu Glu Lys Thr Lys Lys Asp Leu Gly Leu Gly
1               5                   10                  15

Ser Ile Thr Thr Gln Gln Pro Glu Ser Asn Ile Leu Asp Ile Asp Leu
            20                  25                  30

Arg Pro Ala Ser Ala Trp Thr Leu Tyr Ala Val Ala Thr Thr Phe Val
        35                  40                  45

Thr Pro Met Leu Arg His Ser Ile Glu Asn Ser Ser Val Asn Val Ser
    50                  55                  60

Leu Thr Ala Ile Ala Asn Gln Ala Thr Val Leu Met Gly Leu Gly Lys
65                  70                  75                  80

Gly Trp Pro Leu Ser Lys Met Asp Ile Gly Val Pro Leu Leu Ala Ile
                85                  90                  95

Gly Cys Tyr Ser Gln Val Asn Pro Ile Thr Leu Thr Ala Ala Leu Phe
            100                 105                 110

Leu Leu Val Ala His Tyr Ala Ile Ile Gly Pro Gly Leu Gln Ala Lys
        115                 120                 125

Ala Thr Arg Glu Ala Gln Lys Arg Ala Ala Ala Gly Ile Met Lys Asn
    130                 135                 140

Pro Thr Val Asp Gly Ile Thr Val Ile Asp Leu Asp Pro Ile Pro Tyr
145                 150                 155                 160

Asp Pro Lys Phe Glu Lys Gln Leu Gly Gln Val Met Leu Leu Val Leu
                165                 170                 175

Cys Val Thr Gln Val Leu Met Met Arg Thr Thr Trp Ala Leu Cys Glu
            180                 185                 190

Ala Leu Thr Leu Ala Thr Gly Pro Ile Ser Thr Leu Trp Glu Gly Asn
        195                 200                 205

Pro Gly Arg Phe Trp Asn Thr Thr Ile Ala Val Ser Met Ala Asn Ile
    210                 215                 220

Phe Arg Gly Ser Tyr Leu Ala Gly Ala Gly Leu Leu Phe Ser Ile Met
225                 230                 235                 240

Lys Asn Thr Thr Asn Thr Arg Arg
                245

<210> SEQ ID NO 219
<211> LENGTH: 900
<212> TYPE: PRT
<213> ORGANISM: Dengue virus
```

```
<400> SEQUENCE: 219

Gly Thr Gly Asn Ile Gly Glu Thr Leu Gly Glu Lys Trp Lys Ser Arg
1               5                   10                  15

Leu Asn Ala Leu Gly Lys Ser Glu Phe Gln Ile Tyr Lys Lys Ser Gly
            20                  25                  30

Ile Gln Glu Val Asp Arg Thr Leu Ala Lys Glu Gly Ile Lys Arg Gly
        35                  40                  45

Glu Thr Asp His His Ala Val Ser Arg Gly Ser Ala Lys Leu Arg Trp
    50                  55                  60

Phe Val Glu Arg Asn Met Val Thr Pro Glu Gly Lys Val Val Asp Leu
65                  70                  75                  80

Gly Cys Gly Arg Gly Gly Trp Ser Tyr Tyr Cys Gly Gly Leu Lys Asn
                85                  90                  95

Val Arg Glu Val Lys Gly Leu Thr Lys Gly Gly Pro Gly His Glu Glu
            100                 105                 110

Pro Ile Pro Met Ser Thr Tyr Gly Trp Asn Leu Val Arg Leu Gln Ser
        115                 120                 125

Gly Val Asp Val Phe Phe Thr Pro Pro Glu Lys Cys Asp Thr Leu Leu
    130                 135                 140

Cys Asp Ile Gly Glu Ser Ser Pro Asn Pro Thr Val Glu Ala Gly Arg
145                 150                 155                 160

Thr Leu Arg Val Leu Asn Leu Val Glu Asn Trp Leu Asn Asn Asn Thr
                165                 170                 175

Gln Phe Cys Ile Lys Val Leu Asn Pro Tyr Met Pro Ser Val Ile Glu
            180                 185                 190

Lys Met Glu Ala Leu Gln Arg Lys Tyr Gly Gly Ala Leu Val Arg Asn
        195                 200                 205

Pro Leu Ser Arg Asn Ser Thr His Glu Met Tyr Trp Val Ser Asn Ala
    210                 215                 220

Ser Gly Asn Ile Val Ser Ser Val Asn Met Ile Ser Arg Met Leu Ile
225                 230                 235                 240

Asn Arg Phe Thr Met Arg His Lys Lys Ala Thr Tyr Glu Pro Asp Val
                245                 250                 255

Asp Leu Gly Ser Gly Thr Arg Asn Ile Gly Ile Glu Ser Glu Ile Pro
            260                 265                 270

Asn Leu Asp Ile Ile Gly Lys Arg Ile Glu Lys Ile Lys Gln Glu His
        275                 280                 285

Glu Thr Ser Trp His Tyr Asp Gln Asp His Pro Tyr Lys Thr Trp Ala
    290                 295                 300

Tyr His Gly Ser Tyr Glu Thr Lys Gln Thr Gly Ser Ala Ser Ser Met
305                 310                 315                 320

Val Asn Gly Val Val Arg Leu Leu Thr Lys Pro Trp Asp Val Val Pro
                325                 330                 335

Met Val Thr Gln Met Ala Met Thr Asp Thr Thr Pro Phe Gly Gln Gln
            340                 345                 350

Arg Val Phe Lys Glu Lys Val Asp Thr Arg Thr Gln Glu Pro Lys Glu
        355                 360                 365

Gly Thr Lys Lys Leu Met Lys Ile Thr Ala Glu Trp Leu Trp Lys Glu
    370                 375                 380

Leu Gly Lys Lys Lys Thr Pro Arg Met Cys Thr Arg Glu Glu Phe Thr
385                 390                 395                 400

Arg Lys Val Arg Ser Asn Ala Ala Leu Gly Ala Ile Phe Thr Asp Glu
                405                 410                 415
```

Asn Lys Trp Lys Ser Ala Arg Glu Ala Val Glu Asp Ser Arg Phe Trp
            420                 425                 430

Glu Leu Val Asp Lys Glu Arg Asn Leu His Leu Glu Gly Lys Cys Glu
            435                 440                 445

Thr Cys Val Tyr Asn Met Met Gly Lys Arg Glu Lys Lys Leu Gly Glu
450                 455                 460

Phe Gly Lys Ala Lys Gly Ser Arg Ala Ile Trp Tyr Met Trp Leu Gly
465                 470                 475                 480

Ala Arg Phe Leu Glu Phe Glu Ala Leu Gly Phe Leu Asn Glu Asp His
                485                 490                 495

Trp Phe Ser Arg Glu Asn Ser Leu Ser Gly Val Glu Gly Glu Gly Leu
            500                 505                 510

His Lys Leu Gly Tyr Ile Leu Arg Asp Val Ser Lys Lys Glu Gly Gly
            515                 520                 525

Ala Met Tyr Ala Asp Asp Thr Ala Gly Trp Asp Thr Arg Ile Thr Leu
            530                 535                 540

Glu Asp Leu Lys Asn Glu Glu Met Val Thr Asn His Met Glu Gly Glu
545                 550                 555                 560

His Lys Lys Leu Ala Glu Ala Ile Phe Lys Leu Thr Tyr Gln Asn Lys
                565                 570                 575

Val Val Arg Val Gln Arg Pro Thr Pro Arg Gly Thr Val Met Asp Ile
            580                 585                 590

Ile Ser Arg Arg Asp Gln Arg Gly Ser Gly Gln Val Gly Thr Tyr Gly
            595                 600                 605

Leu Asn Thr Phe Thr Asn Met Glu Ala Gln Leu Ile Arg Gln Met Glu
            610                 615                 620

Gly Glu Gly Val Phe Lys Ser Ile Gln His Leu Thr Val Thr Glu Glu
625                 630                 635                 640

Ile Ala Val Gln Asn Trp Leu Ala Arg Val Gly Arg Glu Arg Leu Ser
                645                 650                 655

Arg Met Ala Ile Ser Gly Asp Asp Cys Val Val Lys Pro Leu Asp Asp
            660                 665                 670

Arg Phe Ala Ser Ala Leu Thr Ala Leu Asn Asp Met Gly Lys Val Arg
            675                 680                 685

Lys Asp Ile Gln Gln Trp Glu Pro Ser Arg Gly Trp Asn Asp Trp Thr
            690                 695                 700

Gln Val Pro Phe Cys Ser His His Phe His Glu Leu Ile Met Lys Asp
705                 710                 715                 720

Gly Arg Val Leu Val Val Pro Cys Arg Asn Gln Asp Glu Leu Ile Gly
                725                 730                 735

Arg Ala Arg Ile Ser Gln Gly Ala Gly Trp Ser Leu Arg Glu Thr Ala
            740                 745                 750

Cys Leu Gly Lys Ser Tyr Ala Gln Met Trp Ser Leu Met Tyr Phe His
            755                 760                 765

Arg Arg Asp Leu Arg Leu Ala Ala Asn Ala Ile Cys Ser Ala Val Pro
            770                 775                 780

Ser His Trp Val Pro Thr Ser Arg Thr Thr Trp Ser Ile His Ala Lys
785                 790                 795                 800

His Glu Trp Met Thr Ala Glu Asp Met Leu Thr Val Trp Asn Arg Val
                805                 810                 815

Trp Ile Gln Glu Asn Pro Trp Met Glu Asp Lys Thr Pro Val Glu Ser
            820                 825                 830

-continued

```
Trp Glu Glu Ile Pro Tyr Leu Gly Lys Arg Glu Asp Gln Trp Cys Gly
            835                 840                 845

Ser Leu Ile Gly Leu Thr Ser Arg Ala Thr Trp Ala Lys Asn Ile Gln
        850                 855                 860

Thr Ala Ile Asn Gln Val Arg Ser Leu Ile Gly Asn Glu Glu Tyr Thr
865                 870                 875                 880

Asp Tyr Met Pro Ser Met Lys Arg Phe Arg Arg Glu Glu Glu Glu Ala
                885                 890                 895

Gly Val Leu Trp
            900

<210> SEQ ID NO 220
<211> LENGTH: 15
<212> TYPE: PRT
<213> ORGANISM: Dengue virus

<400> SEQUENCE: 220

Gly Leu Phe Pro Val Ser Leu Pro Ile Thr Ala Ala Ala Trp Tyr
1               5                   10                  15

<210> SEQ ID NO 221
<211> LENGTH: 15
<212> TYPE: PRT
<213> ORGANISM: Dengue virus

<400> SEQUENCE: 221

Gly Lys Thr Lys Arg Tyr Leu Pro Ala Ile Val Arg Glu Ala Ile
1               5                   10                  15

<210> SEQ ID NO 222
<211> LENGTH: 15
<212> TYPE: PRT
<213> ORGANISM: Dengue virus

<400> SEQUENCE: 222

Gly Leu Pro Ile Arg Tyr Gln Thr Pro Ala Ile Arg Ala Glu His
1               5                   10                  15

<210> SEQ ID NO 223
<211> LENGTH: 15
<212> TYPE: PRT
<213> ORGANISM: Dengue virus

<400> SEQUENCE: 223

Ile Gly Cys Tyr Ser Gln Val Asn Pro Ile Thr Leu Thr Ala Ala
1               5                   10                  15

<210> SEQ ID NO 224
<211> LENGTH: 9
<212> TYPE: PRT
<213> ORGANISM: Dengue virus

<400> SEQUENCE: 224

Ile Thr Glu Ala Glu Leu Thr Gly Tyr
1               5

<210> SEQ ID NO 225
<211> LENGTH: 10
<212> TYPE: PRT
<213> ORGANISM: Dengue virus

<400> SEQUENCE: 225

Arg Ser Cys Thr Leu Pro Pro Leu Arg Tyr
```

```
<210> SEQ ID NO 226
<211> LENGTH: 9
<212> TYPE: PRT
<213> ORGANISM: Dengue virus

<400> SEQUENCE: 226

Met Thr Asp Asp Ile Gly Met Gly Val
1               5

<210> SEQ ID NO 227
<211> LENGTH: 9
<212> TYPE: PRT
<213> ORGANISM: Dengue virus

<400> SEQUENCE: 227

Leu Thr Asp Ala Leu Ala Leu Gly Met
1               5

<210> SEQ ID NO 228
<211> LENGTH: 9
<212> TYPE: PRT
<213> ORGANISM: Dengue virus

<400> SEQUENCE: 228

Val Ile Asp Leu Asp Pro Ile Pro Tyr
1               5

<210> SEQ ID NO 229
<211> LENGTH: 9
<212> TYPE: PRT
<213> ORGANISM: Dengue virus

<400> SEQUENCE: 229

Tyr Thr Asp Tyr Met Pro Ser Met Lys
1               5

<210> SEQ ID NO 230
<211> LENGTH: 9
<212> TYPE: PRT
<213> ORGANISM: Dengue virus

<400> SEQUENCE: 230

Arg Leu Ile Thr Val Asn Pro Ile Val
1               5

<210> SEQ ID NO 231
<211> LENGTH: 9
<212> TYPE: PRT
<213> ORGANISM: Dengue virus

<400> SEQUENCE: 231

Ile Met Ala Val Gly Met Val Ser Ile
1               5

<210> SEQ ID NO 232
<211> LENGTH: 9
<212> TYPE: PRT
<213> ORGANISM: Dengue virus

<400> SEQUENCE: 232

Gly Leu Leu Thr Val Cys Tyr Val Leu
1               5
```

<210> SEQ ID NO 233
<211> LENGTH: 10
<212> TYPE: PRT
<213> ORGANISM: Dengue virus

<400> SEQUENCE: 233

Leu Leu Val Ile Ser Gly Leu Phe Pro Val
1 5 10

<210> SEQ ID NO 234
<211> LENGTH: 9
<212> TYPE: PRT
<213> ORGANISM: Dengue virus

<400> SEQUENCE: 234

Ala Ala Ala Trp Tyr Leu Trp Glu Val
1 5

<210> SEQ ID NO 235
<211> LENGTH: 9
<212> TYPE: PRT
<213> ORGANISM: Dengue virus

<400> SEQUENCE: 235

Tyr Leu Pro Ala Ile Val Arg Glu Ala
1 5

<210> SEQ ID NO 236
<211> LENGTH: 10
<212> TYPE: PRT
<213> ORGANISM: Dengue virus

<400> SEQUENCE: 236

Asp Leu Met Arg Arg Gly Asp Leu Pro Val
1 5 10

<210> SEQ ID NO 237
<211> LENGTH: 9
<212> TYPE: PRT
<213> ORGANISM: Dengue virus

<400> SEQUENCE: 237

Ala Leu Ser Glu Leu Pro Glu Thr Leu
1 5

<210> SEQ ID NO 238
<211> LENGTH: 9
<212> TYPE: PRT
<213> ORGANISM: Dengue virus

<400> SEQUENCE: 238

Ile Ile Leu Glu Phe Phe Leu Ile Val
1 5

<210> SEQ ID NO 239
<211> LENGTH: 9
<212> TYPE: PRT
<213> ORGANISM: Dengue virus

<400> SEQUENCE: 239

Lys Leu Ala Glu Ala Ile Phe Lys Leu
1 5

<210> SEQ ID NO 240

```
<211> LENGTH: 9
<212> TYPE: PRT
<213> ORGANISM: Dengue virus

<400> SEQUENCE: 240

Ser Gln Ile Gly Ala Gly Val Tyr Lys
1               5

<210> SEQ ID NO 241
<211> LENGTH: 10
<212> TYPE: PRT
<213> ORGANISM: Dengue virus

<400> SEQUENCE: 241

Gly Thr Ser Gly Ser Pro Ile Ile Asp Lys
1               5                   10

<210> SEQ ID NO 242
<211> LENGTH: 9
<212> TYPE: PRT
<213> ORGANISM: Dengue virus

<400> SEQUENCE: 242

Lys Thr Phe Asp Ser Glu Tyr Val Lys
1               5

<210> SEQ ID NO 243
<211> LENGTH: 10
<212> TYPE: PRT
<213> ORGANISM: Dengue virus

<400> SEQUENCE: 243

Arg Ile Tyr Ser Asp Pro Leu Ala Leu Lys
1               5                   10

<210> SEQ ID NO 244
<211> LENGTH: 9
<212> TYPE: PRT
<213> ORGANISM: Dengue virus

<400> SEQUENCE: 244

Ala Thr Val Leu Met Gly Leu Gly Lys
1               5

<210> SEQ ID NO 245
<211> LENGTH: 9
<212> TYPE: PRT
<213> ORGANISM: Dengue virus

<400> SEQUENCE: 245

Ser Thr Tyr Gly Trp Asn Leu Val Arg
1               5

<210> SEQ ID NO 246
<211> LENGTH: 9
<212> TYPE: PRT
<213> ORGANISM: Dengue virus

<400> SEQUENCE: 246

Thr Val Met Asp Ile Ile Ser Arg Arg
1               5

<210> SEQ ID NO 247
<211> LENGTH: 10
<212> TYPE: PRT
```

<213> ORGANISM: Dengue virus

<400> SEQUENCE: 247

Arg Gln Met Glu Gly Glu Gly Val Phe Lys
1 5 10

<210> SEQ ID NO 248
<211> LENGTH: 9
<212> TYPE: PRT
<213> ORGANISM: Dengue virus

<400> SEQUENCE: 248

Arg Thr Thr Trp Ser Ile His Ala Lys
1 5

<210> SEQ ID NO 249
<211> LENGTH: 10
<212> TYPE: PRT
<213> ORGANISM: Dengue virus

<400> SEQUENCE: 249

Arg Pro Thr Phe Ala Ala Gly Leu Leu Leu
1 5 10

<210> SEQ ID NO 250
<211> LENGTH: 9
<212> TYPE: PRT
<213> ORGANISM: Dengue virus

<400> SEQUENCE: 250

Leu Pro Ala Ile Val Arg Glu Ala Ile
1 5

<210> SEQ ID NO 251
<211> LENGTH: 10
<212> TYPE: PRT
<213> ORGANISM: Dengue virus

<400> SEQUENCE: 251

Ala Pro Thr Arg Val Val Ala Ala Glu Met
1 5 10

<210> SEQ ID NO 252
<211> LENGTH: 9
<212> TYPE: PRT
<213> ORGANISM: Dengue virus

<400> SEQUENCE: 252

Val Pro Asn Tyr Asn Leu Ile Ile Met
1 5

<210> SEQ ID NO 253
<211> LENGTH: 10
<212> TYPE: PRT
<213> ORGANISM: Dengue virus

<400> SEQUENCE: 253

Ala Pro Ile Met Asp Glu Glu Arg Glu Ile
1 5 10

<210> SEQ ID NO 254
<211> LENGTH: 10
<212> TYPE: PRT
<213> ORGANISM: Dengue virus

<400> SEQUENCE: 254

Thr Pro Glu Gly Ile Ile Pro Ser Met Phe
1               5                   10

<210> SEQ ID NO 255
<211> LENGTH: 9
<212> TYPE: PRT
<213> ORGANISM: Dengue virus

<400> SEQUENCE: 255

Lys Pro Arg Trp Leu Asp Ala Arg Ile
1               5

<210> SEQ ID NO 256
<211> LENGTH: 10
<212> TYPE: PRT
<213> ORGANISM: Dengue virus

<400> SEQUENCE: 256

Arg Pro Ala Ser Ala Trp Thr Leu Tyr Ala
1               5                   10

<210> SEQ ID NO 257
<211> LENGTH: 8
<212> TYPE: PRT
<213> ORGANISM: Dengue virus

<400> SEQUENCE: 257

Thr Pro Met Leu Arg His Ser Ile
1               5

<210> SEQ ID NO 258
<211> LENGTH: 10
<212> TYPE: PRT
<213> ORGANISM: Dengue virus

<400> SEQUENCE: 258

Ser Pro Asn Pro Thr Val Glu Ala Gly Arg
1               5                   10

<210> SEQ ID NO 259
<211> LENGTH: 10
<212> TYPE: PRT
<213> ORGANISM: Dengue virus

<400> SEQUENCE: 259

Thr Pro Arg Met Cys Thr Arg Glu Glu Phe
1               5                   10

<210> SEQ ID NO 260
<211> LENGTH: 9
<212> TYPE: PRT
<213> ORGANISM: Dengue virus

<400> SEQUENCE: 260

Arg Pro Thr Pro Arg Gly Thr Val Met
1               5

<210> SEQ ID NO 261
<211> LENGTH: 15
<212> TYPE: PRT
<213> ORGANISM: Dengue virus

<400> SEQUENCE: 261

Ala Phe Leu Arg Phe Leu Thr Ile Pro Pro Thr Ala Gly Ile Leu
1               5                   10                  15

<210> SEQ ID NO 262
<211> LENGTH: 15
<212> TYPE: PRT
<213> ORGANISM: Dengue virus

<400> SEQUENCE: 262

Gly Val Thr Tyr Leu Ala Leu Leu Ala Ala Phe Lys Val Arg Pro
1               5                   10                  15

<210> SEQ ID NO 263
<211> LENGTH: 15
<212> TYPE: PRT
<213> ORGANISM: Dengue virus

<400> SEQUENCE: 263

Met Ala Val Gly Met Val Ser Ile Leu Ala Ser Ser Leu Leu Lys
1               5                   10                  15

<210> SEQ ID NO 264
<211> LENGTH: 15
<212> TYPE: PRT
<213> ORGANISM: Dengue virus

<400> SEQUENCE: 264

Thr Phe Thr Met Arg Leu Leu Ser Pro Val Arg Val Pro Asn Tyr
1               5                   10                  15

<210> SEQ ID NO 265
<211> LENGTH: 15
<212> TYPE: PRT
<213> ORGANISM: Dengue virus

<400> SEQUENCE: 265

Ser Arg Ala Ile Trp Tyr Met Trp Leu Gly Ala Arg Phe Leu Glu
1               5                   10                  15

<210> SEQ ID NO 266
<211> LENGTH: 9
<212> TYPE: PRT
<213> ORGANISM: Dengue virus

<400> SEQUENCE: 266

Ile Thr Glu Ala Glu Leu Thr Gly Tyr
1               5

<210> SEQ ID NO 267
<211> LENGTH: 9
<212> TYPE: PRT
<213> ORGANISM: Dengue virus

<400> SEQUENCE: 267

Ser Thr Glu Ile Gln Leu Thr Asp Tyr
1               5

<210> SEQ ID NO 268
<211> LENGTH: 9
<212> TYPE: PRT
<213> ORGANISM: Dengue virus

<400> SEQUENCE: 268

Thr Thr Glu Ile Gln Leu Thr Asp Tyr
1               5

<210> SEQ ID NO 269
<211> LENGTH: 9
<212> TYPE: PRT
<213> ORGANISM: Dengue virus

<400> SEQUENCE: 269

Thr Ser Glu Ile Gln Leu Ile Asp Tyr
1               5

<210> SEQ ID NO 270
<211> LENGTH: 9
<212> TYPE: PRT
<213> ORGANISM: Dengue virus

<400> SEQUENCE: 270

Thr Ser Glu Ile Gln Leu Thr Asp Tyr
1               5

<210> SEQ ID NO 271
<211> LENGTH: 9
<212> TYPE: PRT
<213> ORGANISM: Dengue virus

<400> SEQUENCE: 271

Ile Ala Glu Ala Glu Leu Thr Gly Tyr
1               5

<210> SEQ ID NO 272
<211> LENGTH: 9
<212> TYPE: PRT
<213> ORGANISM: Dengue virus

<400> SEQUENCE: 272

Ile Ala Glu Ala Glu Leu Thr Asp Tyr
1               5

<210> SEQ ID NO 273
<211> LENGTH: 9
<212> TYPE: PRT
<213> ORGANISM: Dengue virus

<400> SEQUENCE: 273

Ile Thr Asp Ala Glu Leu Thr Gly Tyr
1               5

<210> SEQ ID NO 274
<211> LENGTH: 9
<212> TYPE: PRT
<213> ORGANISM: Dengue virus

<400> SEQUENCE: 274

Ser Thr Glu Ala Glu Leu Thr Gly Tyr
1               5

<210> SEQ ID NO 275
<211> LENGTH: 9
<212> TYPE: PRT
<213> ORGANISM: Dengue virus

<400> SEQUENCE: 275

Thr Thr Glu Ala Glu Leu Thr Gly Tyr
1               5

```
<210> SEQ ID NO 276
<211> LENGTH: 9
<212> TYPE: PRT
<213> ORGANISM: Dengue virus

<400> SEQUENCE: 276

Ile Ser Glu Ala Glu Leu Thr Asp Tyr
1               5

<210> SEQ ID NO 277
<211> LENGTH: 9
<212> TYPE: PRT
<213> ORGANISM: Dengue virus

<400> SEQUENCE: 277

Ile Thr Glu Ala Glu Leu Thr Gly Tyr
1               5

<210> SEQ ID NO 278
<211> LENGTH: 9
<212> TYPE: PRT
<213> ORGANISM: Dengue virus

<400> SEQUENCE: 278

Thr Val Glu Ala Val Leu Leu Glu Tyr
1               5

<210> SEQ ID NO 279
<211> LENGTH: 9
<212> TYPE: PRT
<213> ORGANISM: Dengue virus

<400> SEQUENCE: 279

Thr Val Glu Ala Val Leu Pro Glu Tyr
1               5

<210> SEQ ID NO 280
<211> LENGTH: 9
<212> TYPE: PRT
<213> ORGANISM: Dengue virus

<400> SEQUENCE: 280

Thr Val Glu Ala Ile Leu Pro Glu Tyr
1               5

<210> SEQ ID NO 281
<211> LENGTH: 9
<212> TYPE: PRT
<213> ORGANISM: Dengue virus

<400> SEQUENCE: 281

Thr Ala Glu Ala Ile Leu Pro Glu Tyr
1               5

<210> SEQ ID NO 282
<211> LENGTH: 9
<212> TYPE: PRT
<213> ORGANISM: Dengue virus

<400> SEQUENCE: 282

Thr His Glu Ala Leu Leu Pro Glu Tyr
1               5

<210> SEQ ID NO 283
<211> LENGTH: 9
```

```
<212> TYPE: PRT
<213> ORGANISM: Dengue virus

<400> SEQUENCE: 283

Ile Thr Glu Ala Ile Leu Pro Glu Tyr
1               5

<210> SEQ ID NO 284
<211> LENGTH: 9
<212> TYPE: PRT
<213> ORGANISM: Dengue virus

<400> SEQUENCE: 284

Thr Thr Glu Val Ile Leu Pro Glu Tyr
1               5

<210> SEQ ID NO 285
<211> LENGTH: 9
<212> TYPE: PRT
<213> ORGANISM: Dengue virus

<400> SEQUENCE: 285

Thr Thr Glu Ala Ile Leu Pro Glu Tyr
1               5

<210> SEQ ID NO 286
<211> LENGTH: 9
<212> TYPE: PRT
<213> ORGANISM: Dengue virus

<400> SEQUENCE: 286

Ser Val Glu Val Glu Leu Pro Asp Tyr
1               5

<210> SEQ ID NO 287
<211> LENGTH: 9
<212> TYPE: PRT
<213> ORGANISM: Dengue virus

<400> SEQUENCE: 287

Ser Val Glu Val Lys Leu Pro Asp Tyr
1               5

<210> SEQ ID NO 288
<211> LENGTH: 10
<212> TYPE: PRT
<213> ORGANISM: Dengue virus

<400> SEQUENCE: 288

Arg Ser Cys Thr Leu Pro Pro Leu Arg Tyr
1               5                   10

<210> SEQ ID NO 289
<211> LENGTH: 10
<212> TYPE: PRT
<213> ORGANISM: Dengue virus

<400> SEQUENCE: 289

Arg Ser Cys Thr Leu Pro Pro Leu Arg Phe
1               5                   10

<210> SEQ ID NO 290
<211> LENGTH: 10
<212> TYPE: PRT
<213> ORGANISM: Dengue virus
```

<400> SEQUENCE: 290

Arg Ser Cys Thr Leu Pro Pro Leu Arg Tyr
1               5                   10

<210> SEQ ID NO 291
<211> LENGTH: 10
<212> TYPE: PRT
<213> ORGANISM: Dengue virus

<400> SEQUENCE: 291

Arg Ser Cys Thr Leu Pro Pro Leu Arg Tyr
1               5                   10

<210> SEQ ID NO 292
<211> LENGTH: 10
<212> TYPE: PRT
<213> ORGANISM: Dengue virus

<400> SEQUENCE: 292

Arg Ser Cys Thr Met Pro Pro Leu Arg Phe
1               5                   10

<210> SEQ ID NO 293
<211> LENGTH: 9
<212> TYPE: PRT
<213> ORGANISM: Dengue virus

<400> SEQUENCE: 293

Met Thr Asp Asp Ile Gly Met Gly Val
1               5

<210> SEQ ID NO 294
<211> LENGTH: 9
<212> TYPE: PRT
<213> ORGANISM: Dengue virus

<400> SEQUENCE: 294

Ala Ser Asp Arg Met Gly Met Gly Met
1               5

<210> SEQ ID NO 295
<211> LENGTH: 9
<212> TYPE: PRT
<213> ORGANISM: Dengue virus

<400> SEQUENCE: 295

Ala Ser Asp Met Met Gly Met Gly Thr
1               5

<210> SEQ ID NO 296
<211> LENGTH: 9
<212> TYPE: PRT
<213> ORGANISM: Dengue virus

<400> SEQUENCE: 296

Ala Ser Asp Lys Met Gly Met Gly Thr
1               5

<210> SEQ ID NO 297
<211> LENGTH: 9
<212> TYPE: PRT
<213> ORGANISM: Dengue virus

<400> SEQUENCE: 297

Ala Ser Asp Asn Met Gly Met Gly Thr
1               5

<210> SEQ ID NO 298
<211> LENGTH: 9
<212> TYPE: PRT
<213> ORGANISM: Dengue virus

<400> SEQUENCE: 298

Val Ser Asp Arg Met Gly Met Gly Thr
1               5

<210> SEQ ID NO 299
<211> LENGTH: 9
<212> TYPE: PRT
<213> ORGANISM: Dengue virus

<400> SEQUENCE: 299

Ala Ser Asp Arg Met Gly Met Gly Thr
1               5

<210> SEQ ID NO 300
<211> LENGTH: 9
<212> TYPE: PRT
<213> ORGANISM: Dengue virus

<400> SEQUENCE: 300

Met Ala Asp Asp Ile Gly Met Gly Val
1               5

<210> SEQ ID NO 301
<211> LENGTH: 9
<212> TYPE: PRT
<213> ORGANISM: Dengue virus

<400> SEQUENCE: 301

Met Thr Asp Glu Met Gly Met Gly Val
1               5

<210> SEQ ID NO 302
<211> LENGTH: 9
<212> TYPE: PRT
<213> ORGANISM: Dengue virus

<400> SEQUENCE: 302

Ile Thr Asp Asp Ile Gly Met Gly Val
1               5

<210> SEQ ID NO 303
<211> LENGTH: 9
<212> TYPE: PRT
<213> ORGANISM: Dengue virus

<400> SEQUENCE: 303

Met Thr Asp Asp Ile Gly Met Gly Val
1               5

<210> SEQ ID NO 304
<211> LENGTH: 9
<212> TYPE: PRT
<213> ORGANISM: Dengue virus

<400> SEQUENCE: 304

Ala Ser Asp Arg Thr Gly Met Gly Val

```
1               5

<210> SEQ ID NO 305
<211> LENGTH: 9
<212> TYPE: PRT
<213> ORGANISM: Dengue virus

<400> SEQUENCE: 305

Ala Ser Asp Lys Met Gly Met Gly Val
1               5

<210> SEQ ID NO 306
<211> LENGTH: 9
<212> TYPE: PRT
<213> ORGANISM: Dengue virus

<400> SEQUENCE: 306

Ala Thr Asp Arg Met Gly Met Gly Val
1               5

<210> SEQ ID NO 307
<211> LENGTH: 9
<212> TYPE: PRT
<213> ORGANISM: Dengue virus

<400> SEQUENCE: 307

Ala Ser Asp Arg Met Gly Met Gly Val
1               5

<210> SEQ ID NO 308
<211> LENGTH: 9
<212> TYPE: PRT
<213> ORGANISM: Dengue virus

<400> SEQUENCE: 308

Leu Thr Asp Ala Leu Ala Leu Gly Met
1               5

<210> SEQ ID NO 309
<211> LENGTH: 9
<212> TYPE: PRT
<213> ORGANISM: Dengue virus

<400> SEQUENCE: 309

Leu Gly Asp Gly Leu Ala Ile Gly Ile
1               5

<210> SEQ ID NO 310
<211> LENGTH: 9
<212> TYPE: PRT
<213> ORGANISM: Dengue virus

<400> SEQUENCE: 310

Leu Gly Asp Gly Phe Ala Met Gly Ile
1               5

<210> SEQ ID NO 311
<211> LENGTH: 9
<212> TYPE: PRT
<213> ORGANISM: Dengue virus

<400> SEQUENCE: 311

Leu Gly Asp Gly Leu Ala Met Gly Ile
1               5
```

```
<210> SEQ ID NO 312
<211> LENGTH: 9
<212> TYPE: PRT
<213> ORGANISM: Dengue virus

<400> SEQUENCE: 312

Leu Thr Asp Ala Ile Ala Leu Gly Ile
1               5

<210> SEQ ID NO 313
<211> LENGTH: 9
<212> TYPE: PRT
<213> ORGANISM: Dengue virus

<400> SEQUENCE: 313

Leu Thr Asp Ala Trp Ala Leu Gly Met
1               5

<210> SEQ ID NO 314
<211> LENGTH: 9
<212> TYPE: PRT
<213> ORGANISM: Dengue virus

<400> SEQUENCE: 314

Leu Thr Asp Ala Leu Ala Leu Gly Ile
1               5

<210> SEQ ID NO 315
<211> LENGTH: 9
<212> TYPE: PRT
<213> ORGANISM: Dengue virus

<400> SEQUENCE: 315

Leu Thr Asp Ala Leu Ala Leu Gly Met
1               5

<210> SEQ ID NO 316
<211> LENGTH: 9
<212> TYPE: PRT
<213> ORGANISM: Dengue virus

<400> SEQUENCE: 316

Met Ala Asn Gly Val Ala Leu Gly Leu
1               5

<210> SEQ ID NO 317
<211> LENGTH: 9
<212> TYPE: PRT
<213> ORGANISM: Dengue virus

<400> SEQUENCE: 317

Met Ala Asn Gly Ile Ala Leu Gly Leu
1               5

<210> SEQ ID NO 318
<211> LENGTH: 9
<212> TYPE: PRT
<213> ORGANISM: Dengue virus

<400> SEQUENCE: 318

Leu Ile Ser Gly Ile Ser Leu Gly Leu
1               5

<210> SEQ ID NO 319
```

```
<211> LENGTH: 9
<212> TYPE: PRT
<213> ORGANISM: Dengue virus

<400> SEQUENCE: 319

Phe Ile Asp Gly Leu Ser Leu Gly Leu
1               5

<210> SEQ ID NO 320
<211> LENGTH: 9
<212> TYPE: PRT
<213> ORGANISM: Dengue virus

<400> SEQUENCE: 320

Leu Ile Asp Gly Ile Ser Leu Gly Leu
1               5

<210> SEQ ID NO 321
<211> LENGTH: 9
<212> TYPE: PRT
<213> ORGANISM: Dengue virus

<400> SEQUENCE: 321

Leu Ile Asp Gly Ile Ala Leu Gly Leu
1               5

<210> SEQ ID NO 322
<211> LENGTH: 9
<212> TYPE: PRT
<213> ORGANISM: Dengue virus

<400> SEQUENCE: 322

Phe Ile Asp Gly Ile Ser Leu Gly Leu
1               5

<210> SEQ ID NO 323
<211> LENGTH: 9
<212> TYPE: PRT
<213> ORGANISM: Dengue virus

<400> SEQUENCE: 323

Val Ile Asp Leu Asp Pro Ile Pro Tyr
1               5

<210> SEQ ID NO 324
<211> LENGTH: 9
<212> TYPE: PRT
<213> ORGANISM: Dengue virus

<400> SEQUENCE: 324

Thr Ile Asp Leu Asp Pro Val Val Tyr
1               5

<210> SEQ ID NO 325
<211> LENGTH: 9
<212> TYPE: PRT
<213> ORGANISM: Dengue virus

<400> SEQUENCE: 325

Ala Ile Asp Leu Asp Pro Val Val Tyr
1               5

<210> SEQ ID NO 326
<211> LENGTH: 9
<212> TYPE: PRT
```

<213> ORGANISM: Dengue virus

<400> SEQUENCE: 326

Val Ile Asp Leu Glu Pro Ile Pro Tyr
1               5

<210> SEQ ID NO 327
<211> LENGTH: 9
<212> TYPE: PRT
<213> ORGANISM: Dengue virus

<400> SEQUENCE: 327

Val Ile Asp Leu Asp Pro Ile Pro Tyr
1               5

<210> SEQ ID NO 328
<211> LENGTH: 9
<212> TYPE: PRT
<213> ORGANISM: Dengue virus

<400> SEQUENCE: 328

Thr Ile Asp Leu Asp Ser Val Ile Phe
1               5

<210> SEQ ID NO 329
<211> LENGTH: 9
<212> TYPE: PRT
<213> ORGANISM: Dengue virus

<400> SEQUENCE: 329

Thr Ile Asp Leu Asp Pro Val Ile Tyr
1               5

<210> SEQ ID NO 330
<211> LENGTH: 9
<212> TYPE: PRT
<213> ORGANISM: Dengue virus

<400> SEQUENCE: 330

Thr Ile Ala Leu Asp Pro Val Ile Tyr
1               5

<210> SEQ ID NO 331
<211> LENGTH: 9
<212> TYPE: PRT
<213> ORGANISM: Dengue virus

<400> SEQUENCE: 331

Val Ile Asp Leu Glu Pro Ile Ser Tyr
1               5

<210> SEQ ID NO 332
<211> LENGTH: 9
<212> TYPE: PRT
<213> ORGANISM: Dengue virus

<400> SEQUENCE: 332

Tyr Thr Asp Tyr Met Pro Ser Met Lys
1               5

<210> SEQ ID NO 333
<211> LENGTH: 9
<212> TYPE: PRT
<213> ORGANISM: Dengue virus

<400> SEQUENCE: 333

Tyr Ser Asp Tyr Met Thr Ser Met Lys
1               5

<210> SEQ ID NO 334
<211> LENGTH: 9
<212> TYPE: PRT
<213> ORGANISM: Dengue virus

<400> SEQUENCE: 334

Tyr Leu Asp Tyr Met Ala Ser Met Lys
1               5

<210> SEQ ID NO 335
<211> LENGTH: 9
<212> TYPE: PRT
<213> ORGANISM: Dengue virus

<400> SEQUENCE: 335

Tyr Ile Asp Tyr Met Thr Ser Met Lys
1               5

<210> SEQ ID NO 336
<211> LENGTH: 9
<212> TYPE: PRT
<213> ORGANISM: Dengue virus

<400> SEQUENCE: 336

Tyr Leu Asp Phe Met Thr Ser Met Lys
1               5

<210> SEQ ID NO 337
<211> LENGTH: 9
<212> TYPE: PRT
<213> ORGANISM: Dengue virus

<400> SEQUENCE: 337

Tyr Leu Asp Tyr Met Thr Ser Met Lys
1               5

<210> SEQ ID NO 338
<211> LENGTH: 9
<212> TYPE: PRT
<213> ORGANISM: Dengue virus

<400> SEQUENCE: 338

Tyr Leu Asp Tyr Met Ile Ser Met Lys
1               5

<210> SEQ ID NO 339
<211> LENGTH: 9
<212> TYPE: PRT
<213> ORGANISM: Dengue virus

<400> SEQUENCE: 339

Tyr Ile Asp Tyr Met Pro Ser Met Lys
1               5

<210> SEQ ID NO 340
<211> LENGTH: 9
<212> TYPE: PRT
<213> ORGANISM: Dengue virus

<400> SEQUENCE: 340

Tyr Met Asp Tyr Met Pro Ser Met Lys
1               5

<210> SEQ ID NO 341
<211> LENGTH: 9
<212> TYPE: PRT
<213> ORGANISM: Dengue virus

<400> SEQUENCE: 341

Tyr Thr Asp Tyr Met Pro Ser Met Lys
1               5

<210> SEQ ID NO 342
<211> LENGTH: 9
<212> TYPE: PRT
<213> ORGANISM: Dengue virus

<400> SEQUENCE: 342

Phe Leu Asp Tyr Met Pro Ser Met Lys
1               5

<210> SEQ ID NO 343
<211> LENGTH: 9
<212> TYPE: PRT
<213> ORGANISM: Dengue virus

<400> SEQUENCE: 343

Tyr Ala Asp Tyr Met Pro Val Met Lys
1               5

<210> SEQ ID NO 344
<211> LENGTH: 9
<212> TYPE: PRT
<213> ORGANISM: Dengue virus

<400> SEQUENCE: 344

Tyr Met Asp Tyr Met Pro Val Met Lys
1               5

<210> SEQ ID NO 345
<211> LENGTH: 9
<212> TYPE: PRT
<213> ORGANISM: Dengue virus

<400> SEQUENCE: 345

Tyr Val Asp Tyr Met Pro Ala Met Lys
1               5

<210> SEQ ID NO 346
<211> LENGTH: 9
<212> TYPE: PRT
<213> ORGANISM: Dengue virus

<400> SEQUENCE: 346

Tyr Val Asp Tyr Met Pro Val Met Arg
1               5

<210> SEQ ID NO 347
<211> LENGTH: 9
<212> TYPE: PRT
<213> ORGANISM: Dengue virus

<400> SEQUENCE: 347

Tyr Val Asp Tyr Met Pro Val Met Lys
1               5

<210> SEQ ID NO 348
<211> LENGTH: 9
<212> TYPE: PRT
<213> ORGANISM: Dengue virus

<400> SEQUENCE: 348

Arg Leu Ile Thr Val Asn Pro Ile Val
1               5

<210> SEQ ID NO 349
<211> LENGTH: 9
<212> TYPE: PRT
<213> ORGANISM: Dengue virus

<400> SEQUENCE: 349

Arg Val Ile Thr Ala Asn Pro Ile Val
1               5

<210> SEQ ID NO 350
<211> LENGTH: 9
<212> TYPE: PRT
<213> ORGANISM: Dengue virus

<400> SEQUENCE: 350

Arg Leu Val Thr Ala Asn Pro Ile Val
1               5

<210> SEQ ID NO 351
<211> LENGTH: 9
<212> TYPE: PRT
<213> ORGANISM: Dengue virus

<400> SEQUENCE: 351

Arg Leu Ile Thr Ala Asn Pro Ile Val
1               5

<210> SEQ ID NO 352
<211> LENGTH: 9
<212> TYPE: PRT
<213> ORGANISM: Dengue virus

<400> SEQUENCE: 352

Arg Leu Ile Thr Val Asn Pro Val Val
1               5

<210> SEQ ID NO 353
<211> LENGTH: 9
<212> TYPE: PRT
<213> ORGANISM: Dengue virus

<400> SEQUENCE: 353

Arg Leu Ile Thr Val Asn Pro Ile Ile
1               5

<210> SEQ ID NO 354
<211> LENGTH: 9
<212> TYPE: PRT
<213> ORGANISM: Dengue virus

<400> SEQUENCE: 354

Arg Leu Ile Thr Val Asn Pro Ile Val
1               5

```
<210> SEQ ID NO 355
<211> LENGTH: 9
<212> TYPE: PRT
<213> ORGANISM: Dengue virus

<400> SEQUENCE: 355

Arg Leu Thr Thr Val Asn Pro Ile Val
1               5

<210> SEQ ID NO 356
<211> LENGTH: 9
<212> TYPE: PRT
<213> ORGANISM: Dengue virus

<400> SEQUENCE: 356

Arg Leu Ile Thr Ala Asn Pro Ile Val
1               5

<210> SEQ ID NO 357
<211> LENGTH: 9
<212> TYPE: PRT
<213> ORGANISM: Dengue virus

<400> SEQUENCE: 357

Arg Leu Ile Thr Ala Asn Pro Val Val
1               5

<210> SEQ ID NO 358
<211> LENGTH: 9
<212> TYPE: PRT
<213> ORGANISM: Dengue virus

<400> SEQUENCE: 358

Arg Val Ile Ser Ala Thr Pro Leu Ala
1               5

<210> SEQ ID NO 359
<211> LENGTH: 9
<212> TYPE: PRT
<213> ORGANISM: Dengue virus

<400> SEQUENCE: 359

Arg Val Ile Ser Ser Thr Pro Leu Ala
1               5

<210> SEQ ID NO 360
<211> LENGTH: 9
<212> TYPE: PRT
<213> ORGANISM: Dengue virus

<400> SEQUENCE: 360

Arg Ile Ile Ser Ser Thr Pro Leu Ala
1               5

<210> SEQ ID NO 361
<211> LENGTH: 9
<212> TYPE: PRT
<213> ORGANISM: Dengue virus

<400> SEQUENCE: 361

Arg Val Ile Ser Ser Thr Pro Phe Ala
1               5

<210> SEQ ID NO 362
<211> LENGTH: 9
```

```
<212> TYPE: PRT
<213> ORGANISM: Dengue virus

<400> SEQUENCE: 362

Arg Ile Ile Ser Ser Thr Pro Phe Ala
1               5

<210> SEQ ID NO 363
<211> LENGTH: 9
<212> TYPE: PRT
<213> ORGANISM: Dengue virus

<400> SEQUENCE: 363

Arg Ile Ile Ser Ser Ile Pro Phe Ala
1               5

<210> SEQ ID NO 364
<211> LENGTH: 9
<212> TYPE: PRT
<213> ORGANISM: Dengue virus

<400> SEQUENCE: 364

Ile Met Ala Val Gly Met Val Ser Ile
1               5

<210> SEQ ID NO 365
<211> LENGTH: 9
<212> TYPE: PRT
<213> ORGANISM: Dengue virus

<400> SEQUENCE: 365

Ile Met Ala Val Gly Val Val Ser Ile
1               5

<210> SEQ ID NO 366
<211> LENGTH: 9
<212> TYPE: PRT
<213> ORGANISM: Dengue virus

<400> SEQUENCE: 366

Val Met Ala Val Gly Ile Val Ser Ile
1               5

<210> SEQ ID NO 367
<211> LENGTH: 9
<212> TYPE: PRT
<213> ORGANISM: Dengue virus

<400> SEQUENCE: 367

Ile Met Ala Ile Gly Ile Val Ser Ile
1               5

<210> SEQ ID NO 368
<211> LENGTH: 9
<212> TYPE: PRT
<213> ORGANISM: Dengue virus

<400> SEQUENCE: 368

Ile Met Ala Val Gly Ile Val Ser Ile
1               5

<210> SEQ ID NO 369
<211> LENGTH: 9
<212> TYPE: PRT
<213> ORGANISM: Dengue virus
```

-continued

<400> SEQUENCE: 369

Val Met Ala Val Gly Met Val Ser Ile
1               5

<210> SEQ ID NO 370
<211> LENGTH: 9
<212> TYPE: PRT
<213> ORGANISM: Dengue virus

<400> SEQUENCE: 370

Ile Met Ala Val Gly Met Val Ser Ile
1               5

<210> SEQ ID NO 371
<211> LENGTH: 9
<212> TYPE: PRT
<213> ORGANISM: Dengue virus

<400> SEQUENCE: 371

Val Met Ala Ile Gly Leu Val Ser Ile
1               5

<210> SEQ ID NO 372
<211> LENGTH: 9
<212> TYPE: PRT
<213> ORGANISM: Dengue virus

<400> SEQUENCE: 372

Val Met Ala Val Gly Leu Val Ser Ile
1               5

<210> SEQ ID NO 373
<211> LENGTH: 9
<212> TYPE: PRT
<213> ORGANISM: Dengue virus

<400> SEQUENCE: 373

Met Met Ala Val Gly Leu Val Ser Leu
1               5

<210> SEQ ID NO 374
<211> LENGTH: 9
<212> TYPE: PRT
<213> ORGANISM: Dengue virus

<400> SEQUENCE: 374

Ile Met Ala Val Gly Leu Val Ser Leu
1               5

<210> SEQ ID NO 375
<211> LENGTH: 9
<212> TYPE: PRT
<213> ORGANISM: Dengue virus

<400> SEQUENCE: 375

Gly Leu Leu Thr Val Cys Tyr Val Leu
1               5

<210> SEQ ID NO 376
<211> LENGTH: 9
<212> TYPE: PRT
<213> ORGANISM: Dengue virus

<400> SEQUENCE: 376

Gly Met Leu Ile Thr Cys Tyr Val Ile
1               5

<210> SEQ ID NO 377
<211> LENGTH: 9
<212> TYPE: PRT
<213> ORGANISM: Dengue virus

<400> SEQUENCE: 377

Gly Met Leu Ile Ala Cys Tyr Val Ile
1               5

<210> SEQ ID NO 378
<211> LENGTH: 9
<212> TYPE: PRT
<213> ORGANISM: Dengue virus

<400> SEQUENCE: 378

Gly Pro Leu Thr Val Cys Tyr Val Leu
1               5

<210> SEQ ID NO 379
<211> LENGTH: 9
<212> TYPE: PRT
<213> ORGANISM: Dengue virus

<400> SEQUENCE: 379

Gly Leu Leu Thr Val Cys Tyr Val Leu
1               5

<210> SEQ ID NO 380
<211> LENGTH: 9
<212> TYPE: PRT
<213> ORGANISM: Dengue virus

<400> SEQUENCE: 380

Gly Met Leu Ile Ala Cys Tyr Val Ile
1               5

<210> SEQ ID NO 381
<211> LENGTH: 9
<212> TYPE: PRT
<213> ORGANISM: Dengue virus

<400> SEQUENCE: 381

Gly Leu Leu Ile Ala Cys Tyr Val Ile
1               5

<210> SEQ ID NO 382
<211> LENGTH: 9
<212> TYPE: PRT
<213> ORGANISM: Dengue virus

<400> SEQUENCE: 382

Gly Leu Leu Leu Ala Ala Tyr Met Met
1               5

<210> SEQ ID NO 383
<211> LENGTH: 9
<212> TYPE: PRT
<213> ORGANISM: Dengue virus

<400> SEQUENCE: 383

Gly Leu Leu Leu Ala Ala Tyr Val Met

```
1               5
```

<210> SEQ ID NO 384
<211> LENGTH: 10
<212> TYPE: PRT
<213> ORGANISM: Dengue virus

<400> SEQUENCE: 384

```
Arg Ile Tyr Ser Asp Pro Leu Ala Leu Lys
1               5                   10
```

<210> SEQ ID NO 385
<211> LENGTH: 10
<212> TYPE: PRT
<213> ORGANISM: Dengue virus

<400> SEQUENCE: 385

```
Arg Thr Tyr Ser Asp Pro Gln Ala Leu Arg
1               5                   10
```

<210> SEQ ID NO 386
<211> LENGTH: 10
<212> TYPE: PRT
<213> ORGANISM: Dengue virus

<400> SEQUENCE: 386

```
Arg Thr Tyr Ser Asp Pro Leu Ala Leu Arg
1               5                   10
```

<210> SEQ ID NO 387
<211> LENGTH: 10
<212> TYPE: PRT
<213> ORGANISM: Dengue virus

<400> SEQUENCE: 387

```
Arg Thr Tyr Ser Asp Pro Leu Ala Leu Lys
1               5                   10
```

<210> SEQ ID NO 388
<211> LENGTH: 10
<212> TYPE: PRT
<213> ORGANISM: Dengue virus

<400> SEQUENCE: 388

```
Arg Ile Tyr Ser Asp Pro Leu Thr Leu Lys
1               5                   10
```

<210> SEQ ID NO 389
<211> LENGTH: 10
<212> TYPE: PRT
<213> ORGANISM: Dengue virus

<400> SEQUENCE: 389

```
Lys Ile Tyr Ser Asp Pro Leu Ala Leu Lys
1               5                   10
```

<210> SEQ ID NO 390
<211> LENGTH: 10
<212> TYPE: PRT
<213> ORGANISM: Dengue virus

<400> SEQUENCE: 390

```
Arg Ile Tyr Ser Glu Pro Arg Ala Leu Lys
1               5                   10
```

<210> SEQ ID NO 391
<211> LENGTH: 10
<212> TYPE: PRT
<213> ORGANISM: Dengue virus

<400> SEQUENCE: 391

Arg Ile Tyr Ser Asp Pro Leu Ala Leu Lys
1               5                   10

<210> SEQ ID NO 392
<211> LENGTH: 10
<212> TYPE: PRT
<213> ORGANISM: Dengue virus

<400> SEQUENCE: 392

Arg Thr Tyr Ser Asp Pro Leu Ala Pro Lys
1               5                   10

<210> SEQ ID NO 393
<211> LENGTH: 10
<212> TYPE: PRT
<213> ORGANISM: Dengue virus

<400> SEQUENCE: 393

Arg Thr Tyr Ser Asp Pro Leu Ala Leu Lys
1               5                   10

<210> SEQ ID NO 394
<211> LENGTH: 10
<212> TYPE: PRT
<213> ORGANISM: Dengue virus

<400> SEQUENCE: 394

Arg Ile Tyr Ser Asp Pro Leu Ala Leu Lys
1               5                   10

<210> SEQ ID NO 395
<211> LENGTH: 10
<212> TYPE: PRT
<213> ORGANISM: Dengue virus

<400> SEQUENCE: 395

Arg Val Tyr Ala Asp Pro Met Ala Leu Gln
1               5                   10

<210> SEQ ID NO 396
<211> LENGTH: 10
<212> TYPE: PRT
<213> ORGANISM: Dengue virus

<400> SEQUENCE: 396

Arg Val Tyr Ala Asp Pro Met Ala Leu Lys
1               5                   10

<210> SEQ ID NO 397
<211> LENGTH: 9
<212> TYPE: PRT
<213> ORGANISM: Dengue virus

<400> SEQUENCE: 397

Ala Thr Val Leu Met Gly Leu Gly Lys
1               5

<210> SEQ ID NO 398

```
<211> LENGTH: 9
<212> TYPE: PRT
<213> ORGANISM: Dengue virus

<400> SEQUENCE: 398

Ala Ala Ile Leu Met Gly Leu Asp Lys
1               5

<210> SEQ ID NO 399
<211> LENGTH: 9
<212> TYPE: PRT
<213> ORGANISM: Dengue virus

<400> SEQUENCE: 399

Ala Thr Val Leu Met Gly Leu Gly Lys
1               5

<210> SEQ ID NO 400
<211> LENGTH: 9
<212> TYPE: PRT
<213> ORGANISM: Dengue virus

<400> SEQUENCE: 400

Ala Thr Val Leu Met Gly Leu Gly Arg
1               5

<210> SEQ ID NO 401
<211> LENGTH: 9
<212> TYPE: PRT
<213> ORGANISM: Dengue virus

<400> SEQUENCE: 401

Ala Val Val Leu Met Gly Leu Asn Lys
1               5

<210> SEQ ID NO 402
<211> LENGTH: 9
<212> TYPE: PRT
<213> ORGANISM: Dengue virus

<400> SEQUENCE: 402

Ala Val Val Leu Met Gly Leu Asp Lys
1               5

<210> SEQ ID NO 403
<211> LENGTH: 9
<212> TYPE: PRT
<213> ORGANISM: Dengue virus

<400> SEQUENCE: 403

Ala Ala Val Leu Met Gly Leu Gly Lys
1               5

<210> SEQ ID NO 404
<211> LENGTH: 9
<212> TYPE: PRT
<213> ORGANISM: Dengue virus

<400> SEQUENCE: 404

Ser Thr Tyr Gly Trp Asn Leu Val Arg
1               5

<210> SEQ ID NO 405
<211> LENGTH: 9
<212> TYPE: PRT
```

<213> ORGANISM: Dengue virus

<400> SEQUENCE: 405

Ala Ala Tyr Gly Trp Asn Leu Val Lys
1               5

<210> SEQ ID NO 406
<211> LENGTH: 9
<212> TYPE: PRT
<213> ORGANISM: Dengue virus

<400> SEQUENCE: 406

Ala Thr Tyr Gly Trp Asn Leu Val Lys
1               5

<210> SEQ ID NO 407
<211> LENGTH: 9
<212> TYPE: PRT
<213> ORGANISM: Dengue virus

<400> SEQUENCE: 407

Ser Thr Tyr Gly Trp Asn Leu Val Arg
1               5

<210> SEQ ID NO 408
<211> LENGTH: 9
<212> TYPE: PRT
<213> ORGANISM: Dengue virus

<400> SEQUENCE: 408

Ser Thr Tyr Gly Trp Asn Leu Val Lys
1               5

<210> SEQ ID NO 409
<211> LENGTH: 9
<212> TYPE: PRT
<213> ORGANISM: Dengue virus

<400> SEQUENCE: 409

Ser Thr Tyr Gly Trp Asn Val Val Lys
1               5

<210> SEQ ID NO 410
<211> LENGTH: 9
<212> TYPE: PRT
<213> ORGANISM: Dengue virus

<400> SEQUENCE: 410

Ser Thr Tyr Gly Trp Asn Ile Val Lys
1               5

<210> SEQ ID NO 411
<211> LENGTH: 9
<212> TYPE: PRT
<213> ORGANISM: Dengue virus

<400> SEQUENCE: 411

Ala Thr Tyr Gly Trp Asn Leu Val Lys
1               5

<210> SEQ ID NO 412
<211> LENGTH: 9
<212> TYPE: PRT
<213> ORGANISM: Dengue virus

```
<400> SEQUENCE: 412

Thr Val Met Asp Ile Ile Ser Arg Arg
1               5

<210> SEQ ID NO 413
<211> LENGTH: 9
<212> TYPE: PRT
<213> ORGANISM: Dengue virus

<400> SEQUENCE: 413

Thr Val Met Asp Ile Ile Ser Arg Arg
1               5

<210> SEQ ID NO 414
<211> LENGTH: 9
<212> TYPE: PRT
<213> ORGANISM: Dengue virus

<400> SEQUENCE: 414

Thr Val Met Asp Val Ile Ser Arg Arg
1               5

<210> SEQ ID NO 415
<211> LENGTH: 9
<212> TYPE: PRT
<213> ORGANISM: Dengue virus

<400> SEQUENCE: 415

Thr Val Leu Asp Ile Ile Ser Arg Arg
1               5

<210> SEQ ID NO 416
<211> LENGTH: 9
<212> TYPE: PRT
<213> ORGANISM: Dengue virus

<400> SEQUENCE: 416

Thr Val Met Asp Ile Ile Ser Arg Lys
1               5

<210> SEQ ID NO 417
<211> LENGTH: 9
<212> TYPE: PRT
<213> ORGANISM: Dengue virus

<400> SEQUENCE: 417

Thr Val Met Asp Ile Ile Ser Arg Arg
1               5

<210> SEQ ID NO 418
<211> LENGTH: 9
<212> TYPE: PRT
<213> ORGANISM: Dengue virus

<400> SEQUENCE: 418

Thr Val Met Asp Ile Ile Ser Arg Lys
1               5

<210> SEQ ID NO 419
<211> LENGTH: 9
<212> TYPE: PRT
<213> ORGANISM: Dengue virus

<400> SEQUENCE: 419
```

```
Ala Val Met Asp Ile Ile Ser Arg Lys
1               5
```

<210> SEQ ID NO 420
<211> LENGTH: 10
<212> TYPE: PRT
<213> ORGANISM: Dengue virus

<400> SEQUENCE: 420

```
Arg Gln Met Glu Gly Glu Gly Val Phe Lys
1               5                   10
```

<210> SEQ ID NO 421
<211> LENGTH: 10
<212> TYPE: PRT
<213> ORGANISM: Dengue virus

<400> SEQUENCE: 421

```
Arg Gln Met Glu Ser Glu Glu Ile Phe Ser
1               5                   10
```

<210> SEQ ID NO 422
<211> LENGTH: 10
<212> TYPE: PRT
<213> ORGANISM: Dengue virus

<400> SEQUENCE: 422

```
Arg Gln Met Glu Ser Glu Gly Ile Val Ser
1               5                   10
```

<210> SEQ ID NO 423
<211> LENGTH: 10
<212> TYPE: PRT
<213> ORGANISM: Dengue virus

<400> SEQUENCE: 423

```
Arg Gln Met Glu Ser Glu Gly Ile Phe Phe
1               5                   10
```

<210> SEQ ID NO 424
<211> LENGTH: 10
<212> TYPE: PRT
<213> ORGANISM: Dengue virus

<400> SEQUENCE: 424

```
Arg Gln Met Glu Ser Glu Gly Ile Ile Leu
1               5                   10
```

<210> SEQ ID NO 425
<211> LENGTH: 10
<212> TYPE: PRT
<213> ORGANISM: Dengue virus

<400> SEQUENCE: 425

```
Arg Gln Met Glu Ser Glu Gly Ile Phe Ser
1               5                   10
```

<210> SEQ ID NO 426
<211> LENGTH: 10
<212> TYPE: PRT
<213> ORGANISM: Dengue virus

<400> SEQUENCE: 426

```
Arg Gln Met Glu Ser Glu Gly Ile Phe Leu
1               5                   10
```

<210> SEQ ID NO 427
<211> LENGTH: 10
<212> TYPE: PRT
<213> ORGANISM: Dengue virus

<400> SEQUENCE: 427

Arg Gln Met Glu Gly Glu Gly Val Phe Arg
1               5                   10

<210> SEQ ID NO 428
<211> LENGTH: 10
<212> TYPE: PRT
<213> ORGANISM: Dengue virus

<400> SEQUENCE: 428

Arg Gln Met Glu Gly Glu Gly Ile Phe Arg
1               5                   10

<210> SEQ ID NO 429
<211> LENGTH: 10
<212> TYPE: PRT
<213> ORGANISM: Dengue virus

<400> SEQUENCE: 429

Arg Gln Met Glu Gly Glu Gly Leu Phe Lys
1               5                   10

<210> SEQ ID NO 430
<211> LENGTH: 10
<212> TYPE: PRT
<213> ORGANISM: Dengue virus

<400> SEQUENCE: 430

Arg Gln Met Glu Gly Glu Gly Val Phe Lys
1               5                   10

<210> SEQ ID NO 431
<211> LENGTH: 10
<212> TYPE: PRT
<213> ORGANISM: Dengue virus

<400> SEQUENCE: 431

Arg Gln Met Glu Gly Glu Gly Val Phe Lys
1               5                   10

<210> SEQ ID NO 432
<211> LENGTH: 10
<212> TYPE: PRT
<213> ORGANISM: Dengue virus

<400> SEQUENCE: 432

Arg Gln Met Glu Gly Glu Gly Ile Phe Lys
1               5                   10

<210> SEQ ID NO 433
<211> LENGTH: 10
<212> TYPE: PRT
<213> ORGANISM: Dengue virus

<400> SEQUENCE: 433

Arg Gln Met Glu Gly Glu Gly Val Leu Thr
1               5                   10

```
<210> SEQ ID NO 434
<211> LENGTH: 10
<212> TYPE: PRT
<213> ORGANISM: Dengue virus

<400> SEQUENCE: 434

Arg Gln Met Glu Gly Glu Gly Val Leu Ser
1               5                   10

<210> SEQ ID NO 435
<211> LENGTH: 10
<212> TYPE: PRT
<213> ORGANISM: Dengue virus

<400> SEQUENCE: 435

Arg Gln Met Glu Gly Glu Asp Val Leu Ser
1               5                   10

<210> SEQ ID NO 436
<211> LENGTH: 10
<212> TYPE: PRT
<213> ORGANISM: Dengue virus

<400> SEQUENCE: 436

Arg Gln Met Glu Ala Glu Gly Val Ile Thr
1               5                   10

<210> SEQ ID NO 437
<211> LENGTH: 9
<212> TYPE: PRT
<213> ORGANISM: Dengue virus

<400> SEQUENCE: 437

Arg Thr Thr Trp Ser Ile His Ala Lys
1               5

<210> SEQ ID NO 438
<211> LENGTH: 9
<212> TYPE: PRT
<213> ORGANISM: Dengue virus

<400> SEQUENCE: 438

Arg Thr Thr Trp Ser Ile His Ala His
1               5

<210> SEQ ID NO 439
<211> LENGTH: 9
<212> TYPE: PRT
<213> ORGANISM: Dengue virus

<400> SEQUENCE: 439

Arg Thr Thr Trp Ser Ile His Ala Arg
1               5

<210> SEQ ID NO 440
<211> LENGTH: 9
<212> TYPE: PRT
<213> ORGANISM: Dengue virus

<400> SEQUENCE: 440

Arg Thr Thr Trp Ser Ile His Ala Thr
1               5

<210> SEQ ID NO 441
<211> LENGTH: 9
```

<212> TYPE: PRT
<213> ORGANISM: Dengue virus

<400> SEQUENCE: 441

Arg Thr Thr Trp Ser Ile His Ala Ser
1               5

<210> SEQ ID NO 442
<211> LENGTH: 9
<212> TYPE: PRT
<213> ORGANISM: Dengue virus

<400> SEQUENCE: 442

Arg Thr Thr Trp Ser Ile His Ala Lys
1               5

<210> SEQ ID NO 443
<211> LENGTH: 9
<212> TYPE: PRT
<213> ORGANISM: Dengue virus

<400> SEQUENCE: 443

Arg Thr Thr Trp Ser Ile His Ala His
1               5

<210> SEQ ID NO 444
<211> LENGTH: 9
<212> TYPE: PRT
<213> ORGANISM: Dengue virus

<400> SEQUENCE: 444

Arg Thr Thr Trp Ser Ile His Ala His
1               5

<210> SEQ ID NO 445
<211> LENGTH: 10
<212> TYPE: PRT
<213> ORGANISM: Dengue virus

<400> SEQUENCE: 445

Arg Pro Thr Phe Ala Ala Gly Leu Leu Leu
1               5                   10

<210> SEQ ID NO 446
<211> LENGTH: 10
<212> TYPE: PRT
<213> ORGANISM: Dengue virus

<400> SEQUENCE: 446

Arg Pro Met Leu Ala Val Gly Leu Leu Phe
1               5                   10

<210> SEQ ID NO 447
<211> LENGTH: 10
<212> TYPE: PRT
<213> ORGANISM: Dengue virus

<400> SEQUENCE: 447

Arg Pro Met Phe Ala Met Gly Leu Leu Phe
1               5                   10

<210> SEQ ID NO 448
<211> LENGTH: 10
<212> TYPE: PRT
<213> ORGANISM: Dengue virus

<400> SEQUENCE: 448

Arg Pro Met Phe Ala Val Gly Leu Leu Ile
1               5                   10

<210> SEQ ID NO 449
<211> LENGTH: 10
<212> TYPE: PRT
<213> ORGANISM: Dengue virus

<400> SEQUENCE: 449

Arg Pro Met Phe Ala Val Gly Leu Leu Phe
1               5                   10

<210> SEQ ID NO 450
<211> LENGTH: 10
<212> TYPE: PRT
<213> ORGANISM: Dengue virus

<400> SEQUENCE: 450

Arg Pro Thr Phe Ala Ala Gly Leu Phe Leu
1               5                   10

<210> SEQ ID NO 451
<211> LENGTH: 10
<212> TYPE: PRT
<213> ORGANISM: Dengue virus

<400> SEQUENCE: 451

Arg Pro Thr Phe Ala Val Gly Leu Val Leu
1               5                   10

<210> SEQ ID NO 452
<211> LENGTH: 10
<212> TYPE: PRT
<213> ORGANISM: Dengue virus

<400> SEQUENCE: 452

Arg Pro Thr Phe Ala Val Gly Leu Leu Leu
1               5                   10

<210> SEQ ID NO 453
<211> LENGTH: 10
<212> TYPE: PRT
<213> ORGANISM: Dengue virus

<400> SEQUENCE: 453

Arg Pro Thr Phe Ala Ala Gly Leu Leu Leu
1               5                   10

<210> SEQ ID NO 454
<211> LENGTH: 10
<212> TYPE: PRT
<213> ORGANISM: Dengue virus

<400> SEQUENCE: 454

Gln Pro Phe Leu Ala Leu Gly Phe Phe Met
1               5                   10

<210> SEQ ID NO 455
<211> LENGTH: 10
<212> TYPE: PRT
<213> ORGANISM: Dengue virus

<400> SEQUENCE: 455

```
Gln Pro Phe Leu Thr Leu Gly Phe Phe Leu
1               5                   10

<210> SEQ ID NO 456
<211> LENGTH: 10
<212> TYPE: PRT
<213> ORGANISM: Dengue virus

<400> SEQUENCE: 456

Gln Pro Phe Leu Ala Leu Gly Phe Phe Leu
1               5                   10

<210> SEQ ID NO 457
<211> LENGTH: 10
<212> TYPE: PRT
<213> ORGANISM: Dengue virus

<400> SEQUENCE: 457

Ser Pro Arg Tyr Val Leu Gly Val Phe Leu
1               5                   10

<210> SEQ ID NO 458
<211> LENGTH: 10
<212> TYPE: PRT
<213> ORGANISM: Dengue virus

<400> SEQUENCE: 458

Ser Pro Gly Tyr Val Leu Gly Val Phe Leu
1               5                   10

<210> SEQ ID NO 459
<211> LENGTH: 10
<212> TYPE: PRT
<213> ORGANISM: Dengue virus

<400> SEQUENCE: 459

Ser Pro Gly Tyr Val Leu Gly Ile Phe Leu
1               5                   10

<210> SEQ ID NO 460
<211> LENGTH: 9
<212> TYPE: PRT
<213> ORGANISM: Dengue virus

<400> SEQUENCE: 460

Leu Pro Ala Ile Val Arg Glu Ala Ile
1               5

<210> SEQ ID NO 461
<211> LENGTH: 9
<212> TYPE: PRT
<213> ORGANISM: Dengue virus

<400> SEQUENCE: 461

Leu Pro Ala Ile Ile Arg Glu Ala Ile
1               5

<210> SEQ ID NO 462
<211> LENGTH: 9
<212> TYPE: PRT
<213> ORGANISM: Dengue virus

<400> SEQUENCE: 462

Leu Pro Ala Ile Val Arg Glu Ala Ile
```

```
<210> SEQ ID NO 463
<211> LENGTH: 9
<212> TYPE: PRT
<213> ORGANISM: Dengue virus

<400> SEQUENCE: 463

Leu Pro Ala Met Val Arg Glu Ala Ile
1               5

<210> SEQ ID NO 464
<211> LENGTH: 9
<212> TYPE: PRT
<213> ORGANISM: Dengue virus

<400> SEQUENCE: 464

Leu Pro Ala Ile Val Arg Glu Ala Ile
1               5

<210> SEQ ID NO 465
<211> LENGTH: 9
<212> TYPE: PRT
<213> ORGANISM: Dengue virus

<400> SEQUENCE: 465

Leu Pro Thr Ile Val Arg Glu Ala Ile
1               5

<210> SEQ ID NO 466
<211> LENGTH: 9
<212> TYPE: PRT
<213> ORGANISM: Dengue virus

<400> SEQUENCE: 466

Leu Pro Ala Val Val Arg Glu Ala Ile
1               5

<210> SEQ ID NO 467
<211> LENGTH: 9
<212> TYPE: PRT
<213> ORGANISM: Dengue virus

<400> SEQUENCE: 467

Leu Pro Ala Ile Val Arg Glu Ala Ile
1               5

<210> SEQ ID NO 468
<211> LENGTH: 9
<212> TYPE: PRT
<213> ORGANISM: Dengue virus

<400> SEQUENCE: 468

Leu Pro Ala Ile Ile Arg Glu Ala Ile
1               5

<210> SEQ ID NO 469
<211> LENGTH: 9
<212> TYPE: PRT
<213> ORGANISM: Dengue virus

<400> SEQUENCE: 469

Leu Pro Ser Ile Val Arg Glu Ala Leu
1               5
```

<210> SEQ ID NO 470
<211> LENGTH: 10
<212> TYPE: PRT
<213> ORGANISM: Dengue virus

<400> SEQUENCE: 470

Ala Pro Thr Arg Val Val Ala Ala Glu Met
1 5 10

<210> SEQ ID NO 471
<211> LENGTH: 10
<212> TYPE: PRT
<213> ORGANISM: Dengue virus

<400> SEQUENCE: 471

Ala Pro Thr Arg Val Val Ala Ser Glu Thr
1 5 10

<210> SEQ ID NO 472
<211> LENGTH: 10
<212> TYPE: PRT
<213> ORGANISM: Dengue virus

<400> SEQUENCE: 472

Ala Pro Thr Arg Val Val Ala Ala Glu Met
1 5 10

<210> SEQ ID NO 473
<211> LENGTH: 10
<212> TYPE: PRT
<213> ORGANISM: Dengue virus

<400> SEQUENCE: 473

Ala Pro Thr Arg Val Val Ala Ser Glu Met
1 5 10

<210> SEQ ID NO 474
<211> LENGTH: 10
<212> TYPE: PRT
<213> ORGANISM: Dengue virus

<400> SEQUENCE: 474

Ala Pro Pro Arg Val Val Pro Ala Glu Met
1 5 10

<210> SEQ ID NO 475
<211> LENGTH: 10
<212> TYPE: PRT
<213> ORGANISM: Dengue virus

<400> SEQUENCE: 475

Ala Pro Thr Arg Val Val Ala Ala Glu Met
1 5 10

<210> SEQ ID NO 476
<211> LENGTH: 10
<212> TYPE: PRT
<213> ORGANISM: Dengue virus

<400> SEQUENCE: 476

Ala Pro Thr Arg Val Val Ala Ala Glu Met
1 5 10

<210> SEQ ID NO 477

```
<211> LENGTH: 10
<212> TYPE: PRT
<213> ORGANISM: Dengue virus

<400> SEQUENCE: 477

Ala Pro Thr Arg Val Val Ala Ala Glu Met
1               5                   10

<210> SEQ ID NO 478
<211> LENGTH: 9
<212> TYPE: PRT
<213> ORGANISM: Dengue virus

<400> SEQUENCE: 478

Val Pro Asn Tyr Asn Leu Ile Ile Met
1               5

<210> SEQ ID NO 479
<211> LENGTH: 9
<212> TYPE: PRT
<213> ORGANISM: Dengue virus

<400> SEQUENCE: 479

Val Pro Asn Tyr Asn Met Ile Ile Val
1               5

<210> SEQ ID NO 480
<211> LENGTH: 9
<212> TYPE: PRT
<213> ORGANISM: Dengue virus

<400> SEQUENCE: 480

Val Pro Asn Tyr Asn Met Ile Ile Met
1               5

<210> SEQ ID NO 481
<211> LENGTH: 9
<212> TYPE: PRT
<213> ORGANISM: Dengue virus

<400> SEQUENCE: 481

Val Pro Asn Tyr Asn Met Ile Val Met
1               5

<210> SEQ ID NO 482
<211> LENGTH: 9
<212> TYPE: PRT
<213> ORGANISM: Dengue virus

<400> SEQUENCE: 482

Val Pro Asn Tyr Asn Leu Ile Ile Met
1               5

<210> SEQ ID NO 483
<211> LENGTH: 9
<212> TYPE: PRT
<213> ORGANISM: Dengue virus

<400> SEQUENCE: 483

Val Pro Asn Tyr Asn Leu Ile Val Met
1               5

<210> SEQ ID NO 484
<211> LENGTH: 9
<212> TYPE: PRT
```

<213> ORGANISM: Dengue virus

<400> SEQUENCE: 484

Val Pro Asn Tyr Asn Leu Val Val Met
1 5

<210> SEQ ID NO 485
<211> LENGTH: 9
<212> TYPE: PRT
<213> ORGANISM: Dengue virus

<400> SEQUENCE: 485

Val Pro Asn Tyr Asn Leu Val Ile Met
1 5

<210> SEQ ID NO 486
<211> LENGTH: 9
<212> TYPE: PRT
<213> ORGANISM: Dengue virus

<400> SEQUENCE: 486

Val Ser Asn Tyr Asn Leu Ile Ile Met
1 5

<210> SEQ ID NO 487
<211> LENGTH: 9
<212> TYPE: PRT
<213> ORGANISM: Dengue virus

<400> SEQUENCE: 487

Val Pro Asn Tyr Asn Leu Ile Ile Met
1 5

<210> SEQ ID NO 488
<211> LENGTH: 9
<212> TYPE: PRT
<213> ORGANISM: Dengue virus

<400> SEQUENCE: 488

Val Pro Asn Tyr Asn Leu Ile Val Met
1 5

<210> SEQ ID NO 489
<211> LENGTH: 10
<212> TYPE: PRT
<213> ORGANISM: Dengue virus

<400> SEQUENCE: 489

Ala Pro Ile Met Asp Glu Glu Arg Glu Ile
1 5 10

<210> SEQ ID NO 490
<211> LENGTH: 10
<212> TYPE: PRT
<213> ORGANISM: Dengue virus

<400> SEQUENCE: 490

Ala Ile Ile Gln Asp Glu Glu Arg Asp Ile
1 5 10

<210> SEQ ID NO 491
<211> LENGTH: 10
<212> TYPE: PRT
<213> ORGANISM: Dengue virus

```
<400> SEQUENCE: 491

Ala Val Ile Gln Asp Glu Glu Lys Asp Ile
1               5                   10

<210> SEQ ID NO 492
<211> LENGTH: 10
<212> TYPE: PRT
<213> ORGANISM: Dengue virus

<400> SEQUENCE: 492

Ala Ala Ile Gln Asp Glu Glu Arg Asp Ile
1               5                   10

<210> SEQ ID NO 493
<211> LENGTH: 10
<212> TYPE: PRT
<213> ORGANISM: Dengue virus

<400> SEQUENCE: 493

Ala Val Ile Gln Asp Glu Glu Arg Asp Ile
1               5                   10

<210> SEQ ID NO 494
<211> LENGTH: 10
<212> TYPE: PRT
<213> ORGANISM: Dengue virus

<400> SEQUENCE: 494

Ala Pro Ile Met Asp Asp Glu Arg Glu Ile
1               5                   10

<210> SEQ ID NO 495
<211> LENGTH: 10
<212> TYPE: PRT
<213> ORGANISM: Dengue virus

<400> SEQUENCE: 495

Ala Pro Ile Ile Asp Glu Glu Arg Glu Ile
1               5                   10

<210> SEQ ID NO 496
<211> LENGTH: 10
<212> TYPE: PRT
<213> ORGANISM: Dengue virus

<400> SEQUENCE: 496

Ala Pro Ile Val Asp Glu Glu Arg Glu Ile
1               5                   10

<210> SEQ ID NO 497
<211> LENGTH: 10
<212> TYPE: PRT
<213> ORGANISM: Dengue virus

<400> SEQUENCE: 497

Ala Pro Ile Met Asp Glu Glu Arg Glu Ile
1               5                   10

<210> SEQ ID NO 498
<211> LENGTH: 10
<212> TYPE: PRT
<213> ORGANISM: Dengue virus

<400> SEQUENCE: 498
```

Ala Pro Ile Gln Asp Glu Glu Lys Asp Ile
1               5                   10

<210> SEQ ID NO 499
<211> LENGTH: 10
<212> TYPE: PRT
<213> ORGANISM: Dengue virus

<400> SEQUENCE: 499

Ser Pro Ile Gln Asp Glu Glu Arg Asp Ile
1               5                   10

<210> SEQ ID NO 500
<211> LENGTH: 10
<212> TYPE: PRT
<213> ORGANISM: Dengue virus

<400> SEQUENCE: 500

Ala Pro Ile Gln Asp Glu Glu Arg Asp Ile
1               5                   10

<210> SEQ ID NO 501
<211> LENGTH: 10
<212> TYPE: PRT
<213> ORGANISM: Dengue virus

<400> SEQUENCE: 501

Ala Pro Ile Gln Asp Lys Glu Arg Asp Ile
1               5                   10

<210> SEQ ID NO 502
<211> LENGTH: 10
<212> TYPE: PRT
<213> ORGANISM: Dengue virus

<400> SEQUENCE: 502

Ser Pro Ile Glu Asp Ile Glu Arg Glu Ile
1               5                   10

<210> SEQ ID NO 503
<211> LENGTH: 10
<212> TYPE: PRT
<213> ORGANISM: Dengue virus

<400> SEQUENCE: 503

Thr Pro Glu Gly Ile Ile Pro Ser Met Phe
1               5                   10

<210> SEQ ID NO 504
<211> LENGTH: 10
<212> TYPE: PRT
<213> ORGANISM: Dengue virus

<400> SEQUENCE: 504

Thr Pro Glu Gly Ile Ile Pro Ala Leu Tyr
1               5                   10

<210> SEQ ID NO 505
<211> LENGTH: 10
<212> TYPE: PRT
<213> ORGANISM: Dengue virus

<400> SEQUENCE: 505

Thr Pro Glu Gly Ile Ile Pro Ala Leu Phe
1               5                   10

```
<210> SEQ ID NO 506
<211> LENGTH: 10
<212> TYPE: PRT
<213> ORGANISM: Dengue virus

<400> SEQUENCE: 506

Thr Pro Glu Gly Ile Ile Pro Ser Leu Phe
1               5                   10

<210> SEQ ID NO 507
<211> LENGTH: 10
<212> TYPE: PRT
<213> ORGANISM: Dengue virus

<400> SEQUENCE: 507

Thr Pro Glu Gly Ile Ile Pro Ser Met Phe
1               5                   10

<210> SEQ ID NO 508
<211> LENGTH: 10
<212> TYPE: PRT
<213> ORGANISM: Dengue virus

<400> SEQUENCE: 508

Thr Pro Glu Gly Ile Ile Pro Ala Leu Phe
1               5                   10

<210> SEQ ID NO 509
<211> LENGTH: 10
<212> TYPE: PRT
<213> ORGANISM: Dengue virus

<400> SEQUENCE: 509

Thr Pro Glu Gly Ile Ile Pro Thr Leu Phe
1               5                   10

<210> SEQ ID NO 510
<211> LENGTH: 10
<212> TYPE: PRT
<213> ORGANISM: Dengue virus

<400> SEQUENCE: 510

Leu Leu Val Ile Ser Gly Leu Phe Pro Val
1               5                   10

<210> SEQ ID NO 511
<211> LENGTH: 10
<212> TYPE: PRT
<213> ORGANISM: Dengue virus

<400> SEQUENCE: 511

Leu Leu Ala Ile Ser Gly Val Tyr Pro Leu
1               5                   10

<210> SEQ ID NO 512
<211> LENGTH: 10
<212> TYPE: PRT
<213> ORGANISM: Dengue virus

<400> SEQUENCE: 512

Leu Leu Ala Val Ser Gly Met Tyr Pro Leu
1               5                   10
```

```
<210> SEQ ID NO 513
<211> LENGTH: 10
<212> TYPE: PRT
<213> ORGANISM: Dengue virus

<400> SEQUENCE: 513

Leu Leu Ala Val Ser Gly Val Tyr Pro Leu
1               5                   10

<210> SEQ ID NO 514
<211> LENGTH: 10
<212> TYPE: PRT
<213> ORGANISM: Dengue virus

<400> SEQUENCE: 514

Leu Leu Val Ile Ser Gly Val Tyr Pro Met
1               5                   10

<210> SEQ ID NO 515
<211> LENGTH: 10
<212> TYPE: PRT
<213> ORGANISM: Dengue virus

<400> SEQUENCE: 515

Leu Leu Ala Val Ser Gly Val Tyr Pro Ile
1               5                   10

<210> SEQ ID NO 516
<211> LENGTH: 10
<212> TYPE: PRT
<213> ORGANISM: Dengue virus

<400> SEQUENCE: 516

Leu Leu Ala Ala Ser Gly Val Tyr Pro Met
1               5                   10

<210> SEQ ID NO 517
<211> LENGTH: 10
<212> TYPE: PRT
<213> ORGANISM: Dengue virus

<400> SEQUENCE: 517

Leu Leu Ala Ile Ser Gly Val Tyr Pro Met
1               5                   10

<210> SEQ ID NO 518
<211> LENGTH: 10
<212> TYPE: PRT
<213> ORGANISM: Dengue virus

<400> SEQUENCE: 518

Leu Leu Ala Val Ser Gly Val Tyr Pro Met
1               5                   10

<210> SEQ ID NO 519
<211> LENGTH: 10
<212> TYPE: PRT
<213> ORGANISM: Dengue virus

<400> SEQUENCE: 519

Leu Leu Val Val Ser Gly Leu Phe Pro Val
1               5                   10

<210> SEQ ID NO 520
<211> LENGTH: 10
```

<212> TYPE: PRT
<213> ORGANISM: Dengue virus

<400> SEQUENCE: 520

Leu Leu Val Ile Ser Gly Leu Phe Pro Ala
1 5 10

<210> SEQ ID NO 521
<211> LENGTH: 10
<212> TYPE: PRT
<213> ORGANISM: Dengue virus

<400> SEQUENCE: 521

Leu Leu Val Ile Ser Gly Leu Phe Pro Ile
1 5 10

<210> SEQ ID NO 522
<211> LENGTH: 10
<212> TYPE: PRT
<213> ORGANISM: Dengue virus

<400> SEQUENCE: 522

Leu Leu Val Ile Ser Gly Val Phe Pro Val
1 5 10

<210> SEQ ID NO 523
<211> LENGTH: 10
<212> TYPE: PRT
<213> ORGANISM: Dengue virus

<400> SEQUENCE: 523

Leu Leu Val Ile Ser Gly Leu Phe Pro Val
1 5 10

<210> SEQ ID NO 524
<211> LENGTH: 10
<212> TYPE: PRT
<213> ORGANISM: Dengue virus

<400> SEQUENCE: 524

Leu Leu Ile Val Ser Gly Ile Phe Pro Cys
1 5 10

<210> SEQ ID NO 525
<211> LENGTH: 10
<212> TYPE: PRT
<213> ORGANISM: Dengue virus

<400> SEQUENCE: 525

Leu Leu Ile Val Ser Gly Ile Phe Pro Tyr
1 5 10

<210> SEQ ID NO 526
<211> LENGTH: 10
<212> TYPE: PRT
<213> ORGANISM: Dengue virus

<400> SEQUENCE: 526

Leu Leu Ile Val Ser Gly Val Phe Pro Tyr
1 5 10

<210> SEQ ID NO 527
<211> LENGTH: 10
<212> TYPE: PRT
<213> ORGANISM: Dengue virus

```
<400> SEQUENCE: 527

Leu Ile Thr Val Ser Gly Leu Tyr Pro Leu
1               5                   10

<210> SEQ ID NO 528
<211> LENGTH: 9
<212> TYPE: PRT
<213> ORGANISM: Dengue virus

<400> SEQUENCE: 528

Ala Ala Ala Trp Tyr Leu Trp Glu Val
1               5

<210> SEQ ID NO 529
<211> LENGTH: 9
<212> TYPE: PRT
<213> ORGANISM: Dengue virus

<400> SEQUENCE: 529

Leu Phe Val Trp Cys Phe Trp Gln Lys
1               5

<210> SEQ ID NO 530
<211> LENGTH: 9
<212> TYPE: PRT
<213> ORGANISM: Dengue virus

<400> SEQUENCE: 530

Leu Phe Leu Trp Tyr Phe Trp Gln Lys
1               5

<210> SEQ ID NO 531
<211> LENGTH: 9
<212> TYPE: PRT
<213> ORGANISM: Dengue virus

<400> SEQUENCE: 531

Leu Phe Val Trp His Phe Trp Gln Lys
1               5

<210> SEQ ID NO 532
<211> LENGTH: 9
<212> TYPE: PRT
<213> ORGANISM: Dengue virus

<400> SEQUENCE: 532

Phe Phe Val Trp Tyr Phe Trp Gln Lys
1               5

<210> SEQ ID NO 533
<211> LENGTH: 9
<212> TYPE: PRT
<213> ORGANISM: Dengue virus

<400> SEQUENCE: 533

Pro Phe Val Trp Tyr Phe Trp Gln Lys
1               5

<210> SEQ ID NO 534
<211> LENGTH: 9
<212> TYPE: PRT
<213> ORGANISM: Dengue virus

<400> SEQUENCE: 534
```

```
Leu Phe Val Trp Tyr Phe Trp Gln Lys
1               5

<210> SEQ ID NO 535
<211> LENGTH: 9
<212> TYPE: PRT
<213> ORGANISM: Dengue virus

<400> SEQUENCE: 535

Ala Ala Ala Trp Tyr Leu Trp Glu Thr
1               5

<210> SEQ ID NO 536
<211> LENGTH: 9
<212> TYPE: PRT
<213> ORGANISM: Dengue virus

<400> SEQUENCE: 536

Ala Ala Ala Trp Tyr Leu Trp Glu Ala
1               5

<210> SEQ ID NO 537
<211> LENGTH: 9
<212> TYPE: PRT
<213> ORGANISM: Dengue virus

<400> SEQUENCE: 537

Ala Ala Ala Trp Tyr Leu Trp Glu Val
1               5

<210> SEQ ID NO 538
<211> LENGTH: 9
<212> TYPE: PRT
<213> ORGANISM: Dengue virus

<400> SEQUENCE: 538

Leu Leu Val Trp His Ala Trp Gln Lys
1               5

<210> SEQ ID NO 539
<211> LENGTH: 9
<212> TYPE: PRT
<213> ORGANISM: Dengue virus

<400> SEQUENCE: 539

Met Leu Val Trp His Thr Trp Gln Lys
1               5

<210> SEQ ID NO 540
<211> LENGTH: 9
<212> TYPE: PRT
<213> ORGANISM: Dengue virus

<400> SEQUENCE: 540

Leu Leu Val Trp His Thr Trp Gln Lys
1               5

<210> SEQ ID NO 541
<211> LENGTH: 9
<212> TYPE: PRT
<213> ORGANISM: Dengue virus

<400> SEQUENCE: 541

Met Ala Leu Trp Tyr Ile Trp Gln Val
```

<210> SEQ ID NO 542
<211> LENGTH: 9
<212> TYPE: PRT
<213> ORGANISM: Dengue virus

<400> SEQUENCE: 542

Met Thr Leu Trp Tyr Met Trp Gln Val
1               5

<210> SEQ ID NO 543
<211> LENGTH: 9
<212> TYPE: PRT
<213> ORGANISM: Dengue virus

<400> SEQUENCE: 543

Met Ala Leu Trp Tyr Met Trp Gln Val
1               5

<210> SEQ ID NO 544
<211> LENGTH: 9
<212> TYPE: PRT
<213> ORGANISM: Dengue virus

<400> SEQUENCE: 544

Tyr Leu Pro Ala Ile Val Arg Glu Ala
1               5

<210> SEQ ID NO 545
<211> LENGTH: 9
<212> TYPE: PRT
<213> ORGANISM: Dengue virus

<400> SEQUENCE: 545

Tyr Leu Pro Ala Ile Ile Arg Glu Ala
1               5

<210> SEQ ID NO 546
<211> LENGTH: 9
<212> TYPE: PRT
<213> ORGANISM: Dengue virus

<400> SEQUENCE: 546

Tyr Leu Pro Ala Ile Val Arg Glu Ala
1               5

<210> SEQ ID NO 547
<211> LENGTH: 9
<212> TYPE: PRT
<213> ORGANISM: Dengue virus

<400> SEQUENCE: 547

Tyr Leu Pro Ala Met Val Arg Glu Ala
1               5

<210> SEQ ID NO 548
<211> LENGTH: 9
<212> TYPE: PRT
<213> ORGANISM: Dengue virus

<400> SEQUENCE: 548

Ser Leu Pro Ala Ile Val Arg Glu Ala
1               5

```
<210> SEQ ID NO 549
<211> LENGTH: 9
<212> TYPE: PRT
<213> ORGANISM: Dengue virus

<400> SEQUENCE: 549

Tyr Leu Pro Ala Ile Val Arg Glu Ala
1               5

<210> SEQ ID NO 550
<211> LENGTH: 9
<212> TYPE: PRT
<213> ORGANISM: Dengue virus

<400> SEQUENCE: 550

Tyr Leu Pro Thr Ile Val Arg Glu Ala
1               5

<210> SEQ ID NO 551
<211> LENGTH: 9
<212> TYPE: PRT
<213> ORGANISM: Dengue virus

<400> SEQUENCE: 551

Tyr Leu Pro Ala Val Val Arg Glu Ala
1               5

<210> SEQ ID NO 552
<211> LENGTH: 9
<212> TYPE: PRT
<213> ORGANISM: Dengue virus

<400> SEQUENCE: 552

Tyr Leu Pro Ala Ile Val Arg Glu Ala
1               5

<210> SEQ ID NO 553
<211> LENGTH: 9
<212> TYPE: PRT
<213> ORGANISM: Dengue virus

<400> SEQUENCE: 553

Tyr Leu Pro Ala Ile Ile Arg Glu Ala
1               5

<210> SEQ ID NO 554
<211> LENGTH: 9
<212> TYPE: PRT
<213> ORGANISM: Dengue virus

<400> SEQUENCE: 554

Ile Leu Pro Ser Ile Val Arg Glu Ala
1               5

<210> SEQ ID NO 555
<211> LENGTH: 10
<212> TYPE: PRT
<213> ORGANISM: Dengue virus

<400> SEQUENCE: 555

Asp Leu Met Arg Arg Gly Asp Leu Pro Val
1               5                   10

<210> SEQ ID NO 556
```

```
<211> LENGTH: 10
<212> TYPE: PRT
<213> ORGANISM: Dengue virus

<400> SEQUENCE: 556

Asp Leu Leu Arg Arg Gly Asp Leu Pro Val
1               5                   10

<210> SEQ ID NO 557
<211> LENGTH: 10
<212> TYPE: PRT
<213> ORGANISM: Dengue virus

<400> SEQUENCE: 557

Glu Leu Met Arg Arg Gly Asp Leu Pro Val
1               5                   10

<210> SEQ ID NO 558
<211> LENGTH: 10
<212> TYPE: PRT
<213> ORGANISM: Dengue virus

<400> SEQUENCE: 558

Asp Leu Met Lys Arg Gly Asp Leu Pro Val
1               5                   10

<210> SEQ ID NO 559
<211> LENGTH: 10
<212> TYPE: PRT
<213> ORGANISM: Dengue virus

<400> SEQUENCE: 559

Glu Leu Met Arg Arg Gly Asp Leu Pro Val
1               5                   10

<210> SEQ ID NO 560
<211> LENGTH: 10
<212> TYPE: PRT
<213> ORGANISM: Dengue virus

<400> SEQUENCE: 560

Asp Leu Met Arg Arg Gly Asp Leu Pro Val
1               5                   10

<210> SEQ ID NO 561
<211> LENGTH: 10
<212> TYPE: PRT
<213> ORGANISM: Dengue virus

<400> SEQUENCE: 561

Glu Leu Met Arg Arg Gly His Leu Pro Val
1               5                   10

<210> SEQ ID NO 562
<211> LENGTH: 10
<212> TYPE: PRT
<213> ORGANISM: Dengue virus

<400> SEQUENCE: 562

Glu Leu Met Arg Arg Gly Asp Leu Pro Val
1               5                   10

<210> SEQ ID NO 563
<211> LENGTH: 10
<212> TYPE: PRT
```

<213> ORGANISM: Dengue virus

<400> SEQUENCE: 563

Glu Leu Met Lys Arg Gly Asp Leu Pro Val
1 5 10

<210> SEQ ID NO 564
<211> LENGTH: 10
<212> TYPE: PRT
<213> ORGANISM: Dengue virus

<400> SEQUENCE: 564

Glu Leu Met Arg Arg Gly Asp Leu Pro Val
1 5 10

<210> SEQ ID NO 565
<211> LENGTH: 9
<212> TYPE: PRT
<213> ORGANISM: Dengue virus

<400> SEQUENCE: 565

Ala Leu Ser Glu Leu Pro Glu Thr Leu
1 5

<210> SEQ ID NO 566
<211> LENGTH: 9
<212> TYPE: PRT
<213> ORGANISM: Dengue virus

<400> SEQUENCE: 566

Ala Leu Glu Glu Leu Pro Asp Thr Ile
1 5

<210> SEQ ID NO 567
<211> LENGTH: 9
<212> TYPE: PRT
<213> ORGANISM: Dengue virus

<400> SEQUENCE: 567

Ala Val Glu Glu Leu Pro Asp Thr Ile
1 5

<210> SEQ ID NO 568
<211> LENGTH: 9
<212> TYPE: PRT
<213> ORGANISM: Dengue virus

<400> SEQUENCE: 568

Ala Met Glu Glu Leu Pro Asp Thr Ile
1 5

<210> SEQ ID NO 569
<211> LENGTH: 9
<212> TYPE: PRT
<213> ORGANISM: Dengue virus

<400> SEQUENCE: 569

Ala Leu Ser Glu Leu Ala Glu Thr Leu
1 5

<210> SEQ ID NO 570
<211> LENGTH: 9
<212> TYPE: PRT
<213> ORGANISM: Dengue virus -continued

```
<400> SEQUENCE: 570

Ala Leu Gly Glu Leu Pro Glu Thr Leu
1               5

<210> SEQ ID NO 571
<211> LENGTH: 9
<212> TYPE: PRT
<213> ORGANISM: Dengue virus

<400> SEQUENCE: 571

Ala Leu Ser Glu Leu Pro Glu Thr Leu
1               5

<210> SEQ ID NO 572
<211> LENGTH: 9
<212> TYPE: PRT
<213> ORGANISM: Dengue virus

<400> SEQUENCE: 572

Ala Val Glu Glu Leu Pro Glu Thr Met
1               5

<210> SEQ ID NO 573
<211> LENGTH: 9
<212> TYPE: PRT
<213> ORGANISM: Dengue virus

<400> SEQUENCE: 573

Ala Leu Asn Glu Leu Thr Glu Ser Leu
1               5

<210> SEQ ID NO 574
<211> LENGTH: 9
<212> TYPE: PRT
<213> ORGANISM: Dengue virus

<400> SEQUENCE: 574

Ala Leu Asn Glu Leu Pro Glu Ser Leu
1               5

<210> SEQ ID NO 575
<211> LENGTH: 9
<212> TYPE: PRT
<213> ORGANISM: Dengue virus

<400> SEQUENCE: 575

Ile Ile Leu Glu Phe Phe Leu Ile Val
1               5

<210> SEQ ID NO 576
<211> LENGTH: 9
<212> TYPE: PRT
<213> ORGANISM: Dengue virus

<400> SEQUENCE: 576

Ile Ile Leu Lys Phe Phe Leu Met Val
1               5

<210> SEQ ID NO 577
<211> LENGTH: 9
<212> TYPE: PRT
<213> ORGANISM: Dengue virus

<400> SEQUENCE: 577
```

Ile Ile Leu Glu Phe Leu Leu Met Val
1               5

<210> SEQ ID NO 578
<211> LENGTH: 9
<212> TYPE: PRT
<213> ORGANISM: Dengue virus

<400> SEQUENCE: 578

Ile Met Leu Glu Phe Phe Leu Met Val
1               5

<210> SEQ ID NO 579
<211> LENGTH: 9
<212> TYPE: PRT
<213> ORGANISM: Dengue virus

<400> SEQUENCE: 579

Ile Ile Leu Glu Phe Phe Leu Met Val
1               5

<210> SEQ ID NO 580
<211> LENGTH: 9
<212> TYPE: PRT
<213> ORGANISM: Dengue virus

<400> SEQUENCE: 580

Ile Ile Leu Glu Phe Phe Leu Met Val
1               5

<210> SEQ ID NO 581
<211> LENGTH: 9
<212> TYPE: PRT
<213> ORGANISM: Dengue virus

<400> SEQUENCE: 581

Ile Ile Leu Glu Phe Phe Leu Ile Val
1               5

<210> SEQ ID NO 582
<211> LENGTH: 9
<212> TYPE: PRT
<213> ORGANISM: Dengue virus

<400> SEQUENCE: 582

Ile Ile Leu Glu Phe Phe Met Met Val
1               5

<210> SEQ ID NO 583
<211> LENGTH: 9
<212> TYPE: PRT
<213> ORGANISM: Dengue virus

<400> SEQUENCE: 583

Ile Val Leu Glu Phe Phe Met Met Val
1               5

<210> SEQ ID NO 584
<211> LENGTH: 9
<212> TYPE: PRT
<213> ORGANISM: Dengue virus

<400> SEQUENCE: 584

Ile Ile Leu Glu Phe Phe Leu Met Val
1               5

<210> SEQ ID NO 585
<211> LENGTH: 9
<212> TYPE: PRT
<213> ORGANISM: Dengue virus

<400> SEQUENCE: 585

Lys Leu Ala Glu Ala Ile Phe Lys Leu
1               5

<210> SEQ ID NO 586
<211> LENGTH: 9
<212> TYPE: PRT
<213> ORGANISM: Dengue virus

<400> SEQUENCE: 586

Leu Leu Ala Lys Ala Ile Phe Lys Leu
1               5

<210> SEQ ID NO 587
<211> LENGTH: 9
<212> TYPE: PRT
<213> ORGANISM: Dengue virus

<400> SEQUENCE: 587

Gln Leu Ala Lys Ser Ile Phe Lys Leu
1               5

<210> SEQ ID NO 588
<211> LENGTH: 9
<212> TYPE: PRT
<213> ORGANISM: Dengue virus

<400> SEQUENCE: 588

Leu Leu Ala Thr Ser Val Phe Lys Leu
1               5

<210> SEQ ID NO 589
<211> LENGTH: 9
<212> TYPE: PRT
<213> ORGANISM: Dengue virus

<400> SEQUENCE: 589

Leu Leu Ala Lys Ser Ile Phe Lys Leu
1               5

<210> SEQ ID NO 590
<211> LENGTH: 9
<212> TYPE: PRT
<213> ORGANISM: Dengue virus

<400> SEQUENCE: 590

Leu Leu Ala Thr Ala Ile Phe Lys Leu
1               5

<210> SEQ ID NO 591
<211> LENGTH: 9
<212> TYPE: PRT
<213> ORGANISM: Dengue virus

<400> SEQUENCE: 591

Leu Leu Ala Thr Ser Ile Phe Lys Leu
1               5

```
<210> SEQ ID NO 592
<211> LENGTH: 9
<212> TYPE: PRT
<213> ORGANISM: Dengue virus

<400> SEQUENCE: 592

Leu Leu Ala Ser Ser Ile Phe Lys Leu
1               5

<210> SEQ ID NO 593
<211> LENGTH: 9
<212> TYPE: PRT
<213> ORGANISM: Dengue virus

<400> SEQUENCE: 593

Lys Leu Ala Glu Ala Ile Phe Arg Leu
1               5

<210> SEQ ID NO 594
<211> LENGTH: 9
<212> TYPE: PRT
<213> ORGANISM: Dengue virus

<400> SEQUENCE: 594

Arg Leu Ala Glu Ala Ile Phe Lys Leu
1               5

<210> SEQ ID NO 595
<211> LENGTH: 9
<212> TYPE: PRT
<213> ORGANISM: Dengue virus

<400> SEQUENCE: 595

Lys Leu Ala Glu Ala Val Phe Lys Leu
1               5

<210> SEQ ID NO 596
<211> LENGTH: 9
<212> TYPE: PRT
<213> ORGANISM: Dengue virus

<400> SEQUENCE: 596

Lys Leu Ala Glu Ala Ile Phe Lys Leu
1               5

<210> SEQ ID NO 597
<211> LENGTH: 9
<212> TYPE: PRT
<213> ORGANISM: Dengue virus

<400> SEQUENCE: 597

Gln Leu Ala Ser Ala Ile Phe Lys Leu
1               5

<210> SEQ ID NO 598
<211> LENGTH: 9
<212> TYPE: PRT
<213> ORGANISM: Dengue virus

<400> SEQUENCE: 598

Leu Leu Ala Asn Ala Ile Phe Lys Leu
1               5

<210> SEQ ID NO 599
<211> LENGTH: 9
```

```
<212> TYPE: PRT
<213> ORGANISM: Dengue virus

<400> SEQUENCE: 599

Arg Leu Ala Asn Ala Ile Phe Lys Leu
1               5

<210> SEQ ID NO 600
<211> LENGTH: 9
<212> TYPE: PRT
<213> ORGANISM: Dengue virus

<400> SEQUENCE: 600

Gln Leu Ala Asn Ala Ile Phe Lys Leu
1               5

<210> SEQ ID NO 601
<211> LENGTH: 9
<212> TYPE: PRT
<213> ORGANISM: Dengue virus

<400> SEQUENCE: 601

Thr Leu Ala Lys Ala Ile Phe Lys Leu
1               5

<210> SEQ ID NO 602
<211> LENGTH: 9
<212> TYPE: PRT
<213> ORGANISM: Dengue virus

<400> SEQUENCE: 602

Ile Leu Ala Lys Ala Ile Phe Lys Leu
1               5

<210> SEQ ID NO 603
<211> LENGTH: 9
<212> TYPE: PRT
<213> ORGANISM: Dengue virus

<400> SEQUENCE: 603

Ser Gln Ile Gly Ala Gly Val Tyr Lys
1               5

<210> SEQ ID NO 604
<211> LENGTH: 9
<212> TYPE: PRT
<213> ORGANISM: Dengue virus

<400> SEQUENCE: 604

Ser Gln Val Gly Val Gly Val Phe Gln
1               5

<210> SEQ ID NO 605
<211> LENGTH: 9
<212> TYPE: PRT
<213> ORGANISM: Dengue virus

<400> SEQUENCE: 605

Ser Gln Ile Gly Ala Gly Val Tyr Arg
1               5

<210> SEQ ID NO 606
<211> LENGTH: 9
<212> TYPE: PRT
<213> ORGANISM: Dengue virus
```

<400> SEQUENCE: 606

Ser Gln Ile Gly Thr Gly Val Tyr Lys
1               5

<210> SEQ ID NO 607
<211> LENGTH: 9
<212> TYPE: PRT
<213> ORGANISM: Dengue virus

<400> SEQUENCE: 607

Ser Gln Ile Gly Val Gly Val Tyr Lys
1               5

<210> SEQ ID NO 608
<211> LENGTH: 9
<212> TYPE: PRT
<213> ORGANISM: Dengue virus

<400> SEQUENCE: 608

Ser Gln Ile Gly Ala Gly Val Tyr Lys
1               5

<210> SEQ ID NO 609
<211> LENGTH: 9
<212> TYPE: PRT
<213> ORGANISM: Dengue virus

<400> SEQUENCE: 609

Thr Gln Val Gly Val Gly Ile Gln Lys
1               5

<210> SEQ ID NO 610
<211> LENGTH: 9
<212> TYPE: PRT
<213> ORGANISM: Dengue virus

<400> SEQUENCE: 610

Thr Gln Val Gly Val Gly Val His Lys
1               5

<210> SEQ ID NO 611
<211> LENGTH: 9
<212> TYPE: PRT
<213> ORGANISM: Dengue virus

<400> SEQUENCE: 611

Thr Gln Val Gly Val Gly Val Gln Lys
1               5

<210> SEQ ID NO 612
<211> LENGTH: 9
<212> TYPE: PRT
<213> ORGANISM: Dengue virus

<400> SEQUENCE: 612

Thr Gln Val Gly Val Gly Ile His Ile
1               5

<210> SEQ ID NO 613
<211> LENGTH: 9
<212> TYPE: PRT
<213> ORGANISM: Dengue virus

<400> SEQUENCE: 613

Thr Gln Val Gly Val Gly Ile His Thr
1               5

<210> SEQ ID NO 614
<211> LENGTH: 9
<212> TYPE: PRT
<213> ORGANISM: Dengue virus

<400> SEQUENCE: 614

Thr Gln Val Gly Val Gly Ile His Met
1               5

<210> SEQ ID NO 615
<211> LENGTH: 9
<212> TYPE: PRT
<213> ORGANISM: Dengue virus

<400> SEQUENCE: 615

Thr Gln Val Gly Val Gly Val His Val
1               5

<210> SEQ ID NO 616
<211> LENGTH: 10
<212> TYPE: PRT
<213> ORGANISM: Dengue virus

<400> SEQUENCE: 616

Gly Thr Ser Gly Ser Pro Ile Ile Asp Lys
1               5                   10

<210> SEQ ID NO 617
<211> LENGTH: 10
<212> TYPE: PRT
<213> ORGANISM: Dengue virus

<400> SEQUENCE: 617

Gly Thr Ser Gly Ser Pro Ile Val Ser Arg
1               5                   10

<210> SEQ ID NO 618
<211> LENGTH: 10
<212> TYPE: PRT
<213> ORGANISM: Dengue virus

<400> SEQUENCE: 618

Gly Thr Ser Gly Ser Pro Ile Val Asn Arg
1               5                   10

<210> SEQ ID NO 619
<211> LENGTH: 10
<212> TYPE: PRT
<213> ORGANISM: Dengue virus

<400> SEQUENCE: 619

Gly Thr Ser Gly Ser Pro Ile Ile Asp Lys
1               5                   10

<210> SEQ ID NO 620
<211> LENGTH: 10
<212> TYPE: PRT
<213> ORGANISM: Dengue virus

<400> SEQUENCE: 620

Gly Thr Ser Gly Ser Pro Ile Ala Asp Lys

```
1               5                  10
```

<210> SEQ ID NO 621
<211> LENGTH: 10
<212> TYPE: PRT
<213> ORGANISM: Dengue virus

<400> SEQUENCE: 621

```
Gly Thr Ser Gly Ser Pro Ile Val Asp Arg
1               5                  10
```

<210> SEQ ID NO 622
<211> LENGTH: 10
<212> TYPE: PRT
<213> ORGANISM: Dengue virus

<400> SEQUENCE: 622

```
Gly Thr Ser Gly Ser Pro Ile Val Asp Lys
1               5                  10
```

<210> SEQ ID NO 623
<211> LENGTH: 10
<212> TYPE: PRT
<213> ORGANISM: Dengue virus

<400> SEQUENCE: 623

```
Gly Thr Ser Gly Ser Pro Ile Ile Asn Lys
1               5                  10
```

<210> SEQ ID NO 624
<211> LENGTH: 10
<212> TYPE: PRT
<213> ORGANISM: Dengue virus

<400> SEQUENCE: 624

```
Gly Thr Ser Gly Ser Pro Ile Ile Asn Arg
1               5                  10
```

<210> SEQ ID NO 625
<211> LENGTH: 10
<212> TYPE: PRT
<213> ORGANISM: Dengue virus

<400> SEQUENCE: 625

```
Gly Ser Ser Gly Ser Pro Ile Ile Asn Arg
1               5                  10
```

<210> SEQ ID NO 626
<211> LENGTH: 10
<212> TYPE: PRT
<213> ORGANISM: Dengue virus

<400> SEQUENCE: 626

```
Gly Thr Ser Gly Ser Pro Ile Val Asn Arg
1               5                  10
```

<210> SEQ ID NO 627
<211> LENGTH: 10
<212> TYPE: PRT
<213> ORGANISM: Dengue virus

<400> SEQUENCE: 627

```
Gly Thr Ser Gly Ser Pro Ile Ile Asn Lys
1               5                  10
```

<210> SEQ ID NO 628
<211> LENGTH: 10
<212> TYPE: PRT
<213> ORGANISM: Dengue virus

<400> SEQUENCE: 628

Gly Thr Ser Gly Ser Pro Ile Ile Asn Arg
1               5                   10

<210> SEQ ID NO 629
<211> LENGTH: 9
<212> TYPE: PRT
<213> ORGANISM: Dengue virus

<400> SEQUENCE: 629

Lys Thr Phe Asp Ser Glu Tyr Val Lys
1               5

<210> SEQ ID NO 630
<211> LENGTH: 9
<212> TYPE: PRT
<213> ORGANISM: Dengue virus

<400> SEQUENCE: 630

Lys Thr Phe Asp Thr Glu Tyr Gln Lys
1               5

<210> SEQ ID NO 631
<211> LENGTH: 9
<212> TYPE: PRT
<213> ORGANISM: Dengue virus

<400> SEQUENCE: 631

Lys Thr Phe Asp Thr Glu Tyr Thr Lys
1               5

<210> SEQ ID NO 632
<211> LENGTH: 9
<212> TYPE: PRT
<213> ORGANISM: Dengue virus

<400> SEQUENCE: 632

Lys Thr Phe Asp Thr Glu Tyr Ile Lys
1               5

<210> SEQ ID NO 633
<211> LENGTH: 9
<212> TYPE: PRT
<213> ORGANISM: Dengue virus

<400> SEQUENCE: 633

Lys Thr Phe Asp Phe Glu Tyr Ile Lys
1               5

<210> SEQ ID NO 634
<211> LENGTH: 9
<212> TYPE: PRT
<213> ORGANISM: Dengue virus

<400> SEQUENCE: 634

Lys Thr Phe Asp Ser Glu Tyr Ile Lys
1               5

<210> SEQ ID NO 635

```
<211> LENGTH: 9
<212> TYPE: PRT
<213> ORGANISM: Dengue virus

<400> SEQUENCE: 635

Lys Thr Phe Asp Ser Glu Tyr Ala Lys
1 5

<210> SEQ ID NO 636
<211> LENGTH: 9
<212> TYPE: PRT
<213> ORGANISM: Dengue virus

<400> SEQUENCE: 636

Lys Thr Phe Asp Ser Glu Tyr Val Lys
1 5

<210> SEQ ID NO 637
<211> LENGTH: 9
<212> TYPE: PRT
<213> ORGANISM: Dengue virus

<400> SEQUENCE: 637

Lys Thr Phe Asp Thr Glu Tyr Gln Arg
1 5

<210> SEQ ID NO 638
<211> LENGTH: 9
<212> TYPE: PRT
<213> ORGANISM: Dengue virus

<400> SEQUENCE: 638

Lys Thr Phe Asn Thr Glu Tyr Gln Lys
1 5

<210> SEQ ID NO 639
<211> LENGTH: 9
<212> TYPE: PRT
<213> ORGANISM: Dengue virus

<400> SEQUENCE: 639

Lys Thr Phe Asp Thr Glu Tyr Gln Lys
1 5

<210> SEQ ID NO 640
<211> LENGTH: 9
<212> TYPE: PRT
<213> ORGANISM: Dengue virus

<400> SEQUENCE: 640

Lys Thr Phe Asp Thr Glu Tyr Pro Lys
1 5

<210> SEQ ID NO 641
<211> LENGTH: 9
<212> TYPE: PRT
<213> ORGANISM: Dengue virus

<400> SEQUENCE: 641

Lys Pro Arg Trp Leu Asp Ala Arg Ile
1 5

<210> SEQ ID NO 642
<211> LENGTH: 9
<212> TYPE: PRT

<213> ORGANISM: Dengue virus

<400> SEQUENCE: 642

Arg Pro Arg Trp Leu Asp Ala Arg Thr
1               5

<210> SEQ ID NO 643
<211> LENGTH: 9
<212> TYPE: PRT
<213> ORGANISM: Dengue virus

<400> SEQUENCE: 643

Lys Pro Arg Trp Leu Asp Ala Arg Thr
1               5

<210> SEQ ID NO 644
<211> LENGTH: 9
<212> TYPE: PRT
<213> ORGANISM: Dengue virus

<400> SEQUENCE: 644

Lys Pro Arg Trp Leu Asp Ala Lys Ile
1               5

<210> SEQ ID NO 645
<211> LENGTH: 9
<212> TYPE: PRT
<213> ORGANISM: Dengue virus

<400> SEQUENCE: 645

Lys Pro Arg Trp Leu Asp Pro Arg Ile
1               5

<210> SEQ ID NO 646
<211> LENGTH: 9
<212> TYPE: PRT
<213> ORGANISM: Dengue virus

<400> SEQUENCE: 646

Lys Pro Arg Trp Leu Asp Ala Arg Ile
1               5

<210> SEQ ID NO 647
<211> LENGTH: 9
<212> TYPE: PRT
<213> ORGANISM: Dengue virus

<400> SEQUENCE: 647

Arg Pro Arg Trp Leu Asp Ala Arg Thr
1               5

<210> SEQ ID NO 648
<211> LENGTH: 9
<212> TYPE: PRT
<213> ORGANISM: Dengue virus

<400> SEQUENCE: 648

Arg Pro Arg Trp Leu Asp Ala Arg Ile
1               5

<210> SEQ ID NO 649
<211> LENGTH: 9
<212> TYPE: PRT
<213> ORGANISM: Dengue virus

<400> SEQUENCE: 649

Arg Pro Arg Trp Leu Asp Ala Arg Val
1               5

<210> SEQ ID NO 650
<211> LENGTH: 9
<212> TYPE: PRT
<213> ORGANISM: Dengue virus

<400> SEQUENCE: 650

Arg Pro Lys Trp Leu Asp Ala Arg Val
1               5

<210> SEQ ID NO 651
<211> LENGTH: 10
<212> TYPE: PRT
<213> ORGANISM: Dengue virus

<400> SEQUENCE: 651

Arg Pro Ala Ser Ala Trp Thr Leu Tyr Ala
1               5                   10

<210> SEQ ID NO 652
<211> LENGTH: 10
<212> TYPE: PRT
<213> ORGANISM: Dengue virus

<400> SEQUENCE: 652

His Pro Ala Ser Ala Trp Thr Leu Tyr Ala
1               5                   10

<210> SEQ ID NO 653
<211> LENGTH: 10
<212> TYPE: PRT
<213> ORGANISM: Dengue virus

<400> SEQUENCE: 653

Arg Pro Ala Ser Ala Trp Thr Leu Tyr Ala
1               5                   10

<210> SEQ ID NO 654
<211> LENGTH: 10
<212> TYPE: PRT
<213> ORGANISM: Dengue virus

<400> SEQUENCE: 654

Arg Pro Ala Ser Ala Trp Thr Leu Tyr Ala
1               5                   10

<210> SEQ ID NO 655
<211> LENGTH: 10
<212> TYPE: PRT
<213> ORGANISM: Dengue virus

<400> SEQUENCE: 655

His Pro Ala Ser Ala Trp Ile Leu Tyr Ala
1               5                   10

<210> SEQ ID NO 656
<211> LENGTH: 10
<212> TYPE: PRT
<213> ORGANISM: Dengue virus

<400> SEQUENCE: 656

His Pro Ala Ser Ala Trp Thr Leu Tyr Ala
1               5                   10

<210> SEQ ID NO 657
<211> LENGTH: 10
<212> TYPE: PRT
<213> ORGANISM: Dengue virus

<400> SEQUENCE: 657

Arg Pro Ala Ser Ala Trp Thr Leu Tyr Ala
1               5                   10

<210> SEQ ID NO 658
<211> LENGTH: 8
<212> TYPE: PRT
<213> ORGANISM: Dengue virus

<400> SEQUENCE: 658

Thr Pro Met Leu Arg His Ser Ile
1               5

<210> SEQ ID NO 659
<211> LENGTH: 8
<212> TYPE: PRT
<213> ORGANISM: Dengue virus

<400> SEQUENCE: 659

Thr Pro Met Leu Arg His Thr Ile
1               5

<210> SEQ ID NO 660
<211> LENGTH: 8
<212> TYPE: PRT
<213> ORGANISM: Dengue virus

<400> SEQUENCE: 660

Thr Pro Met Met Arg His Thr Ile
1               5

<210> SEQ ID NO 661
<211> LENGTH: 8
<212> TYPE: PRT
<213> ORGANISM: Dengue virus

<400> SEQUENCE: 661

Thr Pro Met Leu Arg His Ser Ile
1               5

<210> SEQ ID NO 662
<211> LENGTH: 8
<212> TYPE: PRT
<213> ORGANISM: Dengue virus

<400> SEQUENCE: 662

Thr Pro Met Leu Arg His Thr Ile
1               5

<210> SEQ ID NO 663
<211> LENGTH: 8
<212> TYPE: PRT
<213> ORGANISM: Dengue virus

<400> SEQUENCE: 663

Thr Pro Met Leu Arg His Thr Ile
1               5

<210> SEQ ID NO 664
<211> LENGTH: 10
<212> TYPE: PRT
<213> ORGANISM: Dengue virus

<400> SEQUENCE: 664

Ser Pro Asn Pro Thr Val Glu Ala Gly Arg
1               5                   10

<210> SEQ ID NO 665
<211> LENGTH: 10
<212> TYPE: PRT
<213> ORGANISM: Dengue virus

<400> SEQUENCE: 665

Ser Pro Asn Pro Thr Ile Glu Glu Gly Arg
1               5                   10

<210> SEQ ID NO 666
<211> LENGTH: 10
<212> TYPE: PRT
<213> ORGANISM: Dengue virus

<400> SEQUENCE: 666

Ser Pro Ser Pro Thr Val Glu Ala Gly Arg
1               5                   10

<210> SEQ ID NO 667
<211> LENGTH: 10
<212> TYPE: PRT
<213> ORGANISM: Dengue virus

<400> SEQUENCE: 667

Ser Pro Asn Pro Thr Val Asp Ala Gly Arg
1               5                   10

<210> SEQ ID NO 668
<211> LENGTH: 10
<212> TYPE: PRT
<213> ORGANISM: Dengue virus

<400> SEQUENCE: 668

Ser Pro Asn Pro Thr Val Glu Ala Gly Pro
1               5                   10

<210> SEQ ID NO 669
<211> LENGTH: 10
<212> TYPE: PRT
<213> ORGANISM: Dengue virus

<400> SEQUENCE: 669

Ser Pro Asn Pro Thr Ile Glu Ala Gly Arg
1               5                   10

<210> SEQ ID NO 670
<211> LENGTH: 10
<212> TYPE: PRT
<213> ORGANISM: Dengue virus

<400> SEQUENCE: 670

Ser Pro Asn Pro Thr Val Glu Ala Gly Arg
1               5                   10

```
<210> SEQ ID NO 671
<211> LENGTH: 10
<212> TYPE: PRT
<213> ORGANISM: Dengue virus

<400> SEQUENCE: 671

Ser Pro Ser Pro Thr Val Glu Glu Gly Arg
1               5                   10

<210> SEQ ID NO 672
<211> LENGTH: 10
<212> TYPE: PRT
<213> ORGANISM: Dengue virus

<400> SEQUENCE: 672

Ser Pro Ser Leu Thr Val Glu Glu Ser Arg
1               5                   10

<210> SEQ ID NO 673
<211> LENGTH: 10
<212> TYPE: PRT
<213> ORGANISM: Dengue virus

<400> SEQUENCE: 673

Ser Pro Ser Pro Ile Val Glu Glu Ser Arg
1               5                   10

<210> SEQ ID NO 674
<211> LENGTH: 10
<212> TYPE: PRT
<213> ORGANISM: Dengue virus

<400> SEQUENCE: 674

Ser Pro Ser Pro Thr Val Glu Glu Ser Arg
1               5                   10

<210> SEQ ID NO 675
<211> LENGTH: 10
<212> TYPE: PRT
<213> ORGANISM: Dengue virus

<400> SEQUENCE: 675

Ser Ser Asn Pro Thr Ile Glu Glu Gly Arg
1               5                   10

<210> SEQ ID NO 676
<211> LENGTH: 10
<212> TYPE: PRT
<213> ORGANISM: Dengue virus

<400> SEQUENCE: 676

Thr Pro Arg Met Cys Thr Arg Glu Glu Phe
1               5                   10

<210> SEQ ID NO 677
<211> LENGTH: 10
<212> TYPE: PRT
<213> ORGANISM: Dengue virus

<400> SEQUENCE: 677

Lys Pro Arg Ile Cys Thr Arg Glu Glu Phe
1               5                   10

<210> SEQ ID NO 678
<211> LENGTH: 10
```

```
<212> TYPE: PRT
<213> ORGANISM: Dengue virus

<400> SEQUENCE: 678

Arg Pro Arg Ile Cys Thr Arg Ala Glu Phe
1               5                   10

<210> SEQ ID NO 679
<211> LENGTH: 10
<212> TYPE: PRT
<213> ORGANISM: Dengue virus

<400> SEQUENCE: 679

Lys Pro Arg Ile Cys Thr Arg Ala Glu Phe
1               5                   10

<210> SEQ ID NO 680
<211> LENGTH: 10
<212> TYPE: PRT
<213> ORGANISM: Dengue virus

<400> SEQUENCE: 680

Thr Arg Arg Met Cys Thr Arg Glu Glu Phe
1               5                   10

<210> SEQ ID NO 681
<211> LENGTH: 10
<212> TYPE: PRT
<213> ORGANISM: Dengue virus

<400> SEQUENCE: 681

Thr Pro Arg Ile Cys Thr Arg Glu Glu Phe
1               5                   10

<210> SEQ ID NO 682
<211> LENGTH: 10
<212> TYPE: PRT
<213> ORGANISM: Dengue virus

<400> SEQUENCE: 682

Ile Pro Arg Met Cys Thr Arg Glu Glu Phe
1               5                   10

<210> SEQ ID NO 683
<211> LENGTH: 10
<212> TYPE: PRT
<213> ORGANISM: Dengue virus

<400> SEQUENCE: 683

Thr Pro Arg Met Cys Thr Arg Glu Glu Phe
1               5                   10

<210> SEQ ID NO 684
<211> LENGTH: 10
<212> TYPE: PRT
<213> ORGANISM: Dengue virus

<400> SEQUENCE: 684

Lys Pro Arg Leu Cys Pro Arg Glu Glu Phe
1               5                   10

<210> SEQ ID NO 685
<211> LENGTH: 10
<212> TYPE: PRT
<213> ORGANISM: Dengue virus
```

<400> SEQUENCE: 685

Lys Pro Arg Leu Cys Thr Arg Glu Glu Phe
1               5                   10

<210> SEQ ID NO 686
<211> LENGTH: 10
<212> TYPE: PRT
<213> ORGANISM: Dengue virus

<400> SEQUENCE: 686

Arg Pro Arg Leu Cys Thr Arg Glu Glu Phe
1               5                   10

<210> SEQ ID NO 687
<211> LENGTH: 10
<212> TYPE: PRT
<213> ORGANISM: Dengue virus

<400> SEQUENCE: 687

Asn Pro Arg Leu Cys Thr Lys Glu Glu Phe
1               5                   10

<210> SEQ ID NO 688
<211> LENGTH: 10
<212> TYPE: PRT
<213> ORGANISM: Dengue virus

<400> SEQUENCE: 688

Ser Pro Arg Leu Cys Thr Arg Glu Glu Phe
1               5                   10

<210> SEQ ID NO 689
<211> LENGTH: 10
<212> TYPE: PRT
<213> ORGANISM: Dengue virus

<400> SEQUENCE: 689

Thr Pro Arg Leu Cys Thr Arg Glu Glu Phe
1               5                   10

<210> SEQ ID NO 690
<211> LENGTH: 10
<212> TYPE: PRT
<213> ORGANISM: Dengue virus

<400> SEQUENCE: 690

Ser Pro Arg Leu Cys Thr Lys Glu Glu Phe
1               5                   10

<210> SEQ ID NO 691
<211> LENGTH: 10
<212> TYPE: PRT
<213> ORGANISM: Dengue virus

<400> SEQUENCE: 691

Asn Pro Arg Leu Cys Thr Arg Glu Glu Phe
1               5                   10

<210> SEQ ID NO 692
<211> LENGTH: 10
<212> TYPE: PRT
<213> ORGANISM: Dengue virus

<400> SEQUENCE: 692

Lys Pro Arg Leu Cys Thr Arg Glu Glu Phe
1               5                   10

<210> SEQ ID NO 693
<211> LENGTH: 9
<212> TYPE: PRT
<213> ORGANISM: Dengue virus

<400> SEQUENCE: 693

Arg Pro Thr Pro Arg Gly Thr Val Met
1               5

<210> SEQ ID NO 694
<211> LENGTH: 9
<212> TYPE: PRT
<213> ORGANISM: Dengue virus

<400> SEQUENCE: 694

Arg Pro Val Lys Asn Gly Thr Val Met
1               5

<210> SEQ ID NO 695
<211> LENGTH: 9
<212> TYPE: PRT
<213> ORGANISM: Dengue virus

<400> SEQUENCE: 695

Arg Pro Ala Arg Asn Gly Thr Val Met
1               5

<210> SEQ ID NO 696
<211> LENGTH: 9
<212> TYPE: PRT
<213> ORGANISM: Dengue virus

<400> SEQUENCE: 696

Arg Pro Ala Lys Asn Gly Thr Val Met
1               5

<210> SEQ ID NO 697
<211> LENGTH: 9
<212> TYPE: PRT
<213> ORGANISM: Dengue virus

<400> SEQUENCE: 697

Arg Pro Ala Lys Ser Gly Thr Val Met
1               5

<210> SEQ ID NO 698
<211> LENGTH: 9
<212> TYPE: PRT
<213> ORGANISM: Dengue virus

<400> SEQUENCE: 698

Arg Pro Thr Pro Arg Gly Thr Val Leu
1               5

<210> SEQ ID NO 699
<211> LENGTH: 9
<212> TYPE: PRT
<213> ORGANISM: Dengue virus

<400> SEQUENCE: 699

Arg Pro Thr Pro Lys Gly Thr Val Met

<210> SEQ ID NO 700
<211> LENGTH: 9
<212> TYPE: PRT
<213> ORGANISM: Dengue virus

<400> SEQUENCE: 700

Arg Pro Thr Pro Ile Gly Thr Val Met
1               5

<210> SEQ ID NO 701
<211> LENGTH: 9
<212> TYPE: PRT
<213> ORGANISM: Dengue virus

<400> SEQUENCE: 701

Arg Pro Thr Pro Arg Gly Thr Val Met
1               5

<210> SEQ ID NO 702
<211> LENGTH: 9
<212> TYPE: PRT
<213> ORGANISM: Dengue virus

<400> SEQUENCE: 702

Arg Pro Thr Pro Lys Gly Thr Val Met
1               5

<210> SEQ ID NO 703
<211> LENGTH: 9
<212> TYPE: PRT
<213> ORGANISM: Dengue virus

<400> SEQUENCE: 703

Arg Pro Thr Pro Thr Gly Thr Val Met
1               5

<210> SEQ ID NO 704
<211> LENGTH: 9
<212> TYPE: PRT
<213> ORGANISM: Dengue virus

<400> SEQUENCE: 704

Arg Pro Thr Pro Arg Gly Ala Val Met
1               5

<210> SEQ ID NO 705
<211> LENGTH: 9
<212> TYPE: PRT
<213> ORGANISM: Dengue virus

<400> SEQUENCE: 705

Arg Pro Thr Pro Lys Gly Ala Val Met
1               5

<210> SEQ ID NO 706
<211> LENGTH: 15
<212> TYPE: PRT
<213> ORGANISM: Dengue virus

<400> SEQUENCE: 706

Ala Phe Leu Arg Phe Leu Thr Ile Pro Pro Thr Ala Gly Ile Leu
1               5                   10                  15

```
<210> SEQ ID NO 707
<211> LENGTH: 15
<212> TYPE: PRT
<213> ORGANISM: Dengue virus

<400> SEQUENCE: 707

Ala Phe Leu Arg Phe Leu Ala Ile Pro Pro Thr Ala Gly Ile Val
1               5                   10                  15

<210> SEQ ID NO 708
<211> LENGTH: 15
<212> TYPE: PRT
<213> ORGANISM: Dengue virus

<400> SEQUENCE: 708

Ala Leu Leu Arg Phe Leu Ala Ile Pro Pro Thr Ala Gly Ile Leu
1               5                   10                  15

<210> SEQ ID NO 709
<211> LENGTH: 15
<212> TYPE: PRT
<213> ORGANISM: Dengue virus

<400> SEQUENCE: 709

Ala Phe Leu Thr Phe Leu Ala Ile Pro Pro Thr Ala Gly Ile Leu
1               5                   10                  15

<210> SEQ ID NO 710
<211> LENGTH: 15
<212> TYPE: PRT
<213> ORGANISM: Dengue virus

<400> SEQUENCE: 710

Ala Phe Leu Arg Phe Leu Ala Ile Pro Pro Thr Ala Gly Ile Leu
1               5                   10                  15

<210> SEQ ID NO 711
<211> LENGTH: 15
<212> TYPE: PRT
<213> ORGANISM: Dengue virus

<400> SEQUENCE: 711

Ala Phe Leu Arg Phe Leu Thr Ile Ser Pro Thr Ala Gly Ile Leu
1               5                   10                  15

<210> SEQ ID NO 712
<211> LENGTH: 15
<212> TYPE: PRT
<213> ORGANISM: Dengue virus

<400> SEQUENCE: 712

Ala Phe Leu Arg Phe Leu Thr Ile Pro Pro Thr Val Gly Ile Leu
1               5                   10                  15

<210> SEQ ID NO 713
<211> LENGTH: 15
<212> TYPE: PRT
<213> ORGANISM: Dengue virus

<400> SEQUENCE: 713

Ala Phe Leu Arg Phe Leu Thr Ile Pro Pro Thr Ala Gly Ile Leu
1               5                   10                  15

<210> SEQ ID NO 714
```

```
<211> LENGTH: 15
<212> TYPE: PRT
<213> ORGANISM: Dengue virus

<400> SEQUENCE: 714

Ala Phe Leu Arg Phe Leu Ala Ile Pro Pro Thr Ala Gly Ile Leu
1               5                   10                  15

<210> SEQ ID NO 715
<211> LENGTH: 15
<212> TYPE: PRT
<213> ORGANISM: Dengue virus

<400> SEQUENCE: 715

Ala Phe Leu Arg Phe Leu Ala Ile Pro Pro Thr Ala Gly Val Leu
1               5                   10                  15

<210> SEQ ID NO 716
<211> LENGTH: 15
<212> TYPE: PRT
<213> ORGANISM: Dengue virus

<400> SEQUENCE: 716

Thr Phe Leu Arg Val Leu Ser Ile Pro Pro Thr Ala Gly Ile Leu
1               5                   10                  15

<210> SEQ ID NO 717
<211> LENGTH: 15
<212> TYPE: PRT
<213> ORGANISM: Dengue virus

<400> SEQUENCE: 717

Gly Val Thr Tyr Leu Ala Leu Leu Ala Ala Phe Lys Val Arg Pro
1               5                   10                  15

<210> SEQ ID NO 718
<211> LENGTH: 15
<212> TYPE: PRT
<213> ORGANISM: Dengue virus

<400> SEQUENCE: 718

Gly Thr Thr Tyr Leu Ala Leu Met Ala Thr Phe Arg Met Arg Pro
1               5                   10                  15

<210> SEQ ID NO 719
<211> LENGTH: 15
<212> TYPE: PRT
<213> ORGANISM: Dengue virus

<400> SEQUENCE: 719

Gly Met Thr Tyr Leu Ala Leu Met Ala Thr Phe Lys Met Arg Pro
1               5                   10                  15

<210> SEQ ID NO 720
<211> LENGTH: 15
<212> TYPE: PRT
<213> ORGANISM: Dengue virus

<400> SEQUENCE: 720

Gly Thr Thr Tyr Leu Ala Leu Met Ala Thr Leu Lys Met Arg Pro
1               5                   10                  15

<210> SEQ ID NO 721
<211> LENGTH: 15
<212> TYPE: PRT
```

<213> ORGANISM: Dengue virus

<400> SEQUENCE: 721

Gly Thr Thr His Leu Ala Leu Met Ala Thr Phe Lys Met Arg Pro
1               5                   10                  15

<210> SEQ ID NO 722
<211> LENGTH: 15
<212> TYPE: PRT
<213> ORGANISM: Dengue virus

<400> SEQUENCE: 722

Gly Thr Thr Tyr Leu Ala Leu Met Ala Thr Phe Lys Met Arg Pro
1               5                   10                  15

<210> SEQ ID NO 723
<211> LENGTH: 15
<212> TYPE: PRT
<213> ORGANISM: Dengue virus

<400> SEQUENCE: 723

Gly Val Thr Tyr Leu Ala Leu Leu Ala Thr Phe Lys Val Arg Pro
1               5                   10                  15

<210> SEQ ID NO 724
<211> LENGTH: 15
<212> TYPE: PRT
<213> ORGANISM: Dengue virus

<400> SEQUENCE: 724

Gly Val Thr Tyr Leu Ala Leu Leu Ala Ala Tyr Lys Val Arg Pro
1               5                   10                  15

<210> SEQ ID NO 725
<211> LENGTH: 15
<212> TYPE: PRT
<213> ORGANISM: Dengue virus

<400> SEQUENCE: 725

Gly Val Thr Tyr Leu Ala Leu Leu Ala Ala Phe Arg Val Arg Pro
1               5                   10                  15

<210> SEQ ID NO 726
<211> LENGTH: 15
<212> TYPE: PRT
<213> ORGANISM: Dengue virus

<400> SEQUENCE: 726

Gly Val Thr Tyr Leu Ala Leu Leu Ala Ala Phe Lys Val Arg Pro
1               5                   10                  15

<210> SEQ ID NO 727
<211> LENGTH: 15
<212> TYPE: PRT
<213> ORGANISM: Dengue virus

<400> SEQUENCE: 727

Gly Val Thr Tyr Leu Ala Leu Ile Ala Thr Phe Glu Ile Gln Pro
1               5                   10                  15

<210> SEQ ID NO 728
<211> LENGTH: 15
<212> TYPE: PRT
<213> ORGANISM: Dengue virus -continued

<400> SEQUENCE: 728

Gly Val Thr Cys Leu Ala Leu Ile Ala Thr Phe Lys Ile Gln Pro
1               5                   10                  15

<210> SEQ ID NO 729
<211> LENGTH: 15
<212> TYPE: PRT
<213> ORGANISM: Dengue virus

<400> SEQUENCE: 729

Gly Val Thr Tyr Leu Ala Leu Ile Ala Thr Phe Lys Val Gln Pro
1               5                   10                  15

<210> SEQ ID NO 730
<211> LENGTH: 15
<212> TYPE: PRT
<213> ORGANISM: Dengue virus

<400> SEQUENCE: 730

Gly Val Thr Tyr Leu Ala Leu Ile Ala Thr Phe Lys Ile Gln Pro
1               5                   10                  15

<210> SEQ ID NO 731
<211> LENGTH: 15
<212> TYPE: PRT
<213> ORGANISM: Dengue virus

<400> SEQUENCE: 731

Gly Gln Thr His Leu Ala Ile Met Ala Val Phe Lys Met Ser Pro
1               5                   10                  15

<210> SEQ ID NO 732
<211> LENGTH: 15
<212> TYPE: PRT
<213> ORGANISM: Dengue virus

<400> SEQUENCE: 732

Gly Gln Ile His Leu Ala Ile Met Ala Val Phe Lys Met Ser Pro
1               5                   10                  15

<210> SEQ ID NO 733
<211> LENGTH: 15
<212> TYPE: PRT
<213> ORGANISM: Dengue virus

<400> SEQUENCE: 733

Gly Gln Thr His Leu Ala Ile Met Ile Val Phe Lys Met Ser Pro
1               5                   10                  15

<210> SEQ ID NO 734
<211> LENGTH: 15
<212> TYPE: PRT
<213> ORGANISM: Dengue virus

<400> SEQUENCE: 734

Gly Gln Val His Leu Ala Ile Met Ala Val Phe Lys Met Ser Pro
1               5                   10                  15

<210> SEQ ID NO 735
<211> LENGTH: 15
<212> TYPE: PRT
<213> ORGANISM: Dengue virus

<400> SEQUENCE: 735

-continued

Gly Gln Ile His Leu Ala Ile Met Thr Met Phe Lys Met Ser Pro
1               5                   10                  15

<210> SEQ ID NO 736
<211> LENGTH: 15

<210> SEQ ID NO 743
<211> LENGTH: 15
<212> TYPE: PRT
<213> ORGANISM: Dengue virus

<400> SEQUENCE: 743

Met Ala Val Gly Leu Val Ser Ile Leu Ala Ser Ser Leu Leu Arg
1               5                   10                  15

<210> SEQ ID NO 744
<211> LENGTH: 15
<212> TYPE: PRT
<213> ORGANISM: Dengue virus

<400> SEQUENCE: 744

Met Ala Val Gly Leu Val Ser Leu Leu Gly Ser Ala Leu Leu Lys
1               5                   10                  15

<210> SEQ ID NO 745
<211> LENGTH: 15
<212> TYPE: PRT
<213> ORGANISM: Dengue virus

<400> SEQUENCE: 745

Thr Phe Thr Met Arg Leu Leu Ser Pro Val Arg Val Pro Asn Tyr
1               5                   10                  15

<210> SEQ ID NO 746
<211> LENGTH: 15
<212> TYPE: PRT
<213> ORGANISM: Dengue virus

<400> SEQUENCE: 746

Thr Phe Thr Met Arg Leu Leu Ser Pro Val Arg Val Pro Asn Tyr
1               5                   10                  15

<210> SEQ ID NO 747
<211> LENGTH: 15
<212> TYPE: PRT
<213> ORGANISM: Dengue virus

<400> SEQUENCE: 747

Pro Phe Thr Met Arg Leu Leu Ser Pro Val Arg Val Pro Asn Tyr
1               5                   10                  15

<210> SEQ ID NO 748
<211> LENGTH: 15
<212> TYPE: PRT
<213> ORGANISM: Dengue virus

<400> SEQUENCE: 748

Thr Phe Thr Met Arg Leu Leu Ser Pro Ile Arg Val Pro Asn Tyr
1               5                   10                  15

<210> SEQ ID NO 749
<211> LENGTH: 15
<212> TYPE: PRT
<213> ORGANISM: Dengue virus

<400> SEQUENCE: 749

Thr Phe Thr Met Arg Leu Leu Ser Pro Val Arg Val Pro Asn Tyr
1               5                   10                  15

<210> SEQ ID NO 750
<211> LENGTH: 15
<212> TYPE: PRT
<213> ORGANISM: Dengue virus

<400> SEQUENCE: 750

Thr Phe Thr Met Arg Leu Leu Ser Pro Val Arg Val Ser Asn Tyr
1               5                   10                  15

<210> SEQ ID NO 751
<211> LENGTH: 15
<212> TYPE: PRT
<213> ORGANISM: Dengue virus

<400> SEQUENCE: 751

Pro Phe Thr Met Arg Leu Leu Ser Pro Val Arg Val Pro Asn Tyr
1               5                   10                  15

<210> SEQ ID NO 752
<211> LENGTH: 15
<212> TYPE: PRT
<213> ORGANISM: Dengue virus

<400> SEQUENCE: 752

Thr Phe Thr Met Arg Leu Leu Ser Pro Val Arg Val Pro Asn Tyr
1               5                   10                  15

<210> SEQ ID NO 753
<211> LENGTH: 15
<212> TYPE: PRT
<213> ORGANISM: Dengue virus

<400> SEQUENCE: 753

Thr Phe Thr Thr Lys Leu Leu Ser Ser Thr Arg Val Pro Asn Tyr
1               5                   10                  15

<210> SEQ ID NO 754
<211> LENGTH: 15
<212> TYPE: PRT
<213> ORGANISM: Dengue virus

<400> SEQUENCE: 754

Thr Phe Thr Thr Arg Leu Leu Ser Ser Thr Arg Val Pro Asn Tyr
1               5                   10                  15

<210> SEQ ID NO 755
<211> LENGTH: 15
<212> TYPE: PRT
<213> ORGANISM: Dengue virus

<400> SEQUENCE: 755

Ser Arg Ala Ile Trp Tyr Met Trp Leu Gly Ala Arg Phe Leu Glu
1               5                   10                  15

<210> SEQ ID NO 756
<211> LENGTH: 15
<212> TYPE: PRT
<213> ORGANISM: Dengue virus

<400> SEQUENCE: 756

Ser Arg Ala Ile Trp Tyr Val Trp Leu Gly Ala Arg Phe Leu Glu
1               5                   10                  15

<210> SEQ ID NO 757
<211> LENGTH: 15

<210> SEQ ID NO 757
<211> LENGTH: 15
<212> TYPE: PRT
<213> ORGANISM: Dengue virus

<400> SEQUENCE: 757

Ser Arg Ala Ile Trp Tyr Met Trp Leu Gly Ala Ala Phe Leu Glu
1               5                   10                  15

<210> SEQ ID NO 758
<211> LENGTH: 15
<212> TYPE: PRT
<213> ORGANISM: Dengue virus

<400> SEQUENCE: 758

Ser Arg Ala Ile Trp Tyr Met Trp Leu Gly Ala Arg Phe Leu Glu
1               5                   10                  15

<210> SEQ ID NO 759
<211> LENGTH: 15
<212> TYPE: PRT
<213> ORGANISM: Dengue virus

<400> SEQUENCE: 759

Ser Arg Ala Ile Trp Tyr Met Trp Leu Gly Ala Arg Phe Leu Glu
1               5                   10                  15

<210> SEQ ID NO 760
<211> LENGTH: 15
<212> TYPE: PRT
<213> ORGANISM: Dengue virus

<400> SEQUENCE: 760

Ser Arg Ala Ile Trp Tyr Met Trp Leu Gly Ala Arg Phe Leu Glu
1               5                   10                  15

<210> SEQ ID NO 761
<211> LENGTH: 15
<212> TYPE: PRT
<213> ORGANISM: Dengue virus

<400> SEQUENCE: 761

Ser Arg Ala Ile Trp Tyr Met Trp Leu Gly Val Arg Tyr Leu Glu
1               5                   10                  15

<210> SEQ ID NO 762
<211> LENGTH: 15
<212> TYPE: PRT
<213> ORGANISM: Dengue virus

<400> SEQUENCE: 762

Ser Arg Ala Ile Trp Tyr Met Trp Leu Gly Ala Arg Tyr Leu Glu
1               5                   10                  15

<210> SEQ ID NO 763
<211> LENGTH: 15
<212> TYPE: PRT
<213> ORGANISM: Dengue virus

<400> SEQUENCE: 763

Ser Arg Ala Ile Trp Tyr Met Trp Leu Gly Ala Arg Phe Leu Glu
1               5                   10                  15